US007799899B2

(12) United States Patent
Ackerly et al.

(10) Patent No.: US 7,799,899 B2
(45) Date of Patent: Sep. 21, 2010

(54) COMPOSITIONS AND METHODS RELATING TO STOP-1

(75) Inventors: Heidi Ackerly, Belmont, CA (US); Avi Ashkenazi, San Mateo, CA (US); David Eberhard, San Francisco, CA (US); Gretchen Frantz, San Francisco, CA (US); Dorothy French, San Carlos, CA (US); Germaine G. Fuh, Pacifica, CA (US); Jo-Anne S. Hongo, Redwood City, CA (US); Chingwei V. Lee, Foster City, CA (US); Scot A. Masters, San Carlos, CA (US); Helga A. Raab, San Francisco, CA (US); Evgeny Varfolomeev, Burlingame, CA (US); Beni B. Wolf, Redwood City, CA (US); Robert Maurice Pitti, El Cerrito, CA (US); Liliana Soroceanu, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 750 days.

(21) Appl. No.: 10/553,491

(22) PCT Filed: Apr. 16, 2004

(86) PCT No.: PCT/US2004/011793

§ 371 (c)(1),
(2), (4) Date: Apr. 18, 2007

(87) PCT Pub. No.: WO2004/094476

PCT Pub. Date: Nov. 4, 2004

(65) Prior Publication Data

US 2008/0050377 A1 Feb. 28, 2008

Related U.S. Application Data

(60) Provisional application No. 60/463,656, filed on Apr. 16, 2003.

(51) Int. Cl.
C07K 16/00 (2006.01)
(52) U.S. Cl. .................. 530/387.1; 424/130.1
(58) Field of Classification Search ............... None
See application file for complete search history.

(56) References Cited

U.S. PATENT DOCUMENTS

| 5,821,337 | A | 10/1998 | Carter et al. |
| 6,476,195 | B1 | 11/2002 | Komatsoulis et al. |
| 6,680,197 | B2 | 1/2004 | Jiang et al. |
| 7,414,112 | B2 | 8/2008 | Grimaldi et al. |
| 2002/0161211 | A1 | 10/2002 | Lindner et al. |
| 2003/0068688 | A1 | 4/2003 | Baker et al. |
| 2005/0147602 | A1 | 7/2005 | Lindner |
| 2009/0136997 | A1 | 5/2009 | Eaton et al. |

FOREIGN PATENT DOCUMENTS

| EP | 1179540 A1 | 2/2002 |
| WO | WO 92/09690 | 6/1992 |
| WO | WO 98/54963 | 12/1998 |
| WO | WO 00/06698 | 2/2000 |
| WO | WO 00/12708 | 3/2000 |
| WO | WO 00/52151 | 9/2000 |
| WO | WO 00/60076 | 10/2000 |
| WO | WO 00/71581 A1 | 11/2000 |
| WO | WO 00/73346 A1 | 12/2000 |
| WO | WO 00/78960 A2 | 12/2000 |
| WO | WO 00/78961 A1 | 12/2000 |
| WO | WO 01/16318 A2 | 3/2001 |
| WO | WO 01/53455 A2 | 7/2001 |
| WO | WO 01/62891 A2 | 8/2001 |
| WO | WO 01/68848 A2 | 9/2001 |
| WO | WO 02/00690 A2 | 1/2002 |
| WO | WO 02/08284 A2 | 1/2002 |
| WO | WO 02/16602 A2 | 2/2002 |
| WO | WO 02/42487 A2 | 5/2002 |
| WO | WO 02/071928 A2 | 9/2002 |

OTHER PUBLICATIONS

Rudikoff et al (Proc Natl Acad Sci USA 1982 vol. 79 p. 1979).*
MacCallum et al. J. Mol. Biol. (1996) 262, 732-745.*
Pascalis et al. The Journal of Immunology (2002) 169, 3076-3084.*
Casset et al. (2003) BBRC 307, 198-205.*
Vajdos et al. Journal of Molecular Biology (2002) 320, 415-428.*
Holm et al. Molecular Immunology (2007) 44, 1075-1084.*
Chen et al. J. Mol. Bio. (1999) 293, 865-881.*
Wu et al. J. Mol. Biol. (1999) 294, 151-162.*
Mueller et al. (PNAS 1992) vol. 89. pp. 11832-11836.*
Holt et al., "Domain antibodies: proteins for therapy" *Trends Biotechnol.* 21(11):484-490 (Nov. 2003).
Pyagay et al., "Collagen triple helix repeat containing 1, a novel secreted protein in injured and diseased arteries, inhibits collagen expression and promotes cell migration" *Circ Res.* (online: Dec. 23, 2004) 96(2):261-268.
Presentation given by Larry Helms, USPTO SPE, at the Biotechnology/Chemical/Pharmaceutical Customer Partnership on Jun. 13, 2007, "Enablement Issues in the Examination of Antibodies".
"Partial European Search Report issued in counterpart EP Application No. 09004416.5".

* cited by examiner

*Primary Examiner*—Larry R. Helms
*Assistant Examiner*—Meera Natarajan
(74) *Attorney, Agent, or Firm*—Danielle M. Pasqualone

(57) ABSTRACT

The present invention provides novel polypeptides, antibodies, antagonists, agonists, potentiators, nucleic acid molecules, compositions and methods relating to the STOP-1 polypeptide that are useful for treating and preventing diseases and for medical diagnosis and research. The present invention also provides consensus sequences and specific sequences for antibodies that specifically bind to STOP-1 that are useful in the methods described herein.

19 Claims, 74 Drawing Sheets

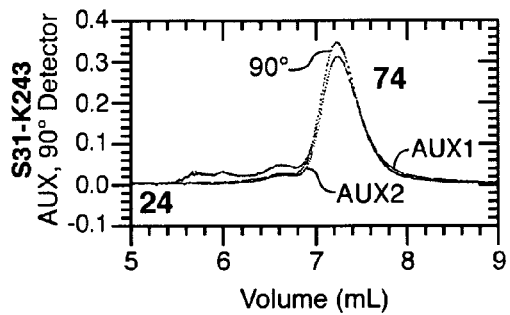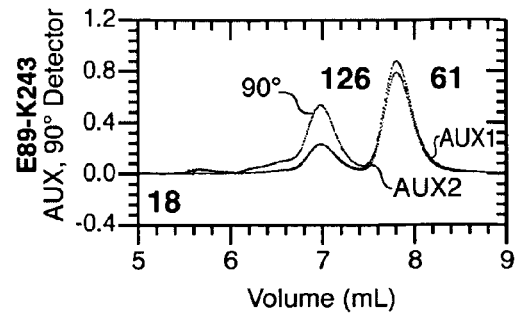
FIG. 6A  FIG. 6B
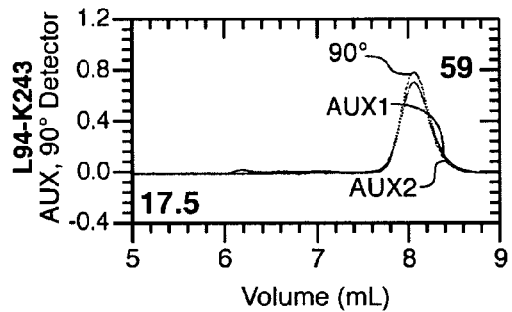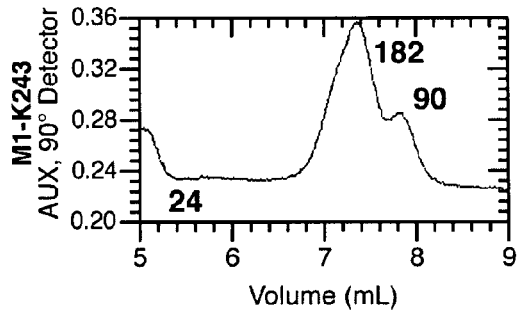
FIG. 6C  FIG. 7A
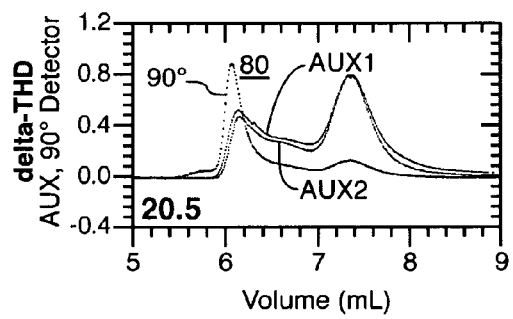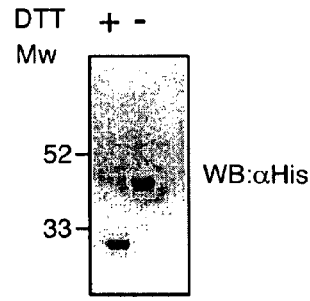
FIG. 7B  FIG. 7C

FIG. 18

| | H1 | | | | | | H2 | | | | | | | | | | | H3 | | | | | | | | | | | | | | Name |
|---|---|---|---|---|---|---|---|---|---|---|---|---|---|---|---|---|---|---|---|---|---|---|---|---|---|---|---|---|---|---|---|---|
| 28 | 29 | 30 | 31 | 32 | 33 | 49 | 50 | 51 | 52 | 52a | 53 | 54 | 55 | 56 | 57 | 58 | 92 | 93 | 94 | 95 | 96 | 97 | 98 | 99 | 100 | 100a | 100b | 100c | 101 | 102 | |
| T | I | S | G | S | D | G | R | I | S | P | Y | G | G | N | T | N | C | A | R | V | G | G | L | K | L | L | - | F | D | Y | S7 |
| T | I | - | T | N | D | A | T | I | Y | P | Y | G | G | Y | T | Y | C | A | R | G | G | G | M | D | G | Y | V | M | D | Y | S16 |
| T | I | - | N | N | D | G | Y | I | S | P | P | S | G | A | T | Y | C | A | R | M | V | G | M | R | R | G | V | M | D | Y | F5 |
| T | I | - | N | N | Y | G | Y | I | S | P | P | S | G | A | T | Y | C | A | R | M | V | G | M | R | R | G | V | M | D | Y | F6 |
| T | I | - | S | N | W | A | W | I | A | P | Y | S | G | A | T | D | C | A | R | E | E | G | G | L | Y | W | - | F | F | Y | S4 |
| T | I | - | S | Y | G | G | R | I | S | P | S | N | G | S | T | Y | C | A | K | C | S | V | R | - | - | - | - | F | A | Y | S9 |
| T | I | - | S | G | W | A | W | I | A | P | Y | S | G | A | T | D | C | A | R | E | E | G | G | L | Y | W | V | F | D | Y | F13 |
| T | I | - | S | G | W | A | W | I | A | P | Y | S | G | A | T | D | C | A | R | E | E | G | G | L | Y | W | V | F | D | Y | F47 |

FIG. 21

| | Phage | | | | Fab | | | | IgG | | | |
|---|---|---|---|---|---|---|---|---|---|---|---|---|
| | 762 S/S | 762 F/F | | | 762 S/S | 762 F/S | 762 F/F | | 762 S/S | 762 F/F | | |
| S4 | 3nM | 0.9nM | | | 3.6nM (1.9nM) | 32nM | 13.4nM | | 0.5nM | 3.1nM | | |
| S7 | 35nM | 2.7nM | | | 113nM | 57nM | n/a | | 7.3nM | 41nM | | |

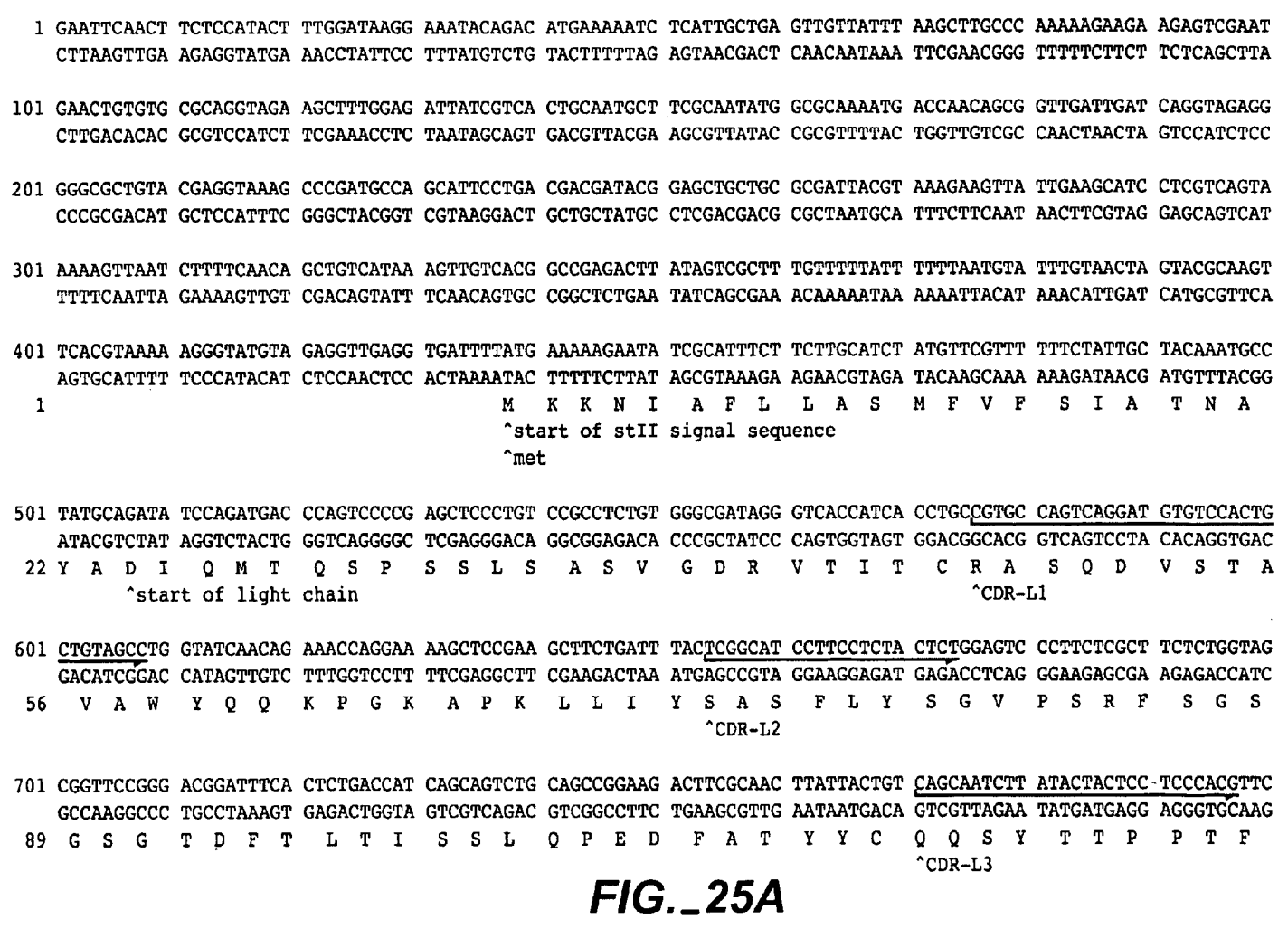

FIG._25A

```
 801 GGACAGGGTA CCAAGGTTGGA GATCAAACGA ACTGTGGCTG CACCATCTGT CTTCATCTTC CGGCCATCTG ATGAGCAGTT GAAATCTGGA ACTGCCTCTG
     CCTGTCCCAT GGTTCCACCT CTAGTTTGCT TGACACCGAC GTGGTAGACA GAAGTAGAAG GCCGGTAGAC TACTCGTCAA CTTTAGACCT TGACGGAGAC
 122 G  Q  G  T   K  V  E   I  K  R    T  V  A  A   P  S  V  F   I  F  P  P   S  D  E  Q   L  K  S  G   T  A  S  V

901 TTGTGTGCCT GCTGAATAAC TTCTATCCCA GAGAGGCCAA AGTACAGTGG AAGGTGGATA ACGCCCTCCA ATCGGGTAAC TCCCAGGAGA GTGTCACAGA
     AACACACGGA CGACTTATTG AAGATAGGGT CTCTCCGGTT TCATGTCACC TTCCACCTAT TGCGGGAGGT TAGCCCATTG AGGGTCCTCT CACAGTGTCT
 156 V  C  L  L   N  N  F   Y  P  R    E  A  K  V   Q  W  K  V   D  N  A  L   Q  S  G  N   S  Q  E  S   V  T  E

1001 GCAGGACAGC AAGGACAGCA CCTACAGCCT CAGCAGCACC CTGACGCTGA GCAAAGCAGA CTACGAGAAA CACAAAGTCT ACGCCTGCGA AGTCACCCAT
     CGTCCTGTCG TTCCTGTCGT GGATGTCGGA GTCGTCGTGG GACTGCGACT CGTTTCGTCT GATGCTCTTT GTGTTTCAGA TGCGGACGCT TCAGTGGGTA
 189 Q  D  S  K   D  S  T   Y  S  L    S  S  T  L   T  L  S  K   A  D  Y  E   K  H  K  V   Y  A  C  E   V  T  H

1101 CAGGGCCTGA GCTCGCCCGT CACAAAGAGC TTCAACAGGG GAGAGTGTGG TGCCAGTCCC CGGTATGGCTG ATCCGAACCG TTTCCGCGGT AAGGACCTGG
     GTCCCGGACT CGAGCGGGCA GTGTTTCTCG AAGTTGTCCC CTCTCACACC ACGGTCAGGG GCCATACCGAC TAGGCTTGGC AAAGGCGCCA TTCCTGGACC
 222 Q  G  L  S   S  P  V   T  K  S    F  N  R  G   E  C  G  A   S  S  G  M   A  D  P  N   R  F  R  G   K  D  L  A
                                                                    ^end of light chain, start of gD tag 1201 CATAACTCGA GGCTGATCCT CTACGCCGGA CGCATCGTGG CCCTAGTACC CAAGTTCACG CAAGTTCACG GTTCAAGTGC ATTTTCCCA ACTCCACTAA
     GTATTGAGCT CCGACTAGGA GATGCGGCCT GCGTAGCACC GGGATCATGC GTTCAAGTGC CAAGTTCACG CAAGTTCACG TAAATCTTTT
 256                                                                                                               ^start of stII
 -23
                                                                                                                   M  K  K 1301 GAATATCGCA TTTCTTCTTG CATCTATGTT CGTTTTTTCT ATTGCTACAA TAACGGTACC ACGGCGTACC TGAGGTTCAG CTGGTGGAGT CCTGGTGCAG
     CTTATAGCGT AAAGAAGAAC GTAGATACAA GCAAAAAAGA TAACGATGTT ATTGCCATGG TGCCGCATGG ACTCCAAGTC GACCACCTCA GGACCACGTC
 -20 N  I  A  F   L  L  A   S  M  F   V  F  S   I  A  T  N   A  Y  A   E  V  Q   L  V  E  S   G  G  G   L  V  Q
                                                            ^start of heavy chain 1401 CCAGGGGGCT CACTCCGTTT GTCCTGTGCA GCTTCTGGCT TCAACATTAA AGACACCTAT ATACACTGGG TGCGTCAGGC CCCGGGTAAG GGCCTGGAAT
     GGTCCCCCGA GTGAGGCAAA CAGGACACGT CGAAGACCGA AGTTGTAATT TCTGTGGATA TATGTGACCC ACGCAGTCCG GGGCCCATTC CCGGACCTTA
  14 P  G  G  S   L  R  L   S  C  A   A  S  G   F  N  I  K   D  T  Y   I  H  W   V  R  Q  A   P  G  K   G  L  E  W
                                          ^CDR-H1
```

FIG._25B

```
1501 GGGTTGCAAG GATTATCCT ACGAATGTT ATACTAGATA TGCCGATAGC GTTCACTATT AAGCCGCAGAC ACATCCAAAA ACACAGCCTA
     CCCAACGTTC CTAAATAGGA TGCTTACCAA TATGATCTAT ACGGCTATCG CAGTTGTATA TTCGCGTCTG TGTAGGTTTT TGTGTCGGAT
  48  V  K  G   R  F  T  I    S  A  D  T    S  K  N  T  A  Y
        ˆCDR-H2

1601 CCTACAAATG AACAGCTTAA GAGCTGAGGA CACTGCCGTC TATTATTGTA GCCGCTGGGG AGGGGACGGC TTCTATGCTA TGGACTACTG GGGTCAAGGA
     GGATGTTTAC TTGTCGAATT CTCGACTCCT GTGACGGCAG ATAATAACAT CGGCGACCCC TCCCCTGCCG AAGATACGAT ACCTGATGAC CCCAGTTCCT
  81  L  Q  M   N  S  L  R   A  E  D   T  A  V  Y  Y  C  S   R  W  G   G  D  G   F  Y  A  M   D  Y  W   G  Q  G
                                                              ˆCDR-H3

1701 ACACTAGTCA CCGTCTCCTC GGCCTCCACC AAGGGCCCAT CGGTCTTCCC CCTGGCACCC TCCTCCAAGA GCACCTCTGG GGGCACAGCG GCCCTGGGCT
     TGTGATCAGT GGCAGAGGAG CCGGAGGTGG TTCCCGGGTA GCCAGAAGGG GGACCGTGGG AGGAGTTCT CGTGGAGACC CCCGTGTCGC CGGGACCCGA
 114  T  L  V   T  V  S  S    A  S  T   K  G  P  S   V  F  P   L  A  P   S  S  K  S   T  S  G   G  T  A   A  L  G  C

1801 GCCTGGTCAA GGACTACTTC CCCGAACCGG TGACGGTGTC GTGGAACTCA GGCGCCCTGA CCAGCGGCGT GCACACCTTC CCGGCTGTCC TACAGTCCTC
     CGGACCAGTT CCTGATGAAG GGGCTTGGCC ACTGCCACAG CACCTTGAGT CCGCGGGACT GGTCGCCGCA CGTGTGGAAG GGCCGACAGG ATGTCAGGAG
 148  L  V  K   D  Y  F   P  E  P  V   T  V  S   W  N  S   G  A  L  T   S  G  V   H  T  F   P  A  V  L   Q  S  S

1901 AGGACTCTAC TCCCTCAGCA GCGTGGTGAC CGTGCCCTCC AGCAGCTTGG GCACCCAGAC CTACATCTGC AACGTGAATC ACAAGCCCAG CAACACCAAG
     TCCTGAGATG AGGGAGTCGT CGCACCACTG GCACGGGAGG TCGTCGAACC CGTGGGTCTG GATGTAGACG TTGCACTTAG TGTTCGGGTC GTTGTGGTTC
 181  G  L  Y   S  L  S  S    V  V  T   V  P  S   S  S  L  G   T  Q  T   Y  I  C   N  V  N  H   K  P  S   N  T  K

2001 GTCGACAAGA AAGTTGAGCC CAAATCTTGT GACAAAACTC ACCTCAGTGG CGGTGGCTCT GGTTCCGGTG ATTTTGATTA TGAAAAGATG GCAAACGCTA
     CAGCTGTTCT TTCAACTCGG GTTTAGAACA CTGTTTTGAG TGGAGTCACC GCCACCGAGA CCAAGGCCAC TAAAACTAAT ACTTTTCTAC CGTTTGCGAT
 214  V  D  K   K  V  E  P   K  S  C   D  K  T  H   L  S  G   G  G  S   G  S  G  D   F  D  Y   E  K  M   A  N  A  N
                                            ˆend of heavy chain
                                                                            ˆstart of gene III coat protein (267-end)

2101 ATAAGGGGGC TATGACCGAA AATGCCGATG AAAACGCGCT ACAGTCTGAC AACTTGATTC TGTCGCTACT GATTACGGTC CTGCTATCGA
     TATTCCCCCG ATACTGGCTT TTACGGCTAC TTTTGCGCGA TGTCAGACTG TTGAACTAAG ACAGCGATGA CTAATGCCAC GACGATAGCT
 248  K  G  A   M  T  E   N  A  D  E   N  A  L   Q  S  D   A  K  G  K   L  D  S   V  A  T   D  Y  G  A   A  I  D
```

*FIG._25C*

```
2201 TGGTTTCATT GGTGACGTTT CCGGCCTTGC TAATGGTAAT GGTGCTACTG GTGATTTTGC TGGCTCTAAT TCCCAAATGG CTCAAGTCGG TGACGGTGAT
     ACCAAAGTAA CCACTGCAAA GGCCGGAACG ATTACCATTA CCACGATGAC CCGAGATTA AGGGTTACC AGGTTCAGCG ACTGCCACTA
281    G  F  I   G  D  V  S   G  L  A    N  G  N    G  A  T  G   D  F  A    G  S  N    S  Q  M  A   Q  V  G    D  G  D

2301 AATTCACCTT TAATGAATAA TTCCGTCAA TATTTACCTT CCCTCCCTCA ATCGGTTGAA TGTCGCCCTT TTGTCTTTAG CGCTGGTAAA CCATATGAAT
     TTAAGTGGAA ATTACTTATT AAAGGCAGTT ATAAATGGAA GGGAGGGAGT TAGCCAACTT ACAGCGGGAA AACAGAAATC GCGACCATTT GGTATACTTA
314   N  S  P  L   M  N  N    F  R  Q    Y  L  P  S   L  P  Q    S  V  E    C  R  P  F   V  F  S    A  G  K    P  Y  E  F

2401 TTTCTATTGA TTGTGACAAA ATAAACTTAT TCCGTGGTGT CTTTGCGTTT CTTTTATATG TTGCCACCTT TATGTATGTA TTTTCTACGT TTGCTAACAT
     AAAGATAACT AACACTGTTT TATTTGAATA AGGCACCACA GAAACGCAAA GAAAATATAC AACGGTGGAA ATACATACAT AAAAGATGCA AACGATTGTA
348    S  I  D   C  D  K    I  N  L  F   R  G  V    F  A  F    L  L  Y  V   A  T  F    M  Y  V    F  S  T  F   A  N  I

2501 ACTGCGTAAT AAGGAGTCTT AATCATGCCA GTTCTTTTGG CTATACCCTT GTCTGCCTCC CCGCGTTGCG TCGGCGTGCA TGGAGCCGGG
     TGACGCATTA TTCCTCAGAA TTAGTACGGT CAAGAAAACC GATATGGGAA CAGACGGAGG GGCGCAACGC AGCCGCACGT ACCTCGGCCC
381   L  R  N    K  E  S  Q

2601 CCACCTCGAC CTGAATGGAA GCCGGCGGCA GCCGGCGGCA CCTCGCTAAC GGATTCACCA CTCCAAGAAT TGGAGCCAAT CAATTCTTGC GGAGAACTGT GAATGCGCAA
     GGTGGAGCTG GACTTACCTT CGGCCGCCGT CGGCCGCCGT GGAGCGATTG CCTAAGTGGT GAGGTTCTTA ACCTCGGTTA GTTAAGAACG CCTCTTGACA CTTACGCGTT

2701 ACCAACCCTT GGCAGAACAT ATCCATCGCG TCCGCCATCT CCAGCAGCCG CACGCGGCGC ATCTCGGGCA GGTTGGGTC CTGGCCACGG GTGCGCATGA
     TGGTTGGGAA CCGTCTTGTA TAGGTAGCGC AGGCGGTAGA GGTCGTCGGC GTGCGCCGCG TAGAGCCCGT CCAACCCAG GACCGGTGCC CACGCGTACT

2801 TCGTGCTCCT GTCGTTGAGG ACCCGGCTAG GCTGGGCGGG TTGCCTTACT AACGGAATGA CCAATCGTCT TACTTAGTGG CGAACCTGAA GCCGACTGCTG
     AGCACGAGGA CAGCAACTCC TGGGCCGATC CGACCCGCCC AACGGAATGA CCAATCGTCT TACTTAGTGG CGAACCTGAA GCCGACTGCTG CGCTGACGAC

2901 CTGCAAAACG TCTGCGACCT GAGCAACAAC ATGAATGGTC TTCGGTTTCC GTGTTTCGTA AAGTCTGGAA ACGGGAAGT CAGCGCCCTG CACCATTATG
     GACGTTTTGC AGACGCTGGA CTCGTTGTTG TACTTACCAG AAGCCAAAGG CACAAAGCAT TTCAGACCTT TGCCCTTCA GTCGCGGGAC GTGGTAATAC

3001 TTCCGGGATCT GCATCGCAGG ATGCTGCTGG CTACCCCTGT GAACACCTAC CTTGTGGATG TAGACATAAT TGCTTCGCGA CCGTAACTGG GACTCACTGA AAAGAGACCA
     AAGGCCTAGA CGTAGCGTCC TACGACGACC GATGGGGACA CTTGTGGATG TAGACATAAT TGCTTCGCGA CCGTAACTGG GACTCACTGA AAAGAGACCA
```

*FIG._25D*

```
3101 CCCGCCGCAT CCATACCGCC AGTTGTTAC CCTCACAACG TTCCAGTAAC CGGGCATGTT CATCATCAGT AACCCGTATC GTGAGCATCC TCTCTCGTTT
     GGGCGGCGTA GGTATGGCGG TCAACAAATG GGAGTGTTGC AAGGTCATTG GCCCGTACAA GTAGTAGTCA TTGGGCATAG CACTCGTAGG AGAGAGCAAA

3201 CATCGGTATC ATTACCCCA TGAACAGAAA TTCCCCCTTA CACGGAGGCA TCAAGTGACC AAACAGGAAA AAACCGCCCT TAACATGGCC CGCTTTATCA
     GTAGCCATAG TAATGGGGGT ACTTGTCTTT AAGGGGGAAT GTGCCTCCGT AGTTCACTGG TTTGTCCTTT TTTGGCGGGA ATTGTACCGG GCGAAATAGT

3301 GAAGCCAGAC ATTAACGCTT CTGGAGAAAC TCAACGAGCT GAACAGGCAG ACATCTGTGA ATCGCTTCAC GACCACGCTG ATGAGCTTTA
     CTTCGGTCTG TAATTGCGAA GACCTCTTTG AGTTGCTCGA CCTTGCCCTA CTTGTCCGTC TGTAGACACT TAGCGAAGTG CTGGTGCGAC TACTCGAAAT

3401 CCGCAGGATC CGGAAATTGT AAACGTTAAT ATTTTGTTAA AATTCCCGTT TAAATCAGCT CATTTTTAA CCAATAGGCC GAAATCGGCA
     GGCGTCCTAG GCCTTTAACA TTTGCAATTA TAAAACAATT TTAAGCGCAA ATTTAGTCGA GTAAAAAATT GGTATCCGG CTTTAGCCGT

3501 AAATCCCTTA TAAATCAAAA GAATAGACCG AGATAGGGTT GAGTGTTGTT CCAGTTTGGA ACAAGAGTCC ACTATTAAAG AACGTGGACT CCAACGTCAA
     TTTAGGGAAT ATTTAGTTTT CTTATCTGGC TCTATCCCAA CTCACAACAA GGTCAAACCT TGTTCTCAGG TGATAATTTC TTGCACCTGA GGTTGCAGTT

3601 AGGGCGAAAA ACCGTCTATC AGGGCTATGG CCCACTACGT GAACCATACAC CCTAATCAAG TTTTTGGG TCGAGGTGCC GTAAAGCACT AAATCGAAC
     TCCCGCTTTT TGGCAGATAG TCCCGATAG GGGTGATGCA CTTGGTAGTG GGATTAGTTC AAAAAACCCC AGCTCCACGG CATTTCGTGA TTTAGCCTTG

3701 CCTAAAGGGA GCCCCCCGATT TAGAGCTTGA CGGGGAAAGC CGGCGAACGT GGGCGAACTG CGGCTCTTT AGGGCGCGTC CGGATCCTGC AGGGCGCTGG
     GGATTTCCCT CGGGGGCTAA ATCTCGAACT GCCCCTTTCG GCCGCTTGCA CCGCTCTTTC CTTCCCTTCT TCGCTTTTCC CCTAGGACG TCCCGCGACC

3801 CAAGTGTAGC GGTCACGCTG CGCGTAACCA CGCGCTTAAT GCGGCCGCTAC AGGGGCCGTC CCCCGCGATG TCCCCGCAG GCCTAGGACG AGCCACTACT
     GTTCACATCG CCAGTGCGAC GCGCATTTGGT GCGCGAATTA CGCCGGCGATG TCCCGCGCAG AGGGGCGCTAC AGGGGCGCGT GAGCGCGCAA AGCCACTACT

3901 CGGTGAAAAC CTCTGACACA TGCAGCTCCC GGAGACGGTC ACAGCTTGTC TGTAAGCGGA TGCCGGGAGC AGACAAGCCC GTCAGGGCGT GTCAGCGGGT
     GCCACTTTTG GAGACTGTGT ACGTCGAGGG CCTCTGCCAG TGTCGAACAG ACATTCGCCT ACGGCCCTCG TCTGTTCGGG CAGTCCCGCG CAGTCGCCCA

4001 GTTGGCGGGT GTCGGGGCGC CAGCCATGACC AGCCAGTGG GCGATAGCGG CAGTCACGTA AGTGTATACT GGCTTAACTA TGCGGCATCA GAGCAGATTG TACTGAGAGT
     CAACCGCCCA CAGCCCGCG TCGGTACTGG TCGGTCACC CGCTATCGCC GTCAGTGCAT TCACATATGA CCGAATTGAT ACCCGTAGT CTCGTCTAAC ATGACTCTCA
```

FIG._25E

```
4101  GACCATATG CGGTGTGAAA TACCGCACAG ATGGCTAAGG AGAAATACC GCATCAGGCG CTCTTCCGCT TCCTCGCTCA CTGACTCGCT GCGCTCCGTC
      CGTGGTATAC GCCACACTTT ATGGCCGTGTC TACCGATTCC TCTTTTATGG CGTAGTCCGC GAGAAGGCGA AGGAGCGAGT GACTGAGCGA CGCGAGCCAG

4201  GTTCGGCTGC GGCGAGCCGT ATCAGCTCAC TCAAAGGCGG TAATACGGTT ATCCACAGAA TCAGGGGATA AGGCAGGAAA GAACATGTGA GCAAAAGGCC
      CAAGCCGACG CCGCTCGCCA TAGTCGAGTG AGTTTCCGCC ATTATGCCAA TAGGTGTCTT AGTCCCCTAT TCCGTCCTTT CTTGTACACT CGTTTTCCGG

4301  AGCAAAAGGC CAGGAACCGT AAAAAGGCCG CGTTGCTGGC GTTTTTCCAT AGGCTCCGCC CCCCTGACGA GCATCACAAA AATCGACGCT CAAGTCAGAG
      TCGTTTTCCG GTCCTTGGCA TTTTTCCGGC GCAACGACCG CAAAAAGGTA TCCGAGGCGG GGGGACTGCT CGTAGTGTTT TTAGCTGCGA GTTCAGTCTC

4401  GTGGCGAAAC CCGACAGGAC TATAAAGATA CCAGGCGTTT CCCCCTGGAA GCTCCCTCGT GCGCTCTCCT GTTCCGACCC TGCCGCTTAC CGGATACCTG
      CACCGCTTTG GGCTGTCCTG ATATTTCTAT GGTCGCAAA GGGGGACCTT CGAGGGAGCA CGCGAGAGGA CAAGGCTGGG ACGGCGAATG GCCTATGGAC

4501  TCCGCCTTTC TCCCTTCGGG AAGCGTGGCG CTTTCTCATA GCTCACGCTG TAGGTATCTC AGTTCGGTGT AGTCGTTCG CTCCAAGCTG GGCTGTGTGC
      AGGCGGAAAG AGGGAAGCCC TTCGCACCGC GAAAGAGTAT CGAGTGCGAC ATCCATAGAG TCAAGCCACA TCAGCAAGC GAGGTTCGAC CCGACACACG

4601  ACGAACCCCC CGTTCAGCCC GACCGCTGCG CCTTATCCGG TAACTATCGT CTTGAGTCCA ACCCGGTAAG ACACGACTTA TCGCCACTGG CAGCAGCCAC
      TGCTTGGGGG GCAAGTCGGG CTGGCGACGC GGAATAGGCC ATTGATAGCA GAACTCAGT TGGGCCATTC TGTGCTGAAT AGCGGTGACC GTCGTCGGTG

4701  TGGTAACAGG ATTAGCAGAG CGAGGTATGT AGGCGGTGCT ACAGAGTTCT TGAAGTGGTG GCCTAACTAC GGATTGATG GCTACACTA GAAGGACAGT ATTTGGTATC
      ACCATTGTCC TAATCGTCTC GCTCCATACA TCCGCCACGA TGTCTCAAGA ACTTCACCAC CGGATTGAT CCGATGTGAT CTTCCTGTCA TAAACCATAG

4801  TGCGCTCTGC TGAAGCCAGT TACCTTCGGA AAAAGAGTTG GTAGCTCTTG ATCCGGCAAA CAAACCACCG CTGGTAGCGG TGGTTTTTT GTTTGCAAGC
      ACGCCAGACG ACTTCGGTCA ATGGAAGCCT TTTTCTCAAC CATCGAGAAC TAGGCCGTTT GTTTGGTGGC GACCATCGCC ACCAAAAAAA CAAACGTTCG

4901  AGCAGATTAC GCGCAGAAAA AAAGGATCTC AAGAAGATCC TTTGATCTTT TCTACGGGGT CTGACGCTCA GTGGAACGAA AACTCACGTT AAGGGATTTT
      TCGCTCTAATG CGCGTCTTTT TTTCCTAGAG TTCTTCTAGG AAACTAGAAA AGATGCCCCA GACTGCGAGT CACCTTGCTT TTGAGTGCAA TTCCCTAAAA

5001  GGTCATGAGA TTATCAAAAA GGATCTTCAC CTAGATCCTT TTAAATTAAA AATGAAGTTT TAAATCAATC ATTAGTTAG TAAAGTATAT TTGGTCTGAC
      CCAGTACTCT AATAGTTTTT CCTAGAAGTG GATCTAGGAA AATTTAATTT TACTTCAAA ATTTAATTAG TTACTTCATA TAAAGTATAT AACCAGACTG
```

FIG._25F

```
5101 AGTTACCAAT GCTTAATCAG TGAGGCACCT ATCTCAGCGA TCTGTCTATT TCGTTCATCC ATAGTTGCCT GACTCCCCGT CGTGTAGATA ACTACGATAC
     TCAATGGTTA CGAATTAGTC ACTCCGTGGA TAGAGTCGCT AGACAGATAA AGCAAGTAGG TATCAACGGA CTGAGGGGCA GCACATCTAT TGATGCTATG

5201 GGGAGGGCTT ACCATCTGGC CCCAGTGCTG CAATGATACC GCGAGACCCA CGCTCACCGG CTCCAGATTT ATCAGCAATA AACCAGCCAG CCGGAAGGGC
     CCCTCCCGAA TGGTAGACCG GGGTCACGAC GTTACTATGG CGCTCTGGGT GCGAGTGGCC GAGGTCTAAA TAGTCGTTAT TTGGTCGGTC GGCCTTCCCG

5301 CGAGCGCAGA AGTGGTCCTG CAACTTTATC CGCCTCCATC CAGTCTATTA ATTGTTGCCG GGAAGCTAGA GTAAGTAGTT CGCCAGTTAA TAGTTTGCGC
     GCTCGCGTCT TCACCAGGAC GTTGAAATAG GCGGAGGTAG GTCAGATAAT TAACAACGGC CCTTCGATCT CATTCATCAA GCGGTCAATT ATCAAACGCG

5401 AACGTTGTTG CCATTGCTGC AGGCATCGTG GTGTCACGCT CGTCGTTTGG TATGGCTTCA TTTCAGCTCCG GTTCCCAACG ATCAAGGCGA GTTACATGAT
     TTGCAACAAC GGTAACGACG TCCGTAGCAC CACAGTGCGA GCAGCAAACC ATACCGAAGT AAGTCGAGGC CAAGGGTTGC TAGTTCCGCT CAATGTACTA

5501 CCCCCATGTT GTGCAAAAAA GCGGTTAGCT CCTTCGGTCC TCCGATCGTT GTCAGAAGTA AGTTGGCCGC AGTGTTATCA CTCATGGTTA TGGCAGCACT
     GGGGGTACAA CACGTTTTTT CGCCAATCGA GGAAGCCAGG AGGCTAGCAA CAGTCTTCAT TCAACCGGCG TCACAATAGT GAGTACCAAT ACCGTCGTGA

5601 GCATAAATTCT CTTACTGTCA TGCCATCCGT AAGATGCTTT TCTGTGACTG GTGAGTACTC AACCAAGTCA TTCTGAGAAT AGTGTATGCG GCGACCGAGT
     CGTATTAAGA GAATGACAGT ACGGTAGGCA TTCTACGAAA AGACACTGAC CACTCATGAG TTGGTTCAGT AAGACTCTTA TCACATACGC CGCTGGCTCA

5701 TGCTCTTGCC CGGCGTCAAC ACGGGATAAT ACCGCGCCAC ATAGCAGAAC TTTAAAAGTG CTCATCATTG GAAAACGTTC TTCGGGGCGA AAACTCTCAA
     ACGAGAACGG GCCGCAGTTG TGCCCTATTA TGGCGCGGTG TATCGTCTTG AAATTTTCAC GAGTAGTAAC CTTTGCAAG AAGCCCCGCT TTTGAGAGTT

5801 GGATCTTACC GCTGTTGAGA TCCAGTTCGA TGTAACCCAC TGTGCACCCC AACTGATCTT CAGCCATCTTT TACTTTCACC AGCGTTTCTG GGTGAGCAAA
     CCTAGAATGG CGACAACTCT AGGTCAAGCT ACATTGGGTG ACACGTGGG TTGACTAGAA GTCGTAGAAA ATGAAAGTGG TCGCAAAGAC CCACTGTTT

5901 AACAGGAAGG CAAAATGCCG CAAAAAAGGG AATAAGGGCG ACACGGAAAT GTTGAATACT CATACTCTTC CTTTTTTCAAT ATTATTGAAG CATTTATCAG
     TTGTCCTTCC GTTTTACGGC GTTTTTTCCC TTATTCCCGC TGTGCCTTTA CAACTTATGA GTATGAGAAG GAAAAAGTTA TAATAACTTC GTAAATAGTC

6001 GGTTATTGTC TCATGAGCGG ATACATATTT GAATGTATTT AGAAAATAA ACAAATAGGG GTTCCCGCGCA CATTCCCCG AAAAGTGCCA CCTGACGTCT
     CCAATAACAG AGTACTCGCC TATGTATAAA CTTACATAAA TCTTTTATTT TGTTTATCCC CAAGGGCGCGT GTAAGGGGC TTTTCACGGT GGACTGCAGA
```

FIG._25G

```
6101  AAGAAACCAT TATTATCATG ACATTAACCT ATAAAAATAG GCGTATCACG AGGCCCTTTC GTCTTCAATA CAGGTAGACC TTTCGTAGAG ATGTACAGTG
      TTCTTTGGTA ATAATAGTAC TGTAATTGGA TATTTTTATC CGCATAGTGC TCCGGGAAAG CAGAAGTTAT GTCCATCTGG AAAGCATCTC TACATGTCAC

6201  AAATCCCCGA AATTATACAC ATGACTGAAG GAAGGGAGCT CGTCATTCCC TGCCGGGTTA CGTCACCTAA CATCACTGTT ACTTAAAAA AGTTTCCACT
      TTTAGGGGCT TTAATATGTG TACTGACTTC CTTCCCTCGA GCAGTAAGGG ACGGCCCAAT GCAGTGGATT GTAGTGACAA TGAAATTTTT TCAAAGGTGA

6301  TGACACTTTG ATCCCTGATG GAAAACGCAT AGTAGAAAGG GCTTCATCAT ATCAAATGCA ACGTACAAAG AAATAGGGCT TCTGACCTGT
      ACTGTGAAAC TAGGGACTAC CTTTTGCGTA TCATCTTTCC CGAAGTAGTA TAGTTTACGT TGCATGTTTC TTTATCCCGA AGACTGGACA

6401  GAAGCAACAG TCAATGGGCA TTTGTATAAG ACAAACTATC TCACACATCG ACAATACAGG TAGACCTTTC GTAGAGATGT ACAGTGAAAT
      CTTCGTTGTC AGTTACCCGT AAACATATTC TGTTTGATAG AGTGTGTAGC TGTTATGTCC ATCTGGAAAG CATCTCTACA TGTCACTTTA

6501  CCCCGAAATT ATACACATGA CTGAAGGAAG GGAGCTCGTC ATTCCCTGCC GGGTTACGTC ACCTAACATC ACTGTTACTT TAAAAAAGTT TCCACTTGAC
      GGGGCTTTAA TATGTGTACT GACTTCCTTC CCTCGAGCAG TAAGGGACGG CCCAATGCAG TGGATTGTAG TGACAATGAA ATTTTTTCAA AGGTGAACTG

6601  ACTTTGATCC CTGATGGAAA ACGCATATCA GAAAGGGCTT CATCATATCA AATGCAACGT ACAAAGAAAT AGGGCTTCTG ACCTGTGAAG
      TGAAACTAGG GACTACCTTT TGCGTATAGT CTTTCCCGAA GTAGTATAGT TTACGTTGCA TGTTTCTTTA TCCCGAAGAC TGGACACTTC

6701  CAACAGTCAA TGGGCATTTG TATAAGACAA ACTATCTCAC ACATCGACAA ACCAATACAA TCTACAGGTA GACCTTTCGT AGAGATGTAC AGTGAAATCC
      GTTGTCAGTT ACCCGTAAAC ATATTCTGTT TGATAGAGTG TGTAGCTGTT AGGTTATGTT AGATGTCCAT CTGGAAAGCA TCTCTACATG TCACTTTAGG

6801  CCGAAATTAT ACACATGACT GAAGGAAGGG AGCTCGTCAT TCCCTGCCGG GTTACGTCAC CTAACATCAC TGTTACTTTA AAAAAGTTTC CACTTGACAC
      GGCTTTAATA TGTGTACTGA CTTCCTTCCC TCGAGCAGTA AGGGACGGCC CAATGCAGTG GATTGTAGTG ACAATGAAAT TTTTCAAAG GTGAACTGTG

6901  TTTGATCCCT GATGGAAAAC GCATTTCAA GGACAGTAGA AAGGGCTTCA TCATATCAAA TGCAACGTAC AAAGAAATAG GCCTTCTGAC CTGTGAAGCA
      AAACTAGGGA CTACCTTTTG CGTAAAGTT CCTGTCATCT TTCCCGAAGT AGTATAGTTT ACGTTGCATG TTTCTTTATC CGGAAGACTG GACACTTCGT

7001  ACAGTCAATG GGCATTGTA TAAGACAAAC TATCTCACAC ATCGACAAAT CAATACAATC
      TGTCAGTTAC CCGTAAACAT ATTCTGTTTG ATAGAGTGTG TAGCTGTTTG GTTATGTTAG
```

FIG._25H

```
  1 GAATTCAACT TCTCCATACT TTGGATAAGG AAATACAGAC ATGAAAAATC TCATTGCTGA GTTGTTATTT AAGCTTGCCC AAAAAGAAGA AGAGTCGAAT
    CTTAAGTTGA AGAGGTATGA AACCTATTCC TTTATGTCTG TACTTTTTAG AGTAACGACT CAACAATAAA TTCGAACGGG TTTTTCTTCT TCTCAGCTTA

101 GAACTGTGTG CGCAGGTAGA AGCTTTGGAG ATTATCGTCA CTGCCAATGCT TCCCAATATG GGGCAAAATG ACCAACAGCG GTTGATTGAT CAGGTAGAGG
    CTTGACACAC GCGTCCATCT TCGAAACCTC TAATAGCAGT GACGTTACGA AGCGTTATAC CCCGTTTTAC TGGTTGTCGC CAACTAACTA GTCCATCTCC

201 GGGCGCTGTA CGAGGTAAAG CCCGATGCCA GCATTCCTGA CGACGATACG GAGCTGCTGC CTCGACGACG GCGATTACGT AAAGAAGTTA TTGAAGCATC CTCGTCAGTA
    CCCGCGACAT GCTCCATTTC GGGCTACGGT CGTAAGGACT GCTGCTATGC CTCGACGACG CGCTAATGCA TTTCTTCAAT AACTTCGTAG GAGCAGTCAT

301 AAAAGTTAAT CTTTTCAACA GCTGTCATCG AGTTGTCACG GCCGAGACTT ATAGTCGCTT TGTTTTTATT TGTTTTAATGTA GTACCAAGT
    TTTTCAATTA GAAAAGTTGT CGACAGTATT TCAACAGTGC CGGCTCTGAA TATCAGCGAA ACAAAAATAA ACAAAATTACAT CATGCGTTCA

401 TCACGTAAAA AGGGTATGTA GAGGTTGAGG TGATTTTATG AAAAAGAATA TCGCATTTCT TCTTGCATCT ATGTTCGTTT TTTCTATTGC TACAAATGCC
    AGTGCATTTT TCCCATACAT CTCCAACTCC ACTAAAATAC TTTTTCTTAT AGCGTAAAGA AGAACGTAGA TACAAGCAAA AAAGATAACG ATGTTTACGG

1                                               M  K  K  N  I  A  F  L  L  A  S  M  F  V  F  S  I  A  T  N  A
                                                  ^start of stII sequence 501 TATGCATCCG ATATCCAGAT GACCCAGTCC CCGAGCTCCC TGTCCGCCTC TGTGGGCGAT AGGGTCACCA TCACCTGCCG TGCCAGTCAG GATGTGTCCA
    ATACGTAGGC TATAGGTCTA CTGGGTCAGG GGCTCGAGGG ACAGGCGGAG ACACCCGCTA TCCCAGTGGT AGTGGACGGC ACGGTCAGTC CTACACAGGT 22   Y  A  S  D  I  Q  M  T  Q  S  P  S  S  L  S  A  S  V  G  D  R  V  T  I  T  C  R  A  S  Q  D  V  S  T
      ^light chain start                                                                       ^CDR-L1

601 CTGCTGTAGC CTGGTATCAA CAGAAACCAG GAAAAGCTCC GAAGCTTCTG ATTTACTCGG CATCCTTTCCT CTACTCTGGA GTCCCTTCTC GCTTCTCTGG
    GACGACATCG GACCATAGTT GTCTTTGGTC CTTTTCGAGG CTTCGAAGAC TAAATGAGCC GTAGGAAGGA GATGAGACCT CAGGGAAGAC CGAAGAGACC

56   A  V  A  W  Y  Q  Q  K  P  G  K  A  P  K  L  L  I  Y  S  A  S  F  L  Y  S  G  V  P  S  R  F  S  G
                                                         ^CDR-L2

701 TAGCGGTTCC GGGACGGATT TCACTCTGAC CATCAGCAGT CTGCAGCCGG AAGACTTCGC AACTTATTAC TGTCAGCAAT CTTATACTAC TCCTCCCACG
    ATCGCCAAGG CCCTGCCTAA AGTGAGACTG GTAGTCGTCA GACGTCGGCC TTCTGAAGCG TTGAATAATG ACAGTCGTTA GAATATGATG AGGAGGGTGC

89   S  G  S  G  T  D  F  T  L  T  I  S  S  L  Q  P  E  D  F  A  T  Y  Y  C  Q  Q  S  Y  T  T  P  P  T
                                                                                  ^CDR-L3
```

*FIG._26A*

```
801  TTCGGACAGG GTACCAAGGT GGAGATCAAA CGAACTGTCC CTTGCACCAT TGTCTTCATC TTCCCGCCAT CTGATGAGCA GTTGAAATCT GGAACTGCCT
     AAGCCTGTCC CATGGTTCCA CCTCTAGTTT GCTTGACACC GAACTGTGGTA ACAGAAGTAG AAGGGCGGTA GACTACTCGT CAACTTTAGA CCTTGACGGA
122  F  G  Q  G  T  K  V  E  I  K  R  T  V  A  A  P  S  V  F  I  F  P  P  S  D  E  Q  L  K  S  G  T  A  S

901  CTGTTGTGTG CCTGCTGAAT AACTTCTATC CCAGAGAGGC CAAAGTACAG TGGAAGGTGG ATAACGCCCT CCAATCGGGT AACTCCCAGG AGAGTGTCAC
     GACAACACAC GGACGACTTA TTGAAGATAG GGTCTCTCCG GTTTCATGTC ACCTTCCACC TATTGCGGGA GGTTAGCCCA TTGAGGGTCC TCTCACAGTG
156  V  V  C  L  L  N  N  F  Y  P  R  E  A  K  V  Q  W  K  V  D  N  A  L  Q  S  G  N  S  Q  E  S  V  T

1001 AGAGCAGGAC AGCAAGGACA GCACCTACAG CCTCAGCAGC ACCCTGACGC TGAGCAAAGC AGACTACGAG AAACACAAAG TCTACGCCTG CGAAGTCACC
     TCTCGTCCTG TCGTTCCTGT CGTGGATGTC GGAGTCGTCG TGGGACTGCG ACTCGTTTCG TCTGATGCTC TTTGTGTTTC AGATGCGGAC GCTTCAGTGG
189  E  Q  D  S  K  D  S  T  Y  S  L  S  S  T  L  T  L  S  K  A  D  Y  E  K  H  K  V  Y  A  C  E  V  T

1101 CATCAGGGCC TGAGCTCGCC CGTCACAAAG AGCTTCAACA GGGGAGAGTG TCCCCTCCTA GCAGTCGTTGT TCGAAGTTGC CTGATCCGAA CCGTTCCGGC GGTAAGGACC
     GTAGTCCCGG ACTCGAGCGG GCAGTGTTTC TCGAAGTTGT CCCCCTCTCAC ACCACGGTCG AGGCCATACC GACTAGGCTT GGCAAAGGCG CCAATTCCTGG
222  H  Q  G  L  S  S  P  V  T  K  S  F  N  R  G  E  C  G  A  S  S  G  M  A  D  P  N  R  F  R  G  K  D  L
                                                                    ^end of light chain, start of gD tag 1201 TGGCATAACT CGAGGCTGAT CCTCTACGCC GGACGCATCG TGGCCCTAGT ACGCAAGTTC ACGTAAAAAG GGTAACTAGA GGTTGAGGTG ATTTTATGAA
     ACCGTATTGA GCTCCGACTA GGAGATGCGG CCTGCGTAGC ACCGGGATCA TGCGTTCAAG TGCATTTTTC CCAATGATCT CCAACTCCAC TAAAATACTT
256  A  Q                                                                                        M  K
-23                                                                                              ^start of stII 1301 AAAGAATATC GCATTCTTTC TTGCATCTAT GTTCGTTTTT TCTATTGCTA CAAACGCGTA CGCTGAGGTT CAGCTGGTGG AGTCTGGCGG TGGCCTGGTG
     TTTCTTATAG CGTAAGAAAG AACGTAGATA CAAGCAAAAA AGATAACGAT GTTTGCGCAT GCGACTCCAA GTCGACCACC TCAGACCGCC ACCGGACCAC
-21  K  N  I  A  F  L  L  A  S  M  F  V  F  S  I  A  T  N  A  Y  A  E  V  Q  L  V  E  S  G  G  G  L  V
                                               ^start of heavy chain 1401 CAGCCAGGGG GCTCACTCCG TTTGTCCTGT GCAGCTTCTG GCTTCAACAT TAAAGACACC TATATACACT GGGTGCGTCA GGCCCCGGGT AAGGGCCTGG
     GTCGGTCCCC CGAGTGAGGC AAACAGGACA CGTCGAAGAC CGAAGTTGTA ATTTCTGTGG ATATATGTGA CCCACGCAGT CCGGGGCCCA TTCCCGGACC
13   Q  P  G  G  S  L  R  L  S  C  A  A  S  G  F  N  I  K  D  T  Y  I  H  W  V  R  Q  A  P  G  K  G  L  E
                                    ^CDR-H1
```

FIG.—26B

```
1501 AATGGGTTGC AAGGATTTAT CCTACGAATG GTTATACTAG ATATGCCGAT AGCCGTTCAC TATAAGCGCA GACACATCCA AAAACACAGC
     TTACCCAACG TTCCTAAATA GGATGCTTAC CAATATGATC TATACGGCTA TCGCAGTTCC CGGCAAAGTG ATATTCGCGT CTGTGTAGGT TTTTGTGTCG
  47  W  V  A  R  I  Y  P  T  N  G  Y  T  R  Y  A  D  S  V  K  G  R  F  T  I  S  A  D  T  S  K  N  T  A
              ^CDR-H2

1601 CTACCTACAA ATGAACAGTT TAAGAGCTGA GGACACTGCC GTCTATTATT GTAGCCGCTG GGGAGGGGAC GGCTTCTATG CCGAAGATAC GATACCTGAT CTGGGGTCAA
     GATGGATGTT TACTTGTCGA ATTCTCGACT CCTGTGACGG CAGATAATAA CATCGGCGAC CCCTCCCCTG CCGAAGATAC GATACCTGAT GACCCCAGTT
  80  Y  L  Q  M  N  S  L  R  A  E  D  T  A  V  Y  Y  C  S  R  W  G  G  D  G  F  Y  A  M  D  Y  W  G  Q
                                                        ^CDR-H3

1701 GGAACACTAG TCACCGTCTC CTCGGCCTCC ACCAAGGGCC CATCGGTCTT CCCCCTGGCA CCCTCCTCCA AGAGCACCTC TGGGGGCACA GCGGCCCTGG
     CCTTGTGATC AGTGGCAGAG GAGCCGGAGG TGGTTCCCGG GTAGCCAGAA GGGGGACCGT GGGAGGAGGT TCTCGTGGAG ACCCCCGTGT CGCCGGGACC
 113  G  T  L  V  T  V  S  S  A  S  T  K  G  P  S  V  F  P  L  A  P  S  S  K  S  T  S  G  G  T  A  A  L  G

1801 GCTGCCTGGT CAAGGACTAC TTCCCCGAAC CGGTGACGGT GTCGTGGAAC TCAGGCGCCC TGACCAGCGG CGTGCACACC TTCCCGGCTG TCCTACAGTC
     CGACGGACCA GTTCCTGATG AAGGGGCTTG GCCACTGCCA CAGCACCTTG AGTCCGCGGG ACTGGTCGCC GCACGTGTGG AAGGGCCGAC AGGATGTCAG
 147  C  L  V  K  D  Y  F  P  E  P  V  T  V  S  W  N  S  G  A  L  T  S  G  V  H  T  F  P  A  V  L  Q  S

1901 CTCAGGACTC TACTCCCTCA GCAGCGTGGT GACCGTGCCC TCCAGCAGCT TGGGCACCCA GACCTACATC TGCAACGTGA ATCACAAGCC CAGCAACACC
     GAGTCCTGAG ATGAGGGAGT CGTCGCACCA CTGGCACGGG AGGTCGTCGA ACCCGTGGGT CTGGATGTAG ACGTTGCACT TAGTGTTCGG GTCGTTGTGG
 180  S  G  L  Y  S  L  S  S  V  V  T  V  P  S  S  S  L  G  T  Q  T  Y  I  C  N  V  N  H  K  P  S  N  T

2001 AAGGTCGACA AGAAAGTTGA AGAACTCAAA AGACTCAAAA CTTGTCCGGA GCCCAAATCT TGTGACAAAA CTCACGGGCG CATGAAACAG CTACTTTCTT CCAGTTCTGT GATCTCCTGT CCAGAGAAGA GCTACTCTCC AAGAACTACC
     TTCCAGCTGT TCTTTCAACT CTTGAGTTTT CGGGTTTAGA ACACTGTTTT GAGTGCCCGC GTACTTTGTC GATGAAAGAA GGTCAAGACT AGAGGAAGGT CTCAGAGACG CAGACTTTCT CGATGAGAGG TTCTTGATGG
 213  K  V  D  K  K  V  E  P  K  S  C  D  K  T  H  G  R  M  K  Q  L  E  D  K  V  E  E  L  L  S  K  N  Y  H
                                                        ^end of heavy chain, start of leucine zipper 2101 ACCTAGAGAA TGAAGTGGCA AGACTCAAGA AACTTGTCGG GGAGCGCGGA AAGCTTAGTG GCGGTGGCTC TGGTTCCGGT GATTTGATT ATGAAAAGAT
     TGGATCTCTT ACTTCACCGT TCTGAGTTTT TTGAACAGCC CCTCGCGCCT TTCGAATCAC CGCCACCGAG ACCAAGGCCA CTAAAACTAA TACTTTCTA
 247  L  E  N  E  V  A  R  L  K  K  L  V  G  E  R  G  K  L  S  G  G  G  S  G  S  G  D  F  D  Y  E  K  M
     end of leucine zipper, start of gene III coat protein (267-end)^
```

FIG._26C

```
2201  GGCAAACGCT AATAAGGGGG CTATGACCGA AAATGCCGAT GAAAACGCGC TACAGTCTGA CGCTAAAGGC AAACTTGATT CTGTCGCTAC TGATTACGGT
      CCGTTTGCGA TTATTCCCCC GATACTGGCT TTTACGGCTA CTTTTGCGCG ATGTCAGACT GCGATTTCCG TTTGAACTAA GACAGCGATG ACTAATGCCA
280    A   N    K   G    A    M   T    E    N    A    D    E    N    A    L    Q   S    D    A    K   G    K   L    D   S    V   A    T    D   Y   G

2301  GCTGCTATCG ATGGTTTCAT TGGTGACGTT TCCGGCCTTG CTAATGGTAA TGGTGCTACT GGTGATTTTG CTGGCTCTAA TTCCCAAATG GCTCAAGTCG
      CGACGATAGC TACCAAAGTA ACCACTGCAA AGGCCGGAAC GATTACCATT ACCACGATGA CCACTAAAAC GACCGAGATT AAGGGTTTAC CGAGTTCAGC
313    A   A    I   D    G   F   I    G    D   V    S    G    L    A    N    G    N    G    A    T    G    D   F   A    G    S   N    S   Q   M    A   Q   V    G

2401  GTGACGGTGA TAATTCACCT TTAATGAATA ATTCCGTCA ATATTACCT TCCCTCCCTC AATCGGTTGA ATGTCGCCCT TTTGTCTTTA GCGCTGGTAA
      CACTGCCACT ATTAAGTGGA AATTACTTAT TAAAGGCAGT TATAAATGGA AGGGAGGGAG TTAGCCAACT TACAGCGGGA AAACAGAAAT CGCGACCATT
347    D   G    D    N    S   P    L   M   N   N    F   R    Q    Y   L    P    S    L   P    Q    S   V    E    C    R    P    F   V   F    S    A   G   K

2501  ACCATATGAA TTTTCTATTG ATTGTGACAA AATAAACTTA TTCCGTGGTG TCTTTGCGTT TCTTTTATAT GTTGCCACCT TTATGTATGT ATTTTCTACG
      TGGTATACTT AAAAGATAAC TAACACTGTT TTATTTGAAT AAGGCACCAC AGAAACGCAA AGAAAATATA CAACGGTGGA AATACATACA TAAAAGATGC
380    P   Y    E    F    S    I   D    C    D   K    I   N    L    F    R    G   V    F    A   F    L    L    Y    V    A   T    F    M   Y   V    F    S    T

2601  TTTGCTAACA TACTGCGTAA TAAGGAGTCT TAATCATGCC AGTTCTTTTG GCTAGCGCCG CCCTATACCT TGTCTGCCTC CCCGCGTTGC GTCGCGGTGC
      AAACGATTGT ATGACGCATT ATTCCTCAGA ATTAGTACGG TCAAGAAAAC CGATCGCGGC GGGATATGGA ACAGACGGAG GGGCGCAACG CAGCGCCACG
413    F    A    N    I    L    R    N    K    E   S    Q

2701  ATGGAGCCGG GCCACCTCGA CCTGAATGGA AGCCGGCGGC ACCTCGCTAA CGGATTCACC ACTCCAAGAA TTGGAGCCAA TCAATTCTTG CGGAGAACTG
      TACCTCGGCC CGGTGGAGCT GGACTTACCT TCGGCCGCCG TGGAGCGATT GCCTAAGTGG TGAGGTTCTT AGTTAAGAAC GCCTCTTGAC

2801  TGAATGCGCA AACCAACCCT TGGTTGGAA GTCCGCCATC TATCCATCGC CCAGCAGCC TCCAGCAGCC GCACGCGGCG CATCTCGGGC AGCGTTGGGT CCTGCCACG
      ACTTACGCGT TTGGTTGGGA ACCGTCTTGT ATAGGTAGCG GGTCGTCGG AGGTCGTCGG CGTGCGCCGC GTAGAGCCCG TCGAACCCA GGACCGGTGC

2901  GGTGCGCATG ATCCTGCTCC TGTCGTTGAG GACCCGGCTA GGCTGGCGGG GTTGCCTTAC TGGTTAGCAG AATGAATCAC CGATACGCGA GCGAACGTGA
      CCACGCGTAC TAGGACGAGG ACAGCACGAGG CTGGGCCGAT CCGACCGCCC CAACGGAATG ACCAATCGTC TTACTTAGTG GCTATGCGCT CGCTTGCACT

3001  ACCGACTGCT GCTGCAAAAC GTCTGCCGACC TGAGCAACAA CATGAATGGT CTTCCGGTTTC CGTGTTTCGT AAAGTCTGGA AACGCGGAAG TCAGCGCCCT
      TCGCTGACGA CGACGTTTTG CAGACGCTGG ACTCCGTTGTT GTACTTACCA GAAGCCAAAG TTTCAGACCT TGGGCCCCTTC AGTCGCGGGA
```

FIG.—26D

```
3101 GCACCATTAT GTTCCGGATC TGCATCGCAG GATGCTGCTG GCTACCCTGT GGAACACCTA CATCTGTATT AACGAAGCGC TGGCATTGAC CCTGAGTGAT
     CGTGGTAATA CAAGGCCTAG ACGTAGCGTC CTACGACGAC CGATGGGACA CCTTGTGGAT GTAGACATAA TTGCTTCGCG ACCGTAACTG GGACTCACTA

3201 TTTTCTCTGG TCCCGCCGCA TCCATACCGC CAGTTGTTTA CCCTCACAAC GTTCCAGTAA CCGGGCATGT TCATCATCAG TAACCCGTAT CGTGAGCATC
     AAAAGAGACC AGGGCGGCGT AGGTATGGCG GTCAACAAAT GGGAGTGTTG CAAGGTCATT GGCCCGTACA AGTAGTAGTC ATTGGGCATA GCACTCGTAG

3301 CTCTCTCGTT TCATCGGTAT CATTACCCCC ATGAACACAGAA ATTCCCCCTT ACACGGAGGC ATCAAGTGAC CAAACAGGAA AAAACCGCCC TTAACATGC
     GAGAGAGCAA AGTAGCCATA GTAATGGGGG TACTTGTCTT TAAGGGGGAA TGTGCCTCCG TAGTTCACTG GTTTGTCCTT TTTTGGCGGG AATTGTACCG

3401 CCGCTTTATC AGAAGCCAGA CATTAACGCT TCTGGAGAAA CTCAACGAGC TGGACGCGGA GACATCTGTG AATCGCTTCA CGACCACGCT
     GGCGAAATAG TCTTCGGTCT GTAATTGCGA AGACCTCTTT GAGTTGCTCG ACCTGCGCCT ACTGTCCGT CTGTAGACAC TTAGCGAAGT GCTGGTGCGA

3501 GATGAGCTTT ACCGCAGGAT CCCGAAATTG TAAACGTTAA TATTTTGTTA AAATTCGCGT TAAATTTTG TTAAATCAGC TCATTTTTA ACCAATAGGC
     CTACTCGAAA TGGCGTCCTA GGGCTTTAAC ATTTGCAATT ATAAAACAAT TTTAAGCGCA ATTTAAAAAC AATTTAGTCG AGTAAAAAAT TGGTTATCCG

3601 CGAAATCGGC AAAATCCCTT ATAAATCAAA AGAATAGACC GAGATAGGGT TGAGTGTTGT TCCAGTTTGT AACAAGAGTC CACTATTAAA GAACGTGGAC
     GCTTTAGCCG TTTTAGGGAA TATTTAGTTT TCTTATCTGG CTCTATCCCA ACTCACAACA AGGTCAAACC TTGTTCTCAG GTGATAATTT CTTGCACCTG

3701 TCCAACGTCA AAGGGCGAAA AACCGTCTAT CAGGGCTATG GCCCACTACG TGAACCATCA CCCTAATCAA GTTTTTTGGG GTCGAGGTGC CGTAAAGCAC
     AGGTTGCAGT TTCCCGCTTT TTGGCAGATA GTCCCGATAC CGGGTGATGC ACTTGGTAGT GGGATTAGTT CAAAAAACCC CAGCTCCACG GCATTTCGTG

3801 TAAATCGGAA CCCTAAAGGG AGCCCCCGAT TTAGAGCTTG ACGGGGAAAG CCGGCGAACG TGGCGAGAAA GGAAGGGAAG AAAGCGAAAG GAGCGGGCGC
     ATTTAGCCTT GGGATTTCCC TCGGGGGCTA AATCTCGAAC TGCCCCTTTC GGCCGCTTGC ACCGCTCTTT CCTTCCCTTC TTTCGCTTTC CTCGCCCGCG

3901 TAGGGCGCTG GCAAGTGTAG CGGTCACGCT GCGCGTAACC CCGCGCTTAA TGCGCCGCTA CAGGGCGCGT CAGGGCGCGT CCGGATCCTG CCTCGCGCGT
     ATCCCGCGAC CGTTCACATC GCCAGTGCGA CGCGCATTGG GGCGCGAATT ACGCGGCGAT GTCCCGCGCA GTCCCGCGCA GGCCTAGGAC GGAGCGCGCA

4001 TTCGGTGATG ACGGTGAAAA CCTCTGACAC ATGCAGCTCC CGGAGACGGT CACAGCTTGT CTGTAAGCGG ATGCCGGGAG CAGACAAGCC CGTCAGGGCG
     AAGCCACTAC TGCCACTTTT GGAGACTGTG TACGTCGAGG GCCTCTGCCA GTGTCGAACA GACATTCGCC TACGGCCCTC GTCTGTTCGG GCAGTCCCGC

4101 CGTCAGCGGG TGTTCGGCCGGG CAGCAGCCG CAGCCATGAC GGTCAGTCAG AGCGATAGCC GAGTGTATAC TGGCTTAACT ATGCGGCATC AGAGCAGATT
     GCAGTCGCCC ACAACGCCCC ACAGCCCGC GTCGGTACTG CCAGTCAGTC TCGCTATCGG CTCACATATG ACCGAATTGA TACGCCGTAG TCTCGTCTAA
```

FIG._26E

```
4201 GTACTGAGAG TGCACCATAT GCGGTGTGAA ATACCGCACA GATGCGTAAG GAGAAAATAC CGCATCAGGC GCTCTTCCGC TTCCTCGCTC ACTGACTCGC
     CATGACTCTC ACGTGGTATA CGCCACACTT TATGGCGTGT CTACGCATTC CTCTTTTATG GCGTAGTCCG CGAGAAGGCG AAGGAGCGAG TGACTGAGCG

4301 TGCGCTCGGT CGTTCGGCTG CGGCGAGCGG TATCAGCTCA CTCAAAGGCG GTAATACGGT TATCCACAGA ATCAGGGGAT AACGCAGGAA AGAACATGTG
     ACGCGAGCCA GCAAGCCGAC GCCGCTCGCC ATAGTCGAGT GAGTTTCCGC CATTATGCCA ATAGGTGTCT TAGTCCCCTA TTGCGTCCTT TCTTGTACAC

4401 AGCAAAAGGC CAGGAACCGG TAAAAAGGCC GCGTTGCTGG CGTTTTTCCA TAGGCTCCGC CCCCCTGACG AGCATCACAA AAATCGACGC
     TCGTTTTCCG GTCCTTGGCC ATTTTTCCGG CGCAACGACC GCAAAAAGGT ATCCGAGGCG GGGGGACTGC TCGTAGTGTT TTTAGCTGCG

4501 TCAAGTCAGA GGTGGCGAAA CCCGACAGGA CTATAAAGAT ACCAGGCGTT TCCCCCTGGA AGCTCCCTCG TGCGCTCTCC TGTTCCGACC CTGCCGCTTA
     AGTTCAGTCT CCACCGCTTT GGGCTGTCCT GATATTTCTA TGGTCCGCAA AGGGGGACCT TCGAGGGAGC ACGCGAGAGG ACAAGGCTGG GACGGCGAAT

4601 CCGGATACCT GTCCGCCTTT CTCCCTTCGG GAAGCGTGGC GCTTTCTCAT AGCTCACGCT GTAGGTATCT CAGTTCGGTG TAGGTCGTTC GCTCCAAGCT
     GGCCTATGGA CAGGCGGAAA GAGGGAAGCC CTTCGCACCG CGAAAGAGTA TCGAGTGCGA CATCCATAGA GTCAAGCCAC ATCCAGCAAG CGAGGTTCGA

4701 GGGCTGTGTG CACGAACCCC CCGTTCAGCC CGACCGCTGC GCCTTATCCG GTAACTATCG TCTTGAGTCC AACCCGGTAA GACACGACTT ATCGCCACTG
     CCCGACACAC GTGCTTGGGG GGCAAGTCGG GCTGGCGACG CGGAATAGGC CATTGATAGC AGAACTCAGG TTGGGCCATT CTGTGCTGAA TAGCGGTGAC

4801 GCAGCAGCCA CTGGTAACAG GATTAGCAGA GCGAGGTATG TAGGCGGTGC TACAGAGTTC TTGAAGTGGT GGCCTAACTA CGGCTACACT AGAAGGACAG
     CGTCGTCGGT GACCATTGTC CTAATCGTCT CGCTCCATAC ATCCGCCACG AGTCTCAAG AACTTCACCA CCGGATTGAT GCCGATGTGA TCTTCCTGTC

4901 TATTTGGTAT CTGCGCTCTG CTGAAGCCAG TTACCTTCGG AAAAAGAGTT GGTAGCTCTT GATCCGGCAA ACAAACCACC GCTGGTAGCG GTGGTTTTTT
     ATAAACCATA GACGCGAGAC GACTTCGGTC AATGGAAGCC TTTTTCTCAA CCATCGAGAA CTAGGCCGTT TGTTTGGTGG CGACCATCGC CACCAAAAAA

5001 TGTTTGCAAG CAGCAGATTA CGCGCAGAAA AAAAGGATCT CAAGAAGATC CTTTGATCTT TTCTACGGGG TCTGACGCTC AGTGGAACGA AAACTCACGT
     ACAAACGTTC GTCGTCTAAT GCGCGTCTTT TTTTCCTAGA GTTCTTCTAG GAAACTAGAA AAGATGCCCC AGACTGCGAG TCACCTTGCT TTTGAGTGCA

5101 TAAGGGATTT TGGTCATGAG ATTATCAAAA AGGATCTTCA CCTAGATCCT TTAAATTAA AAATGAAGTT TTAAATCAAT CTAAAGTATA TATGAGTAAA
     ATTCCCTAAA ACCAGTACTC TAATAGTTTT TCCTAGAAGT GGATCTAGGA AATTTAATT TTTACTTCAA AATTTAGTTA GATTTCATAT ATACTCATTT

5201 CTTGGTCTGA CAGTTACCAA TGCTTAATCA GTGAGGCACC TATCTCAGCG ATCTGTCTAT TTCGTTCATC CATAGTTGCC TGACTCCCCG TCGTGTAGAT
     GAACCAGACT GTCAATGGTT ACGAATTAGT CACTCCGTGG ATAGAGTCGC TAGACAGATA AAGCAAGTAG GTATCAACGG ACTGAGGGGC AGCACATCTA
```

FIG._26F

```
5301 AACTACGATA CGGGAGGGCT TACCATCTGG CCCCAGTGCT GCAATGATAC CGCGAGACCC ACGCTCACCG GCTCCAGATT TATCAGCAAT AAACCAGCCA
     TTGATGCTAT GCCCTCCCGA ATGGTAGACC GGGGTCACGA CGTTACTATG GCGCTCTGGG TGCGAGTGGC CGAGGTCTAA ATAGTCGTTA TTTGGTCGGT

5401 GCCGAAGGG CCGAGCGCAG AAGTGGTCCT GCAACTTTAT CCGCCTCCAT CCAGTCTATT AATTGTTGCC GGGAAGCTAG AGTAAGTAGT TCGCCAGTTA
     CGGCCTTCCC GGCTCGCGTC TTCACCAGGA CGTTGAAATA GGCGGAGGTA GGTCAGATAA TTAACAACGG CCCTTCGATC TCATTCATCA AGCGGTCAAT

5501 ATAGTTTGCG CAACGTTGTT GCCATTGCTG CAGGCATCGT GGTGTCACGC TCGTCGTTTG GTATGGCTTC ATTCAGCTCC GGTTCCCAAC GATCAAGGCG
     TATCAAACGC GTTGCAACAA CGGTAACGAC GTCCGTAGCA CCACAGTGCG AGCAGCAAAC CATACCGAAG TAAGTCGAGG CCAAGGGTTG CTAGTTCCGC

5601 AGTTACATGA TCCCCCATGT TGTGCAAAAA AGCGGTTAGC TCCTTCGGTC CTCCGATCGT TGTCAGAAGT AAGTTGGCCG CAGTGTTATC ACTCATGGTT
     TCAATGTACT AGGGGGTACA ACACGTTTTT TCGCCAATCG AGGAAGCCAG GAGGCTAGCA ACAGTCTTCA TTCAACCGGC GTCACAATAG TGAGTACCAA

5701 ATGGCAGCAC TGCATAATTC TCTTACTGTC ATGCCATCCG TAAGATGCTT TTCTGTGACT GGTGAGTACT CAACCAGTC ATTCTGAGAA TAGTGTATGC
     TACCGTCGTG AGTATTAAG AGAATGACAG TACGGTAGGC ATTCTACGAA AAGACACTGA CCACTCATGA GTTGGTTCAG TAAGACTCTT ATCACATACG

5801 GGCGACCGAG TTGCTCTTGC CCGGCGTCAA CACGGGATAA TACCGCGCCA CATAGCAGAA CTTTAAAAGT GCTCATCATT GGAAAACGTT CTTCGGGGCG
     CCGCTGGCTC AACGAGAACG GGCCCGCAGTT GTGCCCTATT ATGGCGCGGT GTATCGTCTT GAAATTTTCA CGAGTAGTAA CCTTTTGCAA GAAGCCCGC

5901 AAAACTCTCA AGGATCTTAC CGCTGTTGAG ATCCAGTTCG ATGTAACCCA CTCGTGCACC CAACTGATCT TCAGCATCTT TTACTTTCAC CAGCGTTTCT
     TTTTGAGAGT TCCTAGAATG GCGACAACTC TAGGTCAAGC TACATTGGGT GAGCACGTGG GTTGACTAGA AGTCGTAGAA AATGAAAGTG GTCGCAAAGA

6001 GGGTGAGCAA AAACAGGAAG GCAAAAATGC CGCAAAAAAGG GAATAAGGGC GACACGGAAA TGTTGAATAC TCATACTCTT CCTTTTTCAA TATTATTGAA
     CCCACTCGTT TTTGTCCTTC CGTTTTTACGG CGTTTTTTCC CTTATTCCCG CTGTGCCTTT ACAACTTATG AGTATGAGAA GGAAAAAGTT ATAATAACTT

6101 GCATTATCA GGGTTATTGT CTCATGAGCG GATACATATT TGAATGTATT TAGAAAAATA AACAAATAGG GGTTCCGCGC ACATTTCCCC GAAAAGTGCC
     CGTAAATAGT CCCAATACA GAGTACTCGC CTATGTATAA ACTTACATAA ATCTTTTTAT TTGTTTATCC CCAAGGCGCG TGTAAAGGGG CTTTTCACGG

6201 ACCTGACGTC TAAGAAACCA TTATTATCAT GACATTAACC TATAAAAATA GGCGTATCAC GAGGCCCTTT CGTCTTCAAT ACAGGTAGAC CTTTCGTAGA
     TGGACTGCAG ATTCTTTGGT AATAATAGTA CTGTAATTGG ATATTTTTAT CCGCATAGTG CTCCGGGAAA GCAGAAGTTA TGTCCATCTG GAAAGCATCT

6301 GATGTACAGT GAAATCCCCG AAATTATACA CATGACTGAA GGAAGGGAGC TCGTCATTCC CTGCCGGGTT ACGTCACCTA ACATCACTGT TACTTAAAA
     CTACATGTCA CTTTAGGGGC TTTAATATGT GTACTGACTT CCTTCCCTCG AGCAGTAAGG GACGGCCCAA TGCAGTGGAT TGTAGTGACA ATGAAATTTT
```

FIG._26G

```
6401  AAGTTTCCAC TTGACACTTT GATCCCTGAT GGAAAACGCA TAATCTGGGA CAGTAGAAAG GGCTTCATCA TATCAAATGC AACGTACAAA GAAATAGGGC
      TTCAAAGGTG AACTGTGAAA CTAGGGACTA CCTTTTGCGT ATTAGACCCT GTCATCTTTC CCGAAGTAGT ATAGTTTACG TTGCATGTTT CTTTATCCCG

6501  TTCTGACCTG TGAAGCAACA GTCAATGGGC ATTTGTATAA GACAAACTAT CTCACACATC GACAAACCAA TACAATACAG GTAGACCTTT CGTAGAGATG
      AAGACTGGAC ACTTCGTTGT CAGTTACCCG TAAACATATT CTGTTTGATA GAGTGTGTAG CTGTTTGGTT ATGTTATGTC CATCTGGAAA GCATCTCTAC

6601  TACAGTGAAA TCCCCGAAAT TATACACATG GGGAGCTCGT CATTCCCTGC CGGGTTACGT CACCTAAACAT CACTGTTACT TTAAAAAAGT
      ATGTCACTTT AGGGGCTTTA ATATGTGTAC TGACTTCCTT GCCCAATGCA GTGGATTGTA AATTTTTCA

6701  TTCCACTTGA CACTTTGATC CCTGATGGAA AACGCATATAA CTGGGACAGT AGAAAGGGCT TCATCATATC AAATGCAACG TACAAAGAAA TAGGGCTTCT
      AAGGTGAACT GTGAAACTAG GGACTACCTT TGCGTATTA GACCCTGTCA TCTTTCCCGA AGTAGTATAG TTTACGTTGC ATGTTTCTTT ATCCCGAAGA

6801  GACCTGTGAA GCAACAGTCA ATGGGCATTT GTATAAGACA AACTATCTCA CACATCGACA AACCAATACA ATCTACAGGT AGACCTTTCG TAGAGATGTA
      CTGGACACTT CGTTGTCAGT TACCCGTAAA CATATTCTGT TTGATAGAGT GTGTAGCTGT TTGGTTATGT TAGATGTCCA TCTGGAAAGC ATCTCTACAT

6901  CAGTGAAATC CCCGAAATTA TACACATGAC TGAAGGAAGG GAGCTCGTCA TTCCCTGCCG GGTTACGTCA CCTAACATCA CTGTTACTTT AAAAAAGTTT
      GTCACTTTAG GGGCTTTAAT ATGTGTACTG ACTTCCTTCC CTCGAGCAGT AAGGGACGGC CCAATGCAGT GGATTGTAGT GACAATGAAA TTTTTTCAAA

7001  CCACTTGACA CTTTGATCCC TGATGGAAAA CGCATAATCT GGGACAGTAG AAAGGGCTTC ATCATATCAA ATGCAACGTA CAAAGAAATA GGGCTTCTGA
      GGTGAACTGT GAAACTAGGG ACTACCTTTT GCGTATTAGA CCCTGTCATC TTTCCCGAAG TAGTATAGTT TACGTTGCAT GTTTCTTTAT CCCGAAGACT

7101  CCTGTGAAGC AACAGTCAAT GGGCATTTGT ATAAGACAAA CTATCTCACA CATCGACAAA CCAATACAAT C
      GGACACTTCG TTGTCAGTTA CCCGTAAACA TATTCTGTTT GATAGAGTGT GTAGCTGTTT GGTTATGTTA G
```

FIG. 26H

```
  1 ATGAAAAGA ATAATCGCATT TCTTCTTGCA TCTATGTTCG TTTTTTCTAT TGCTACAAAT GCCTATGCAG ATATCCAGAT GACCCAGTCC CCGAGCTCCC
    TACTTTTTCT TATAGCGTAA AGAAGAACGT AGATACAAGC AAAAAAGATA ACGATGTTTA CGGATACGTC TATAGGTCTA CTGGGTCAGG GGCTCGAGGG
  1 M  K  K  N  I  A  F  L  L  A  S  M  F  V  F  L  L  Q  T  N  A  Y  A  D  I  Q  M  T  Q  S  P  S  S  L
    ^met                                                                       ^start of light chain
    ^start of stII signal sequence 101 TGTCCGCCTC TGTGGGCGAT AGGGTCACCA TCACCTGCCG TGCCAGTCAG GATGTGTCCA CTGCTGTAGC CTGGTATCAA CAGAAACCAG GAAAAGCTCC
    ACAGGCGGAG ACACCCGCTA TCCCAGTGGT AGTGGACGGC ACGGTCAGTC GACCATAGGT GACGACATCG GACCATAGTT GTCTTTGGTC CTTTTCGAGG
 35 S  V  G  D  R  V  T  I  T  C  R  A  S  Q  D  V  S  T  A  V  A  W  Y  Q  Q  K  P  G  K  A  P
                                      ^CDR-L1

201 GAAGCTTCTG ATTTACTCGG CATCCTTCCT CTACTCTGGA GTCCCTTCTC GCTTCTCTGG GGGACGGATT TCACTCTGAC CATCAGCAGT
    CTTCGAAGAC TAAATGAGCC GTAGGAAGGA GATGAGACCT CAGGGAAGAG CGAAGAGACC CCCTGCCTAA AGTGAGACTG GTAGTCGTCA
 68 K  L  L  I  Y  S  A  S  F  L  Y  S  G  V  P  S  R  F  S  G  S  G  S  G  T  D  F  T  L  T  I  S  S
              ^CDR-L2

301 CTGCAGCCGG AAGACTTCGC AACTTATTAC TGTCAGCAAC ATTATACTAC TCCTCCCACG TTCGGACAGG GTACCAAGGT GGAGATCAAA CGAACTGTGG
    GACGTCGGCC TTCTGAAGCG TTGAATAATG ACAGTCGTTG TAATATGATG AGGAGGGTGC AAGCCTGTCC CATGGTTCCA CCTCTAGTTT GCTTGACACC
101 L  Q  P  E  D  F  A  T  Y  Y  C  Q  Q  H  Y  T  T  P  P  T  F  G  Q  G  T  K  V  E  I  K  R  T  V  A
                                      ^CDR-L3

401 CTGCACCATC TGTCTTCATC TTCCCGCCAT CTGATGAGCA GTTGAAATCT GGAACTGCCT CTGTTGTGTG CCTGCTGAAT AACTTCTATC CCAGAGAGGC
    GACGTGGTAG ACAGAAGTAG AAGGGCGGTA GACTACTCGT CAACTTTAGA CCTTGACGGA GACAACACAC GGACGACTTA TTGAAGATAG GGTCTCTCCG
135 A  P  S  V  F  I  F  P  P  S  D  E  Q  L  K  S  G  T  A  S  V  V  C  L  L  N  N  F  Y  P  R  E  A

501 CAAAGTACAG TGGAAGGTGG ATAACGCCCT CCAATCGGGT AACTCCCAGG AGAGTGTCAC AGAGCAGGAC AGCAAGGACA GCACCTACAG CCTCAGCAGC
    GTTTCATGTC ACCTTCCACC TATTGCGGGA GGTTAGCCCA TTGAGGGTCC TCTCACAGTG TCTCGTCCTG TCGTTCCTGT CGTGGATGTC GGAGTCGTCG
168 K  V  Q  W  K  V  D  N  A  L  Q  S  G  N  S  Q  E  S  V  T  E  Q  D  S  K  D  S  T  Y  S  L  S  S

601 ACCCTGACGC TGAGCAAAGC TGACTACGAG AAACACAAAG TCTACGCCTG CGAAGTCACC CATCAGGGCC TGAGCTCGCC CGTCACAAAA AGCTTCAACA
    TGGGACTGCG ACTCGTTTCG ACTGATGCTC TTTGTGTTTC AGATGCGGAC GCTTCAGTGG GTAGTCCCGG ACTCGAGCGG GCAGTGTTTT TCGAAGTTGT
201 T  L  T  L  S  K  A  D  Y  E  K  H  K  V  Y  A  C  E  V  T  H  Q  G  L  S  S  P  V  T  K  S  F  N  R
```

FIG._27A

```
701  GGGAGAGTG  TGGTGCCAGC  TCCCGTATGG  CTGATCCGAA  CCGTTTCCGC  GGTAAGGACC  TGGCATAACT  CGAGGCTGAT  CCTCTACGCC  GGACGCATCG
     CCCCTCTCAC  ACCACGGTCG  AGGCATACC   GACTAGGCTT  GGCAAAGCCG  CCATTCCTGG  ACCGTATTGA  GCTCCGACTA  GGAGATGCGG  CCTGCGTAGC
235   G   E   C    G   A   S    S   G   M   A    D   P   N    R   F   R    G   K   D   L    A   Q
                                                         ^end of light chain, start of gD tag 801  TGGCCCTAGT  ACCCAAGTTC  ACGTAAAAAG  GGTAACTAGA  GGTTGAGGTG  ATTTTATGAA  AAAGAATATC  GCATTCTTC   TTGCATCTAT  GTTCGTTTTT
     ACCGGGATCA  TGGCTTCAAG  TGCATTTTTC  CCATTGATCT  CCAACTCCAC  TAAAATACTT  TTTCTTATAG  CGTAAAGAAG  AACGTAGATA  CAAGCAAAAA
                                                         M   K   N   I   A   F   L   L   A   S   M    F   V   F
-23                                                             ^start of stII 901  TCTATTGCTA  CAAACGCGTA  CGCTGAGGTT  CAGCTGGTGG  AGTCTGGCGG  TGGCCTGGTG  CAGCCAGGGG  GCTCACTCCG  TTTGTCCTGT  GCAGCTTCTG
     AGATAACGAT  GTTTGCGCAT  GCGACTCCAA  GTCGACCACC  TCAGACCGCC  ACCGGACCAC  GTCGGTCCCC  CGAGTGAGGC  AAACAGGACA  CGTCGAAGAC
  -8  S   I   A   T    N   A   Y    A   E   V    Q   L   V    E   S   G   G    G   L   V    Q   P   G   G    S   L   R   L   S   C    A   A   S   G
                                                                                                                                          ^CDR-H1

1001 GCTTCACCAT  TAGTGGTTCT  TGGATACACT  GGGTGCGTCA  GGCCCCGGGT  AAGGGCCTGG  AATGGGTTGC  CCTTATAGCG  GCGCTACTGA
     CGAAGTGGTA  ATCACCAAGA  ACCTATGTGA  CCCACGCAGT  CCGGGGCCCA  TTCCCGGACC  TTACCCAACG  GGAATATCGC  CGCGATGACT
  27   F   T   I   S   G   S    W   I   H   W    V   R   Q    A   P   G    K   G   L   E    W   V   A    A   L   I   A    P   Y   S   G    A   T   D
                                                                                                      ^CDR-H2

1101 CTATGCCGAT  AGCCTCAAGG  GCCGTTTCAC  TATAAGGGCA  GACACATCCA  AAAACACAGC  CTACCTACAA  ATGAACAGCT  TAAGAGCTGA  GGACACTGCC
     GATACGGCTA  TCGGAGTTCC  CGGCAAAGTG  ATATTCCCGT  CTGTGTAGGT  TTTTGTGTCG  GATGGATGTT  TACTTGTCGA  ATTCTCGACT  CCTGTGACGG
  60   Y   A   D    S   V   K   G    R   F   T    I   S   A    D   T   S   K   N   T   A    Y   L   Q    M   N   S   L    R   A   E    D   T   A

1201 GTCTATTATT  GTGCAAGAGA  GGGGGGCTTG  CCCCCCGAAC  TGGTCAAGGA  ACACTAGTCA  CCGTCTCCTC  GGCTCCACC   AAGGGCCCAT  CGGTCTTCCC
     CAGATAATAA  CACGTTCTCT  CCCCCCGAAC  GGGGGGCTTG  ACCAGTTCCT  TGTGATCAGT  GGCAGAGGAG  CCGAGGTGG   TTCCCGGGTA  GCCAGAAGGG
  93   V   Y   Y   C    A   R   E    G   G   L    Y   W   F    D   Y   W    G   Q   G    T   L   V   T   V   S   S    A   S   T    K   G   P   S
                        ^CDR-H3

1301 CGGTCTTCCC  CCTGGCACCC  TCCTCCAAGA  GCACCTCTGG  GGGCACAGCG  GCCCTGGGCT  GCCTGGTCAA  GGACTACTTC  CCCGAACCGG  TGACGGTGTC
     GCCAGAAGGG  GGACCGTGGG  AGGAGGTTCT  CGTGGAGACC  CCCGTGTCGC  CGGGACCCGA  CGGACCAGTT  CCTGATGAAG  GGGCTTGGCC  ACTGCCACAG
127    V   F   P    L   A   P    S   S   K   S   T    S   G    G   T   A   A   L   G    C   L   V   K    D   Y   F    P   E   P   V   T   V   S
```

*FIG. _27B*

```
1401  GTGGAACTCA GGCGCCCTGA CCAGCGGCGT GCACACCTTC CCGGCTGTCC AGGACTCCTC CGTGCCCTCC
      CACCTTGAGT CCGCGGGACT GGTCGCCGCA CGTGTGGAAG GGCCGACGAG TCCTGAGATG AGGGAGTCGT
160        W  N  S    G  A  L  T    S  G  V  H    T  F  P  A    V  L  Q  S  S

TACAGTCCTC AGGACTCTAC GGTGGTGAC CGTGCCCTCC
      ATGTCAGGAG TCCTGAGATG GCACCACTG GCACGGGAGG
           G  L  Y    S  L  S  S    V  V  T    V  P  S

1501  AGCAGCTTGG GCACCCAGAC CTACATCTGC AACGTGAATC ACAAGCCCAG CAACACCAAG GTCGACAAGA
      TCGTCGAACC CGTGGGTCTG GATGTAGACG TTGCACTTAG TGTTCGGGTC GTTGTGGTTC CAGCTGTTCT
193        S  S  L    G  T  Q  T    Y  I  C    N  V  N  H    K  P  S    N  T  K

AAGTTGAGCC CAAATCTTGT GACAAAACTC
      TTCAACTCGG GTTTAGAACA CTGTTTTGAG
           V  D  K  K    V  E  P    K  S  C    D  K  T  H

1601  ACCTCAGTGG CGGTGGCTCT GGTTCCGGTG ATTTTGATTA TGAAAAGATG GCAAACGCTA ATAAGGGGGC
      TGGAGTCACC GCCACCGAGA CCAAGGCCAC TAAAACTAAT ACTTTTCTAC CGTTTGCGAT TATTCCCCCG
227     L  S  G    G  G  S    G  S  G    D  F  D  Y    E  K  M    A  N  A  N    K
      ^end of heavy chain
               ^start of gene III coat protein (267-end)

TATGACCGAA AATGCCGATG AAAACGCTCT
      ATACTGGCTT TTACGGCTAC TTTGCGCGA
        G  A    M  T  E    N  A  D  E    N  A  L

1701  ACAGTCTGAC AACTTGATTC TGTCGCTACT GATTACGGTG CTGCTATCGA TGGTTTCATT GGTGACGTTT
      TGTCAGACTG TTGAACTAAG ACAGCGATGA CTAATGCCAC GACGATAGCT ACCAAAGTAA CCACTGCAAA
260     Q  S  D    A  K  G  K    L  D  S    V  A  T    D  Y  G  A    A  I  D

CCGGCCTTGC TAATGGTAAT
      GGCCGGAACG ATTACCATTA
           G  F  I    G  D  V  S    G  L  A    N  G  N

1801  GGTGCTACTG GTGATTTTGC TGATTTCGGT TCCAAGTCGG CTCAAGTTAC GAGTTCAGCC GAGTTTGGTT
      CCACGATGAC CACTAAAACG ACTAAAGCCA AGGTTCAGCC GAGTTCAATG CTCAAGTCGG CTCAAACCAA
293     G  A  T  G    D  F  A    G  S  N    Q  V  G    D  G  D    N  S  P  L

AATTCACCTT TAATGAATAA TATTCCGTCAA TATTTACCTT
      TTAAGTGGAA ATTACTTATT AAAGGCAGTT ATAAATGAA
        M  N  N    F  R  Q    Y  L  P  S

1901  CCCTCCCCTCA ATCGGTTGAA TGTCGCCCTT TTGTCTTTAG CGCTGGTAAA CCATATGAAT TTTCTATTGA
      GGGAGGGGAGT TAGCCAACTT ACAGCGGGAA AACAGAAATC GCGACCATTT GGTATACTTA AAAGATAACT
327     L  P  Q    S  V  E    C  R  P  F    V  F  S    A  G  K    P  Y  E  F    S

TTGTGACAAA ATAAACTTAT TCCGTGGTGT
      AACACTGTTT TATTTGAATA AGGCACCACA
        I  D  C    D  K  I    N  L  F    R  G  V

2001  CTTTGCCTTT CTTTTATATG TTGCCACCTT TATGTATGTA TTTTCTACGT TTGCTAACAT ACTGCGTAAT AAGGAGTCTT AA
      GAAACGGAAA GAAAATATAC AACGGTGGAA ATACATACAT AAAAGATGCA AACGATTGTA TGACGCATTA TTCCTCAGAA TT
360     F  A  F    L  L  Y  V    A  T  F    M  Y  V    F  S  T  F    A  N  I    L  R  N  K  E  S  Q
```

FIG._27C

1   ATGAAAAAGA ATATCGCATT TCTTCTTGCA TCTATGTTCG TTTTTTCTAT TGCTACAAAT GCCTATGCAG ATATCCAGAT GACCCAGTCC CCGAGCTCCC
    TACTTTTTCT TATAGCGTAA AGAAGAACGT AGATACAAGC AGATACAAGC AGATAGCAAGT AAAAAGATA ACGATGTTTA CGGATACGTC TATAGGTCTA CTGGGTCAGG GGCTCGAGG
1   M  K  K  N  I  A  F  L  L  A  S  M  F  V  F  S  I  A  T  N  A  Y  A  D  I  Q  M  T  Q  S  P  S  S  L
    ^met
    ^start of stII signal sequence                                                    ^start of light chain 101 TGTCCGCCTC TGTGGGCGAT AGGGTCACCA TCACCTGCCG TGCCAGTCAG GATGTGTCCA CTGCTGTAGC CTGGTATCAA CAGAAACCAG GAAAAGCTCC
    ACAGGCGGAG ACACCGCTA TCCCAGTGGT AGTGGACGGC ACGTCAGTC CTACACAGGT GACGACATCG GACCATAGTT GTCTTTGGTC CTTTTCGAGG
35  S  A  S  V  G  D  R  V  T  I  T  C  R  A  S  Q  D  V  S  T  A  V  A  W  Y  Q  Q  K  P  G  K  A  P
                                                           ^CDR-L1

201 GAAAGCTTCTG ATTACTCGG CATCCCTTCT CTACTCTGGA GTCCCTTCTC GCTTCTCTGG TAGCGGTTCC GGGACGGATT TCACTCTGAC CATCAGCAGT
    CTTCGAAGAC TAATGAGCC GTAGGGAAGA GATGAGACCT CAGGGAAGAG CGAAGAGACC ATCGCCAAGG CCCTGCCTAA AGTGAGACTG GTAGTCGTCA
68  K  L  L  I  Y  S  A  S  F  L  Y  S  G  V  P  S  R  F  S  G  S  G  S  G  T  D  F  T  L  T  I  S  S
          ^CDR-L2

301 CTGCAGCCGG AAGACTTCGC AACTTATTAC TGTCAGCAAC ATTATACTAC TCCTCCCACG TTCGGACAGG GTACCAAGGT GGAGATCAAA CGAACTGTGG
    GACGTCGGCC TTCTGAAGCG TTGAATAATG ACAGTCGTTG TAATATGATG AGGAGGGTGC AAGCCTGTCC CATGGTTCCA CCTCTAGTTT GCTTGACACC
101 L  Q  P  E  D  F  A  T  Y  Y  C  Q  Q  H  Y  T  T  P  P  T  F  G  Q  G  T  K  V  E  I  K  R  T  V  A
                                         ^CDR-L3

401 CTGCACCATC TGTCTTCATC TTCCCGCCAT CTGATGAGCA GTTGAAATCT GGAACTGCCT CTGTTGTGTG CCTGCTGAAT AACTTCTATC CCAGAGAGGC
    GACGTGGTAG ACAGAAGTAG AAGGGCGGTA GACTACTCGT CAACTTTAGA CCTTGACGGA GACACACAC GGACGACTTA TTGAAGATAG GGTCTCTCCG
135 A  P  S  V  F  I  F  P  P  S  D  E  Q  L  K  S  G  T  A  S  V  V  C  L  L  N  N  F  Y  P  R  E  A

501 CAAAGTACAG TGGAAGGTGG ATAACGCCCT CCAATCGGGT AACTCCCAGG AGAGTGTCAC AGAGCAGGAC AGCAAGGACA GCACCTACAG CCTCAGCAGC
    GTTTCATGTC ACCTTCCACC TATTGCGGGA GGTTAGCCCA TTGAGGGTCC TCTCACAGTG TCTCGTCCTG TCGTTCCTGT CGTGGATGTC GGAGTCGTCG
168 K  V  Q  W  K  V  D  N  A  L  Q  S  G  N  S  Q  E  S  V  T  E  Q  D  S  K  D  S  T  Y  S  L  S  S

601 ACCCTGACGC TGAGCAAAGC AGACTACGAG AAACACAAAG TCTACGCCTG CGAAGTCACC CATCAGGGCC TGAGCTCGCC CGTCACAAAG AGCTTCAACA
    TGGGACTGCG ACTCGTTTCG TCTGATGCTC TTTGTGTTTC AGATGCGGAC GCTTCAGTGG GTAGTCCCGG ACTCGAGCGG GCAGTGTTTC TCGAAGTTGT
201 T  L  T  L  S  K  A  D  Y  E  K  H  K  V  Y  A  C  E  V  T  H  Q  G  L  S  S  P  V  T  K  S  F  N  R

FIG._28A

```
701  GGGGAGAGTG TGGTGCCAGC TCCGGTATGG CTGATCCGAA CCGTTCCGC GGTAAGGACC TGGCATAACT CGAGGCTGAT CCTCTACGCC GGACGCATCG
     CCCCTCTCAC ACCACGGTCG AGGCCATACC GACTAGGCTT GGCAAAGGCG CCATTCCTGG ACCGTATTGA GCTCCGACTA GGAGATGCGG CCTGCGTAGC
235  G  E  C  G  A  S  S  G  M  A  D  P  N  R  F  R  G  K  D  L  A  Q
                      ^end of light chain, start of gD tag 801  TGGCCCTAGT ACGCAAGTTC ACGTAAAAAG GGTAACTAGA GGTTGAGGTG ATTTTATGAA AAAGAATATC GCATTTCTTC TTGCATCTAT GTTCGTTTTT
     ACCGGGATCA TGCGTTCAAG TGCATTTTTC CCATTGATCT CCAACTCCAC TAAAATACTT TTTCTTATAG CGTAAAGAAG AACGTAGATA CAAGCAAAAA
-23                                                M  K  K  N  I  A  F  L  L  A  S  M  F  V  F
                                                   ^start of stII 901  TCTATTGCTA CAAACGCGTA CGCTGAGGTT CAGCTGGTGG AGTCTGGCGG TGGCCTGGTG CAGCCAGGGG GCTCACTCCG TTTGTCCTGT GCAGCTTCTG
     AGATAACGAT GTTTGCGCAT GCGACTCCAA GTCGACCACC TCAGACCGCC ACCGGACCAC GTCGGTCCCC CGAGTGAGGC AAACAGGACA CGTCGAAGAC
-8   S  I  A  T  N  A  Y  A  E  V  Q  L  V  E  S  G  G  G  L  V  Q  P  G  G  S  L  R  L  S  C  A  A  S  G
                      ^start of heavy chain 1001 GCTTCACCAT TAGTAATTAT GGGATACACT GGGTGCGTCA GGCCCCAGGG AAGGGCCTGG AATGGGTTGG TAGGATTTCT CCTTCTAACG GCTCTACTTA
     CGAAGTGGTA ATCATTAATA CCCTATGTGA CCCACGCAGT CCGGGGTCCC TTCCCGGACC TTACCCAACC ATCCTAAAGA GGAAGATTGC CGAGATGAAT
27   F  T  I  S  N  Y  G  I  H  W  V  R  Q  A  P  G  K  G  L  E  W  V  G  R  I  S  P  S  N  G  S  T  Y
                      ^CDR-H1                                           ^CDR-H2

1101 CTATGCCGAT AGCGTCAAGG GCCGTTTCAC TATAAGCGCA GACACATCCA AAAACACAGC CTACCTACAA ATGAACAGCT TAAGAGCTGA GGACACTGCC
     GATACGGCTA TCGCAGTTCC CGGCAAAGTG ATATTCGCGT CTGTGTAGGT TTTTGTGTCG GATGGATGTT TACTTGTCGA ATTCTCGACT CCTGTGACGG
60   Y  A  D  S  V  K  G  R  F  T  I  S  A  D  T  S  K  N  T  A  Y  L  Q  M  N  S  L  R  A  E  D  T  A

1201 GTCTATTATT GTGCAAAATG CTCGGGTCAGG TTCGCTTACT GGGGTCAAGG CCCCAGTTCC TTGTGATCGG AACACTAGTC TGGCAGAGGA GCCGGAGGTG GTTCCCGGGT AGCCAGAGGG
     CAGATAATAA CACGTTTTAC GAGCCCAGTCC AAGCGAATGA CCCCAGTTCC AACACTAGCC TTGTGATCAG ACCGTCTCCT CGGCCTCCAC CAAGGGCCCA TCGGTCTTCC AGCCAGAAGG
93   V  Y  Y  C  A  K  C  S  V  R  F  A  Y  W  G  Q  G  T  L  V  T  V  S  S  A  S  T  K  G  P  S  V  F  P
                      ^CDR-H3
```

FIG._28B

```
1301  CCTGGCACC CTCCTCCAAG AGCACCTCTG GGGGCACAGC GGCCCTGGGC TGCCTGGTCA AGGACTACTT CCCCGAACTC
      GGGACCGTGG GAGGAGGTTC TCGTGGAGAC CCCCGTGTCG CCGGGACCCG ACGGACCAGT TCCTGATGAA GGGGCTTGAG
      GTGACGGTGT CGTGGAACTC
      GCACCGCCACA GCACCTTGAG
127   L  A  P    L  P  S    S  T  S  G    G  T  A    A  L  G    C  L  V  K    D  Y  F    P  E  P    V  T  V  S    W  N  S

1401  AGGGCCCCCTG ACCAGCGGCG TGCACACCTT CCCGGCTGTC CTACAGTCCT CAGGACTCTA CTCCCTCAGC AGCGTGGTGA
      TCCGCGGGAC TGGTCGCCGC ACGTGTGGAA GGGCCGACAG GATGTCAGGA GTCCTGAGAT GAGGGAGTCG TCGCACCACT
      CCGTGCCCTC  CAGCAGCTTG
      GGCACGGGAG  GTCGTCGAAC
160   G  A  L    T  S  G    V  H  T  F    P  A  V    L  Q  S  S    G  L  Y    S  L  S    S  V  V  T    V  P  S    S  S  L

1501  GGCACCCAGA CCTACATCTG CAACGTGAAT CACAAGCCCA GCAACACCAA GGTCGACAAG AAAGTTGAGC CCAAATCTTG TGACAAAACT CACCTCAGTG
      CCGTGGGTCT GGATGTAGAC GTTGCACTTA GTGTTCGGGT CGTTGTGGTT CCAGCTGTTC TTTCAACTCG GGTTTAGAAC ACTGTTTTGA GTGGAGTCAC
193   G  T  Q  T    Y  I  C    N  V  N    H  K  P  S    N  T  K    V  D  K    K  V  E  P    K  S  C    D  K  T    H  L  S  G
                                                                                                       ^"end of heavy chain (267-end)"
                                                                                         start of gene III coat protein 1601  GCGGTGGCTC TGGTTCCGGT GATTTTGATT ATGAAAAGAT GGCAAACGCT AATAAGGGGG CTATGACCGA AAATGCCGAT GAAAACCCGC TACAGTCTGA
      CGCCACCGAG ACCAAGGCCA CTAAAACTAA TACTTTTCTA CCGTTTGCGA TTATTCCCCC GATACTGGCT TTTACGGCTA CTTTTGGCG ATGTCAGACT
227   G  G  S    G  G  S    D  F  D  Y    E  K  M    A  N  A    N  K  G  A    M  T  E    N  A  D    E  N  A  L    Q  S  D 1701  CGCTAAAGGC AAACTTGATT CTGTCGCTAC TGATTACGGT GCTGCTATCG ATGGTTTCAT TGGTGACGTT TCCGGCCTTG CTAATGTAA TGGTGCTACT
      GCGATTTCCG TTTGAACTAA GACAGCGATG ACTAATGCCA CGACGATAGC TACCAAAGTA ACCACTGCAA AGGCCGGAAC GATTACATT ACCACGATGA
260   A  K  G    K  L  D  S    V  A  T    D  Y  G    A  A  I  D    G  F  I    G  D  V    S  G  L  A    N  G  N    G  A  T 1801  GGTGATTTTG CTGGCTCTAA TTCCCAAATG GCTCAAGTCG GTGACGGTGA CACTCAGCC CGAGTTGTAC CGGATGAACG AATTACTATT TATAAATGA
      CCACTAAAAC GACCGAGATT AAGGGTTTAC CGAGTTCAGC CACTGCCACT GTGAGTCGG GCTCAACATG GCCTACTTGC TTAATGATAA ATATTACT
293   G  D  F  A    G  S  N    S  Q  M    A  Q  V  G    D  G  D    N  S  P    L  M  N  N    F  R  Q    Y  L  P    S  L  P  Q 1901  AATCGGTTGA ATGTCGCCCT TTTGTCTTTA GCGCTGGTAA ACCATATGAA TTTTCTATTG ATTGTGACAA AATAAACTTA TTCCGTGGTG TCTTTGCGTT
      TTAGCCAACT TACAGGGGA AAACAGAAAT CGCGACCATT TGGTATACTT AAAAGATAAC TAACACTGTT TTATTTGAAT AAGGCACCAC AGAAACGCAA
327   S  V  E    C  R  P    F  V  F  S    A  G  K    P  Y  E    F  S  I  D    C  D  K    I  N  L    F  R  G  V    F  A  F 2001  TCTTTTATAT GTTGCCACCT TTATGTATGT ATTTTCTACG TTTGCTAACA TACTGCGTAA TAAGGAGTCT TAA
      AGAAAATATA CAACGGTGGA AATACATACA TAAAGATGC AAACGATTGT ATGACGCATT ATTCCTCAGA ATT
360   L  L  Y    V  A  T  F    M  Y  V    F  S  T    F  A  N  I    L  R  N    K  E  S    O
```

FIG._28C

```
  1 ATGAAAAAGA ATATCGCATT TCTTCTTGCA TCTATGTTCG TTTTTTCAT TGCTACAAAT GCCTATGCAT CCGATATCCA GATGACCCAG TCCCGAGCT
    TACTTTTTCT TATAGCGTAA AGAAGAACGT AGATACAAGC AAAAAAGATA ACGATGTTTA CGGATACGTA CGGCTATAGGT CTACTGGGTC AGGGGCTCGA
  1 M  K  K  N  I  A  F  L  L  A  S  M  F  V  F  S  I  A  T  N  A  Y  A  S  D  I  Q  M  T  Q  S  P  S  S
    ^met
    ^start of stII signal sequence                                                 ^light chain start 101 CCCTGTCCGC CTCTGTGGGC GATAGGGTCA CCATCACCTG CCGTGCCAGT CAGGATGTGT CCACTGCTGT AGCCTGGTAT CAACAGAAAC CAGGAAAAGC
    GGGACAGGCG GAGACACCCG CTATCCCAGT GGTAGTGGAC GGCACGGTCA GTCCTACACA GGTGACGACA TCGGACCATA GTTGTCTTTG GTCCTTTTCG
 35 L  S  A  S  V  G  D  R  V  T  I  T  C  R  A  S  Q  D  V  S  T  A  V  A  W  Y  Q  Q  K  P  G  K  A
                                                 ^CDR-L1

201 TCCGAAGCTT CTGATTTACT CGGCATCCTT CCTCTACTCT GGAGTCCCT CTCGCTTCTC TGGTAGCGGT TCCGGGACGG ATTTCACTCT GACCATCAGC
    AGGCTTCGAA GACTAAATGA GCCGTAGGAA GGAGATGAGA CCTCAGGGAA GAGCGAAGAG ACCATCGCCA AGGCCCTGCC TAAAGTGAGA CTGGTAGTCG
 68 P  K  L  L  I  Y  S  A  S  F  L  Y  S  G  V  P  S  R  F  S  G  S  G  S  G  T  D  F  T  L  T  I  S
                       ^CDR-L2

301 AGTCTGCAGC CGGAAGACTT CGCAACTTAT TACTGTCAGC AATCTTATAC ACGTTGACC AGGGTACCAA GGTGGAGATC AAACGAACTG
    TCAGACGTCG GCCTTCTGAA GCGTTGAATA ATGACAGTCG TTAGAATATG TGCAAGCCTG TCCCATGGTT CCACCTCTAG TTTGCTTGAC
101 S  L  Q  P  E  D  F  A  T  Y  Y  C  Q  Q  S  Y  T  T  P  P  T  F  G  Q  G  T  K  V  E  I  K  R  T  V
                                           ^CDR-L3

401 TGGCTGCACC ATCTGTCTTC ATCTTCCCGC CATCTGATGA GCAGTTGAAA TCTGGAACTG CGCTGTCGTG CTGCTGCTG AATAACTTCT ATCCCAGAGA
    ACCGACGTGG TAGACAGAAG TAGAAGGGCG GTAGACTACT CGTCAACTTT AGACCTTGAC GCGACAGCAC GGAGACAACA CACGACGAC TTATTGAAGA TAGGGTCTCT
135 A  A  P  S  V  F  I  F  P  P  S  D  E  Q  L  K  S  G  T  A  S  V  V  C  L  L  N  N  F  Y  P  R  E

501 GGCCAAAGTA CAGTGGAAGG TGGATAACGC CCTCCAATCG GGTAACTGAA CTGAGGG CCATTGAGG AGGAGAGTGT CACAGAGCAG GACAGCAAGG ACAGCACCTA CAGCCTCAGC
    CCGGTTTCAT GTCACCTTCC ACCTATTGCG GGAGGTTAGC CCATTGACTT GACTCCC AGTAACTC TCCTCTCACA GTGTCTCGTC CTGTCGTTCC TGTCGTGGAT GTCGGAGTCG
168 A  K  V  Q  W  K  V  D  N  A  L  Q  S  G  N  S  Q  E  S  V  T  E  Q  D  S  K  D  S  T  Y  S  L  S

601 AGCACCCTGA CGCTGAGCGA AGCAGACTAC GAGAAACACA AAGTCTACGC CTGCGAAGTC ACCCATCAGG GCCTGAGCTC GCCCGTCACA AAGAGCTTCA
    TCGTGGGACT GCGACTCGCT TCGTCTGATG CTCTTTGTGT TTCAGATGCG GACGCTTCAG TGGGTAGTCC CGGACTCGAG CGGGCAGTGT TTCTCGAAGT
201 S  T  L  T  L  S  K  A  D  Y  E  K  H  K  V  Y  A  C  E  V  T  H  Q  G  L  S  S  P  V  T  K  S  F  N
```

FIG._29A

```
701  ACAGGGGAGA GTGTGGTGCC AGTCCCGGTA TGGCTGATCC GAACCGTTTC CGCGGTAAGG ACCTGGCATA ACTCGAGGCT GATCCTCTAC GCCGGACGCA
     TGTCCCCTCT CACACCACGG TCGAGGCCAT ACCGACTAGG CTTGGCAAAG GCGCCATTCC TGGACCGTAT TGAGCTCCGA CTAGGAGATG CGGCCTGCGT
235  R   G  E   C  G   A   S  S   G  M   A  D   P  N   R  F   R  G   K  D   L  A   Q
                  ^end of light chain, start of gD tag 801  TCCTGGCCCT AGTACGCAAG TTCACGCTAAA AAGGGTAACT AGAGGTTGAG TCTCCAACTC GTGATTTTAT GAAAAAGAAT ATCGGCATTTC TTCTTGCATC TATGTTCGTT
     AGGACCGGGA TCATGCGTTC AAGTGCATTT TTCCCATTGA TCTCCAACTC CACTAAAATA CTTTTTCTTA TAGCGTAAAG AAGAACGTAG ATACAAGCAA
-23                                                                   M   K  K   N   I  A   F   L  A   S   M  F   V
                                                                      ^start of stII 901  TTTTCTATTG CTACAAACGC GTACGCTGAG GTTCAGCTGG TGGAGTCTGG CGGTGGCCTG GTGCAGCCAG GGGGCTCACT CCGTTTGTCC TGTGCAGCTT
     AAAAGATAAC GATGTTTGCG CATGCGACTC CAAGTCGACC ACCTCAGACC GCCACCGGAC CACGTCGGTC CCCCGAGTGA GGCAAACAGG ACACGTCGAA
-9   F  S   I   A  T   N   A  Y   A  E   V  Q   L  V   E   S  G   G   G  L   V  Q   P  G   G  S   L  R   L  S   C  A   A  S
                                    ^start of heavy chain                                                          ^CDR-H1

1001 CTGGCTTCAC CATTAGTGGT TCTGATATAC ACTGGGTGCG TCAGGCCCCG GGTAAGGGCC TGGAATGGGT TGGTAGGATT TCTCCTTATG GCGGCAATAC
     GACCGAAGTG GTAATCACCA AGACTATATG TGACCCACGC AGTCCGGGGC CCATTCCCGG ACCTTACCCA ACCATCCTAA AGAGGAATAC CGCCGTTATG
26   G  F   T   I  S   G   S  D   I   H  W   V   R  Q   A   P  G   K   G  L   E   W  V   G   R  I   S   P  Y   G   G  N   T
                                                                                                         ^CDR-H2

1101 TAACTATGCC GATAGCGTCA AGGGCCGTTT CACTATAAGC AGCTACACAT GCAGACACAT CCAAAAACAC CAAATGAACA GCTTAAGAGC TGAGGACACT
     ATTGATACGG CTATCGCAGT TCCCGGCAAA GTGATATTCG TCGTCTGTGTA CGTCTGTGTA GGTTTTTGTG TCGGAATGAT GTTACTTGT CGAATTCTCG ACTCCTGTGA
59   N   Y   A  D   S   V  K   G   R   F   T   I   S   A   D   T   S   K   N   T   A   Y   L   Q   M   N   S   L   R   A   E   D   T

1201 GCCGTCTATT ATTGTGCAAG AGTCGGCGGC TGTTCGACTA TGTTCGACTA CAAAGCTGAT GACCCCAGTT CCTTGTGATC AGTGGCAGGA GAGCCGGAGG TGGTTCCCGG ACCAAGGGCC
     CGGCAGATAA TAACACGTTC TCAGCGCCG GAGTTCAACG ACAAGCTGAT GACCCCAGTT CCTTGTGATC AGTGGCAGGA GAGCCGGAGG TGGTTCCCGG
92   A   V   Y   Y   C   A   R   V   G   G   L   K   L   L   F   D   Y   W   G   Q   G   T   L   V   T   V   S   S   A   S   T   K   G   P
                               ^CDR-H3

1301 CATCGGTCTT CCCCCTGGCA CCCTCCTCCA AGAGCACCTC TGGGGGCACA GCGGCCCTGG GCTGCCTGGT CAAGGACTAC TTCCCCGAAC CGGTGACGGT
     GTAGCCAGAA GGGGGACCGT GGGAGGAGGT TCTCGTGGAG ACCCCCGTGT CGCCGGGACC CGACGGACCA GTTCCTGATG AAGGGGCTTG GCCACTGCCA
126  S   V   F   P   L   A   P   S   S   K   S   T   S   G   G   T   A   A   L   G   C   L   V   K   D   Y   F   P   E   P   V   T   V
```

FIG._29B

```
1401 GTCGTGGAAC TCAGGCGCCC TGACCAGCGG CGTGCACACC TTCCCGGCTG TCCTACAGTC CTCAGGACTC TACTCCCTCA GCAGCCTGGT GACCGTGCCC
     CAGCACCTTG AGTCCGCGGG ACTGGTCGCC GCACGTGTGG AAGGGCCGAC AGGATGTCAG GAGTCCTGAG ATGAGGGAGT CGTCGGACCA CTGGCACGGG
 159 S  W  N  S  G  A  L  T  S  G  V  H  T  F  P  P  A  V  L  Q  S  S  G  L  Y  S  L  S  S  V  V  T  V  P

1501 TCAGCAGCT TGGCACCCA GACTACATC TGCAACGTGA ATCACAAGCC CAGCAACACC AAGGTCGACA AGAAAGTTGA GCCCAAATCT TGTGACAAAA
     AGTCGTCGA ACCCGTGGGT CTGATGTAG ACGTTGCACT TAGTGTTCGG GTCGTTGTGG TTCCAGCTGT TCTTTCAACT CGGGTTTAGA ACACTGTTTT
 192 S  S  S  L  G  T  Q  T  Y  I  C  N  V  N  H  K  P  S  N  T  K  V  D  K  K  V  E  P  K  S  C  D  K  T

1601 CTCACGGCCG CATGAAACAG CTAGAGGACA AGGTCGAAGA GCTACTCTCC AAGAACTACC ACTAGAGAA TGAAGTGGCA AGACTCAAAA AACTTGTCGG
     GAGTGCCGGC GTACTTTGTC GATCCTCCTGT TCCAGCTTCT CGATGAGAGG TTCTTGATGG TGGATCTCTT ACTTCACCGT TCTGAGTTTT TTGAACAGCC
 226 H  G  R  M  K  Q  L  E  D  K  V  E  E  L  L  S  K  N  Y  H  L  E  N  E  V  A  R  L  K  K  L  V  G
     ^end of heavy chain, start of leucine zipper 1701 GGAGCGCGGA AAGCTTAGTG GCGGTGGCTC TGGTTCCGGT GATTTTGATT ATGAAAAGAT GGCAAACGCT AATAAGGGGG CTATGACCGA AAATGCCGAT
     CCTCGCGCCT TTCGAATCAC CGCCACCGAG ACCAAGGCCA CTAAAACTAA TACTTTTCTA CCGTTTGCGA TTATTCCCCC GATACTGGCT TTTACGGCTA
 259 E  R  G  K  L  S  G  G  G  S  G  S  G  D  F  D  Y  E  K  M  A  N  A  N  K  G  A  M  T  E  N  A  D
     ^end of leucine zipper, gene III coat protein (267-end)

1801 GAAAACGCGC TACAGTCTGA CGCTAAAGGC AAACTTGATT CTGTCGCTAC TGATTACGGT GCTGTCTATC TGGTTACGGT ATGGTTTCAT TCCGGCCTTG
     CTTTTGCGCG ATGTCAGACT GCGATTTCCG TTTGAACTAA GACAGCGATG ACTAATGCCA CGACGATAGC ACCAATGCCA TACCAAAGTA AGGCCGGAAC
 292 E  N  A  L  Q  S  D  A  K  G  K  L  D  S  V  A  T  D  Y  G  A  A  I  D  G  F  I  G  D  V  S  G  L  A

1901 CTAATGGTAA TGGTGCTACT GGTGATTTTG CTGGCTCTAA TTCCCAAATG GAGGGTTTAC AAGGTTTCAG GTGACGGTGA TAATTCACCT ATTAAGTGAA
     GATTACCATT ACCACGATGA CCACTAAAAC GACCGAGATT AAGGGTTTAC TTCCAAAGTC CACTGCCACT ATTAAGTGGA AATTACTTAT TAAGGCAGT
 326 N  G  N  G  A  T  G  D  F  A  G  S  N  S  Q  M  A  Q  V  G  D  G  D  N  S  P  L  M  N  N  F  R  Q

2001 ATATTTACCT TCCCTCCCTC AATCGGTTGA ATGTCGCCCT TTTGTCTTTA TACAGCGGGA AAACAGAAAT CCGACCATT TGGTATACTT ATTGTGACAA
     TATAAATGGA AGGGAGGGAG TTAGCCAACT TACAGCGGGA ATGTCGCCCT AAACAGAAAT TGTCGCCATT TGGTATACTT AACTGTGTT TAACACTGTT
 359 Y  L  P  S  L  P  Q  S  V  E  C  R  P  F  V  F  S  A  G  K  P  Y  E  F  S  I  D  C  D  K  I  N  L

2101 TTCCGGTGGTG TCTTTTGCGT TCTTTTATAT GTTGCCACCT TTATGTATGT ATTTTCTACG TTTGCTAACA TACTGCGTAA TAAGGAGTCT TAA
     AAGGCCACCAC AGAAAACGCAA AGAAAATATA CAACGGTGGA AATACATACA TAAAGATGC AAACGATTGT ATGACGCATT ATTCCTCAGA ATT
 392 F  R  G  V  F  A  F  L  L  Y  V  A  T  F  M  Y  V  F  S  T  F  A  N  I  L  R  N  K  E  S  O
```

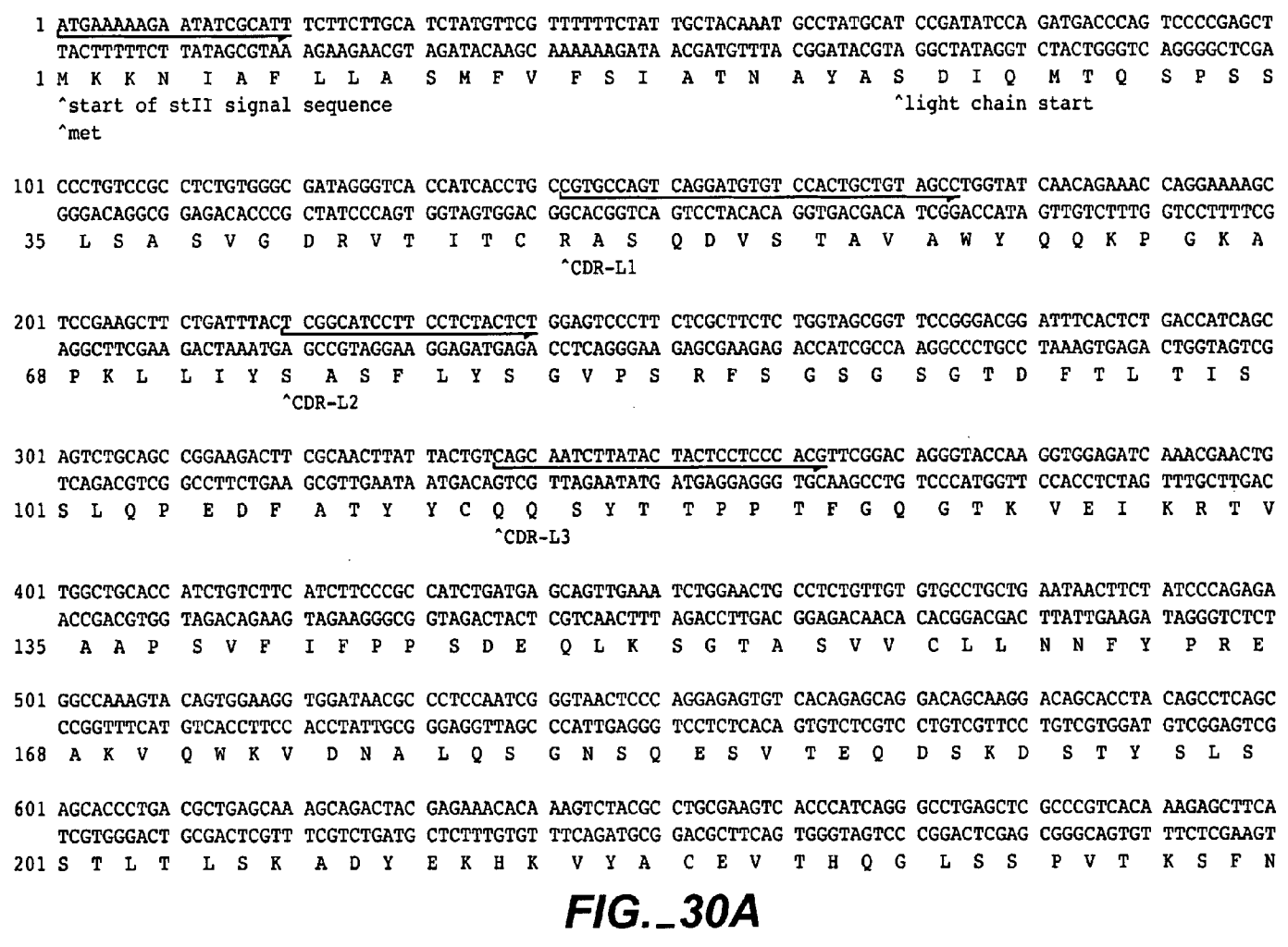

```
701  ACAGGGGAGA GTGTGGTGCC AGTCCCACGG TGGCTGATCC GAACCGTTTC CGGGGTAAGG ACCTGGCATA ACTGGAGGCT GATCCTCTAC GCCGGACGCA
     TGTCCCCTCT CACACCACGG TCGAGGGTGCC ACCGACTAGG CTTGGCAAAG GCCCCATTCC TGGACCGTAT TGAGCTCCGA CTAGGAGATG CGGCCTGCGT
235   R  G  E    C  G  A    S  S  G  M    A  D  P  N    R  F    R  G  K  D    L  A  Q

801  TCGTGGCCCT AGTACGCAAG TTCACGCTAAA AAGGTAACT AGAGGTTGAG GTGATTTTAT GAAAAGAAT ATCGCATTTC TTCTTGCATC TATGTTCGTT
     AGCACCGGGA TCATGCGTTC AAGTGCGATT TTCCCATTGA TCTCCAACTC CACTAAAATA CTTTTCTTA TAGCCGTAAAG AAGAACGTAG ATACAAGCAA
-23                                                                     M  K  K  N    I  A  F  L    L  A  S    M  F  V
                                                                        ^start of stII 901  TTTTCTATTG CTACAAACGC GTACGCTGAG GTTCAGCTGG TGGAGTCTGG CGGTGGCCTG GTGCAGCCAG GGGGCTCACT CCGTTTGTCC TGTGCAGCTT
     AAAAGATAAC GATGTTTGCG CATGCGACTC CAAGTCGACC ACCTCAGACC GCCACCGGAC CACGTCGGTC CCCCGAGTGA GGCAAACAGG ACACGTCGAA
-9    F  S  I  A    T  N  A    Y  A  E    V  Q  L  V    E  S  G    G  G  L    V  Q  P  G    G  S  L    R  L  S    C  A  A  S
      ^start of heavy chain                                                                                              ^CDR-H1

1001 CTGGCTTCAC CATTACTAAT TCCGATATAC ACTGGGTGCG TCAGGCCCCG GGTAAGGGCC TGGAATGGGT TCCTACTATT TATCCTTATG GCCGCTATAC
     GACCGAAGTG GTAATGATTA AGGCTATATG TGACCCACGC AGTCCGGGGC CCATTCCCGG ACCTTACCCA AGGATGATAA ATAGGAATAC CGGCGATATG
26    G  F  T    I  T  N    S  D  I  H    W  V  R    Q  A  P    G  K  G  L    E  W  V    A  T  I    Y  P  Y  G    G  Y  T
                        ^CDR-H2

1101 TTACTATGCC GATAGGGTCA AGGGCCGTTT CACTATATAAGC AGGGTTTGTA CAAATGAACA GCTTAAGAGC TGAGGACACT
     AATGATACGG CTATCGCAGT TCCCGGCAAA GTGATATTCG CGTCTGTGTA GTTTTTGTG TCGGATGGAT GTTACTTGT CGAATTCTCG ACTCCTGTGA
59    Y  Y  A    D  S  V  K    G  R  F    T  I  S    A  D  T  S    K  N  T    A  Y  L    Q  M  N  S    L  R  A    E  D  T

1201 GCCGTCTATT ATTGTGCAAG AGGGGCGGG ATGGACGAC AGTTATGAA TGCAATACCT CAAGGAACAC TAGTGGGGCT CTCCTCGGCC TCCACCAAGG
     CGGCAGATAA TAACGACGTTC TCCCCCGCCC TACCTGCCGA TGCAATACCT ACGTTATGGA GTTCCTTGTG ATCAGTGGCA GAGGAGCCGG AGTGGTTCC
92    A  V  Y  Y    C  A  R    G  G  G    M  D  G  Y    V  M  D    Y  W  G    Q  G  T  L    V  T  V    S  S  A    S  T  K  G
                         ^CDR-H3

1301 GCCCATCCGT CTTCCCCCTG GCACCCTCCT CCAAGAGCAC CTCTGGGGGC ACAGCGGGCC TGGGCTGCCT GGTCAAGGAC TACTTCCCCG AACCGGTGAC
     CGGGTAGGCA GAAGGGGGAC CGTTCGAGGA GGTTCTCGTG GAGACCCCCG TGTCGCCCGG ACCCGACGGA CCAGTTCCTG ATGAAGGGGC TTGGCCACTG
126   P  S  V    F  P  L    A  P  S  S    K  S  T    S  G  G    T  A  A  L    G  C  L    V  K  D    Y  F  P  E    P  V  T
```

FIG._30B

```
1401 GGTGTCGTGG AACTCAGGCG CCCTGACCAG CGGCGTGCAC ACCTTCCCGG CTGTCCTACA GTCCTCAGGA CTCTACTCCC TCAGCAGCGT GGTGACCGTG
     CCACAGCACC TTGAGTCCGC GGGACTGGTC GCCGCACGTG TGGAAGGGCC GACAGGATGT CAGGAGTCCT GAGATGAGGG AGTCGTCGCA CCACTGGCAC
 159  V  S  W  N  S  G  A  L  T  S  G  V  H  T  F  P  A  V  L  Q  S  S  G  L  Y  S  L  S  S  V  V  T  V

1501 CCCTCCAGCA GCTTGGGCAC CCAGACCTAC ATCTGCAACG TGAATCACAA GCCCAGCAAC ACCAAGGTCG ACAAGAAAGT TGAGCCCAAA TCTTGTGACA
     GGGAGGTCGT CGAACCCGTG GGTCTGGATG TAGACGTTGC ACTTAGTGTT CGGGTCGTTG TGGTTCCAGC TGTTCTTTCA ACTCGGGTTT AGAACACTGT
 192  P  S  S  S  L  G  T  Q  T  Y  I  C  N  V  N  H  K  P  S  N  T  K  V  D  K  K  V  E  P  K  S  C  D  K
                                                                                         ^end of heavy chain, start of leucine zipper 1601 AAACTCACGG CCGCATGAAA CACCTAGAGG ACAAGGTCGA AGAGCTACTC TGTTCCAGCT GTCGATCTCC TCTCGATGAG AGTTCTTGA SKNYHLEELL
     TTTGAGTGCC GGCGTACTTT GTGGATCTCC TGTTCCAGCT TCTCGATGAG ACAAGGTCGA AGAGCTACTC CTTAAGAACT CCACCTAGA TGGTGGATCT CTTACTTCAC CGTTCTGAGT TTTTGAACA
 226  T  H  G  R  M  K  Q  L  E  D  K  V  E  E  L  L  S  K  N  Y  H  L  E  N  E  V  A  R  L  K  K  L  V
                                          ^end of leucine zipper 1701 CGGGGACCGC GGAAAGCTTA GTGGCGGTGG CTCTGGTTCC GGTGATTTTG ATTATGAAAA GATGGCAAAC GCTAATAAGG GGGCTATGAC CGAAAATGCC
     GCCCCTGGCG CCTTTCGAAT CACCGCCACC GAGACCAAGG CCACTAAAAC CTAATACTTT CTACCGTTTG CGATTATTCC CCCGATACTG GCTTTTACGG
 259  G  E  R  K  L  S  G  G  G  S  G  S  G  D  F  D  Y  E  K  M  A  N  A  N  K  G  A  M  T  E  N  A 1801 GATGAAAACG CGCTACAGTC TGACGCTAAA GGCAAACTTG ATTCTGTCGC TACTGATTAC GGTGCTGCTA TCGATGGTTT CATTGGTGAC GTTCCGGCC
     CTACTTTTGC GCGATGTCAG ACTGCGATTT CCGTTTGAAC TAAGACAGCG ATGACTAATG CCACGACGAT AGCTACCAAA GTAACCACTG CAAGGCCGG
 292  D  E  N  A  L  Q  S  D  A  K  G  K  L  D  S  V  A  T  D  Y  G  A  A  I  D  G  F  I  G  D  V  S  G  L 1901 TTGCTAATGG TAATGTGCTT ACTGGTGATT TTGCTGGCTC TAATTCCCAA ATGGCTCAAG TCGGTGACGG TGATAATTCA CCTTTAATGA ATAATTCCG
     AACGATTACC ATTACCACGA TGACCACTAA AACGACCGAG ATTACCAGGTT TACCGAGTTC AGCCACTGCC ACTATTAAGT GGAAATTACT TATTAAAGGC
 326  A  N  G  N  G  A  T  G  D  F  A  G  S  N  S  Q  M  A  Q  V  G  D  G  D  N  S  P  L  M  N  N  F  R 2001 TCAATATTTA CCTTCCCTCC CTCAATCGGT CTCAATGTCG CCTTTTGTCT TGAATGTCGA AATTTGGTATA CTTAAAAGAT AACTAACACT GTTTATTTG
     AGTTATAAAT GGAAGGGAGG GAGTTAGCCA GAGTTACAGC GGAAAACAGA AACTTACAGCT TTAAACCATAT GAATTTCTA TTGATTGTGA CAAAATAAAC
 359  Q  Y  L  P  S  L  P  Q  S  V  E  C  R  P  F  V  F  S  A  G  K  P  Y  E  F  S  I  D  C  D  K  I  N 2101 TTATTCCCTG GTGTCTTTGC GTTTCTTTTA TATGTTGCCA CCTTTATGTA CTTTATTTCT ACGTTTGCTA ACATACTGCG TAATAAGGAG TCTTAA
     AATAAGGGAC CACAGAAACG CAAAGAAAAT ATACAACGGT GGAAATACAT ACATAAAAGA TGCAAACGAT TGTATGACGC ATTATTCCTC AGAATT
 392  L  F  R  G  V  F  A  F  L  L  Y  V  A  T  F  M  Y  V  F  S  T  F  A  N  I  L  R  N  K  E  S  Q
```

FIG._30C

```
  1 ATGAAAAAGA ATATCGCATT TCTTCTTGCA TCTATGTTCG TGTTTTCTAT TGCTACAAAT GCCTATGCAT CCGATATCCA GATGACCCAG TCCCCGAGCT
    TACTTTTTCT TATAGCGTAA AGAAGAACGT AGATACAAGC AAAAAGATA ACGATGTTTA CGATACGTA GGCTATAGGT CTACTGGGTC AGGGGCTCGA
  1 M  K  K  N  I  A  F  L  L  A  S  M  F  V  F  S  I  A  T  N  A  Y  A  S  D  I  Q  M  T  Q  S  P  S  S
    ^met                                                                          ^light chain start 101 CCCTGTCCGC CTCTGTGGGC GATAGGGTCA CCATCACCTG CCGTGCCAGT CAGGATGTGT AGCCTGGTAT CAACAGAAAC CAGGAAAAGC
    GGGACAGGCG GAGACACCCG CTATCCCAGT GGTAGTGGAC GGCACGGTCA GTCCTACACA GTCGACGACA TCGGACCATA GTTGTCTTTG GTCCTTTTCG
 35 L  S  A  S  V  G  D  R  V  T  I  T  C  R  A  S  Q  D  V  S  T  A  V  A  W  Y  Q  Q  K  P  G  K  A
                                             ^CDR-L1

201 TCCGAAGCTT CTGATTACT CGGCATCCTT CCTCTACTCT GGAGTCCCTT CTCGCTTCTC TGGTAGCGGT TCCGGGACGG ATTTCACTCT GACCATCAGC
    AGGCTTCGAA GACTAATGA GCCGTAGGAA GGAGATGAGA CCTCAGGGAA GAGCGAAGAG ACCATCGCCA AGGCCCTGCC TAAAGTGAGA CTGGTAGTCG
 68 P  K  L  L  I  Y  S  A  S  F  L  Y  S  G  V  P  S  R  F  S  G  S  G  S  G  T  D  F  T  L  T  I  S
              ^CDR-L2

301 AGTCTGCAGC CGGAAGACTT CGCAACTTAT TACTGTCAGC AATCTATAC TACTCCTCCC ACGTTCGGAC AGGGTACCAA GGTGGAGATC AAACGAACTG
    TCAGACGTCG GCCTTCTGAA GCGTTGAATA ATGACAGTCG TTAGATATATG ATGAGGAGGG TGCAAGCCTG TCCCATGGTT CCACCTCTAG TTTGCTTGAC
101 S  L  Q  P  E  D  F  A  T  Y  Y  C  Q  Q  S  Y  T  T  P  P  T  F  G  Q  G  T  K  V  E  I  K  R  T  V
                                    ^CDR-L3

401 TGGCTGCACC ATCTGTCTTC ATCTTCCCGC CATCTGATGA GCAGTTGAAA TCTGGAACTG CCTCCGTTGT GTGCCTGCTG AATAACTTCT ATCCCAGAGA
    ACCGACGTGG TAGACAGAAG TAGAAGGGCG GTAGACTACT CGTCAACTTT AGACCTTGAC GGAGGACAACA CACGGACGAC TTATTGAAGA TAGGGTCTCT
135 A  A  P  S  V  F  I  F  P  P  S  D  E  Q  L  K  S  G  T  A  S  V  V  C  L  L  N  N  F  Y  P  R  E

501 GGCCAAAGTA CAGTGGAAGG TGGATAACGC CCTCCAATCG GGTAACTCCC AGGAGAGTGT CACAGAGCAG GACAGCAAGG ACAGCACCTA CAGCCTCAGC
    CCGTTTCAT GTCACCTTCC ACCTATTGCG GGAGGTTAGC CCATTGAGGG TCCTCTCACA GTGTCTCGTC CTGTCGTTCC TGTCGTGGAT GTCGGAGTCG
168 A  K  V  Q  W  K  V  D  N  A  L  Q  S  G  N  S  Q  E  S  V  T  E  Q  D  S  K  D  S  T  Y  S  L  S

601 AGCACCCTGA CGCTGAGCAA AGCAGACTAC GAGAAACACA AAGTCTACGC CTGCGAAGTC ACCCATCAGG GCCTGAGCTC GCCCGTCACA AAGAGCTTCA
    TCGTGGGACT GCGACTCGTT TCGTCTGATG CTCTTTGTGT TTCAGATGCG GACGCTTCAG TGGGTAGTCC CGGACTCGAG CGGGCAGTGT TTCTCGAAGT
201 S  T  L  T  L  S  K  A  D  Y  E  K  H  K  V  Y  A  C  E  V  T  H  Q  G  L  S  S  P  V  T  K  S  F  N
```

FIG._31A

```
701  ACAGGGGAGA GTGTGGTGCC AGCTCCGGTA TGGCTGATCC GAACCGTTTC CGCGGTAAGG ACCTGGCATA ACTCGAGGCT GATCCCTAC GCCGACGCA
     TGTCCCCTCT CACACCACGG TCGAGGCCAT ACCGACTAGG CTTGGCAAAG GCGCCATTCC TGGACCGTAT TGAGCTCCGA CTAGGAGATG CGGCCTGCGT
235  R  G  E     C  G  A     S  S  G  M   A  D  P     N  R  F     R  G  K  D     L  A  Q
                              ^end of light chain, start of gD tag
```

```
801  TCGTGGCCCT AGTACGCAAG TTCACGTAAA AGAGGTTGAG GTGATTTAT GAAAAAGAAT ATCGCATTTC TTCTTGCATC TATGTTCGTT
     AGCACCGGGA TCATGCGTTC AAGTGCATTT TCTCCAACTC CACTAAAATA CTTTTTCTTA TAGCGTAAAG AAGAACGTAG ATACAAGCAA
-23                                               M  K  K  N   I  A  F  L     L  A  S     M  F  V
                                                  ^start of stII
```

```
901  TTTTCTATTG CTACAAACGC GTAACGCTGA GTTCAGCTGG TGGAGTCTGG CGGTGGCCTG GTGCAGCCAG GGGGCTCACT CCGTTGTCC  TGTGCAGCTT
     AAAAGATAAC GATGTTTGCG CATTGCGACT CAAGTCGACC ACCTCAGACC GCCACCGGAC CACGTCGGTC CCCCGAGTGA GGCAAACAGG ACACGTCGAA
-9   F  S  I  A   T  N  A   Y  A  E    V  Q  L    V  E  S  G    G  G  L    V  Q  P  G    G  S  L    R  L  S    C  A  A  S
                          ^start of heavy chain                                                                        ^CDR-H1
```

```
1001 CTGGCTTCAC CATTAATAAT TATGATATAC ACTGGGTGCG TCAGGCCCCG GGTAAGGGCC TGGAATGGGT TGGTTATATT ACCAATATAA AGAGGAGGAT CGGCGCGATG
     GACCGAAGTG GTAATTATTA ATACTATATG TGACCCACGC AGTCCGGGGC CCATTCCCGG ACCTTACCCA ACCAATATAA TGGTTATATT TCTCCTCCTA GCCGCGCTAC
26   G  F  T   I  N  N   Y  D  I  H     W  V  R    Q  A  P     G  K  G  L    E  W  V     G  Y  I     S  P  P  S     G  A  T
                ^CDR-H2
```

```
1101 TTACTATGCC GATAGGCGTCA AGGGCCGTTT CACTATAAGC GCAGACACAT CCAAAAACAC AGCCTACCTA CAAATGAACA GCTTAAGAGC ACTCTGTGA
     AATGATACGG CTATCGCAGT TCCCGGCAAA GTGATATTCG CGTCTGTGTA GGTTTTTGTG TCGGATGGAT GTTTACTTGT CGAATTCTCG TGAGACACT
59   Y  Y  A   D  S  V  K    G  R  F     T  I  S    A  D  T  S     K  N  T     A  Y  L    Q  M  N  S    L  R  A     E  D  T
```

```
1201 GCCGTCTATT ATTGTGCAAG AATGGTCGGC ATGCGGAGGG GGGTTATGA CTACTGGGGT CAAGGAACAC GTTCCTTGTG ATCAGTGGCA TAGTCACCGT CTCCTCGGCC TCCACCAAGG
     CGGCAGATAA TAACACGTTC TTACCAGCCG TACGCCTCCC CCCAATACCT GATGACCCCA GTTCCTTGTG CAAGGAACAC TAGTCACCGT ATCAGTGGCA GAGGAGCCGG AGGTGGTTCC
92   A  V  Y  Y   C  A  R    M  V  G    M  R  R  G   V  M  D    Y  W  G     Q  G  T  L    V  T  V     S  S  A     S  T  K  G
                    ^CDR-H3
```

```
1301 GCCCATCGGT CTTCCCCCTG GCACCCTCCT CCAAGAGCAC CTCTGGGGGC ACAGCGGCCC TGGGCTGCCT GGTCAAGGAC TACTTCCCCG AACCGTGAC
     CGGGTAGCCA GAAGGGGGAC CGTGGGAGGA GGTTCTCGTG GAGACCCCCG TGTCGCCGGG ACCCGACGGA CCAGTTCCTG ATGAAGGGGC TTGGCACTG
126  P  S  V   F  P  L  A    P  S  S     K  S  T     S  G  G     T  A  A  L   G  C  L     V  K  D     Y  F  P  P    E  P  V  T
```

FIG._31B

```
1401 GGTGTCTGTGG AACTCAGGCG CCCTGACCAG CGGCGTGCAC ACCTTCCCGG CTGTCCTCAGGA GTCCTCAGGA CTCTACTCCC TCAGCAGCGT GGTGACCGTG
     CCACAGCACC TTGAGTCCGC GGGACTGGTC GCCGCACGTG TGGAAGGGCC GACAGGATGT CAGGAGTCCT GAGATGAGGG AGTCGTCGCA CCACTGGCAC
 159  V  S  W  N  S  G  A  L  T  S  G  V  H  T  F  P  A  V  L  Q  S  S  G  L  Y  S  L  S  S  V  V  T  V

1501 CCCTCCAGCA GCTTGGGCAC CCAGACCTAC ATCTGCAACG TGAATCACAA GCCCAGCAAC ACCAAGGTCG ACAAGAAAGT TGAGCCCAAA TCTTGTGACA
     GGGAGGTCGT CGAACCCGTG GGTCTGGATG TAGACGTTGC ACTTAGTGTT CGGGTCGTTG TGGTTCCAGC ACTTCTTTCA ACTCGGGTTT AGAACACTGT
 192  P  S  S  S  L  G  T  Q  T  Y  I  C  N  V  N  H  K  P  S  N  T  K  V  D  K  K  V  E  P  K  S  C  D  K

1601 AAACTCACGG CCGCATGAAA CAGCTAGAGG ACAAGGTCGA AGAGCTACTC TCCAAGAACT ACCACCTAGA GAATGAAGTG GCAAGACTCA AAAAACTTGT
     TTTGAGTGCC GGCGTACTTT GTCGATCTCC TGTTCCAGCT TCTCGATGAG AGGTTCTTGA TGGTGGATCT CTTACTTCAC CGTTCTGAGT TTTTTGAACA
 226  T  H  G  R  M  K  Q  L  E  D  K  V  E  E  L  L  S  K  N  Y  H  L  E  N  E  V  A  R  L  K  K  L  V
                                ^end of heavy chain, start of leucine zipper 1701 CGGGGAGCGC GGAAAGCTTA GTGGCGGTGG CTCTGGTTCC GGTGATTTTG ATTATGAAAA TAATACTTTT CTACCGTTTG CCCGATACTG GCTTTTACGG
     GCCCCTCGCG CCTTTCGAAT CACCGCCACC GAGACCAAGG CCACTAAAAC CAATACTTTT GATGGCAAAC GATGGCAAGA GCTAATAAGG GGGCTATGAC CGAAATGCC
 259  G  E  R  K  L  S  G  G  G  S  G  S  G  D  F  D  Y  E  K  M  A  N  K  G  A  M  T  E  N  A
           ^end of leucine zipper
           ^gene III coat protein (267-end)

1801 GATGAAAACG CGCTACAGTC TGACGCTAAA GGCAAACTTG ATTCTGTCGC TACTGATTAC GGTGCTGCTA TCGATGGTTT CATTGGTGAC GTTCCGGCC
     CTACTTTTGC GCGATGTCAG ACTGCGATTT CCGTTTGAAC TAAGACAGCG ATGACTAATG CCACGACGAT AGCTACCAAA GTAACCACTG CAAGGCCGG
 292  D  E  N  A  L  Q  S  D  A  K  G  K  L  D  S  V  A  T  D  Y  G  A  A  I  D  G  F  I  G  D  V  S  G  L

1901 TTGCTGGCTC TAATGTGCT ACTCGTGATT TTGCTGGCTC TAATTCCCAA ATGGCTCAAG TCGGTGACGG TGATAATCA CCTTAATGA ATATTTCCG
     AACGATTACC ATTACCACGA TGAGCACTAA AACGACCGAG ATTAAGGGTT TACCGAGTTC AGCCACTGCC ACTATTAGT GGAATTACT TATAAAGGC
 326  A  N  G  N  G  A  T  G  D  F  A  G  S  N  S  Q  M  A  Q  V  G  D  G  D  N  S  P  L  M  N  N  F  R

2001 TCAATATTA CCTTCCCTCC CTCAATCGGT TGAATGTCGC CCTTTTGTCT GGAAAACAGA AATTCCGACC ATTTGGTATA CTTAAAAGAT AACTAACACT GTTTATTTG
     AGTTATAAT GGAAGGGAGG GAGTTAGCCA ACTTACAGCG GGAAAACAGA CCTTTTGTCT TTAAGGCTGG TAAACCATAT GAATTTTCTA TTGATTGTGA CAAATAAAC
 359  Q  Y  L  P  S  L  P  Q  S  V  E  C  R  P  F  V  F  S  A  G  K  P  Y  E  F  S  I  D  C  D  K  I  N

2101 TTATTCCGT GTGTCTTTGC TATGTTGCCA CCTTTATGTA TGTATTTCT ACGTTTGCTA ACATACTGCG TAATAAGGAG TCTTAA
     AATAAGGCA CACAGAAACG CAAAGAAAAT ATACAACGGT GGAAATACAT ACATAAAAGA TGCAAACGAT TGTATGACGC ATTATTCCTC AGAATT
 392  L  F  R  G  V  F  A  F  L  L  Y  V  A  T  F  M  Y  V  F  S  T  F  A  N  I  L  R  N  K  E  S  Q

FIG._31C
```

```
  1 GAATTCAACT TCTCCATACT TTGGATAAGG AAATACAGAC ATGAAAAATC TCATTGCTGA GTTGTTATTT AAGCTTGCCC AAAAAGAAGA AGAGTCGAAT
    CTTAAGTTGA AGAGGTATGA AACCTATTCC TTTATGTCTG TACTTTTTAG AGTAACGACT CAACAATAAA TTCGAACGGG TTTTTCTTCT TCTCAGCTTA

101 GAACTGTGTG CGCAGGTAGA AGCTTTGGAG ATTATCGTCA CTGCAATGCT TCGCAATATG GCGCAAAATG ACCAACAGCG GTTGATTGAT CAGGTAGAGG
    CTTGACACAC GCGTCCATCT TCGAAACCTC TAATAGCAGT GACGTTACGA AGCGTTATAC CGCGTTTTAC TGGTTGTCGC CAACTAACTA GTCCATCTCC

201 GGGCGCTGTA CGAGGTAAAC CCCGATGCCA GCATTCCTGA GCAGCTGCTG CGATTACGT AAAGAAGTTA TTGAAGCATC CTCGTCAGTA
    CCCGCGACAT GCTCCATTGC CGTAAGGACT CGTCGACGAC CGCTAATGCA TTTCTTCAAT AACTTCGTAG GAGCAGTCAT

301 AAAAGTTAAT CTTTTCAACA AGTTGTCACG GCCGAGACTT ATAGTCGCTT TGTTTTTATT TTTTAATGTA GTACGCAAGT
    TTTTCAATTA GAAAAGTTGT CGACAGTATT TCAACAGTGC CGGCTCTGAA TATCAGCGAA ACAAAAATAA AAATTACAT CATGCGTTCA

401 TCACGTAAAA AGGGTATGTA GAGGTTGAGG TGATTTTATG AAAAAGAATA TCGCATTTCT TCTTGCATCT AGAACGTAAGA TACAAGCAAA ATGTTTACGG
    AGTGCATTT TCCCATACAT CTCCAACTCC ACTAAAATAC TTTTTCTTAT AGCGTAAGA AGAACGTAGA TACAAGCAAA ATGTTTACGG
    0             M  K  K  N  I  A  F  L  L  A  S  M  F  V  F  S  I  A  T  N  A
                  ^start of stII signal sequence 501 TATGCAGATA TCCAGATGAC CCAGTCCCCG AGCTCCCTGT CCGCCTCTGT GGGCGATAGG GTCACCATCA CCTGCCGTGC CAGTCAGGAT GTGTCCACTG
    ATACGTCTAT AGGTCTACTG GGTCAGGGGC TCGAGGGACA GGCGGAGACA CCCGCTATCC CAGTGGTAGT GGACGGCACG GTCAGTCCTA CACAGGTGAC
 21  Y  A  D  I  Q  M  T  Q  S  P  S  S  L  S  A  S  V  G  D  R  V  T  I  T  C  R  A  S  Q  D  V  S  T  A
    ^start of light chain
    ^EcoRV                                                                          ^CDR-L1

601 CTGTAGCCTG GTATCAACAG AAACCAGGAA AAGCTCCGAA GCTTCTGATT TACTCGGCAT CCTTCCTCTA CTCTGGAGTC CCTTCTCGCT TCTCTGGTAG
    GACATCGGAC CATAGTTGTC TTTGGTCCTT TTCGAGGCTT CGAAGACTAA ATGAGCCGTA GGAAGGAGAT GAGACCTCAG GGAAGAGCGA AGAGACCATC
 55  V  A  W  Y  Q  Q  K  P  G  K  A  P  K  L  L  I  Y  S  A  S  F  L  Y  S  G  V  P  S  R  F  S  G  S
                                                       ^CDR-L2

701 CGGTTCCGGG ACGGATTTCA CTCTGACCAT CAGCAGTCTG CAGCCGGAAG ACTTCGCAAC TTATTACTGT CAGCAATCTT ATACTACTCC TCCCACGTTC
    GCCAAGGCCC TGCCTAAAGT GAGACTGGTA GTCGTCAGAC GTCGGCCTTC TGAAGCGTTG AATAATGACA GTCGTTAGAA TATGATGAGG AGGGTGCAAG
 88  G  S  G  T  D  F  T  L  T  I  S  S  L  Q  P  E  D  F  A  T  Y  Y  C  Q  Q  S  Y  T  T  P  P  T  F
                                                                                   ^CDR-L3
```

FIG._32A

```
 801 GGACAGGGTA CCAAGGTGGA GATCAAACGA ACTGTGGCTG CACCATCTGT CTTCATCTTC CCGCCATCTG ATGAGCAGTT GAAATCTGGA ACTGCCTCTG
     CCTGTCCCAT GGTTCCACCT CTAGTTTGCT TGACACCGAC GTGGTAGACA GAAGTAGAAG GGCGGTAGAC TACTCGTCAA CTTTAGACCT TGACGGAGAC
 121 G  Q  G  T  K  V  E  I  K  R  T  V  A  A  P  S  V  F  I  F  P  P  S  D  E  Q  L  K  S  G  T  A  S  V
        ^KpnI

901 TTGTGTGCCT GCTGAATAAC TTCTATCCCA GAGAGGCCAA AGTACAGTGG AAGGTGGATA ACGCCCTCCA ATCGGGTAAC TCCCAGGAGA GTGTCACAGA
     AACACACGGA CGACTTATTG AAGATAGGGT CTCTCCGGTT CATGTCACC TTCCACCTAT TGCGGGAGGT TAGCCCATTG AGGGTCCTCT CACAGTGTCT
 155 V  C  L  L  N  N  F  Y  P  R  E  A  K  V  Q  W  K  V  D  N  A  L  Q  S  G  N  S  Q  E  S  V  T  E

1001 GCAGGACAGC AAGGACAGCA CCTACAGCCT CAGCAGCACC CTGACGCTGA GCAAAGCAGA CTACGAGAAA CACAAAGTCT ACGCCTGCGA AGTCACCCAT
     CGTCCTGTCG TTCCTGTCGT GGATGTCGGA GTCGTCGTGG GACTGCGACT CGTTTCGTCT GATGCTCTTT GTGTTTCAGA TGCGGACGCT TCAGTGGGTA
 188 Q  D  S  K  D  S  T  Y  S  L  S  S  T  L  T  L  S  K  A  D  Y  E  K  H  K  V  Y  A  C  E  V  T  H

1101 CAGGGCCTGA GCTCGCCCGT CACAAAGAGC TTCAACAGGG GAGAGTGTGG TGCCAGTCG ACGGTCGAGG CCATACCGAC TAGGCTGCC TTTCCGCGGT AAGGACCTGG
     GTCCCGGACT CGAGCGGGCA GTGTTTCTCG AAGTTGTCCC CTCTCACACC ACGGTCAGC TGCCAGCTCC GGTATGGCTG ATCCGACGG AAAGGCGCCA TTCCTGGACC
 221 Q  G  L  S  S  P  V  T  K  S  F  N  R  G  E  C  G  A  S  S  G  M  A  D  P  N  R  F  R  G  K  D  L  A
                                                             ^end of light chain, start of gD tag 1201 CATAACTCGA GGCTGATCCT CTACGCCGGA CGCATCGTGG CCCTAGTACG CAAGTTCACG GTTCAAGTGC TAAAAGGGT AACTAGAGGT TGAGTGATT TTATGAAAAA
     GTATTGAGCT CCGACTAGGA GATGCGGCCT GCGTAGCACC GGGATCATGC GTTCAAGTGC ATTTTTCCCA TTGATCTCCA ACTCCACTAA AATACTTTTT
 255                                                                                                       M  K  K
   0                                                                                                       ^start of stII 1301 GAATATCGCA TTTCTTCTTG CATCTATGTT CGTTTTTTCT ATTGCTACAA ACGCGTACGC TGAGGTTCAG CTGGTGGAGT CTGGCGGTGG CCTGGTGCAG
     CTTATAGCGT AAAGAAGAAC GTAGATACAA GCAAAAAAGA TAACGATGTT TGCGCATGCG ACTCCAAGTC GACCACCTCA GACCGCCACC GGACCACGTC
 -23 N  I  A  F  L  L  A  S  M  F  V  F  S  I  A  T  N  A  Y  A  E  V  Q  L  V  E  S  G  G  G  L  V  Q
    -20                                                              ^start of heavy chain
                                                            ^BsiWi
```

FIG._32B

```
1401  CCAGGGGGCT CACTCCGTTT GTCCTGTGCA GCTTCTGGCT TCACCATTAG TGGTTCTTGG ATACACTGGG TGCGTCAGGC CCCGGGTAAG GGCCTGGAAT
      GGTCCCCCGA GTGAGGCAAA CAGGACACGT CGAAGACCGA AGTGGTAATC ACCAAGAACC TATGTGACCC ACGCAGTCCG GGGCCCATTC CCGGACCTTA
  14  P  G  G  S  L  R  L  S  C  A  A  S  G  F  T  I  S  G  S  W  I  H  W  V  R  Q  A  P  G  K  G  L  E  W
                                           ^CDR-H1

1501  GGGTTGCTTG GATTGCTCCT TATAGCGGCG CTACTGACTA TGCCGATAGC GTCAAGGGCC GTTTCACTAT AAGCGCAGAC ACATCCAAAA ACACAGCCTA
      CCCAACGAAC CTAACGAGGA ATATCGCCGC GATGACTGAT ACGGCTATCG CAGTTCCCGG CAAAGTGATA TTCGCGTCTG TGTAGGTTTT TGTGTCGGAT
  48  V  A  W  I  A  P  Y  S  G  A  T  D  Y  A  D  S  V  K  G  R  F  T  I  S  A  D  T  S  K  N  T  A  Y
            ^CDR-H2

1601  CCTACAAATG AACAGCTTAA GAGCTGAGGA CACTGCCGTC TATTATTGTG CAAGAGAGG GGGCTTGTAC TGGGTGTTCG ACTACTGGGG TCAAGGAACA
      GGATGTTTAC TTGTCGAATT CTCGACTCCT GTGACGGCAG ATAATAACAC GTTCTCTCCC CCCGAACATG ACCCACAAGC TGATGACCCC AGTTCCTTGT
  81  L  Q  M  N  S  L  R  A  E  D  T  A  V  Y  Y  C  A  R  E  G  L  Y  W  V  F  D  Y  W  G  Q  G  T
                                                           ^CDR-H3

1701  CTAGTCACCG TCTCCTCCGC CTCCACCAAG GGCCCATCGG TCTTCCCCCT GGCACCCCTC TCCAAGAGCA CCTCTGGGGG CACAGCGGCC CTGGGCTGCC
      GATCAGTGGC AGAGGAGGCG GAGGTGGTTC CCGGGTAGCC AGAAGGGGGA CCGTGGGGAG AGGTTCTCGT GGAGACCCCC GTGTCGCCGG GACCCGACGG
 114  L  V  T  V  S  S  A  S  T  K  G  P  S  V  F  P  L  A  P  S  S  K  S  T  S  G  G  T  A  A  L  G  C  L
                                           ^ApaI

1801  TGGTCAAGGA CTACTTCCCC GAACCGGTGA CGGTGTCGTG GAACTCAGGC GCCCTGACCA GCGGCGTGCA CACCTTCCCG GCTGTCCTAC AGTCCTCAGG
      ACCAGTTCCT GATGAAGGGG CTTGGCCACT GCCACAGCAC CTTGAGTCCG CGGGACTGGT CGCCGCACGT GTGGAAGGGC CGACAGGATG TCAGGAGTCC
 148  V  K  D  Y  F  P  E  P  V  T  V  S  W  N  S  G  A  L  T  S  G  V  H  T  F  P  A  V  L  Q  S  S  G

1901  ACTCTACTCC CTCAGCAGCG TGGTGACCGT GCCCTCCAGC AGCTTGGGCA CCCAGACCTA CATCTGCAAC GTGAATCACA AGCCCAGCAA CACCAAGGTC
      TGAGATGAGG GAGTCGTCGC ACCACTGGCA TCGAACCCGT TCGAACCCGT GGGTCTGGAT GTAGACGTTG CACTTAGTGT TCGGGTCGTT GTGGTTCCAG
 181  L  Y  S  L  S  S  V  V  T  V  P  S  S  S  L  G  T  Q  T  Y  I  C  N  V  N  H  K  P  S  N  T  K  V

2001  GACAAGAAAG TTGAGCCCAA ATCTTGTGAC AAAACTCACC TCTAGAGTGG CGGTGGCTCT GGTTCCGGTG ATGCTCGGTT GCCGCCGGGC GTTTTTATG
      CTGTTCTTTC AACTCGGGTT TAGAACACTG TTTTGAGTGG AGATCTCACC GCCACCGAGA CCAAGGCCAC TACGAGCCAA CGGCGGCCCG CAAAAAATAC
 214  D  K  K  V  E  P  K  S  C  D  K  T  H  L  Q

2101  CTAGCGCCGC CCTATACCTT GTCTGCCTCC CCGCGTTGCC TCGCGGTGCA TGGAGCCGGG CCACCTCGAC CTGAATGGAA GCCGGCGGCA CCTCGCTAAC
      GATCGCGGCG GGATATGGAA CAGACGGAGG GGCGCAACGG AGCGCCACGT ACCTCGGCCC GGTGGAGCTG GACTTACCTT CGGCCGCCGT GGAGCGATTG
```

FIG._32C

```
2201  GGATTCACCA CTCCAAGAAT TGGAGCCAAT CAATTCTTGC GGAGAACTGT GAATGCGCAA ACCAACCCTT GGCAGAACAT ATCCATCGCG TCCGCCATCT
      CCTAAGTGGT GAGGTTCTTA ACCTCGGTTA GTTAAGAACG CCTCTTGACA CTTACGCGTT TGGTTGGGAA CCGTCTTGTA TAGGTAGCGC AGGCGGTAGA

2301  CCAGCAGCCG CACGCGGCGC ATCTCGGGCA GCGTTGGGTC CTGGCCACGG GTGCGCATGA TCGTTGTCCT GTCGTTGAGG ACCCGGCTAG GCTGGCGGGG
      GGTCGTCGGC GTGCGCCGCG TAGAGCCCGT CGCAACCCAG GACCGGTACC CACGCGTACT AGCACGAGGA CAGCAACTCC TGGGCCGATC CGACCGCCCC

2401  TTGCCTTACT GGTTAGCAGA ATGAATCACC GATACGCGAG CGAACGTGAA GCCACTGCTG CTGCAAAACG TCTGCGACCT GAGCAACAAC ATGAATGGTC
      AACGGAATGA CCAATCGTCT TACTTAGTGG CTATGCGCTC GCTTGCACTT CGGTGACGAC GACGTTTTGC AGACGCTGGA CTCGTTGTTG TACTTACCAG

2501  TTCGGTTTCC GTGTTTCGTA AAGTCTGAAA ACGCGGAAGT CAGCGCCCTG CACCATTATG TTCCGGATCT GCATCGCAGG ATGCTGCTGG CTACCCTGTG
      AAGCCAAAGG CACAAAGCAT TTCAGACCTT TGCGCCTTCA GTCGCGGGAC GTGGTAATAC AAGGCCTAGA CGTAGCGTCC TACGACGACC GATGGGACAC

2601  GAACACCTAC ATCTGTATTA ACGAAGGCGCT GGCATTGACC TTTCTCTGGT CCCGCCGCAT AGTTGTTAC CCTCACAACG
      CTGTGGATG TAGACATAAT TGCTTCGCGA CCGTAACTGG GACTCACTAA AAAGAGACCA GGGCGGCGTA TCAACAAATG GGAGTGTTGC

2701  TTTCCAGTAAC CGGGCATGTT CATCATCAGT GTGAGCATCC TCTCTCGTTT ATTACCCCCA TGAACAGAAA TTTCCCCTTA
      AAGGTCATTG GCCCGTACAA GTAGTAGTCA CACTCGTAGG AGAGACAAA GTAGCCATAG TAATGGGGT ACTTGTCTTT AAGGGGAAT

2801  CACGGAGGCA TCAAGTGACC AAACAGGAAA ATCGCTTCAC TAACATGGCC CGCTTTATCA GAAGCCAGAC ATTAACGCTT CTGGAGAAAC TCAACGAGCT
      GTGCCTCCGT AGTTCACTGG TTTGTCCTTT TAGCGAAGTG ATTGTACCGG GCGAAATAGT CTTCGGTCTG TAATTGCGAA GACCTCTTTG AGTTGCTCGA

2901  GGACGCGGAT GAACAGGCAG ACATCTGTGA ATCGCTTCAC GACCACGCTG ATGAGCTTTA CCGCAGGATC CGGAAATTGT AAACGTTAAT ATTTTGTTAA
      CCTGCGCCTA CTTGTCCGTC TGTAGACACT TAGCGAAGTG CTGGTGCGAC TACTCGAAAT GGCGTCCTAG GCCTTTAACA TTTGCAATTA TAAAACAATT

3001  AATTCGCGTT AAATTTTTGT TAAATCAGCT CATTTTTAA CCAATAGGCC GAAATCGGCA AAATCCCTTA TAAATCAAAA GAATAGACCG AGATAGGGTT
      TTAAGCGCAA TTTAAAAACA ATTTAGTCGA GTAAAAAATT GGTTATCCGG CTTTAGCCGT TTTAGGGAAT ATTTAGTTTT CTTATCTGGC TCTATCCCAA

3101  GAGTGTTGTT CCAGTTTGGA ACAAGAGTCC ACTATTAAAG AACGTGGACT CCAACGTCAA AGGGCGAAAA ACCGTCTATC AGGGCTATGG CCCACTACGT
      CTCACAACAA GGTCAAACCT TGTTCTCAGG TGATAATTTC TTGCACCTGA GGTTGCAGTT TCCCGCTTTT TGGCAGATAG TCCCGATACC GGGTGATGCA
```

*FIG._32D*

```
3201 GAACCATCAC CCTAATCAAG TTTTTTGGGG TCGAGGTGCC GTAAAGCACT AAATCGGAAC CCTAAAGGGA GCCCCCGATT TAGAGCTTGA CGGGGAAAGC
     CTTGGTAGTG GGATTAGTTC AAAAAACCCC AGCTCCACGG CATTTCGTGA TTTAGCCTTG GGATTTCCCT CGGGGGCTAA ATCTCGAACT GCCCCTTTCG

3301 CGGCGAACGT GGCGAGAAAG GAAGGGAAGA AAGCGAAAGG AGCGGGGCGCT AGGGCGCTGG CAAGTGTAGC GGTCACGCTG CGCGTAACCA CCACACCCGC
     GCCGCTTGCA CCGCTCTTTC CTTCCCTTCT TTCGCTTTCC TCGCCCCGCA TCCCCGCGAC GTTCACATCG CCAGTGCGAC GCGCATTGGT GGTGTGGGCG

3401 CGCGCTTAAT GCGCCGCTAC AGGGCGCGTC CGGATCCTGC CTCGCGCGTT TCGGTGATGA CGGTGAAAAC CTCTGACACA TGCAGCTCCC GGAGACGGTC
     GCGCGAATTA CGCGGCGATG TCCCGCGCAG GCCTAGGACG AGCGCGCAA AGCCACTACT GCCACTTTTG GAGACTGTGT ACGTCGAGGG CCCTCGCCAG

3501 ACAGCTTGTC TGTAAGCGGA TGCCGGGAGC AGACAAGCCC GTCAGCCGGT GTTGGCAGGT GTCGGGGCGC AGCCATGACC CAGTCACGTA
     TGTCGAACAG ACATTCGCCT ACGGCCCTCG TCTGTTCGGG CAGTCGGCCA CAACCGCCCA CAGCCGCCCG TCGGTACTGG GTCAGTGCAT

3601 GCGATAGCGG AGTGTATACT GGCTTAACTA TGCCGCATCA GAGCAGATTG TACTGAGAGT GCACCATATG CGGTGTGAAA TACCGCACAG ATGCGTAAGG
     CGCTATCGCC TCACATAGA CCGATTGAT ACGCCGTAGT CTCGTCTAAC ATGACTCTCA CGTGGTATAC GCCACACTTT ATGGCGTGTC TACGCATTCC

3701 AGAAAATACC GCATCAGGCG CTCTTCCGCT TCCTCGCTCA CTGACTCGCT GCGCTCGGTC GTTCGGCTGC GGCGAGCGGT ATCAGCTCAC TCAAAGGCGG
     TCTTTTATGG CGTAGTCCGC GAGAAGGCGA AGGAGCGAGT GACTGAGCGA CGCGAGCCAG CAAGCCGACG CCGCTCGCCA TAGTCGAGTG AGTTTCCGCC

3801 TAATACGGTT ATCCACAGAA TCAGGGGATA ACGCAGGAAA GAACATGTGA GCAAAAAGGC CAGGAACCGT AAAAAGGCCG CGTTGCTGGC
     ATTATGCCAA TAGGTGTCTT AGTCCCCTAT TGCGTCCTTT CTTGTACACT CGTTTTCCGG GTCCTTGGCA TTTTTCCGGC GCAACGACCG

3901 GTTTTTCCAT AGGCTCCGCC CCCCTGACGA GCATCACAAA AATCGACGCT CAAGTCAGAG GTGGCGAAAC CCGACAGGAC TATAAAGATA CCAGGCGTTT
     CAAAAAGGTA TCCGAGGCGG GGGGACTGCT CGTAGTGTTT TTAGCTGCGA GTTCAGTCTC CACCGCTTTG GGCTGTCCTG ATATTTCTAT GGTCCGCAAA

4001 CCCCCTGGAA GCTCCCTCGT GCGCTCTCCT GTTCCGACCC TGCCGCTTAC CGGATACCTG TCCGCCTTTC TCCCTTCGGG AACCGTGGCG CTTTCTCATA
     GGGGGACCTT CGAGGGAGCA CGCGAGAGGA CAAGGCTGGG ACGGCGAATG GCCTATGGAC AGGCGGAAAG AGGGAAGCCC TTGCCACCGC GAAAGAGTAT

4101 GCTCACGCTG TAGGTATCTC AGTTCGGTGT AGGTCGTTCG CTCCAAGCTG GGCTGTGTGC ACGAACCCCC CGTTCAGCCC GACCGCTGCG CCCTTATCCG
     CGAGTGCGAC ATCCATAGAG TCAAGCCACA TCCAGCAAGC GAGGTTCGAC CCGACACACG TGCTTGGGGG GCAAGTCGGG CTGGCGACGC GGAATAGGCC

4201 TAACTATCGT CTTGAGTCCA ACCCGGTAAG ACACGACTTA TCGCCACTGG CAGCAGCCAC TGGTAACAGG ATTAGCAGAG CGAGGTATGT AGGCGGTGCT
     ATTGATAGCA GAACTCAGGT TGGGCCATTC TGTGCTGAAT AGCGGTGACC GTCGTCGGTG ACCATTGTCC TAATCGTCTC GCTCCATACA TCCGCCACGA
```

*FIG._32E*

```
4301  ACAGAGTTCT TGAAGTGGTG GCCTAACTAC GGCTACACTA GAAGGACAGT ATTTGTATC TGCGCTCTGC TGAAGCCAGT TACCTTCGGA AAAAGAGTTG
      TGTCTCAAGA ACTTCACCAC CGGATTGATG CCGATTGATG CTTCCTGTCA TAAACCATAG ACGCGAGACG ACTTCGGTCA ATGGAAGCCT TTTTCTCAAC

4401  GTAGCTCTTG ATCCGGCAAA CAAACCACCG CTGGTAGCGG TGGTTTTTT GTTGCAAGC AGCAGATTAC GCGCAGAAAA AAAGGATCTC AAGAAGATCC
      CATCGAGAAC TAGGCCGTTT GTTTGGTGGC GACCATCGCC ACCAAAAAAA CAAACGTTCG TCGTCTAATG CGCGTCTTTT TTTCCTAGAG TTCTTCTAGG

4501  TTTGATCTTT TCTACGGGGT CTGACGCTCA GTGGAACGAA AACTCACGTT AAGGGATTTT GGTCATGAGA TTATCAAAAA GGATCTTCAC CTAGATCCTT
      AAACTAGAAA AGATGCCCCA GACTGCGAGT CACCTTGCTT TTGAGTGCAA TTCCCTAAAA CCAGTACTCT AATAGTTTTT CCTAGAAGTG GATCTAGGAA

4601  TTAAATTAAA AATGAAGTTT TAAATCAATC TAAAGTATAT ATGAGTAAAC TTGGTCTGAC AGTTACCAAT GCTTAATCAG TGAGGCACCT ATCTCAGCGA
      AATTTAATT TTACTTCAA ATTTAGTTAG ATTTCATATA TACTCATTTG AACCAGACTG TCAATGGTTA CGAATTAGTC ACTCCGTGGA TAGAGTCGCT

4701  TCTGTCTATT TCGTTCATCC ATAGTTGCCT GACTCCCCGT CGTGTAGATA ACTACGATAC GGGAGGGCTT ACCATCTGGC CCCAGTGCTG CAATGATACC
      AGACAGATAA AGCAAGTAGG TATCAACGGA CTGAGGGGCA GCACATCTAT TGATGCTATG CCCTCCCGAA TGGTAGACCG GGGTCACGAC GTTACTATGG

4801  GCGAGACCCA CGCTCACCGG CTCCAGATTT ATCAGCAATA AACCAGCCAG CCGGAAGGGC CGAGCCAGA AGTGGTCCTG CAACTTTATC CGCCTCCATC
      CGCTCTGGGT GCGAGTGGCC GAGGTCTAAA TAGTCGTTAT TTGGTCGGTC GGCCTTCCCG GCTCGGTCT TCACCAGGAC GTTGAAATAG GCGGAGGTAG

4901  CAGTCTATTA ATTGTTGCCG GGAAGCTAGA GTAAGTAGTT CGCCAGTTAA TAGTTTGCGC AACGTTGTTG CCATTGCTGC AGGCATCGTG GTGTCACGCT
      GTCAGATAAT TAACAACGGC CCTTCGATCT CATTCATCAA GCGGTCAATT ATCAAACGCG TTGCAACAAC GGTAACGACG TCCGTAGCAC CACAGTGCGA

5001  CGTCGTTTGG TATGGCTTCA TTCAGCTCCG GTTCCCAACG ATCAAGGCGA GTTACATGAT CCCCCATGTT GTGCAAAAAA GCGGTTAGCT CCTTCGGTCC
      GCAGCAAACC ATACCGAAGT AAGTCGAGGC CAAGGGTTGC TAGTTCCGCT CAATGTACTA GGGGGTACAA CACGTTTTT CGCCAATCGA GGAAGCCAGG

5101  TCCGATCGTT GTCAGAAGTA AGTTGGCCGC AGTGTTATCA CTCATGGTTA TGGCAGCACT ACCGGCCAAT ACCGTCGTGA CGTATTAAGA ACGTAGGCCA
      AGGCTAGCAA CAGTCTTCAT TCAACCGGCG TCACAATAGT GAGTACCAAT ACCGTCACT GAGTACCAAT ACCGTCGTGA CGTATTAAGA ACGTAGGCCA

5201  TCTGTGACTG GTGAGTACTC AACCAAGTCA TTCTGAGAAT AGTGTATGCG GCGACCGAGT TGCTCTTGCC CGGCGTCAAC ACGAGAACGG GCCGCAGTTG
      AGACACTGAC CACTCATGAG TTGGTTCAGT AAGACTCTTA TCACATACGC CGCTGGCTCA ACGAGAACGG GCCGCAGTTG TGCCCTATTA TGGCGCGGTG
```

FIG._32F

```
5301 ATAGCAGAAC TTTAAAAGTG CTCATCATTG GAAAAACGTTC TTCGGGGCGA AAACTCTCAA GGATCTTACC GCTGTTGAGA TCCAGTTCGA TGTAACCCAC
     TATCGTCTTG AAATTTCAC GAGTAGTAAC CTTTTGCAAG AAGCCCCGCT TTTGAGAGTT CCTAGAATGG CGACAACTCT AGGTCAAGCT ACATTGGGTG

5401 TCGTGCACCC AACTGATCTT CAGCATCTTT TACTTTCACC AGCGTTTCTG GGTGAGCAAA AACAGGAAGG CAAAATGCCG CAAAAAAGGG AATAAGGCG
     AGCACGTGGG TTGACTAGAA GTCGTAGAAT ATGAAAGTGG TCGCAAAGAC CCACTCGTTT TTGTCCTTCC GTTTTACGGC GTTTTTTCCC TTATTCCGC

5501 ACACCGAAAT GTTGAATACT CATACTCTTC CTTTTTCAAT ATTATTGAAG CATTTATCAG GGTTATTGTC TCATGAGCGG ATACATATTT GAATGTATTT
     TGTGCTTTA CAACTTATGA GTATGAGAAG GAAAAAGTTA TAATAACTTC GTAAATAGTC CCAATAACAG AGTACTCGCC TATGTATAAA CTTACATAAA

5601 AGAAAATAA ACAAATAGGG GTTCCGGCCA CATTTCCCCG AAAAGTGCCA CCTGACGTCT AAGAAACCAT TATTATCATG ACATTAACCT ATAAAAATAG
     TCTTTTATT TGTTTATCCC CAAGGCCGT GTAAAGGGGC TTTTCACGGT GGACTGCAGA TTCTTTGGTA ATAATAGTAC TGTAATTGGA TATTTTTATC

5701 GCCTATCACG AGCCCCTTTC GTCTTCAATA CAGGTAGACC TTTCGTAGAG ATGTACAGTG AAATCCCGA AATTATACAC ATGACTGAAG GAAGGAGCT
     CGGATAGTGC TCGGGAAAG CAGAAGTTAT GTCCATCTGG AAAGCATCTC TACATGTCAC TTTAGGGGCT TTAATATGTG TACTGACTTC CTTCCCTG

5801 CGTCATTCCC TGCCGGGTTA CGTCACCTAA CATCACTGTT ACTTTAAAAA AGTTTCCACT TGACACTTTG ATCCCTGATG GAAACGCCAT AATCTGGAC
     GCAGTAAGGG ACCGCCCAAT GCAGTTGGATT GTAGTAGATA TGAAATTTT TCAAAGGTGA ACTGTGAAAC TAGGGACTAC CTTTTGCCTA TTAGACCCTG

5901 AGTAGAAAGG GCTTCATCAT ATCAAATGCA ACGTACAAAG TAGAACACAG AAATAGGGGCT TCTGACCTGT GAAGCAACAG TCAATGGGCA TTTGTATAAG ACAAACTATC
     TCATCTTTCC CGAAGTAGTA TAGTTTACGT TGCATGTTCA ATCTTGTCC AGACTGGACA CTTCGTTGTC AGTTACCCGT AAACATATTC TGTTTGATAG

6001 TCAACATCG ACAAACCAAT ACAATACAGG TAGACCTTTC GTAGAGATGT ACAGTGAAAT CCCGAAATT GGGCTTTAA TGTGTACT GACTTCCTTC CCTCCGAGCAG
     AGTGTGTAGC TGTTTGGTTA TGTTATGTCC ATCTGGAAAG CATCTCTACA TGTCACTTTA GGGCTTTAA ACTTGAACT TATGTACT GACTTCCTTC CCTCCGAGCAG

6101 ATTCCCTGCC GGGTTACGTC ACCTAACATC ACTGTTACTT TAAAAAAGTT TCCACTGAC ACTTTGATCC ACGGCATAATC TGGACAGTA ACCTGTCAT
     TAAGGACGG CCCAATGCAG TGGATTGTAG TGACAATGAA ATTTTTCAA AGGTGAACTG TGAAACTAGG GACTACCTTT TGCGTATTAG ACCTGTCAT

6201 GAAAGGCTT CATCATATCA AATGCAACGT TACGTTGCA TGTTTCTTTA ACAAAGAAAT AGGGCTTCTG TCCCGAAGAC CAACAGTCAA TGGGCATTG TATAAGACAA ACTATCTCAC
     CTTTCCGAA GTAGTATAGT TTACGTTGCA TGTTTCTTTA ACAAAGAAAT AGGGCTTCTG TCCCGAAGAC GTTGTCAGTT ACCCGTAAAC ATATTCTGTT TGATAGAGTG

6301 ACATCACAA ACCAATACAA TCTACAGGTA GACCTTTCGT AGAGATGTAC AGTGAAATCC CCGAAATTAT ACACATGACT GAAGGAAGGG AGCTCGTCAT
     TGTAGTGTT TGGTTATGTT AGATGTCCAT CTGGAAAGCA TCTCTACATG TCACTTTAGG GGCTTTAATA TGTGTACTGA CTTCCTTCCC TCGAGCAGTA

6401 TCCCTCCGG GTTACGTCAC CTAACATCAC TGTTACTTTA AAAAAGTTTC CACTTGACAC TTTGATCCCT GATGGAAAAC GCATAATCTG GACAGTAGA
     AGGGACGCC CAATGCAGTG GATTGTAGTG ACAATGAAAT TTTTTCAAAG GTGAACTGTG AAACTAGGGA CTACCTTTG CGTATTAGAC CCTGTCATCT

6501 AAGGGCTTCA TCATATCAAA TGCAACGTAC AAAGAAAATA G GCTTCTGAC CGAAGACTG ACAGTCAATG GGCATTTGTA TAAGACAAAC TATCTCACAC
     TTCCCGAAGT AGTATAGTTT ACGTTGCATG TTTCTTTATC CCGAAGACTG GACACTTCGT TGTCAGTTAC CCGTAAACAT ATTCTGTTTG ATAGAGTGTG

6601 ATCGACAAAC CAATACAATC
     TAGCTGTTTG GTTATGTTAG
```

*FIG.\_32G*

```
  1 TTCGAGCTCG CCCGACAATTG ATTATTGACT AGTAATTAAT AGTAATCAAT TACGGGGTCA TTAGTTCATA GCCCATATAT GGAGTTCCGC GTTACATAAC
    AAGCTCGAGC GGGCTGTAAC TAATAACTGA TCATTAATTA TCATTAGTTA ATGCCCCAGT AATCAAGTAT CGGGTATATA CCTCAAGGCG CAATGTATTG

101 TTACGGTAAA TGGCCCGCCT GGCTGACCGC CCAACGACCC ACGTCAATAA TGACGTATGT TCCCATAGTA ACGCCAATAG GGACTTTCCA
    AATGCCATTT ACCGGGCGGA CCGACTGGCG GGTTGCTGGG TGCAGTTATT ACTGCATACA AGGGTATCAT TGCGGTTATC CCTGAAAGGT

201 TTGACGTCAA TGGGTGGAGT ATTTACGGTA AACTGCCCAC TTGGCAGTAC ATCAAGTGTA TCATATGCCA AGTACGCCCC CTATTGACGT CAATGACGGT
    AACTGCAGTT ACCCACCTCA TAAATGCCAT TTGACGGGTG AACCGTCATG TAGTTCACAT AGTATACGGT TCATGCGGGG GATAACTGCA GTTACTGCCA

301 AAATGGCCCG CCTGGCATTA TGCCCAGTAC ATGACCTTAT GGGACTTTCC TACTTGGCAG TACATCTACG TATTAGTCAT CGCTATTACC ATGGTGATGC
    TTTACCGGGC GGACCGTAAT ACGGGTCATG TACTGGAATA CCCTGAAAGG ATGAACCGTC ATGTAGATGC ATAATCAGTA GCGATAATGG TACCACTACG

401 GGTTTTGGCA GTACATCAAT GGGCGTGGAT AGCGGTTTGA CTCACGGGGA TTTCCAAGTC TCCACCCCAT TGACGTCAAT GGGAGTTTGT TTTGGCACCA
    CCAAAACCGT CATGTAGTTA CCCGCACCTA TCGCCAAACT GAGTGCCCCT AAAGGTTCAG AGGTGGGGTA ACTGCAGTTA CCCTCAAACA AAACCGTGGT

501 AAATCAACGG GACTTTCCAA AATGTCGTAA CAACTCCGCC CCATTGACGC AAATGGGCGG TAGGCGTGTA CGGTGGGAGG TCTATATAAG CAGAGCTCGT
    TTTAGTTGCC CTGAAAGGTT TTACAGCATT GTTGAGGCGG GGTAACTGCG GGTAACTGCG ATCCGCACAT GCCACCCTCC AGATATATTC GTCTCGAGCA

601 TTAGTGAACC GTCAGATCGC CTGGAGACGC CATCCACGCT GTTTTGACCT CCATAGAAGA CACCGGGACC GATCCAGCCT CCGCGGCCGG GAACGGTGCA
    AATCACTTGG CAGTCTAGCG GACCTCTGCG GTAGGTGCGA CAAAACTGGA GGTATCTTCT GTGGCCCTGG CTAGGTCGGA GGCGCCGGCC CTTGCCACGT

701 TTGGAACGCG GATTCCCCGT GCCAAGAGTG ACGTAAGTAC CGGTTCTCAC TGCATTCATG GCCCTATAGA GTCTATAGGC CCACCCCCTT GGCTTCGTTA GAACGCGGCT ACAATTAATA
    AACCTTGCGC CTAAGGGGCA CGGTTCTCAC TGCATTCATG ACGGTAAGTG TGCATTTCAG GCGGATATCT CAGATATCCG GTGGGGGAA CCGAAGCAAT CTTGCGCCGA TGTTAATTAT

801 CATAACCTTA TGTATCATAC ACATTGGTGA ATTCCAACATT TAGGTGACAC TATAGAATAA CATCCACTTT GCCTTCTCT CCACTCCCAG GTCCAACTGC
    GTATTGGAAT ACATAGTATG TGTATCTAA ATCCACTGTG ATATCTTATT GTAGGTGAAA CGGAAAGAGA CGGAAGAGA GGTGAGGGTC CAGGTTGACG

901 ACCTCGGTTC TATCGATTGA ATTCCACCAT GGGATGGTCA ATTCAGGATC TTTTTCTAGT TGTATCATCC AGCAACTGCA ACTGGAGTAC ATTCAGATAT CCAGATGACC
    TGGAGCCAAG ATAGCTAACT TAAGGTGGTA CCCTACCAGT AAAAAGATCA ACATAGTAGG TCGTTGACGT TGACCTCATG TAAGTCTATA GGTCTACTGG

1                          M   G   W   S    C   I   I   L   F   L   V    A   T   A   T    G   V   H   S    D   I   Q   M   T
                             ^met                                                                          ^Start VL
                                                                                                           ^EcoRV
```

FIG._33A

```
1001 CAGTCCCCGA GCTCCCTGTC CGCCTCTGTG GGCGATAGGG TCACCATCAC CTGCCGTGCC AGTCAGGATG TGTCCACTGC TGTAGCCTGG TATCAACAGA
     GTCAGGGGCT CGAGGACAG GCGGAGACAC CCGCTATCCC AGTGGTAGTG GACGGCACGG TCAGTCCTAC ACAGGTGACG ACATCGGACC ATAGTTGTCT
  25  Q  S  P  S   S  L  S   A  S  V   G  D  R  V   T  I  T   C  R  A   S  Q  D  V   S  T  A   V  A  W   Y  Q  Q  K
                                                               ^CDR-L1

1101 AACCAGGAAA AGCTCCGAAG CTTCTGATTT ACTCGGCATC CTTCCTCGTAC TCTGGAGTCC CTTCTCGCTT CTCTGGTAGC GGGTCCGGGA CGGATTCAC
     TTGGTCCTTT TCGAGGCTTC GAAGACTAAA TGAGCCGTAG GAAGGAGATG AGACCTCAGG GAAGAGCGAA GAGACCATCG CCAAGGCCCT GCCTAAAGTG
  59  P  G  K   A  P  K   L  L  I  Y   S  A  S   F  L  Y   S  G  V  P   S  R  F   S  G  S   G  S  G   T  D  F  T
                          ^CDR-L2

1201 TCTGACCATC AGCAGTCTGC AGCCCGAAGA CTTCGCAACT TATTACTGTC AGCAATCTTA TACTACTCCT CCCACGTTCG GACAGGGTAC CAAGGTGGAG
     AGACTGGTAG TCGTCAGACG TCGGGCTTCT GAAGCGTTGA ATAATGACAG TCGTTAGAAT ATGATGAGGA GGGTGCAAGC CTGTCCCATG GTTCCACCTC
  92  L  T  I   S  S  L  Q   P  E  D   F  A  T   Y  Y  C   Q  Q  S  Y   T  T  P   P  T  F  G   Q  G  T   K  V  E
                                                           ^CDR-L3                                        ^KpnI

1301 ATCAAACGAA CTGTGGCTGC ACCATCTGTC TTCATCTTCC CGCCATCTGA TGAGCAGTTG AAATCTGGAA CTGCTTCTGT TGTGTGCCTG CTGAATAACT
     TAGTTTGCTT GACACCGACG TGGTAGACAG AAGTAGAAGG GCGGTAGACT ACTCGTCAAC TTTAGACCTT GACGAAGACA ACACACGGAC GACTTATTGA
 125  I  K  R  T   V  A  A   P  S  V   F  I  F  P   P  S  D   E  Q  L   K  S  G  T   A  S  V   V  C  L   L  N  N  F
              ^start human kappa 1401 TCTATCCCAG AGAGGCCAAA GTACAGTGGA AGGTGGATAA CGCCCTCCAA TCGGGTAACT CGCCCAGGAG TGTCACAGAG GGGTCCCTC ACAGTGTCTC AGGGCCTGAG CTCCCCGTC
     AGATAGGGTC TCTCCGGTTT CATGTCACCT TCCACCTATT GCGGGAGGTT AGCCCATTGA GCGGGTCCTC ACAGTGTCTC CCCAGGGAG TGTCACAGAG TCCCGGACTC GAGGGGCAG
 159  Y  P  R   E  A  K   V  Q  W  K   V  D  N   A  L  Q   S  G  N  S   Q  E  S   V  T  E   Q  D  S  K   D  S  T 1501 CTACAGCCTC AGCAGCACCC TGACGCTGAG CAAAGCAGAC TACGAGAAAC ACAAAGTCTA CGCCTGCGAA GTCACCCATC AGGGCCTGAG CTCCCCGTC
     GATGTCGGAG TCGTCGTGGG ACTGCGACTC GTTTCGTCTG ATGCTCTTTG TGTTTCAGAT GCGGACGCTT CAGTGGGTAG TCCCGGACTC GAGGGGCAG
 192  Y  S  L   S  S  T  L   T  L  S   K  A  D   Y  E  K  H   K  V  Y   A  C  E   V  T  H  Q   G  L  S   S  P  V 1601 ACAAAGAGCT TCAACAGGGG AGAGTGTTAA GCTTGCCGGC CATGGCCCAA CTTGTTTATT GCAGCTTACA ATGGTTACAA CGTCGAATAA AGCATCACAA
     TGTTTCTCGA AGTTGTCCCC TCTCACAATT CGAACGGCCG GTACCGGGTT GAACAAATAA CGTCGAATGT TACCAATGTT GCAGCTTATA TATTCGTTA TCGTAGTGTT
 225  T  K  S   F  N  R  G   E  C  O
```

*FIG._33B*

```
1701  ATTTCACAAA TAAAGCATTT TTTTCACTGC ATTCTAGTTG TGGTTTGTCC AAACTCATCA ATGTATCTTA TCATGTCTGG ATCGGGAATT AATTCGGCGC
      TAAAGTGTTT ATTTCGTAAA AAAAGTGACG TAAGATCAAC ACCAAACAGG TTTGAGTAGT TACATAGAAT AGTACAGACC TAGCCCTTAA TTAAGCCGCG

1801  AGCACCATGG CCTGAAATAA CCTCTGAAAG AGGAACTTGG TTAGGTATCT TCTGAGGCGG AAAGAACCAG CTGTGGAATG TGTGTCAGTT AGGGTGTGA
      TCGTGGTACC GGACTTTATT GGAGACTTTC TCCTTGAACC AATCCATAGA AGACTCCGCC TTTCTTGGTC GACACCTTAC ACACAGTCAA TCCCACACCT
                                                                                 ^change from C to T, kill KpnI site 1901  AAGTCCCCAG GCTCCCCAGC AGGCAGAAGT ATGCAAAGCA TTAGTCAGCA ACCAGGTGTG GAAAGTCCCC AGGCTCCCCA GCAGGCAGAA
      TTCAGGGGTC CGAGGGGTCG TCCGTCTTCA TACGTTTCGT AATCAGTCGT TGGTCCACAC CTTTCAGGGG TCCGAGGGGT CGTCCGTCTT 2001  GTATGCAAAG CATGCATCTC AATTAGTCAG CAACCATATG TTATTATTAT CCCGCCCCTA ACTCCGCCCA TCCCGCCCCT AACTCCGCCC ATTCTCCGCC
      CATACGTTTC GTACGTAGAG TTAATCAGTC GTTGGTATCA AATAATAATA GGGCGGGGAT TGAGGCGGGT AGGGCGGGGA TTGAGGCGGG TAAGAGGCGG 2101  CCATGGGCTGA CTAATTTTTT TTATTTATGC AGAGGCCGAG GCCGCCCTCG CCTCTGAGCT ATTCCAGAAG TAGTGAGGAG GCTTTTTTGG AGGCCTAGGC
      GGTACCGACT GATTAAAAAA AATAAATACG TCTCCGGCTC CGGCGGGAGC GGAGACTCGA TAAGGTCTTC ATCACTCCTC CGAAAAAACC TCCGGATCCG 2201  TTTTTGCAAAA AGCTGTTAAC AGCTTGGCAC TGGCCGTCGT TTTACAACGT CGTGACTGGG AAAACCCTGG CGTTACCCAA CTTAATCGCC TTGCAGCACA
      AAAACGTTTT TCGACAATTG TCGAACCGTG ACCGGCAGCA AAATGTTGCA GCACTGACCC TTTTGGGACC GCAATGGGTT GAATTAGCGG AACGTCGTGT 2301  TCCCCCCTTC GCCAGCTGGC GTAATAGCGA AGAGGCCCGC ACCGATCGCC CTTCCCAACA GTTGCGTAGC CTGAATGGCG AATGGCGCCT GATGCGGTAT
      AGGGGGGAAG CGGTCGACCG CATTATCGCT TCTCCGGGCG TGGCTAGCGG GAAGGGTTGT CAACGCATCG GACTTACCGC TTACCGCGGA CTACGCCATA 2401  TTTTCTCCTTA CGCATCTGTG CGGTATTTCA CACCGCATTA GTCAAAGCAA CCATAGTACG CGCCCTGTAG AGCGCGCGG GTGTGGTGGT
      AAAGAGGAAT GCGTAGACAC GCCATAAAGT CAGTTTCGTT GGTATCATGC GCGGGACATC GCGGCGCGCC CACACCACCA 2501  TACGCGCAGC CACTTGCCAG CGGGATCGC GCGGGATCGC GGGGATGCTA CGGGCCTAGC CCGCTCCTT TCGCTTTCTT CCCTTCCTTT CTCGCCACGT TCGCCGGCTT TCCCCGTCAA AGGGGCAGTT
      ATGCGCGTCG CACTGGCGAT GTGAACGGTC GCGCTAGCC CCGGGATGGG AGCGAAAGAA GGGAAGGAAA GAGCGGGTGCA AGCGGCCGAA AGGGGCAGTT 2601  GCTCTAAATC GGGGGCTCCC TTTAGGGTTC CGATTTAGTG CTTTACGGCA CCTCGACCCC AAAAAACTTG ATTTGGGTGA TGGTTCACGT AGTGGGCCAT
      CGAGATTTAG CCCCCGAGGG AAATCCCAAG GCTAAATCAC GAAATGCCGT GGAGCTGGGG TTTTTTGAAC TAAACCCACT ACCAAGTGCA TCACCCGGTA
```

FIG._33C

```
2701  CGCCCTGATA GACGGTTTTT CGCCCCTTGA CGTTGGAGTC CACGTTCTTT AATAGTGGAC TCTTGTTCCA AACTGGAACA ACACTCAACC CTATCTCGGG
      GCGGGACTAT CTGCCAAAAA GCGGGAAACT GCAACCTCAG GTGCAAGAAA TTATCACCTG AGAACAAGT TTGACCTTGT TGTGAGTTGG GATAGAGCCC

2801  CTATTCTTTT GATTATAAG GGATTTCGCC GATTTCGGCC TATTGGTTAA AAAATGAGCT GATTTAACAA AAATTTAACG CGAATTTTAA CAAAATATTA
      GATAAGAAAA CTAAATATTC CCTAAAACGG CTAAAGCCGG ATAACCAATT TTTTACTCGA CTAAATTGTT TTTAAATTGC GCTTAAAATT GTTTATAAT

2901  ACGTTTACAA TTTTTATGGTG CACTCTCAGT ACAATCTGCT CTGATGCCGC ATAGTTAAGC CAACTCCCCT ATCGCTACGT GACTGGGTCA TGGCTGCGCC
      TGCAAATGTT AAAATACCAC GTGAGAGTCA TGTTAGACGA GACTACGGCG TATCAATTCG GTTGAGCGA CTGACCCAGT TAGGCATGCA ACCGACGCGG

3001  CCGACACCCG CCAACACCCC CTGACGCGCC TGTCTGCTCC CGGCATCCGC TTACAGACAA GCTGTGACCG TCTCCGGGAG CTGCATGTGT
      GGCTGTGGGC GGTTGTGGGC GACTGCGCGG ACAGACGAGG GCCGTAGGCG AATGTCTGTT CGACACTGGC AGAGGCCCTC GACGTACACA

3101  CAGAGGTTTT CACCGTCATC ACCGAAACGC GCGAGGCAGT ATTCTTGAAG ACGAAAGGGC CTCGTGATAC GCCTATTTT ATAGGTTAAT GTCATGATAA
      GTCTCCAAAA GTGGCAGTAG TGGCTTTGCG CGCTCCGTCA TAAGAACTTC TGCTTCCCCG GAGCACTATG CGGATAAAAA TATCCAATTA CAGTACTATT

3201  TAATGGTTTC TTAGACGTCA GGTGGCACTT TTCGGGGAAA TGTGCGCGGA ACCCCTATTT GTTTATTTTT CTAAATACAT TCAAATATGT ATCCGCTCAT
      ATTACCAAAG AATCTGCAGT CCACCGTGAA AAGCCCCTTT ACACGCGCCT TGGGGATAAA CAAATAAAAA GATTTATGTA AGTTTATACA TAGGCGAGTA

3301  GAGACAATAA CCCTGATAAA TGCTTCAATA ATATTGAAGA AGGAAGAGTA TGAGTATTCA ACATTCCGT GTCGCCCTTA TTCCCTTTTT TGCGGCATTT
      CTCTGTTATT GGGACTATTT ACGAAGTTAT TATAACTTCT TCCTTCTCAT ACTCATAAGT TGTAAAGGCA CAGCGGGAAT AAGGGAAAAA ACGCCGTAAA

3401  TGCCTTCCTG TTTTTGCTCA CCCAGAAACG CTGGTGAAAG TAAAAGATGC TGAAGATCAG TTGGGTGCAC GAGTGGGTTA CATCGAACTG GATCTCAACA
      ACGGAAGGAC AAAAACGAGT GGGTCTTTGC GACCACTTTC ATTTTCTACG ACTTCTAGTC AACCCACGTG CTCACCCAAT GTAGCTTGAC CTAGAGTTGT

3501  GCGGTAAGAT CCTTGAGAGT TTTCGCCCCG AAGAACGTTT TCCAATGATG AGCACTTTTA AAGTTCTGCT ATGTGGCGCG GTATTATCCC GTGATGACGC
      CGCCATTCTA GGAACTCTCA AAAGCGGGGC TTCTTGCAAA AGGTTACTAC TCGTGAAAAT TTCAAGACGA TACACCGCGC CATAATAGGG CACTACTGCG

3601  CGGGCAAGAG CAACTCGGTC GCCGCATACA CTATTCTCAG AATGACTTGG TTGAGTACTC ACCAGTCACA GAAAAGCATC TTACGGATGG CATGACAGTA
      GCCCGTTCTC GTTGAGCCAG CGGCGTATGT GATAAGAGTC TTACTGAACC AACTCATGAG TGGTCAGTGT CTTTTCGTAG AATGCCTACC GTACTGTCAT
```

FIG._33D

```
3701 AGAGAATTAT GCAGTGCTGC CATAACCATG AGTGATAACA CTGCGGCCAA CTTACTTCTG ACAACGATCG GAGGACCGAA GGAGCTAACC GCTTTTTGC
     TCTCTTAATA CGTCACGACG GTATTGGTAC TCACTATTGT GACGCCGGTT GAATGAAGAC TGTTGCTAGC CTCCTGGCTT CCTCGATTGG CGAAAAAACG

3801 ACAACATGGG GGATCATGTA ACTCGCCTTG ATCGTTGGGA ACCGGAGCTG AATGAAGCA TACCAAACGA CGAGCGTGAC ACCACGATGC CAGCAGCAAT
     TGTTGTACCC CCTAGTACAT TGAGCGGAAC TAGCAACCCT TGGCCTCGAC TTACTTCGGT ATGGTTTGCT GCTCGCACTG TGGTGCTACG GTCGTCGTTA

3901 GGCAACAACG TTGCGCAAAC TATTAACTGG CGAACTACTT ACTCTAGCTT CCCGGCAACA ATTAATAGAC TGGATGGAGG CGGATAAAGT TGCAGGACCA
     CCGTTGTTGC AACGCGTTTG ATAATTGACC GCTTGATGAA TGAGATCGAA GGGCCGTTGT TAATTATCTG ACCTACCTCC GCCTATTTCA ACGTCCTGGT

4001 CTTCTGCGCT CGGCCCTTCC GGCTGGCTGG ATAAATCTGG AGCCGGTGAG CGTGGGTCTC GCGGTATCAT TGCAGCACTG GGGCCAGATG
     GAAGACGCGA GCCGGGAAGG CCGACCGACC TATTTAGACC TCGGCCACTC GCACCCAGAG CGCCATAGTA ACGTCGTGAC CCCGGTCTAC

4101 GTAAGCCCTC CCGTATCGTA GTTATCTACA CGACGGGGAG TCAGGCAACT ATGGATGAAC GAAATAGACA GATCGCTGAG ATAGGTGCCT CACTGATTAA
     CATTCGGGAG GGCATAGCAT CAATAGATGT GCTGCCCCTC AGTCCGTTGA TACCTACTTG CTTTATCTGT CTAGCGACTC TATCCACGGA GTGACTAATT

4201 GCATTGGTAA CTGTCAGACC AAGTTTACTC ATATATACTT TAGATTGATT TAAAACTTCA TTTTTAATTT AAAAGGATCT AGGTGAAGAT CCTTTTTGAT
     CGTAACCATT GACAGTCTGG TTCAAATGAG TATATATGAA ATCTAACTAA ATTTTGAAGT AAAAATTAAA TTTTCCTAGA TCCACTTCTA GGAAAAACTA

4301 AATCTCATGA CCAAAATCCC TTAACGTGAG TTTTCGTTCC ACTGAGCGTC AGACCCCGTA GAAAAGATCA AAGGATCTTC TTGAGATCCT TTTTTTCTGC
     TTAGAGTACT GGTTTTAGGG AATTGCACTC AAAAGCAAGG TGACTCGCAG TCTGGGGCAT CTTTTCTAGT TTCCTAGAAG AACTCTAGGA AAAAAAGACG

4401 GCGTAATCTG CTGCTTGCAA ACAAAAAAAC CACCGCTACC AGCGGTGGTT TGTTTGCCGG ATCAAGAGCT ACCAACTCTT TTTCCGAAGG TAACTGGCTT
     CGCATTAGAC GACGAACGTT TGTTTTTTTG GTGGCGATGG TCGCCACCAA ACAAACGGCC TAGTTCTCGA TGGTTGAGAA AAAGGCTTCC ATTGACCGAA

4501 CAGCAGAGCG CAGATACCAA ATACTGTCCT TCTAGTGTAG CCGTAGTTAG GCCACCACTT CAAGAACTCT GTAGCACCGC CTACATACCT CGCTCTGCTA
     GTCGTCTCGC GTCTATGGTT TATGACAGGA AGATCACATC GGCATCAATC CGGTCATGAA GTTCTTGAGA CATCGTGGCG GATGTATGGA GCGAGACGAT

4601 ATCCTGTTAC CAGTGGCTGC TGCCAGTGGC GATAAGTCGT GTCTTACCGG GTTGGACTCA AGACGATAGT TACCGGATAA GGCGCAGCGG TCGGGCTGAA
     TAGGACAATG GTCACCGACG ACGGTCACCG CTATTCAGCA CAGAATGGCC CAACCTGAGT TCTGCTATCA ATGGCCTATT CCGCGTCGCC AGCCCGACTT
```

*FIG. 33E*

```
4701  CGGGGGGTTC GTGCACACAG CCCAGCTTGG AGCGAACGAC CTACACCGAA CTGAGATACC TACAGGCGTGA GCATTGAGAA AGCGCCACGG TTCCCGAAGG
      GCCCCCCAAG CACGTGTGTC GGGTCGAACC TCGCTTGCTG GATGTGGCTT GACTCTATGG ATGTCGCACT CGTAACTCTT TCGCGGTGCG AAGGGCTTCC

4801  GAGAAAGGCG GACAGGTATC CGGTAAGCGG CAGGGTCGAA ACAGGAGAGC GCACGAGGGA GCTTCCAGGG GGAAACGCCT GGTATCTTTA TAGTCCTGTC
      CTCTTTCCGC CTGTCCATAG GCCATTCGCC GTCCCAGCCT GTGCTCTCG CGTGCTCCT CGAAGGTCCC CCTTTGCGA CCATAGAAAT ATCAGGACAG

4901  GGGTTTCGCC ACCTCTGACT TGAGCCGTCGA TTTTTGTGAT GCTCGTCAGG GGGGCGGAGC CTATGGAAAA ACGCCAGCAA CCGGGCCTTT TTACGGTTCC
      CCCAAAGCGG TGGAGACTGA ACTCGCAGCT AAAAACACTA CGAGCAGTCC CCCCGCCTCG GATACCTTTT TGCGGTCGTT GCGCCGGAAA AATGCCAAGG

5001  TGGCCTTTTG CTGGCCTTTT GCTCACATGT TCTTTCCTGC GTTATCCCCT GATTCTGTGG ATAACCGTAT TACCGCCTTT GAGTGAGCTG ATACCGCTCG
      ACCGGAAAAC GACCGGAAAA CGAGTGTACA AGAAAGGACG CAATAGGGGA CTAAGACACC TATTGGCATA ATGGCGGAAA CTCACTCGAC TATGGCGAGC

5101  CCGCAGCCGA ACGACCGAGC GCAGCGAGTC GAAGCGGAAG AGCGCCCAAT AGCGCAAACCG CCTCTCCCCG CGCGTTGGCC GATTCATTAA
      GGCGTCGGCT TGCTGGCTCG CGTCGCTCAG TCACTCGCTC CTTCGCCTTC TCGCGGGTTA TGCGTTTGGC GGAGAGGGGC GCGCAACCGG CTAAGTAATT

5201  TCCAGCTGGC ACGACAGGTT TCCCGACTGG AAAGCGGGCA GTGAGCGCAA CGCAATTAAT GTGAGTTACC TCACTCATTA GGCACCCCAG GCTTTACACT
      AGGTCGACCG TGCTGTCCAA AGGGCTGACC TTTCGCCCGT CACTCGCGTT GCGTTAATTA CACTCAATGG AGTGAGTAAT CCGTGGGGTC CGAAATGTGA

5301  TTATGCTTCC GGCTCGTATG TTGTGTGGAA TTGTGAGCGG ATAACAATTT CACACAGGAA ACAGCTATGA CCATGATTAC GAATTAA
      AATACGAAGG CCGAGCATAC AACACACCTT AACACTCGCC TATTGTTAAA GTGTGTCCTT TGTCGATACT GGTACTAATG CTTAATT
```

FIG._33F

```
  1 ATTCGAGCTC GCCCGACATT GATTATTGAC TAGTTATTAA TAGTAATCAA TTACGGGTC ATTAGTTCAT AGCCCATATA TGGAGTTCCG CGTTACATAA
    TAAGCTCGAG CGGGCTGTAA CTAATAACTG ATCAATAATT ATCATTAGTT AATGCCCCAG TAATCAAGTA TCGGTATAT ACCTCAAGGC GCAATGTATT

101 CTTACGGTAA ATGCCCCGCC TGGCTGACCG CCCAACGACC CCCGCCCATT GACGTCAATA ATGACGTATG TTCCCATAGT AACGCCAATA GGGACTTTCC
    GAATGCCATT TACGGGGCGG ACCGACTGGC GGGTTGCTGG GGGCGGGTAA CTGCAGTTAT TACTGCATAC AAGGGTATCA TTGCGGTTAT CCCTGAAAGG

201 ATTGACGTCA ATGGGTGGAG TATTTACGGT AAACTGCCCA CTTGGCAGTA CATCAAGTGT ATCATATGCC AAGTACGCCC CCTATTGACG TCAATGACGG
    TAACTGCAGT TACCCACCTC ATAAATGCCA TTTGACGGGT GAACCGTCAT GTAGTTCACA TAGTATACGG TTCATGCGGG GGATAACTGC AGTTACTGCC

301 TAAATGGCCC GCCTGGCATT ATGCCCAGTA CATGACCTTA TGGGACTTTC CTACTTGGCA GTACATCTAC GTATTAGTCA TCGCTATTAC CATGGTGATG
    ATTTACCGGG CGGACCGTAA TACGGGTCAT GTACTGGAAT ACCCTGAAAG GATGAACCGT CATGTAGATG CATAATCAGT AGCGATAATG GTACCACTAC

401 CGGTTTTGGC AGTACAATCAA TGGGCGTGGA TAGCGGTTTG ACTCACGGGG ATTTCCAAGT CTCCACCCCA TTGACGTCAA TGGGAGTTTG TTTTGGCACC
    GCCAAAACCG TCATGTTAGTT ACCCGCACCT ATCGCCAAAC TGAGTGCCCC TAAAGGTTCA GAGGTGGGGT AACTGCAGTT ACCCTCAAAC AAAACCGTGG

501 AAAATCAACG GGACTTTCCA AAATGTCGTA ACAACTCCGC CCCATTGACG CAAATGGGCG GTAGGCGTGT ACGGTGGGAG GTCTATATAA GCAGAGCTCG
    TTTTAGTTGC CCTGAAAGGT TTTACAGCAT TGTTGAGGCG GGGTAACTGC GTTTACCCGC CATCCGCACA TGCCACCCTC CAGATATATT CGTCTCGAGC

601 TTTAGTGAAC CGTCAGATCG CCTGGAGACG CCATCCACGC TGTTTTGACC TCCATAGAAG ACACCGGGAC CGATCCAGCC TCCGCGGCCG GGAACGGTGC
    AAATCACTTG GCAGTCTAGC GGACCTCTGC GGTAGGTGCG ACAAAACTGG AGGTATCTTC TGTGGCCCTG GCTAGGTCGG AGGCGCCGGC CCTTGCCACG

701 ATTGGAACGC GGATTCCCCG TGCCAAGAGT GACGTAAGTA CGGGTTCTCA CTGCCATTCAT TGGCTTCGTT AGAACGCGGC TACAATTAAT
    TAACCCTTGCG CCTAGGGGC ACGGTTCTCA CTGCATTCAT AATCCACTT GTACTAGAGTAG TCAGATATC GCCCTATAG TCAGATATCC GGCGGATATC TCAGATATCC ATGGGTTCCC AGCCACTAG AGCCACTAG AGTCCACTAG ATGTTAATTA

801 ACATAACCTT ATGTATCATA CACATACGAT TTAGGTGACA CTATAGAATA CATTCCACTT TGGCCTTTCTC TCCACAGGTG GGTCCAACTG
    TGTATTGGAA TACATAGTAT GTGTATGCTA AATCCACTGT GATATCTTAT GTAAGTGAA ACGAAAGAG AGGAAAGAG AGGTGTCCAC AGTGAGGGT CCAGGTTGAC

901 CACCTCGGTT CTATCGATTG AATTCCACCA TGGGATGGTC ATGTATCATC CTTTTCTAG TAGCAACTGC ATCGTTGACG TTGACCTGCC TACGCTGAGG TTCAGCTGT
    GTGGAGCCAA GATAGCTAAC TTAAGGTGGT ACCCTACCAG TACATAGTAG GAAAAGATC ATCGTTGACG TTGACCTGCC AAGTGAGGGT CCAGGTTGAC AAGTCGACCA

1                              M  G  W  S     C  I  I     L  F  L  V     A  T  A        T  G  A     Y  A  E  V     Q  L  V
                                 ^start signal peptide                                                 ^start of heavy chain
                                 ^met                                                                  ^BsiW1
```

FIG._34A

```
1001 GGAGTCTGGC GGTGGCCTGG TGCAGCCAGG GGGCTCACTC CGTTTGTCCT GTGCAGCTTC TGGCTTCACC ATTAGTGGTT CTTGGATACA CTGGGTGCGT
     CCTCAGACCG CACCGGACC ACGTCGGTCC CCCGAGTGAG GCAAACAGGA CACGTCGAAG ACCGAAGTGG TAATCACCAA GAACCTATGT GACCCACGCA
  25 E  S  G    G  G  L  V    Q  P  G    G  S  L    R  L  S  C    A  A  S    G  F  T    I  S  G  S    W  I  H    W  V  R
                                                                                        ^CDR-H1

1101 CAGGCCCCGG GTAAGGGCTC CATTCCCGGA CCTTACCCAA GCTTGGATTG CTCCTTATAG CGGCGCTACT GACTATGCCG ATAGCGTCAA GGGCCGTTTC ACTATAAGCG
     GTCCGGGGCC CATTCCCGAG GTAAGGGCCT GGAATGGGTT CGAACCTAAC CGAACCTAAT GCCGCGATGA CTGATACGGC TATCGCAGTT CCCGGCAAAG TGATATTCGC
  58 Q  A  P  G  K  G  L  E  W  V    A  W  I  A    P  Y  S    G  A  T    D  Y  A  D    S  V  K    G  R  F    T  I  S  A
                                            ^CDR-H2

1201 CAGACACATC CAAAACACA GCCTACCTAC AAATGAACAG CTTAAGAGCT GAGGACACTG CCGTCTATTA TTGTGCAAGA GAGGGGGGCT TGTACTGGGT
     GTCTGTGTAG GTTTTTGTGT CGGATGGATG TTTACTTGTC GAATTCTCGA CTCCTGTGAC GGCAGATAAT AACACGTTCT CTCCCCCCGA ACATGACCCA
  92 D  T  S    K  N  T    A  Y  L  Q    M  N  S    L  R  A    E  D  T  A    V  Y  Y    C  A  R    E  G  G  L    Y  W  V
                                                                                                        ^CDR-H3

1301 GTTCGACTAC TGGGGTCAAG GAACCCTGGT CACCGTCTCC TCGGCCTCCA CCAAGGGCCC ATCGGTCTTC CCCCTGGCAC CCTCCTCCAA GAGCACCTCT
     CAAGCTGATG ACCCCAGTTC CTTGGGACCA GTGGCAGAGG AGCCGGAGGT GGTTCCCGGG TAGCCAGAAG GGGGACCGTG GGAGGAGGTT CTCGTGGAGA
 125 F  D  Y    W  G  Q  Q    T  L  V    T  V  S    S  A  S  T    K  G  P    S  V  F    P  L  A  P    S  S  K    S  T  S
                                                                        ^Apal 1401 GGGGGCACAG CGGCCCTGGG CTGCCTGGTC AAGGACTACT TCCCCGAACC GGTGACGGTG TCGTGGAACT CAGGCGCCCT GACCAGCGGC GTGCACACCT
     CCCCCGTGTC GCCGGGACCC GACGGACCAG TTCCTGATGA AGGGGCTTGG CCACTGCCAC AGCACCTTGA GTCCGCGGGA CTGGTCGCCG CACGTGTGGA
 158 G  G  T  A    A  L  G    C  L  V    K  D  Y  F    P  E  P    V  T  V    S  W  N  S    G  A  L    T  S  G    V  H  T  F 1501 TCCCGGCTGT CCTACAGTCC TCAGGACTCT ACTCCCTCAG CAGCGTGGTG ACTGTGCCCT CTAGCAGCTT GGGCACCCAG ACCTACATCT GCAACGTGAA
     AGGGCCGACA GGATGTCAGG AGTCCTGAGA TGAGGGAGTC GTCGCACCAC TGACACGGGA GATCGTCGAA CCCGTGGGTC TGGATGTAGA CGTTGCACTT
 192 P  A  V  L    Q  S    S  G  L  Y    S  L  S    S  V  V    T  V  P  S    S  S  L    G  T  Q    T  Y  I  C    N  V  N 1601 TCACAAGCCC AGCAACACCA AGGTGGACAA GAAAGTTGAG CCCAAATCTT GTGACAAAAC TCACACATGC CCACCGTGCC CAGCACCTGA ACTCCTGGGG
     AGTGTTCGGG TCGTTGTGGT TCCACCTGTT CTTTCAACTC GGGTTTAGAA CACTGTTTTG AGTGTGTACG GGTGGCACGG GTCGTGGACT TGAGGACCCC
 225 H  K  P    S  N  T  K    V  D  K    K  V  E    P  K  S  C    D  K  T    H  T  C    P  P  C  P    A  P  E    L  L  G

FIG._34B
```

```
1701 GGACCGTCAG TCTTCCTCTT CCCCCCAAAA CCCAAGGACA CCCTCATGAT CTCCCCGGACC CCTGAGGTCA CATGCCTGGT GGTGACGTG AGCCACGAAG
     CCTGGCAGTC AGAAGGAGAA GGGGGGTTTT GGGTTCCTGT GGGAGTACTA GAGGGCCTGG GGACTCCAGT GTACGCACCA CCACCTGCAC TCGGTGCTTC
 258  G  P  S  V  F  L  F   P   P   P  K   P  K  D  T   L  M  I   S  R  T  P  E  V  T   C  V  V   V  D  V   S  H  E  D

1801 ACCCTGAGGT CAAGTTCAAC TGGTACGTGG ACGGCGTGGA GTGCATAAT CCACGCACCT GCCAAGACAA AGCCGCGGGA GGAGCAGTAC AACAGCACGT ACCGGGTGGT
     TGGGACTCCA GTTCAAGTTG ACCATGCACC TGCCGCACCT CCACGTATTA GGTGCGTGGA CGGTTCTGTT TCGGCGCCCT CCTCGTCATG TTGTCGTGCA TGGCCCACCA
 292  P  E  V   K  F  N   W  Y  V  D   G  V  E   V  H  N   A  K  T  K   P  R  E   E  Q  Y  N  S  T  Y   R  V  V

1901 CAGGGTCCTC ACCGTCCTGC ACCAGGACTG GCTGAATGGC AAGGAGTACA AGTGCAAGGT CTCCAACAAA GCCCTCCCAG CCCCCATCGA GAAAACCATC
     GTCCCAGGAG TGGCAGGACG TGGTCCTGAC CGACTTACCG TTCCTCATGT TCACGTTCCA GAGGTTGTTT CGGGAGGGTC GGGGGTAGCT CTTTTGGTAG
 325  S  V  L   T  V  L   H  Q  D  W   L  N  G   K  E  Y  K   C  K  V   S  N  K   A  L  P  A   P  I  E   K  T  I

2001 TCCAAAGCCA AAGGGCAGCC CCGAGAACCA CAGGTGTACA CCCTGCCCCC ATCCCGGGAA GAGATGACCA AGAACCAGGT CAGCCTGACC TGCCTGGTCA
     AGGTTTCGGT TTCCCGTCGG GGCTCTTGGT GTCCACATGT GGGACGGGGG TAGGGCCCCT CTCTACTGGT TCTTGGTCCA GTCGGACTGG ACGGACCAGT
 358  S  K  A  K   G  Q  P   P  R  E  P   Q  V  Y  T   L  P  P   S  R  E   E  M  T  K   N  Q  V   S  L  T   C  L  V  K

2101 AAGGCTTCTA TCCCAGCGAC ATCGCCGTGG AGTGGGAGAG CAATGGGCAG CCGGAGAACA ACTACAAGAC CACGCCTCCC GTGCTGGACT CCGACGGCTC
     TTCCGAAGAT AGGGTCGCTG TAGCCGGCACC TCACCCTCTC GTTACCCGTC GGCCTCTTGT TGATGTTCTG GTGCGGAGGG CACGACCTGA GGCTGCCGAG
 392  G  F  Y   P  S  D   I  A  V  E   W  E  S   N  G  Q   P  E  N  N   Y  K  T   P  P  P   V  L  D  S   D  G  S

2201 CTTCTTCCTC TACAGCAAGC TCACCGTGGA CAAGAGCAGG TGGCAGCAGG GGAACGTCTT CCTTGCAGAA GAGTACGAGG CACTACGTCC GTGATGCATG CAACCACTAC
     GAAGAAGGAG ATGTCGTTCG AGTGGCACCT GTTCTCGTCC ACCGTCGTCC CCTTGCAGAA GAACGTCTT CTCATGCTCC GTGATGCAGG CACTACTAC GTGGTGATG
 425  F  F  L   Y  S  K   L  T  V  D   K  S  R   W  Q  Q  G   N  V  F   S  C  S   V  M  H  E   A  L  H   N  H  Y

2301 ACGCAGAAGA GCCTCTCCCT GTCTCCGGGT AAATGAGTGC GACGGGCCCTA GAGTCGACCT GCAGAAGCTT GCCCAACTTG TTTATTGCAG
     TGCGTCTTCT CGGAGAGGGA CAGAGGCCCA TTTACTCACG CTGCCGGGAT CTCAGCTGGA CGTCTTCGAA CGGGTTGAAC AAATAACGTC
 458  T  Q  K  S   L  S  L   S  P  G   K  Q

2401 CTTATAATGG TTACAAATAA AGCAATAGCA TCACAAATTT CACAAATAAA GCATTTTTTT CACTGCCATTC TAGTTGTTGGT TTGTCCAAAC TCATCAATGT
     GAATATTACC AATGTTTATT TCGTTATCGT AGTGTTTAAA GTGTTTATTT CGTAAAAAAA GTGACGTAAG ATCAACACCA AACAGGTTTG AGTAGTTACA
```

FIG._34C

```
2501 ATCTTATCAT GTCTGGATCG ATCGGGAATT AATTCGGCGC AGCACCATGG CCTGAAATAA CCTCTGAAAG AGGAACTTGG TTAGTACCT TCTGAGGCGG
     TAGAATAGTA CAGACCTAGC TAGCCCTTAA TTAAGCCGCG TCGTGGTACC GGACTTTATT GGAGACTTTC TCCTTGAACC AATCCATGGA AGACTCCGCC

2601 AAAGAACCAT CTGTGGAATG TGTGTCAGTT AGGGTGTGGA AGTCCCCAG GCTCCCCAGC AGGCAGAAGT ATGCAAAGCA TGCATCTCAA TTAGTCAGCA
     TTTCTTGGTA GACACCTTAC ACACAGTCAA TCCCACACCT TTCAGGGGTC CGAGGGGTCG TCCGTCTTCA TACGTTTCGT ACGTAGAGTT AATCAGTCGT

2701 ACCAGGTGTG GAAAGTCCCC AGGCTCCCCA GCAGGCAGAA GTATGCAAAG CATGCATCTC AATTAGTCAG CAACCATAGT CCCGCCCCTA ACTCCGCCCA
     TGGTCCACAC CTTTCAGGGG TCCGAGGGGT CGTCCGTCTT CATACGTTTC GTACGTAGAG TTAATCAGTC GTTGGTATCA GGGCGGGGAT TGAGGCGGGT

2801 TCCCGCCCCT AACTCCGCCC AGTTCCGCCC ATTCTCCGCC CCATGGCTGA CTAATTTTTT TTATTTATGC AGAGGCCCGAG GCCGCCTCGG CCTCTGAGCT
     AGGGCGGGGA TTGAGGCGGG TCAAGGCGGG TAAGAGGCGG GGTACCGACT GATTAAAAAA AATAAATACG TCTCCGGCTC CGGCGGAGCC GGAGACTCGA

2901 ATTCCAGAAG TAGTGAGGAG GCTTTTTTGG AGGCCTAGGC TTTTTGCAAAA AGCTGTTAAC AGCTTGGCAC TGGCCGTCGT TTTACAACGT CGTGACTGGG
     TAAGGTCTTC ATCACTCCTC CGAAAAAACC TCCGGATCCG AAAACGTTTT TCGACAATTG ACCGGCAGCA AAATGTTGCA GCACTGACCC

3001 AAAACCCTGG CGTTACCCAA CTTAATCGCC TTGCAGCACA TCCCCCCTTC GCCAGTGGCG GTAATAGCGA AGAGGCCCGC ACCGATCGCC CTTCCAACA
     TTTTGGGACC GCAATGGGTT GAATTAGCGG AACGTCGTGT AGGGGGGAAG CGGTCAACCG CATTATCGCT TCTCCGGGCG TGGCTAGCGG GAAGGTTGT

3101 GTTGCGTAGC CTGAATGGCG AATGGCGCCT GATGCGGTAT TTTCTCCTTA CGCATCTGTG CCGTATTTCA CACCGCATAC GTCAAAGCAA CCATAGTACG
     CAACGCATCG GACTTACCGC TTACCGCGGA CTACGCCATA AAAGAGGAAT GCGTAGACAC GGCATAAAGT GTGGCGTATG CAGTTTCGTT GGTATCATGC

3201 CGCCCTGTAG CGGCGCATTA AGCGCGGCGG GTGTGGTGGT TACGCGCAGC GTGACCGCTA CACTTGCCAG CGCCCTAGCG CCCGCTCCTT TCGCTTTCTT
     GCGGGACATC GCCGCGTAAT TCGCGCCGCC CACACCACCA ATGCGCGTCG CACTGGCGAT GTGAACGGTC GCGGGATCGC GGGCGAGGAA AGCGAAAGAA

3301 CCCTTCCTTT CTCGCCACGT TCGCCGGCTT TCCCCGTCAA GCTCTAAATC GGGGGCTCCC TTTAGGGTTC CGATTTAGTG CTTTACGGCA CCTCGACCCC
     GGGAAGGAAA GAGCGGTGCA AGCGGCCGAA AGGGGCAGTT CGAGATTTAG CCCCCGAGGG AAATCCCAAG GCTAAATCAC GAAATGCCGT GGAGCTGGGG

3401 AAAAAACTTG ATTTGGGTGA TGGTTCACGT AGTGGGCCAT CGCCCTGATA CGGCGTTTTT CGCCCTTTGA CGTTGGAGTC CACGTTCTTT AATAGTGGAC
     TTTTTTTGAAC TAAACCCACT ACCAAGTGCA TCACCCGGTA GCGGGACTAT GCCGCAAAAA GCGGGAAACT GCAACCTCAG GTGCAAGAAA TTATCACCTG
```

*FIG._34D*

```
3501  TCTGTTCCA AACTGGAACA ACACTCAACC CTATCTCGGG CTATTCTTTT GATTTATAAG GGATTTGCC GATTTCGGCC TATTGGTTAA AAAATGAGCT
      AGAACAAGGT TTGACCTTGT TGTGAGTTGG GATAGAGCCC GATAAGAAAA CTAAATATTC CCTAAAACGG CTAAAGCCGG ATAACCAATT TTTTACTCGA

3601  GATTTAACAA AAATTAACG CGAATTTTAA CAAATATTA ACGTTACAA TTTTATGTG CACTCTCAGT ACAATCTGCT CTGATGCCGC ATAGTTAAGC
      CTAAATTGTT TTTAAATGT GCTTAAAATT GTTTTATAAT TGCAAATGTT AAAATACCAC GTGAGAGTCA TGTTAGACGA GACTACGGCG TATCAATTCG

3701  CAACTCCGCT ATCGCTACGT GACTGGGTCA TGGCTGCGCC CCGACACCCG CTGACGCGCC CTGACGGGCT TGTCTGCTCC CGGATCCGC
      GTTGAGGCGA TAGCCGATGCA CTGACCCAGT ACCGACGCGG GGCTGTGGGC GACTGCGCGG GACTGCCCGA ACAGACGAGG GCCGTAGGCG

3801  TTACAGACAA GCTGTGACCG TCTCCGGGAG CTGCATGTGT CAGAGGTTTT CACCGTCATC ACCGAAACGC GCGAGGCAGT ATTCTTGAAG ACGAAAGGGC
      AATGTCTGTT CGACACTGGC AGAGGCCCTC GACGTACACA GTCTCCAAAA GTGGCAGTAG TGGCCAGTAG CGCTCCGTCA TAAGAACTTC TGCTTTCCCG

3901  CTCGTGATAC GCCTATTTT ATAGGTTAAT GTCATGATAA TAATGGTTTC TTAGACGTCA GGTGGCACTT TTCGGGGAAA TGTGCGCGGA ACCCCTATTT
      GAGCACTATG CGGATAAAAA TATCCAATTA CAGTAGTATT AATTACCAAAG AATCTGCAGT CCACCGTGAA AAGCCCCTTT ACACGCGCCT TGGGGATAAA

4001  GTTTATTTTT CTAAATATGT TCAAATATGT ATCCGCTCAT GAGACAATAA TGCTTCAATA CCCTGATAAA ATATTGAAAA AGGAAGAGTA TGAGTATTCA
      CAAATAAAAA GATTTATGA AGTTTATACA TAGGGGAGTA CTCTGTTATT CTCTGATATT ACGAAGTTAT TATAACTTTT TCCTTCTCAT ACTCATAAGT

4101  ACATTTCCGT GTCGCCCTTA TTCCCTTTTT TGCGGCATTT TGCCTTCCTG TTTTTGCTCA CCCAGAAACG CTGGTGAAAG TAAAAGATGC TGAAGATCAG
      TGTAAGGCA CAGCGGGAAT AAGGGAAAAA ACGCCGTAAA ACGGAAGGAC AAAAACGAGT GGGTCTTTGC GACCACTTTC ATTTTCTACG ACTTCTAGTC

4201  TTGGGTGCAC GAGTGGGTTA CATCGAACTG GATCTCAACA GCGGTAAGAT CCTTGAGAGT TTTCGCCCCG AAGAAACGTTT TCCAATGATG AGCACTTTTA
      AACCCACGTG CTCACCCAAT GTAGCTTGAC CTAGAGTTGT CGCCATTCTA GGAACTCTCA AAAGCGGGGC TTCTTGCAAA AGGTTACTAC TCGTGAAAAT

4301  AAGTTCTGCT ATGTGGCGCG GTATTATCCC GTATGACGCC GGGCAAGAG CAACTCGGTC GCCGCATACA CTATTCTCAG AATGACTTGG TTGAGTACTC
      TTCAAGACGA TACACCGCGC CATAATAGGG CATACTGCGG CCCGTTCTC GTTGAGCCAG CGGCGTATGT GATAAGAGTC TTACTGAACC AACTCATGAG

4401  ACCAGTCACA GAAAAGCATC TTACGGATGG CATGACAGTA AGAGAATTAT GCAGTGCTGC CATAACCATG AGTGATAACA CTGCGGCCAA CTTACTCTG
      TGGTCAGTGT CTTTTCGTAG AATGCCTACC GTACTGTCAT TCTCTTAATA CGTCACGACG GTATTGGTAC TCACTATTGT GACGCCGGTT GAATGAGAC

4501  ACAACGATCG GAGGACCGAA GGAGCTAACC GCTTTTTTGC ACAACATGGG GGATCATGTA ACTCGCCTTG ATCGTTGGGA ACCGGAGCTG AATGAAGCCA
      TGTTGCTAGC CCTCCTGGCT TCCTCGATTGG CGAAAAACG TGTTGTACCC CCTAGTACAT TGAGCGGAAC TAGCAACCCT TGGCCTCGAC TTACTTCGGT
```

FIG.34E

```
4601  TACCAAACGA CGAGCGTGAC ACCACGATGC CAGCAGCAAT GGCAACAACG TTGCGCAAAC TATTAACTGG CGAACTACTT ACTCTAGCTT CCCGGCAACA
      ATGGTTTGCT GCTCGCACTG TGGTGCTACG GTCGTCGTTA CCGTTGTTGC AACGCGTTTG ATAATTGACC GCTTGATGAA TGAGATCGAA GGGCCGTTGT

4701  ATTAATAGAC TGGATGGAGG CGGATAAAGT TGCAGGACCA CTTCTGCGCT CGGCCCTTCC GGCTGGCTGG TTTATTGCTG ATAAATCTGG AGCCGGTGAG
      TAATTATCTG ACCTACCTCC GCCTATTTCA ACGTCCTGGT AAGACGCGAA GCCGGGAAGG CCGACCGACC AAATAACGAC TATTTAGACC TCGGCCACTC

4801  CGTGGGTCTC GCGTATCAT TCCAGCACTG GGGCCAGATG GTAAGCCCTC CCGTATCGTA GTTATCTACA CGACGGGGAG TCAGGCAACT ATGGATGAAC
      GCACCCAGAG CGCCATAGTA AGGTCGTGAC CCCGGTCTAC CATTCGGGAG GGCATAGCAT CAATAGATGT GCTGCCCCTC AGTCCGTTGA TACCTACTTG

4901  GAAATAGACA GATCGCTGAG ATAGGTGCCT CACTGATTAA GCATTGGTAA CTGTCAGACC AAGTTTACTC ATATATACTT TAGATTGATT TAAAACTTCA
      CTTTATCTGT CTAGCGACTC TATCCACGGA GTGACTAATT CGTAACCATT GACAGTCTGG TTCAAATGAG TATATATGAA ATCTAACTAA ATTTGAAGT

5001  TTTTTAATTT AAAAGGATCT AGTGAAGAT CCTTTTTGAT AATCTCATGA CCAAAATCCC TTAACGTGAG TTTTCGTTCC ACTGAGCGTC AGACCCCGTA
      AAAAATTAAA TTTTCCTAGA TCCACTTCTA GGAAAAACTA TTAGAGTACT GGTTTTAGGG AATTGCACTC AAAAGCAAGG TGACTCGCAG TCTGGGCAT

5101  GAAAGATCA AAGGATCTTC TTGAGATCCT TTTTTTCTGC GCGTAATCTG CTGCTTGCAA ACAAAAAAAC CACCGCTACC AGCGGTGGTT TGTTTGCCG
      CTTTTCTAGT TTCCTAGAAG AACTCTAGGA AAAAAAGACG CGCATTAGAC GACGAACGTT TGTTTTTTTG GTGGCGATGG TCGCCACCAA ACAAACGGCC

5201  ATCAAGAGCT ACCAACTCTT TTTTCCGAAGG TAACTGGCTT CAGCAGAGCG CAGATACCAA ATACTGTCCT TCTAGTGTAG CCGTAGTTAG GCCACCACTT
      TAGTTCTCGA TGGTTGAGAA AAAGGCTTCC ATTGACCGAA GTCGTCTCGC GTCTATGGTT TATGACAGGA AGATCACATC GGCATCAATC CGGTGGTGAA

5301  CAAGAACTCT GTAGCACCGC CTACATACCT CGCTCTGCTA ATCCTGTTAC CAGTGGCTGC GTCACCGACG GATAAGTCGT GTCTTACCGG GTTGGACTCA
      GTTCTTGAGA CATCGTGGCG GATGTATGGA GCGAGACGAT TAGGACAATG GTCACCGACG ACGGTCACCG CTATTCAGCA CAGAATGGCC CAACCTGAGT

5401  AGACGATAGT TACCGGATAA GGCGCAGCGG TCGGGCTGAA CGGGGGGTTC GTGCACACAG CCCAGCTTGG AGCGAACGAC CTACACCGAA CTGAGATACC
      TCTGCTATCA ATGGCCTATT CCGCGTCGCC AGCCCGACTT GCCCCCCAAG CACGTGTGTC GGGTCGAACC TCGCTTGCTG GATGTGGCTT GACTCTATGG

5501  TACAGCGTGA GCATTGAGAA AGCGCCACGC TTCCCGAAGG GAGAAAGGCG GACAGGTATC CGGTAAGCGG CAGGGTCGGA ACAGGAGAGC GCACGAGGGA
      ATGTCGCACT CGTAACTCTT TCGCGGTGCG AAGGGCTTCC CTCTTTCCGC CTGTCCATAG GCCATTCCGC GTCCCAGCCT TGTCCTCTCG CGTGCTCCCT

5601  GCTTCCAGGG GGAAACGCCT GGTATCTTTA TAGTCCTGTC GGGTTTCGCC ACCTCTGACT TGAGCGTCGA TTTTTGTGAT GCTCGTCAGG GGGGCGGAGC
      CGAAGGTCCC CCTTTGCGGA CCATAGAAAT ATCAGGACAG CCCAAAGCGG TGGAGACTGA ACTCGCAGCT AAAAACACTA CGAGCAGTCC CCCCGCCTCG
```

FIG._34F

5701 CTATGGAAAA ACGCCAGCAA CGGCGGCCTT TTACGGTTCC TGGCCTTTTG CTGGCCTTTT GCTCACATGT TCTTTCCTGC GTTATCCCCT GATTCTGTGG
     GATACCTTTT TGCGGTCGTT GCGCCGGAAA AATGCCAAGG ACCGGAAAAC GACCGGAAAA CGAGTGTACA AGAAAGGACG CAATAGGGGA CTAAGACACC

5801 ATAACCGTAT TACCGCCTTT GAGTGAGCTG ATACCGCTCG CCGCAGCCGA ACGACCGAGC GCAGCGAGTC AGTGAGCGAG GAAGCGGAAG AGCGCCCAAT
     TATTGGCATA ATGGCGGAAA CTCACTCGAC TATGGCGAGC GGCGTCGGCT TGCTGGCTCG CGTCGCTCAG TCACTCGCTC CTTCGCCTTC TCGCGGGTTA

5901 ACGCAAACCG CCTCTCCCCG CGCGTTGGCC GATTCATTAA TCCAACTGGC ACGACAGGTT TCCCGACTGG AAAGCGGGCA GTGAGCGCAA CGCAATTAAT
     TGCGTTTGGC GGAGAGGGGC GCGCAACCGG CTAAGTAATT AGTTGACCG TGCTGTCCAA AGGGCTGACC TTTCGCCCGT CACTCGCGTT GCGTTAATTA

6001 GTGAGTTACC TCACTCATTA GGCACCCCAG GCTTTACACT TTATGCTTCC GGCTCGTATG TTGTGTGGAA TTGTGAGCGG ATAACAATTT CACACAGGAA
     CACTCAATGG AGTGAGTAAT CCGTGGGGTC CGAAATGTGA AATACGAAGG CCGAGCATAC AACACACCTT AACACTCGCC TATTGTTAAA GTGTGTCCTT

6101 ACAGCTATGA CCATGATTAC GAATTA
     TGTCGATACT GGTACTAATG CTTAAT

FIG._34G

| LC Frequency | | | | | | | | | |
|---|---|---|---|---|---|---|---|---|---|
| 28 | S 511 | N 262 | V 258 | D 186 | G 178 | I 44 | T 39 | L 16 | X 35 |
| 29 | I | S 272 | V 254 | G 192 | N 147 | X 70 | | | |
| 30 | S 612 | N 176 | K 169 | G 86 | R 81 | Y 63 | T 29 | D 28 | A 17 X 53 |
| 31 | S 849 | N 496 | T 170 | R 47 | I 29 | D 28 | K 25 | G 18 X 69 | |
| 32 | S 676 | Y 128 | W 97 | F 77 | S 61 | D 40 | R 25 | | |
| 50 | Y 1055 | A 341 | D 294 | W 151 | K 116 | L 91 | E 39 | S 30 | X 82 |
| 53 | G 386 | N 438 | T 407 | K 41 | I 23 | R 23 | X 58 | | |
| 91 | S 545 | S 196 | R 169 | A 118 | G 61 | H 41 | X 148 | | |
| 92 | Y 849 | G 356 | N 248 | S 193 | D 114 | L 94 | T 64 | H 43 | I 38 X 91 |
| 93 | Y 362 | N 346 | Q 117 | T 101 | H 66 | G 51 | D 47 | R 35 | X 112 I 24 |
| 94 | S 738 | T 365 | W 288 | Y 172 | L 114 | F 79 | A 46 | P 43 | V 33 N 18 |
| 96 | S 386 | Y 205 | W 176 | F 140 | I 117 | R 115 | P 46 | X 121 | X 40 |
| | L 264 | | | | | | | | |

*FIG. 35*

| Residue | Natural Diversity | Diversity < DNA codon | % good | % covering |
|---|---|---|---|---|
| L1-28 | SNVDGI | SNVDGI<RDT> | 100% | 94% |
| L1-29 | ISVGN | ISVG<RKT> | 100% | 86% |
| L1-29 | | IV<RTT> | 100% | 56% |
| L1-30 | SNKGRYTDA | SNKGGRTTDAAE<RVW> | 92% | 93% |
| L1-31 | SNTRIDKG | SNTTRDKGGAAE<RVW> | 75% | 95% |
| L1-31 | | SNTTRIIK<ANW> | 100% | 94% |
| L1-32 | YNWFSDR | YNFSDATIV<DHT> | 55% | 88% |
| L1-32 | | YFS<THT> | 100% | 77% |
| L2-50 | GADWKLES | GAWLSV<KBG> | 83% | 67% |
| L2-53 | SNTKIR | SNT<AVC> | 100% | 90% |
| L3-91 | YSRAGH | YSAD<KMT> | 75% | 74% |
| | | YS<TMT> | 100% | 66% |
| L3-92 | YGNSDLTHI | YNSDTIFAV<DHT> | 67% | 64% |
| | | YNSDTA<DMC> | 83% | 62% |
| L3-93 | SNQTHGDR | SNTGDA<RVT> | 83% | 80% |
| | | SNTDYAFIV<DHT> | 44% | 76% |
| L3-94 | STWYLFAPVI | STYLFAPVINDH<NHT> | 75% | 78% |
| | | STYFIN<WHT> | 83% | 43% |
| L3-96 | LYWFIRP | LYFPHS<YHT> | 67% | 52% |
| | | LYFIHN<HWT> | 67% | 58% |
| | | LFI<HTT> | 100% | 42% |
| | | LLWR<YKG> | 100% | 47% |
| | | YF<TWT> | 100% | 29% |

*FIG. 36*

Light Chain Designed Diversity
Diversity: ~ 2.9 x 10$^9$

CDR-L1: diversity ~ 7 x 10$^3$

| 28 | 29 | 30 | 31 | 32 |
|---|---|---|---|---|
| RDT | RTT | RVW | RVW | DHT |
| D | I | D | D | A |
| G | V | E | E | D |
| I | | G | G | F |
| N | | K | K | I |
| S | | N | N | N |
| V | | S | S | S |
| | | T | T | T |
| | | R | R | V |
| | | | | Y |

CDR-L2: diversity = 18

| 50 | 53 |
|---|---|
| KBG | AVC |
| A | N |
| G | S |
| L | T |
| S | |
| V | |
| W | |

CDR-L3: diversity ~ 2.3 x 10$^4$

| 91 | 92 | 93 | 94 | 96 |
|---|---|---|---|---|
| KMT | DHT | DHT | NHT | YHT |
| A | A | A | A | F |
| D | D | D | D | H |
| S | F | F | F | L |
| Y | I | I | H | P |
| | N | N | I | S |
| | S | S | L | Y |
| | T | T | N | |
| | V | V | P | |
| | Y | Y | S | |
| | | | T | |
| | | | V | |
| | | | Y | |

FIG. 37

Light Chain Designed Diversity
Diversity: ~ 6.1 x 10$^8$

CDR-L1: diversity ~ 3.4 x 10$^3$

| 28 | 29 | 30 | 31 | 32 |
|---|---|---|---|---|
| RDT | RTT | RVW | ANW | THT |
| D | I | D | I | F |
| G | V | E | K | S |
| I | | G | N | Y |
| N | | K | R | |
| S | | N | S | |
| V | | S | T | |
| | | T | | |
| | | V | | |

CDR-L2: diversity = 18

| 50 | 53 |
|---|---|
| KBG | AVC |
| A | N |
| G | S |
| L | T |
| S | |
| V | |
| W | |

CDR-L3: diversity ~ 1.0 x 10$^4$

| 91 | 92 | 93 | 94 | 96 |
|---|---|---|---|---|
| KMT | DMC | RVT | NHT | YHT |
| A | A | A | A | F |
| D | D | D | D | H |
| S | N | G | F | L |
| Y | S | N | H | P |
| | T | S | I | S |
| | Y | T | L | Y |
| | | | N | |
| | | | P | |
| | | | S | |
| | | | T | |
| | | | V | |
| | | | Y | |

FIG. 38

Light Chain Designed Diversity

CDR-L3: diversity ~ 1.3 x 10³

| 91 | 92 | 93 | 94 | 96 |
|---|---|---|---|---|
| TMT | DMC | RVT | WHT | HTT |
| S | A | A | F | F |
| Y | D | D | I | I |
|  | N | G | N | L |
|  | S | N | S |  |
|  | T | S | T |  |
|  | Y | T | Y |  |

FIG. 39

CDR-L1

| 28 | 29 | 30 | 31 | 32 |
|---|---|---|---|---|
| RDT | RTT | RVW | RVW | DHT |
| D | I | D | D | A |
| G | V | E | E | D |
| I |  | G | G | F |
| N |  | K | K | I |
| S |  | N | N | N |
| V |  | S | S | S |
|  |  | T | T | T |
|  |  | V | V | V |
|  |  |  |  | Y |

CDR-L2

| 50 | 53 |
|---|---|
| DVK | AVM |
| A | N |
| G | K |
| L | R |
| S | S |
| V | T2 |
| W |  |

CDR-L3

| 91 | 92 | 93 | 94 | 96 |
|---|---|---|---|---|
| NRT | NRT | RVM | NNK | TDK |
| C | C | A2 | A | C |
| D | D | D | C | F |
| G | G | E | D | L |
| H | H | G2 | E | W |
| N | N | K | F | Y |
| R | R | N | G | * |
| S | S | R | H |  |
| Y | Y | S | I |  |
|  |  | T2 | L |  |
|  |  |  | M |  |
|  |  |  | N |  |
|  |  |  | P |  |
|  |  |  | Q |  |
|  |  |  | R |  |
|  |  |  | etc |  |
|  |  |  | * |  |

*Amber stop codon is encoded by the degenerate codon

FIG. 40

COMPOSITIONS AND METHODS RELATING TO STOP-1

This application claims benefit from U.S. Provisional Application No. 60/463,656, filed Apr. 16, 2003, which application is incorporated by reference herein in its entirety.

FIELD OF THE INVENTION

The present invention is directed to STOP-1 polypeptides, antibodies, nucleic acid molecules, antagonists, agonists, potentiators and compositions relating to STOP-1, and methods of making and using the same, including methods for diagnosing and treating of tumors in mammals. The present invention further relates to the diagnosis and treatment of disorders involving angiogenesis and vasculogenesis (e.g., cardiovascular as well as oncological disorders).

BACKGROUND AND INTRODUCTION OF THE INVENTION

Uncontrolled cell growth is the cause of many illnesses in a variety of cell types. For example, cancer occurs when there is an increase in the number of abnormal, or neoplastic, cells derived from a normal tissue that proliferate to form a tumor mass. The tumor cells often invade the adjacent tissues and can spread via the blood or lymphatic system to regional lymph nodes and to distant sites via a process called metastasis. In a cancerous growth, a cell proliferates under conditions in which normal cells would not grow. Cancer manifests itself in a wide variety of forms, characterized by different degrees of invasiveness and aggressiveness. Malignant tumors (cancers) are the second leading cause of death in the United States, after heart disease (Boring et al., *CA Cancel J. Clin.* 43:7 (1993)).

Much research has been devoted to discovering new treatments for cell proliferative disorders, such as cancer. Despite recent advances, there is a great need to identify and understand the role of new cellular targets for modulating cell proliferation and to develop alternative or more effective methods of treatment and therapeutic and diagnostic agents. There is also a need to develop alternative therapeutics and methods for treating specific cell types and for treating illnesses caused by or associated with abnormal cell proliferation, such as cancers. For example, desmoplasia is the hyperplasia of fibroblasts and disproportionate formation of fibrous connective tissue, especially in the stroma of carcinomas. Desmoplasia is a hallmark of tumor invasion and malignancy. Desmoid tumors and abdominal fibroids are nodules or relatively large masses of unusually firm scarlike connective tissue resulting from active proliferation of fibroblasts, occurring most frequently in the abdominal muscles of women who have borne children; the fibroblasts infiltrate surrounding muscle and fascia.

In post-natal life, vasculogenesis (endothelial cells forming a primary tubular network) and angiogenesis (the growth or sprouting of new blood vessels from existing vessels) play critical roles in the pathophysiology of neoplastic disorder (Semenza, G. L., (2003) *Ann. Rev. Med.* 54:17-28). The distinction between vasculogenesis and angiogenesis is not absolute and they overlap (Ribatti, D et al., (2001) *Mech. Dev.* 100:157-163). Both require endothelial cell proliferation, migration, three-dimensional reorganization of newly formed aggregates and use similar extracellular matrix adhesive mechanisms (Ribatti, supra). Use of anti-angiogenic therapies such as the antibody against vascular endothelial growth (VEGF) called Avastin have been shown to be useful in treating cancers.

Another cellular protein, referred to herein as STOP-1 or UNQ762, has been shown to be overexpressed in certain tumors (e.g., WO 01/163318, WO 01/68848, WO 02/00690, WO 02/08284, WO 02/16602, WO 02/42487). Polyclonal antibodies against STOP-1 have been reported (e.g., WO 02/42487). Although there has been some discussion of targeting STOP-1 to treat cancers and diseases associated with angiogenesis (e.g., WO 01/163318, WO 01/68848, WO 02/00690, WO 02/08284, WO 02/16602, WO 02/42487, WO 00/71581, WO 02/00690), there is a need to further explore the biology of the STOP-1 protein to identify alternative and more effective therapeutic agents and methods for diagnosis and treatment of uncontrolled cell growth and diseases caused by, associated with or complicated by excessive and insufficient angiogenesis.

The present invention addresses these needs and others by providing new STOP-1 polypeptides, antibodies, nucleic acid molecules, compositions and methods that incorporate further knowledge about the STOP-1 protein. Among other things, the present disclosure shows that STOP-1 is overexpressed in the stroma of several tumor types. The present disclosure shows that overexpression of STOP-1 alone can be tumorigenic. Further, the present disclosure demonstrates that the STOP-1 protein can be secreted and that secretion is required for tumorigenesis. Still further, the present disclosure shows that the glycosylation state of STOP-1 affects whether it is secreted and that elimination of a N-glycosylation site, e.g., by substituting the amino acid at position 186 (Asn) with alanine results in loss of secretion. The present disclosure shows that disulfide bonding between STOP-1 proteins can occur at a cysteine 55 in culture in the triple helix domain of STOP-1. Additionally, the present disclosure shows that the STOP-1 protein can form a complex with itself as a dimer, trimer and hexamer and that the c-terminus of the protein is sufficient for oligomerization, whereas a region related to the triple helix domain of collagen is not required. The present disclosure also shows a plurality of agents that specifically bind to STOP-1, including the C-terminal region and N-terminal region of the protein as well as nucleic acid and protein sequences encoding them. Further, the present disclosure shows that STOP-1 expression can be modulated by overexpression of proteins in the WNT signalling pathway that are know to cause breast cancer in mice, e.g., the overexpression of WNT. Additionally, the present disclosure shows that STOP-1 can be cleaved by proteases that are overexpressed in the same tumors as STOP-1, e.g., MMP-9. Further, the present disclosure shows that a method for producing STOP-1 polypeptides by expressing the polypeptides in proteoglycan synthesis deficient cell lines. The present invention shows that STOP-1 binds to the surface of cells, such as cancer cells and endothelial cells. The present invention provides antagonistic molecules that can inhibit the interaction of STOP-1 with the surface of cells. The present invention provides molecules that can potentiate the binding of STOP-1 with the surface of cells. The present invention also relates to the role of STOP-1 in angiogenesis and vasculogenesis and methods and compositions for treating disorders for which treatment would be improved by modulating angiogenesis and vasculogenesis. This data and others provided herein, together with other disclosure of in present application, teach new, better and/or alternative methods for using the STOP-1 protein or compositions relating thereto.

SUMMARY OF THE INVENTION

The present invention provides new therapeutic agents, diagnostic agents and methods for treating or preventing uncontrolled cell proliferation, including cancer, and other diseases by targeting the activity, expression and regulation of STOP-1. The present invention provides new therapeutic agents, diagnostic agents and methods for treating a any medical condition having suboptimal, excessive or inappropriate angiogenic or vasculogenic events by targeting the activity, expression and regulation of STOP-1.

According to one embodiment, the present invention provides a monoclonal antibody that specifically binds to an oligomeric form of human STOP-1. According to another embodiment, the present invention provides, a monoclonal antibody that specifically binds to amino acids 33-53 or 33-52 of human STOP-1. In yet another embodiment, the present invention includes a monoclonal antibody that specifically binds to amino acids 94-243 of human STOP-1. According to further embodiment, the monoclonal antibody that specifically binds to residues 94-243 of human STOP-1 or residues 33-53 or 33-52 of human STOP-1 also recognizes an oligomeric form of human STOP-1, such as the trimeric form. An antibody according to this invention can be isolated. It is understood that an aforementioned antibody that specifically binds a residue within residues 33-52 or 33-53 of human STOP-1 may also bind to other residues within STOP-1 or non-human equivalents thereof.

In yet another embodiment, the present invention provides monoclonal antibodies having the biological characteristics of an antibody selected from the group consisting of S7 encoded by the nucleic acid molecule deposited on Mar. 25, 2003 as designation V0350-4-S7, S4 encoded by the nucleic acid molecule deposited on Mar. 25, 2003 as designation V0350-2b-S4, S9 encoded by the nucleic acid molecule deposited on Mar. 25, 2003 as designation V0350-2b-S9, S16 encoded by the nucleic acid molecule deposited on Mar. 25, 2003 as designation V0350-4-S16, F5 encoded by the nucleic acid molecule deposited on Mar. 25, 2003 as designation V0350-5 and 6B12 produced by the hybridoma cell line deposited on Mar. 28, 2003 as designation 6B12.1.7 in the American Type Culture Collection (ATCC), 10801 University Blvd., Manassas, Va. 20110-2209, USA, including the deposited antibodies, antibodies comprising a portion of those antibodies and variants thereof. In another embodiment, the present invention provides antibodies that specifically bind to STOP-1, wherein the binding of the antibodies to STOP-1 can be inhibited (e.g., as observed in a competitive ELISA assay) by a second monoclonal antibody selected from one of the aforementioned deposited antibodies.

The present invention also relates to antibodies having the following sequences:

A monoclonal antibody comprising:
(a) a first amino acid sequence comprising:

T-I-X1-X2-X3-X4 wherein X1 is S, N or T;
wherein X2 is G, N, S or A;
wherein X3 is Y, S or T; and
wherein X4 is D or W.
(b) a second amino acid sequence comprising:

X1-X2-I-X3-P-X4-X5-G-X6-T-X7    (SEQ ID NO: 115)

wherein X1 is G or A;
wherein
(1) X2 is an amino acid selected from the group consisting of S, T, A, and X3 is an amino acid selected from the group consisting of R, W and Y; or (2) X3 is an amino acid selected from the group consisting of S, T, A, and X2 is an amino acid selected from the group consisting of R, W and Y;
wherein X4 is Y or F;
wherein X5 is G, S, T or A;
wherein X6 is N, Y or A; and
wherein X7 is N, Y or D; and
(c) a third amino acid sequence comprising the sequence:

(SEQ ID NO: 116)
C-X1-X2-X3-G-G-X4-X5-X6-X7-X8-X9-X10-X11 wherein X1 is A, S or T;
wherein X2 is basic amino acid;
wherein X3 is any amino acid;
wherein X4 is a hydrophobic amino acid;
wherein any one of X5-X8 can be any amino acid or can be missing, and at least one of X5-X8 is an aromatic amino acid or a hydrophobic amino acid;
wherein X9 is an aromatic or hydrophobic amino acid;
wherein X10 is D or A; and
wherein X11 is Y or V.

According to one embodiment, the monoclonal antibody comprises the light chain sequence of FIG. 34. According to another embodiment, the monoclonal antibody is a full-length IgG.

According to one embodiment of this invention, the X1 of the first amino acid sequence is S. According to another embodiment of this invention, the X2 the first amino acid sequence is G. According to yet another embodiment of this invention, X3 of the first amino acid sequence is S. According to one embodiment, the first amino acid sequence is a sequence selected from the group consisting of TISGSD (SEQ ID NO:8), TITNSD (SEQ ID NO:11) and TISGSW (SEQ ID NO:17).

According to yet another embodiment of this invention, X3 of SEQ ID NO:115 is S or A. According to yet another embodiment of this invention, X4 of SEQ ID NO:115 is Y. According to yet another embodiment of this invention, X5 of SEQ ID NO:115 is G or A. According to yet another embodiment of this invention, X6 of SEQ ID NO:115 is N or A. According to one embodiment, SEQ ID NO:115 is a sequence selected from the group consisting of GRISPYGGNTN (SEQ ID NO:9), ATIYPYGGYTY (SEQ ID NO:12) and AWIAPY-SGATD (SEQ ID NO:18).

According to one embodiment of this invention, the X1 of SEQ ID NO:116 is A. According to another embodiment of this invention, the X2 of SEQ ID NO:116 is R. According to yet another embodiment of this invention, X4 of SEQ ID NO:116 is L or M. According to one preferred embodiment of this invention, the aromatic amino acid present in X5-X8 is a tryptophan residue. According to another embodiment, one amino acid of X5-X8 is missing. According to yet another embodiment of this invention, X9 of SEQ ID NO:116 is F. According to one embodiment of this invention, X10 of SEQ ID NO:116 is D. According to one embodiment of this invention, X11 of SEQ ID NO:116 is Y. According to one embodiment, the SEQ ID NO:116 is a sequence selected from the group consisting of CARVGGLKLLFDY (SEQ ID NO:10), CARGGGMDGYVMDY (SEQ ID NO:13) and CAREG-GLYWVFDY (SEQ ID NO:19).

An antibody according to this invention can comprise (a) a first amino acid sequence comprising the sequence TISGSD (SEQ ID NO:8); (b) a second amino acid sequence comprising the sequence GRISPYGGNTN (SEQ ID NO:9); and (c) a third amino acid sequence comprising the sequence CARVG- GLKLLFDY (SEQ ID NO:10), or a variant of said antibody. Alternatively, an antibody according to this invention can comprise (a) a first amino acid sequence comprising the sequence TITNSD (SEQ ID NO:11); (b) a second amino acid sequence comprising the sequence ATIYPYGGYTY (SEQ ID NO:12); and (c) a third amino acid sequence comprising the sequence CARGGGMDGYVMDY (SEQ ID NO:13); or a variant of said antibody. Alternatively, an antibody according to this invention can comprise (a) a first amino acid sequence comprising the sequence TISGSW (SEQ ID NO:17); (b) a second amino acid sequence comprising the sequence AWIAPYSGATD (SEQ ID NO:18); and (c) a third amino acid sequence comprising the sequence CAREGGLYWVFDY (SEQ ID NO:19); or a variant of said antibody. Alternatively, an antibody according to this invention can comprises (a) a first amino acid sequence comprising the sequence TISNYG (SEQ ID NO:20); (b) a a second amino acid sequence comprising the sequence GRISPSNGSTY (SEQ ID NO:21); and (c) a third amino acid sequence comprising the sequence CAKCSVRFAY (SEQ ID NO:22); or a variant of said antibody. Alternatively, an antibody according to this invention can comprise (a) a first amino acid sequence comprising the sequence TINNYD (SEQ ID NO:14); (b) a second amino acid sequence comprising the sequence GYISPPSGATY (SEQ ID NO:15); and (c) third amino acid sequence comprising the sequence CARMVGMRRGVMDY (SEQ ID NO:16); or a variant of said antibody.

In a further embodiment, the first, second and third amino acid sequences described above are located in a human heavy chain wherein the first amino acid sequence is at residues 28-33 of the heavy chain according to the Kabat numbering system, the second amino acid sequence is at residues 49-58 of the heavy chain according to the Kabat numbering system and the third amino acid sequence is at residues 92-102 according to the Kabat numbering system.

In another embodiment, the present invention provides a monoclonal antibody comprising the amino acid sequence of: (a) the heavy chain sequence of FIG. 27; (b) the heavy chain sequence of FIG. 28; (c) the heavy chain sequence of FIG. 29; (d) the heavy chain sequence of FIG. 30; (e) the heavy chain sequence of FIG. 31; or (f) the heavy chain sequence of FIG. 34; or variants thereof. In a further embodiment, the antibodies of this invention further comprise (a) the light chain sequence of FIG. 27, (b) the light chain sequence of FIG. 34; or variants thereof.

In a further embodiment, the antibodies of this invention are chimeric or humanized antibodies. In another embodiment, the antibodies of this invention are antibody fragments. In yet another embodiment of this invention, the antibodies are conjugated to an agent selected from the group consisting of a stromal targeting agent, a growth inhibitory agent, a cytotoxic agent, a detection agent, an agent that improves the bioavailability and an agent that improves the half-life of the antibody. In another embodiment, the antibody of this invention is a multi-specific antibody having a binding specificity for a STOP-1 polypeptide and one or more binding specificities for any other antigen. According to one embodiment, the other antigen is a cell-surface protein or receptor or receptor subunit. According to one preferred embodiment, the cell-surface protein is a natural killer (NK) receptor. According to a more preferred embodiment, the binding of the antibody to the NK receptor activates the natural killer cell.

The present invention provides variants and modifications of STOP-1 polypeptide variants. In one embodiment, the STOP-1 polypeptide variant that cannot be secreted from a cell. In another embodiment, said variant is a human STOP-1 polypeptide that is not glycosylated. In a further embodiment, the variant is a human STOP-1 polypeptide that is mutated at residue 186. The present invention also provides a STOP-1 variant polypeptide comprising STOP-1 that cannot disulfide bind with another STOP-1. According to one embodiment, the variant is a human STOP-1 polypeptide that is mutated at residue 55.

The present invention also provides nucleic acid molecules encoding the antibodies and polypeptides and variants thereof, vectors comprising the nucleic acid molecules, and host cells comprising the nucleic acid molecules of this invention.

The present invention includes compositions comprising an antibody, a polypeptide or a nucleic acid molecule of this invention. According to one embodiment, the composition further comprises a pharmaceutically acceptable carrier. In a further embodiment, the composition comprises a stromal targeting agent. In a further embodiment, the stromal targeting agent is covalently linked to the monoclonal antibody or polypeptide. In yet a further embodiment, the stromal targeting agent recognizes a stromal cell of a tumor.

The present invention provides methods for producing a STOP-1 polypeptide or an anti-STOP-1 antibody of this invention by culturing a cell comprising a nucleic acid according to this invention. According to one embodiment, the method for producing a STOP-1 polypeptide comprises the step of culturing a mammalian cell that comprises a nucleic acid molecule encoding the STOP-1 polypeptide and that is deficient in proteoglycan synthesis. According to another embodiment, the cell line that is deficient in proteoglycan synthesis is deficient in galactosyltransferase I activity. According to one preferred embodiment, the cell line is a CHO-psbg cell line.

The present invention provides a method for determining the presence of a STOP-1 polypeptide in a sample comprising exposing a sample suspected of containing the STOP-1 polypeptide to an anti-STOP-1 antibody and determining binding of said antibody to a component of said sample. According to one embodiment, the antibody is a monoclonal antibody of this invention.

The present invention provides methods for diagnosing or monitoring a cell proliferative disorder, such as a tumor, of a patient comprising the step of comparing the expression of STOP-1 in a normal tissue to the amount of STOP-1 being tested from the patient. In one embodiment, a STOP-1 protein can be detected by an agent such as an antibody of this invention. In another embodiment, STOP-1 mRNA can be detected by an agent such as a nucleic acid molecule that specifically hybridizes to the UNQ6762 mRNA. In a further embodiment, the tumor being tested has a large stromal compartment. In a further embodiment, STOP-1 detection agent is administered at or near the stromal compartment of the tissue being tested. In yet another embodiment, the method further comprises the step of observing or assaying the STOP-1 protein or mRNA in the stromal compartment agent of the normal tissue and tissue being tested. In another embodiment, the antibody is a monoclonal antibody of this invention.

The present invention provides a method of preventing or treating a proliferative disorder in a patient comprising the step of administering to the patient a composition of this invention in an amount effective to inhibit the proliferation of cells in the patient. In one embodiment, the proliferative disorder is desmoplasia. The present invention also provides a method of preventing or inhibiting the growth of a tumor that overexpresses STOP-1 in a patient comprising administering to the patient an antagonist of STOP-1 in an amount effective to inhibit growth of the tumor in the patient. In a further embodiment, the tumor to be treated has stromal compartments. In yet a further embodiment, the tumor having stromal compartments is selected from the group consisting of desmoid tumors, pancreatic cancer, sarcomas (e.g., hemangiosarcoma, rhabdomyosarcoma) and adenocarcinomas (mammary adenocarcinomas, colon adenocarcinomas, gastrointestinal adenocarcinomas and ovarian adenocarcinomas), hepatocellular carcinoma, breast cancer, colon cancer, lung cancer, ovarian cancer, glioma, endometrial cancer and vascular cancer. In a further embodiment, the antagonist is administered at or near a stroma of the tumor. In another embodiment, the tumor is a melanoma or a round cell tumor (e.g., malignant fibrous hystiocytoma).

An antagonist according to this invention is any molecule that partially or fully blocks, inhibits, or neutralizes a biological activity of a native STOP-1 polypeptide and that specifically binds to a native STOP-1 polypeptide, wherein the binding of the antagonistic molecule (1) is to a native STOP-1 polypeptide in oligomeric form, (2) is to residues 94-243 of native human STOP-1 and/or (3) can be inhibited (e.g., as observed in a competitive ELISA assay using STOP-1 and 6B12) by a monoclonal antibody of this invention (e.g., a deposited antibody of this invention, etc.). According to one embodiment, the deposited antibody is the 6B12 antibody. According one embodiment, the antagonist is a polypeptide. According to another embodiment, the antagonist is an antibody of this invention. In another embodiment, the STOP-1 polypeptide that the antagonist inhibits is part of a trimeric complex.

According to another embodiment, the biological activity that is inhibited by the antagonist is the interaction of STOP-1 with a cell that specifically binds STOP-1. According to one embodiment, the cell is a breast cancer cell. According to another embodiment, the cell is an endothelial cell. According to yet another embodiment, the antagonist has an additional property selected from the group consisting of (1) capable of binding to an epitope within human STOP-1 that the 6B12 antibody binds; (2) capable of binding to a residue within at least residues 33-52 of human STOP-1; and (3) capable being competed from binding to STOP-1 by the 6B12 antibody (e.g., as observed in a competitive ELISA assay using STOP-1, the antagonist and the 6B12 antibody).

The present invention provides a method for inhibiting the growth of a cell that overexpresses STOP-1 comprising the step of inhibiting the secretion of STOP-1 from the cell. In one embodiment, secretion is inhibited by inhibiting glycosylation of STOP-1. In another embodiment, the secretion is inhibited by overexpressing a STOP-1 protein that cannot be secreted in the cell. In a further embodiment, the secretion is inhibited by a STOP-1 protein that is mutated at residue 186.

The present invention provides a method for preventing disulfide binding between STOP-1 molecules comprising a step selected from the group consisting of: (1) mutating STOP-1-encoding DNA molecules at residue cysteine 55; (2) expressing STOP-1 proteins that are mutated at residue cysteine 55 in the presence of naturally-occurring STOP-1 proteins; and (3) incubating STOP-1 proteins that are mutated at residue cysteine 55 with naturally-occurring STOP-1 proteins.

The present invention provides a method for cleaving STOP-1 comprising the step of incubating STOP-1 with a protease selected from the group consisting of a matrix metalloprotease-7 (MMP-7) and a matrix metalloprotease-9 (MMP-9). In a further embodiment, the method additionally comprises the step of monitoring the STOP-1 cleavage products produced.

Another embodiment of the present invention is directed to a method for inhibiting the growth of a cell that overexpresses a STOP-1 polypeptide, wherein the method comprises administering an antagonist of STOP-1, wherein the antagonist specifically binds to STOP-1 and is optionally conjugated to one or a combination of the agent(s) selected from the group consisting of a stromal targeting agent, a growth inhibitory agent or cytotoxic agent such as a toxin, including, for example, a maytansinoid or calicheamicin, an antibiotic, a radioactive isotope and a nucleolytic enzyme. Another embodiment of the present invention is directed to a method for inhibiting the growth of a cell that overexpresses a STOP-1 polypeptide, wherein the method comprises administering an agent to a stromal cell of the tumor, wherein the agent is an antagonist of STOP-1 or a nucleic acid molecule encoding a STOP polypeptide. The agent can be administered to the stromal cell directly by a patient or physician or indirectly, through the use of stromal targeting agents that can direct the agent to the stromal cell. The present invention provides an article of manufacture comprising (a) a composition of matter comprising a modified STOP-1 polypeptide, a STOP-1 polypeptide variant, STOP-1 antagonist, STOP-1 agonist, STOP-1 potentiator or a nucleic acid molecule encoding a STOP-1 polypeptide conjugated to a vehicle (e.g., such as antisense therapy or RNAi therapy); (b) a container containing said composition; and (c) a label affixed to said container, or a package insert included in said container referring to the use of said polypeptide variant, modified polypeptide or antagonist in the treatment of a proliferative disorder or a disease associated with abnormal angiogenesis or vasculogenesis (e.g., a package insert). According to one embodiment, the STOP-1 antagonist or potentiator is an antibody of this invention.

The present invention provides methods for testing the activity of STOP-1 and agonists or antagonists of STOP-1. In one embodiment, a method of inducing cell migration in vitro comprising administering to an endothelial cell a STOP-1 polypeptide in an amount effective to induce migration of said cell is provided. According to another embodiment, the present invention provides a method of testing the activity of a candidate antagonist or agonist of STOP-1 comprising the steps of treating a first endothelial cell with STOP-1, treating a second endothelial cell with STOP-1 and the candidate antagonist or agonist, and comparing the migration of the first and second endothelial cells. In one preferred embodiment, the cell used in such migration assay is a HUVEC cell.

The present invention also provides methods of treating a disease or condition associated with excessive, inappropriate or uncontrolled angiogenesis in a mammalian subject. In one embodiment, the method comprises the step of administering to the subject a STOP-1 antagonist in an amount effective to treat the disease, wherein the STOP-1 antagonist has any property selected from the group consisting of (1) binds to residues within human STOP-1 that the 6B12 antibody binds; (2) binds to a residue within at least residues 33-52 of human STOP-1; and (3) can be inhibited from binding to STOP-1 by the 6B12 antibody.

The present invention also contemplates treating patients who would benefit from increased angiogenesis vasculogenesis by administering a therapeutically effective amount of a STOP-1 potentiator, a molecule that enhances STOP-1 binding to cells and/or aggregates STOP-1 on the cell surface. Such a molecule would be administered in an amount effective to increase angiogenesis or vasculogenesis. In one preferred embodiment, the agonist is an anti-STOP-1 antibody that aggregates STOP-1 a cell surface.

The present invention also provides agonists comprising an oligomeric form of STOP-1 polypeptide that comprises greater than three STOP-1 polypeptides. According to one embodiment the agonist comprises six STOP-1 polypeptides. According to another embodiment, the STOP-1 polypeptide is part of an immunoadhesin that is used to form said agonist.

The present invention provides new methods for identifying and evaluating candidate and know STOP-1 antagonists, agonist and potentiators comprising the step of observing or measuring the binding of STOP-1 to a cell in the presence and absence of the antagonist, agonist or potentiator. According to one embodiment, the cell is a cancer cell. In a further embodiment the cell is a breast cancer cell. According to another embodiment, the cell is an endothelial cell.

BRIEF DESCRIPTION OF THE DRAWINGS

FIG. 1 shows an alignment of amino acid sequences encoding STOP-1 from a wide variety of species—human (SEQ ID NO:3), mouse (SEQ ID NO:4), rice fish (SEQ ID NO:5), zebrafish (SEQ ID NO:6) and chicken (SEQ ID NO:7). A consensus sequence is also provided. The arrow indicates a signal sequence cleavage site. Red indicates residues conserved in all species. Capitalized letters in the consensus sequence indicates residues that have been conserved throughout all species. Lower case letters in the consensus sequence indicate residues that are conserved in most species. Residues that that are not conserved in those species appear as a "period." "!" indicates I or V. "$" indicates L or M. "%" indicates F or Y. "#" indicates B, D, E, N, Q or Z.

FIG. 2 shows an amino acid sequence of human STOP-1 (SEQ ID NO:3). A signal sequence is indicated by the boxed amino acids. A triple helix domain is indicated by an underline. A glycosylation site is at amino acid 186.

FIG. 6 shows the oligomerization of human STOP-1 protein expressed using a baculoviral infection system in SF9 insect cells. STOP-1 protein and various deletion mutants were expressed from SF9 cells, separated on a size exclusion column and subjected to light scattering analysis e.g., (A) S31-K243, (13) E89-K243 and (C) L94-K243. The predicted molecular weight of the monomers appear in the left corner of each graph. The numbers appearing next to several peaks refer to the average molecular weight of the complexes in the peak FIG. 7 shows the oligomerization of human STOP-1 protein expressed from mammalian cells. Human STOP-1 protein and various deletion mutants were expressed from CHO cells, separated on a size exclusion column and subjected to light scattering analysis, e.g., (A) M1-K243 and (B) delta-THD (residues 1-54, 94-243, plus histidine tag). The predicted molecular weight of the monomers appear in the left corner of each graph. The numbers appearing next to several peaks refer to an average molecular weight of the complexes in those peaks. Under non-reducing conditions, western blots of secreted full length, his-tagged human STOP-1 protein recombinantly expressed from CHO-psgb cells presented predominantly homodimerized complexes (C). The western blots were probed with anti-his antibody.

FIG. 12 shows the proliferation of 3T3 cells after transfection with (A) human STOP-1 or (B) mouse STOP-1.

FIG. 14 shows that mouse STOP-1 promotes tumorigenesis by 3T3 fibroblasts in a xenograft mouse model.

FIG. 15 shows the mean tumor volume of tumors in mice implanted with 3T3 fibroblasts transfected with vector alone or DNA encoding human STOP-1, RAS protein or LP1.

FIG. 18 shows the amino acid sequences of the CDRs of several phage-derived antibodies having affinity for human STOP-1. "H1," "H2" and "H3" refer to $V_H$-CDR1, $V_H$-CDR2 and $V_H$-CDR3. The numerical header generally corresponds to amino acid positions 28-33, 49-58 and 92-102 according to the Kabat numbering system. The SEQ ID NOs for the listed sequences are as follows:

| H1 | H2 | H3 | Ab Name |
| --- | --- | --- | --- |
| SEQ ID NO: 8 | SEQ ID NO: 9 | SEQ ID NO: 10 | S7 |
| SEQ ID NO: 11 | SEQ ID NO: 12 | SEQ ID NO: 13 | S16 |
| SEQ ID NO: 14 | SEQ ID NO: 15 | SEQ ID NO: 16 | F5, F6 |
| SEQ ID NO: 17 | SEQ ID NO: 18 | SEQ ID NO: 19 | S4, F13, F37 |
| SEQ ID NO: 20 | SEQ ID NO: 21 | SEQ ID NO: 22 | S9 |

Figure 19:
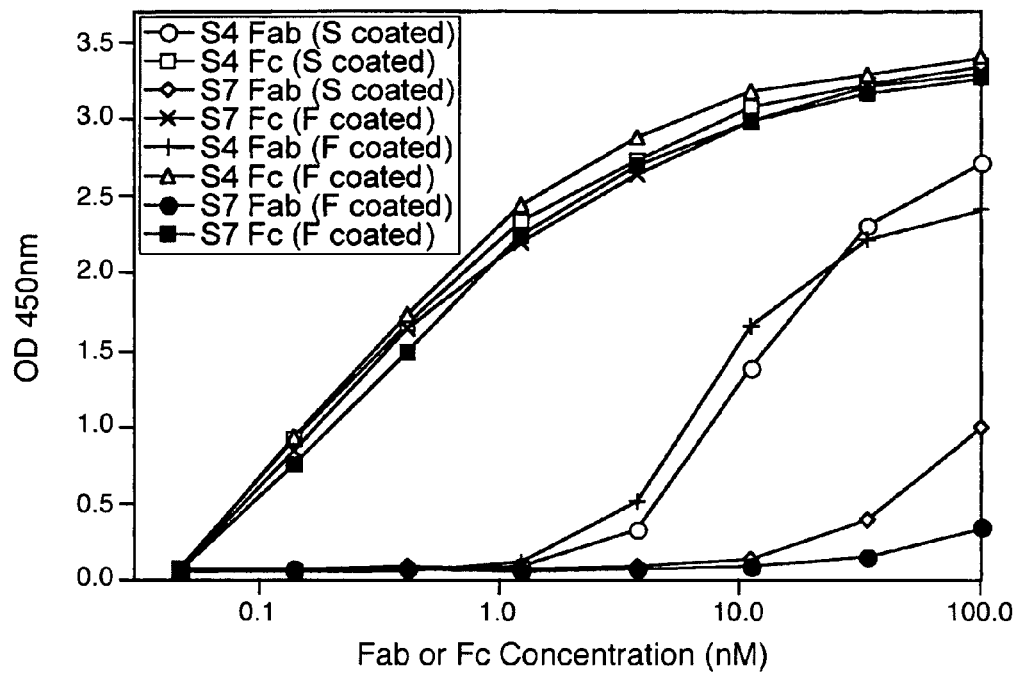

FIG. 19 shows a graph of an ELISA assay to determine an optimal concentration of S4 and S7 Fab or IgG for use in a competition ELISA to determine the affinity of the antibodies for STOP-1. "S coated" refers to a short form (#94-243) of STOP-1 coated on a microtiter plate. "F coated" refers to a full-length form of human STOP-1 coated on a microtiter plate. Approximately 90% of maximal binding was considered to be optimal for use in a competitive ELISA assay. Horse-radish peroxidase-conjugated protein G was used to detect the bound Fab and IgG.

Figure 20A:
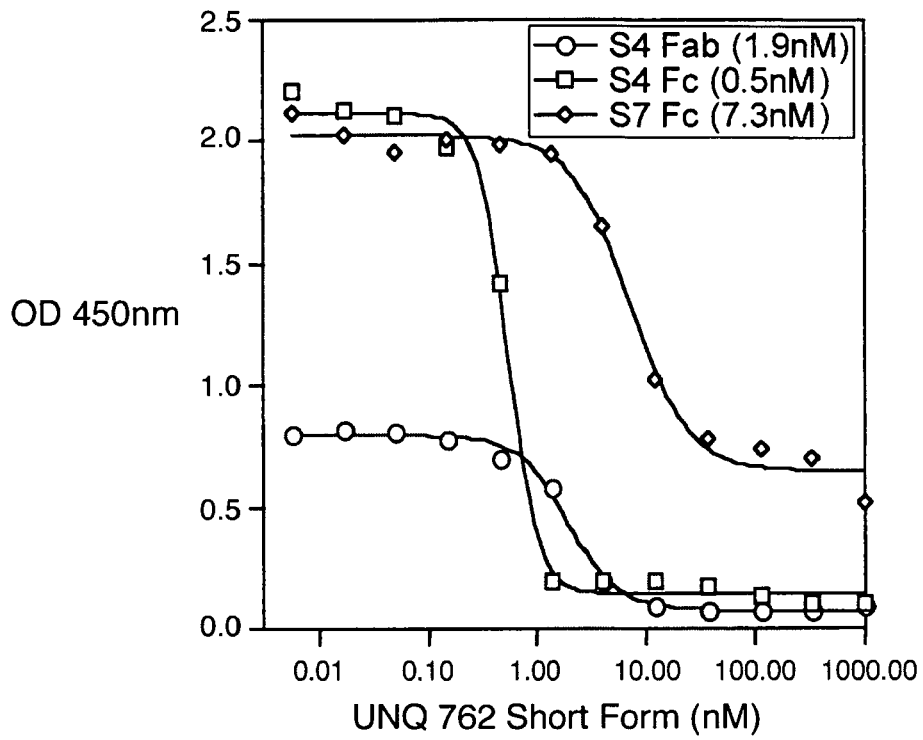
Figure 20B:
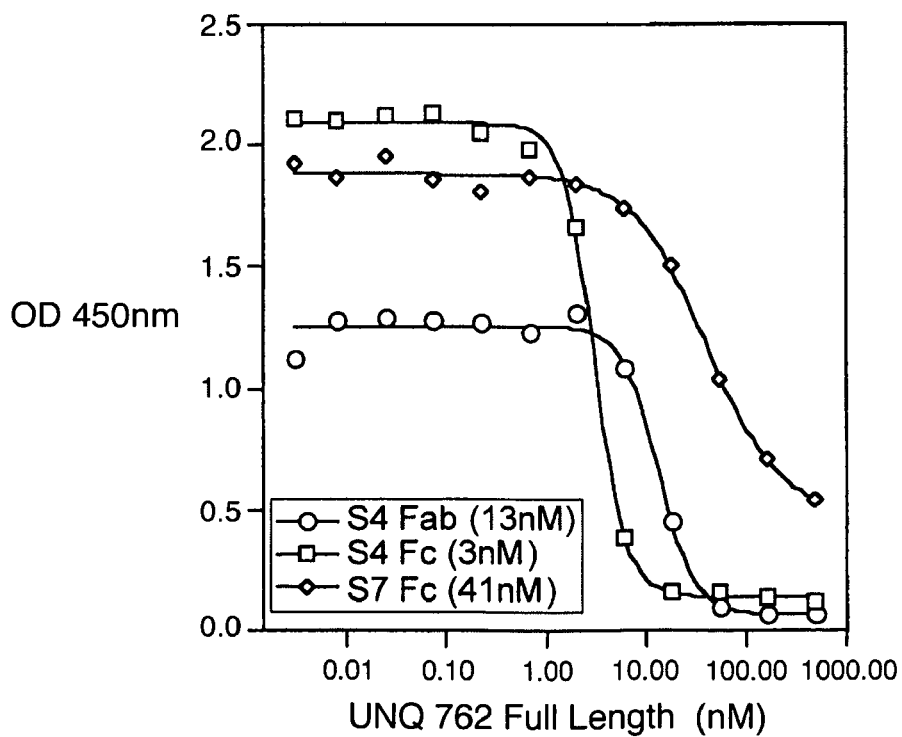

FIG. 20 shows a graph of the results of competitive ELISA to determine the binding affinities of the S4 and S7 Fab or IgG. The plates were coated with short form or full-length human STOP-1 and competed with short form or full length STOP-1, respectively (FIGS. 20A and B, respectively). The calculated binding affinities are indicated in the parentheticals.

FIG. 21 shows a summary of the binding affinities of several phage-derived antibodies against STOP-1. "S/S" refers to an ELISA in which the microtiter plate was coated with a short form of STOP-1 and competed with a short form of STOP-1. "F/S" refers to an ELISA in which the microtiter plate was coated with a full-length form of human STOP-1 and competed with a short form of human STOP-1. "F/F" refers to an ELISA in which the microtiter plate was coated with a full-length form of STOP-1 and competed with a full-length form of STOP-1. The phage used in these studies were the S4-Fab phage and the S7-F(ab)'$_2$ phage.

Figure 22:
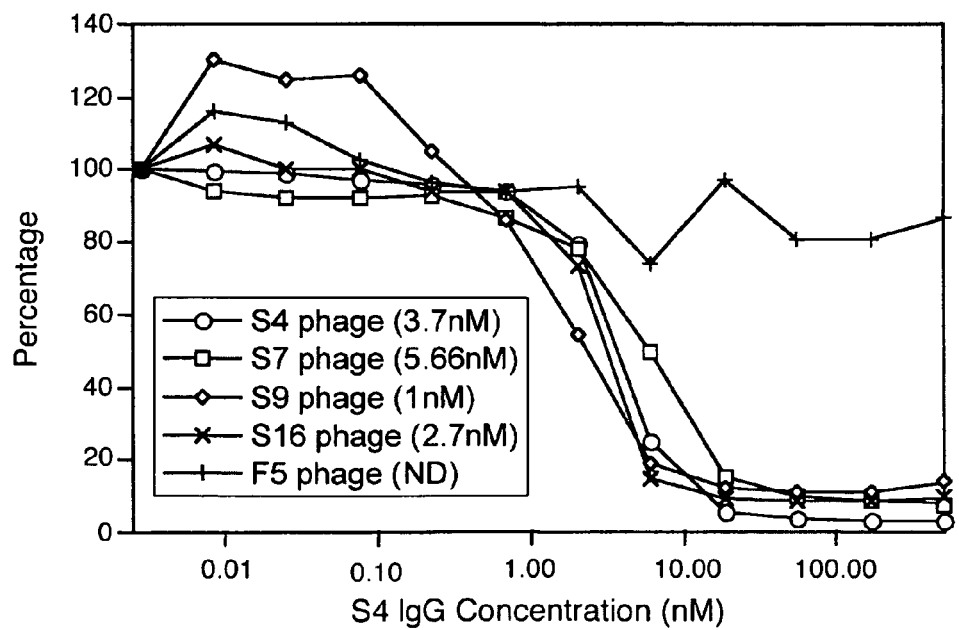

FIG. 22 shows a graph of an ELISA assay in which the plates were coated with human STOP-1, bound with S4 IgG and then competed with S4 (Fab) phage, S7 (F(ab)'$_2$) phage, S9 (Fab) phage, S16 (F(ab)'$_2$) phage and F5 (F(ab)'$_2$) phage. The Y axis refers to percentage unblocked as calculated by dividing the OD450 nm value of the well that blocked S4 IgG by the OD450 nm value of a well without S4 IgG.

Figure 23:
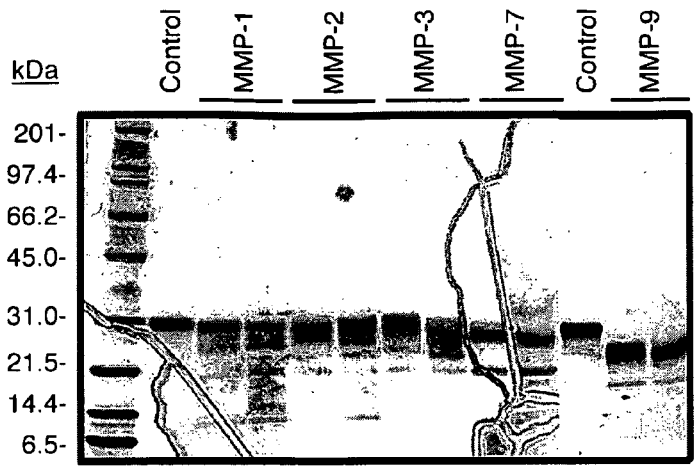

FIG. 23 shows a coomassie stained gel of baculovirus-expressed human STOP-1 protein cleaved by various proteases in vitro. "MMP" refers to matrix metalloprotease.

Figure 24A:
Figure 24B:
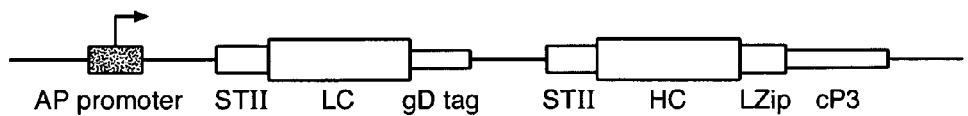
Figure 24C:
Figure 24D:
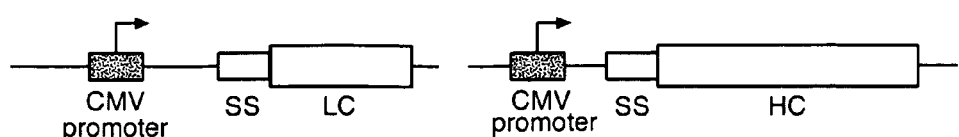

FIG. 24A-D are schematics of phagemids encoding Fab of F(ab)'$_2$ phage display proteins or vectors encoding Fab or IgG proteins. FIG. 24A is a schematic of a Fab-phagemid construct. The construct contains an alkaline phosphatase promoter, an STII signal sequence, a $V_L$ and $C_L$ light chain sequence, a gD tag, another STII signal sequence, a heavy chain $V_H$ and $CH_1$ region and a C-terminal part of the M13 bacteriophage pIII coat protein (cP3). FIG. 24B is a schematic of a F(ab)'$_2$-phagemid construct. The construct contains generally the same sequences as the Fab-phagemid, except it additionally includes a leucine zipper sequence (Zip). FIG. 24C is a schematic of a nucleic acid molecule encoding a Fab protein. FIG. 24D is a schematic of a nucleic acid molecule encoding an IgG protein, which IgG protein includes a $CH_2$ and $CH_3$ sequence.

FIG. 25A-H describe amino acid sequences and a nucleic acid sequence for a phage display anti-Her-2 Fab. More specifically, FIG. 25 shows an amino acid sequence comprising an anti-Her-2 Fab light chain (SEQ ID NO:86), an amino acid sequence comprising an anti-Her-2 Fab heavy chain region (SEQ ID NO:87) and the nucleic acid sequence of a phagemid encoding the amino acid sequences (SEQ ID NO:88).

FIG. 26A-H describe amino acid sequences and a nucleic acid sequence for a phage display anti-Her-2 F(ab)'$_2$. More specifically, FIG. 26 shows an amino acid sequence comprising an anti-Her-2 F(ab)'$_2$ light chain (SEQ ID NO:89), an amino acid sequence comprising an anti-Her-2 F(ab)'$_2$ heavy chain region (SEQ ID NO:90) and the nucleic acid sequence of a phagemid encoding the amino acid sequences (SEQ ID NO:91).

FIG. 27A-C describe amino acid sequences and a nucleic acid sequence for a phage display S4-Fab. More specifically, FIG. 27 shows an amino acid sequence comprising an S4-Fab light chain (SEQ ID NO:92), an amino acid sequence comprising an S4-Fab heavy chain region (SEQ ID NO:93) and a nucleic acid sequence encoding the amino acid sequences (SEQ ID NO:94).

FIG. 28A-C describe amino acid sequences and a nucleic acid sequence for a phage display S9 Fab. More specifically, FIG. 28 shows an amino acid sequence comprising an S9-Fab light chain (SEQ ID NO:95), an amino acid sequence comprising an S9-Fab heavy chain region (SEQ ID NO:96) and a nucleic acid sequence encoding the amino acid sequences (SEQ ID NO:97).

FIG. 29A-C describe amino acid sequences and a nucleic acid sequence for a phage display S7-F(ab)'$_2$. More specifically, FIG. 29 shows an amino acid sequence comprising an S7-F(ab)'$_2$ light chain (SEQ ID NO:98), an amino acid sequence comprising an S7-F(ab)'$_2$ heavy chain region (SEQ ID NO:99) and a nucleic acid sequence encoding the amino acid sequences (SEQ ID NO:100).

FIG. 30A-C describe amino acid sequences and a nucleic acid sequence for a phage display S16-F(ab)'$_2$. More specifically, FIG. 30 shows an amino acid sequence comprising an S16-F(ab)'$_2$ light chain (SEQ ID NO:101), an amino acid sequence comprising an S16-F(ab)'$_2$ heavy chain region (SEQ ID NO:102) and a nucleic acid sequence encoding the amino acid sequences (SEQ ID NO:103).

FIG. 31A-C describe amino acid sequences and a nucleic acid sequence for a phage display F5-F(ab)'$_2$. FIG. 31 shows an amino acid sequence comprising a F5-F(ab)'$_2$ light chain (SEQ ID NO:104), an amino acid sequence comprising an F5-F(ab)'$_2$ heavy chain region (SEQ ID NO:105) and a nucleic acid sequence encoding the amino acid sequences (SEQ ID NO:106).

FIG. 32A-G describe amino acid sequences and a nucleic acid sequence for a S4-Fab. More specifically, FIG. 32 shows an amino acid sequence comprising an S4-Fab light chain (SEQ ID NO:107), an amino acid sequence comprising an S4-Fab heavy chain region (SEQ ID NO:108) and the nucleic acid sequence of a vector encoding the amino acid sequence (SEQ ID NO:109).

FIG. 33A-F describe an S4 light chain sequence of an IgG protein. More specifically, FIG. 33 shows an amino acid sequence comprising an S4 Light Chain (SEQ ID NO:110) and the nucleic acid sequence of a vector encoding the amino acid sequence (SEQ ID NO:111).

FIG. 34A-G describe an S4 heavy chain sequence of an IgG protein. More specifically, FIG. 34 shows an amino acid sequence comprising an S4 Heavy Chain (SEQ ID NO:112) and the nucleic acid sequence of a vector encoding the amino acid sequence (SEQ ID NO:113).

FIG. 35 shows a frequency of amino acids in human antibody light chain sequences from the Kabat database.

FIG. 36 shows one illustrative embodiment of a suitable codon set design.

FIG. 37 is an illustrative embodiment of restricted diversity degenerate (also referred to herein as "nonrandom") codon sets for diversification of CDRs L1, L2 & L3.

FIG. 38 is an illustrative embodiment of restricted diversity degenerate (also referred to herein as "nonrandom") codon sets for diversification of CDRs L1, L2 & L3.

FIG. 39 is an illustrative embodiment of restricted diversity degenerate (also referred to herein as "nonrandom") codon sets for diversification of CDR L3.

FIG. 40 is an illustrative embodiment of a restricted diversity degenerate (also referred to herein as "nonrandom") codon sets for diversification of CDRs L1, L2 & L3.

Figure 41:
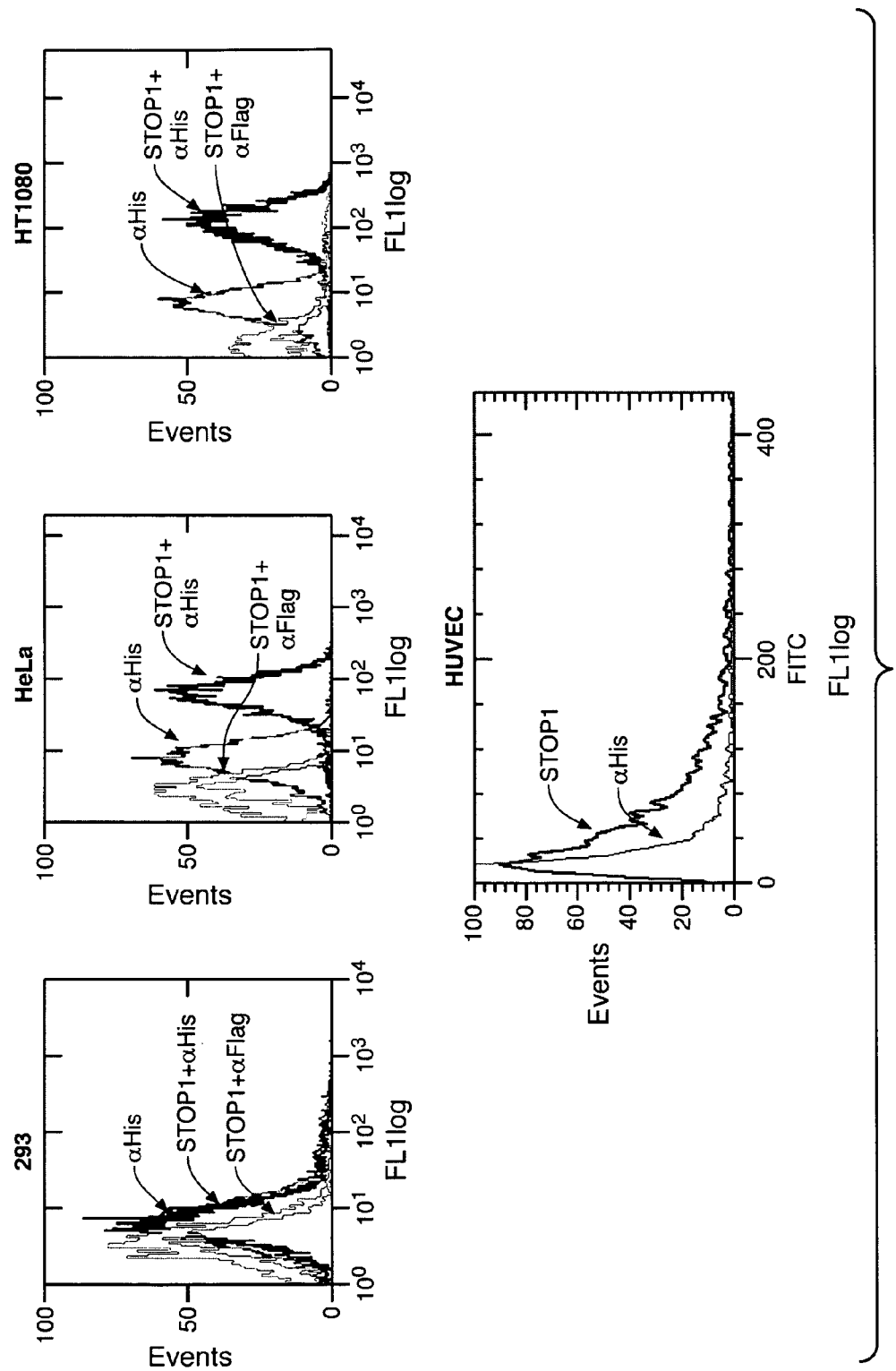

FIG. 41 shows a flow cytometric analysis of populations of 293, HeLa, HT1080 or HUVEC cells treated with either (1) anti-HIS antibodies, (2) anti-HIS antibodies and STOP-1 protein or (3) anti-flag antibodies and STOP-1 protein, followed by treatment with fluorescein isothiocyanate (FITC)-conjugated goat anti-mouse antibodies. A small, insignificant number of cells bound the anti-flag antibodies (i.e., the peaks at far left corner of the x-axis in the 293, HeLa and HT1080 graphs). The x-axis indicates the number of cells (log fluorescein signal intensity). The y-axis indicates the level of fluorescence emitted by the labeled cells (events).

Figure 42:
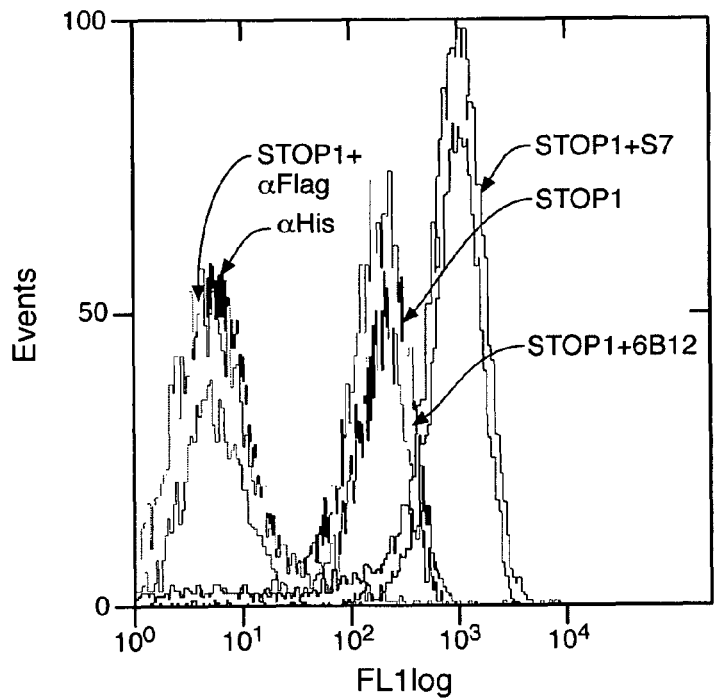

FIG. 42 shows a FACS analysis of populations of HT1080 cells treated with (1) anti-HIS antibodies, (2) anti-HIS antibodies and STOP-1 protein, (3) anti-flag antibodies and STOP-1 protein, (3) STOP-1 protein, (4) STOP-1 protein and S7 antibodies or (5) STOP-1 and 6b12 antibodies, followed by treatment with FITC-conjugated goat anti-mouse antibodies.

Figure 43:
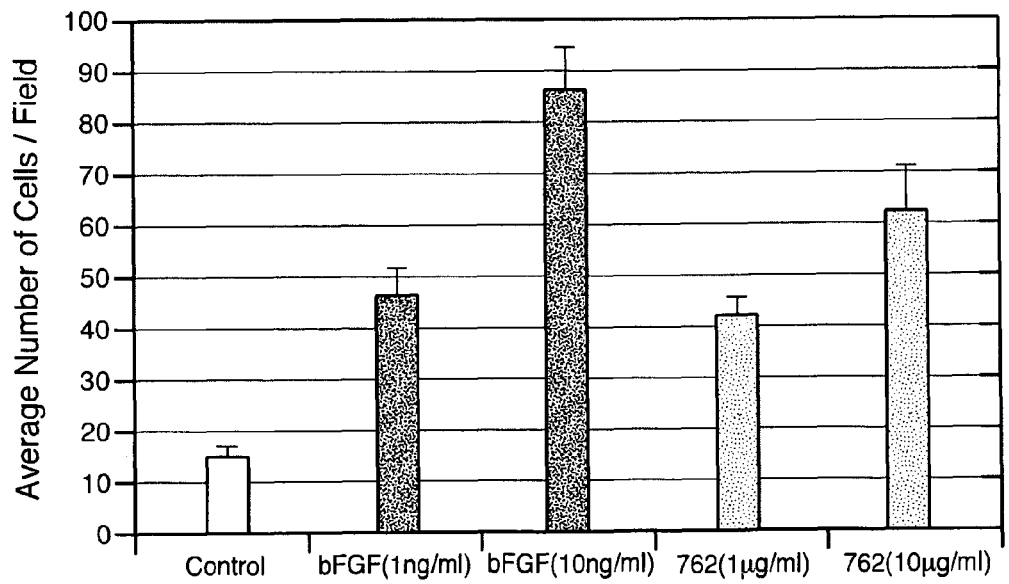

FIG. 43 charts the migration of HT1080 cells (number of cells) in a modified Boyden chemotactic chamber after treatment with bFGF or STOP-1 ("762") or a negative control.

Figure 44:
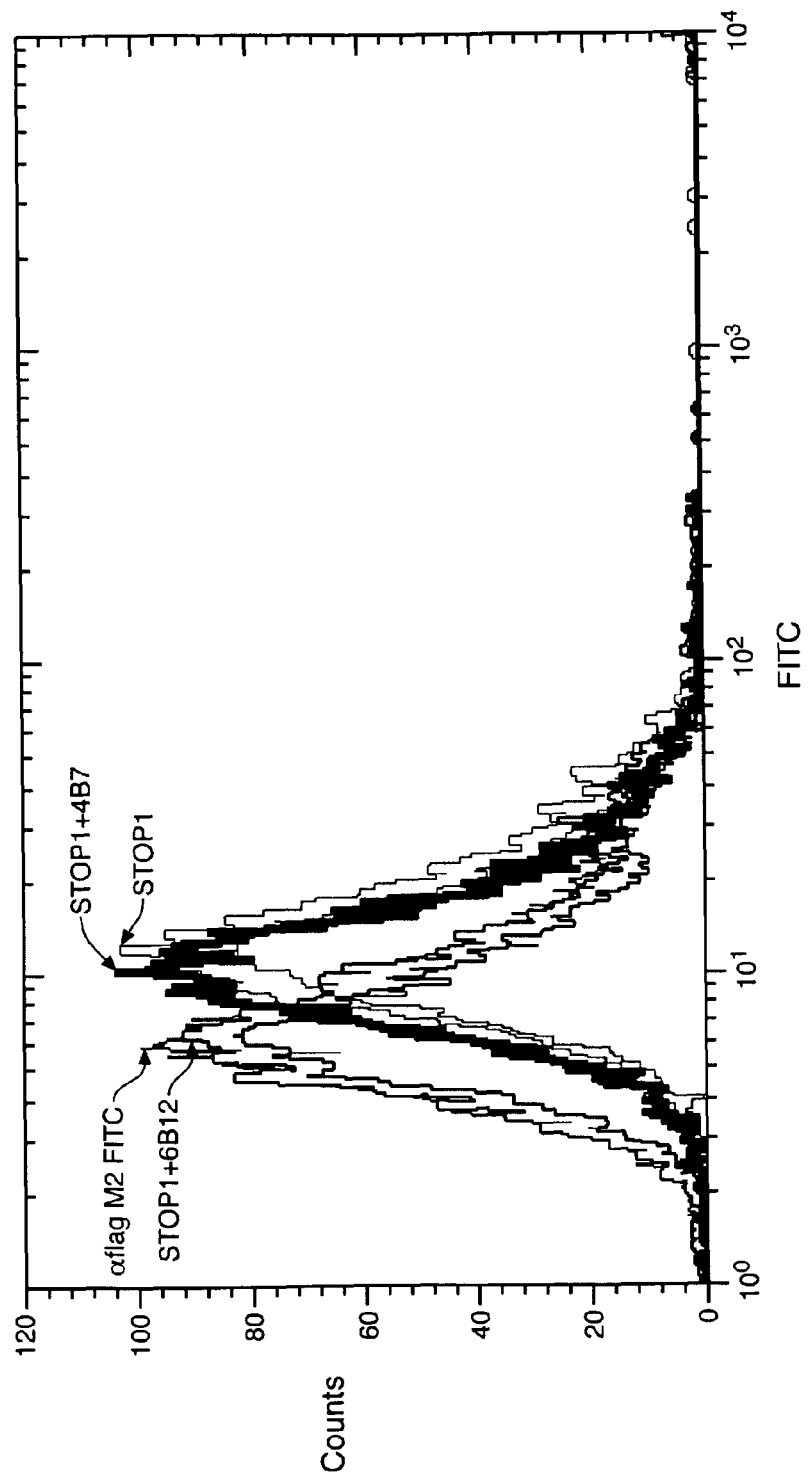

FIG. 44 shows a FACS analysis of STOP-1 binding to MDA435 cells in the presence and absence of an anti-STOP-1 antibody (6B12) or an antibody control (4B7). The detection antibody, anti-flag M2-FITC antibody, did not effect STOP-1 binding.

FIG. 45 is a graph that shows the fold change in STOP-1 mRNA expression after treatment (A) under hypoxic conditions for 8 and 34 hours or (B) under normoxic conditions for 3, 8 and 34 hours, in the presence and absence of recombinant human TNFalpha.

DETAILED DESCRIPTION OF THE INVENTION

Figures 1, 2:
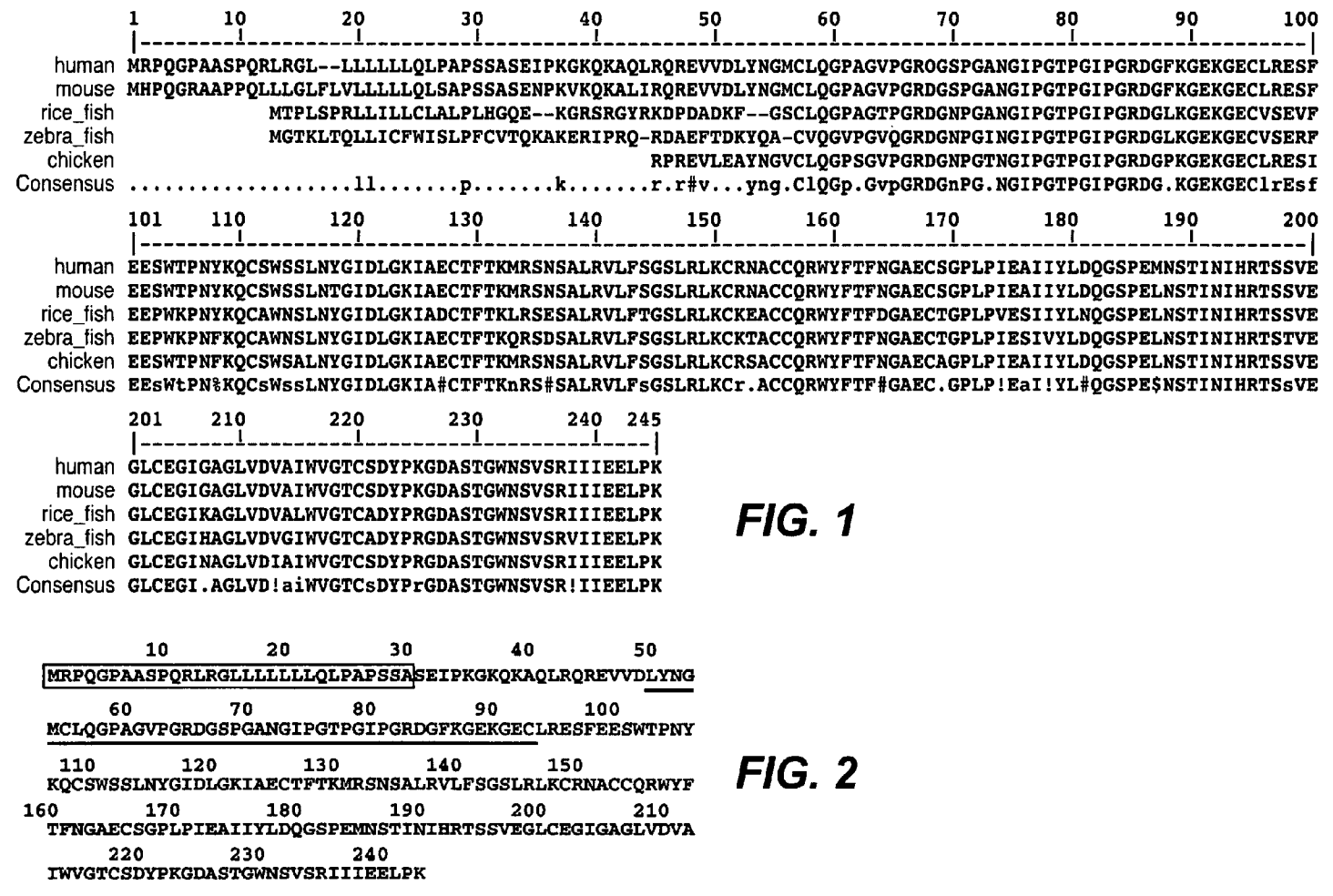

A nucleic acid sequence coding for a STOP-1 protein according to this invention includes, e.g., SEQ ID NO:1 and the nucleic acid molecules encoding the polypeptides of FIG. 1.

```
                                              SEQ ID NO: 1
GGAGAGAGGCGCGCGGGTGAAAGGCGCATTGATGCAGCCTGCGGCGGCCT

CGGAGCGCGGCGGAGCCAGACGCTGACCACGTTCCTCTCCTCGGTCTCCT

CCGCCTCCAGCTCCGCGCTGCCCGGCAGCCGGGAGCCATGCGACCCCAGG

GCCCCGCCGCCTCCCCGCAGCGGCTCCGCGGCCTCCTGCTGCTCCTGCTG

CTGCAGCTGCCCGCGCCGTCGAGCGCCTCTGAGATCCCCAAGGGGAAGCA

AAAGGCGCAGCTCCGGCAGAGGGAGGTGGTGGACCTGTATAATGGAATGT

GCTTACAAGGGCCAGCAGGAGTGCCTGGTCGAGACGGGAGCCCTGGGGCC

AATGTTATTCCGGGTACACCTGGGATCCCAGGTCGGGATGGATTCAAAGG

AGAAAAGGGGGAATGTCTGAGGGAAAGCTTTGAGGAGTCCTGGACACCCA

ACTACAAGCAGTGTTCATGGAGTTCATTGAATTATGGCATAGATCTTGGG

AAAATTGCGGAGTGTACATTTACAAAGATGCGTTCAAATAGTGCTCTAAG

AGTTTTGTTCAGTGGCTCACTTCGGCTAAAATGCAGAAATGCATGCTGTC

AGCGTTGGTATTTCACATTCAATGGAGCTGAATGTTCAGGACCTCTTCCC

ATTGAAGCTATAATTTATTTGGACCAAGGAAGCCCTGAAATGAATTCAAC

AATTAATATTCATCGCACTTCTTCTGTGGAAGGACTTTGTGAAGGAATTG

GTGCTGGATTAGTGGATGTTGCTATCTGGGTTGGCACTTGTTCAGATTAC

CCAAAAGGAGATGCTTCTACTGGATGGAATTCAGTTTCTCGCATCATTAT

TGAAGAACTACCAAAATAAATGCTTTAATTTTCATTTGCTACCTCTTTTT

TTATTATGCCTTGGAATGGTTCACTTAAATGACATTTTAAATAAGTTTAT

GTATACATCTGAATGAAAAGCAAAGCTAAATATGTTTACAGACCAAAGTG

TGATTTCACACTGTTTTTAAATCTAGCATTATTCATTTTGCTTCAATCAA

AAGTGGTTTCAATATTTTTTTAGTTGGTTAGAATACTTTCTTCATAGTC

ACATTCTCTCAACCTATAATTTGGAATATTGTTGTGGTCTTTTGTTTTTT

CTCTTAGTATAGCATTTTTAAAAAAATATAAAAGCTACCAATCTTTGTAC

AATTTGTAAATGTTAAGAATTTTTTTTATATCTGTTAAATAAAAATTATT

TCCAACA
```

The terms "STOP-1," "STOP-1 protein," "STOP-1 polypeptide" (also referred to UNQ762 or 762) as used herein include native sequence polypeptides, polypeptide variants and fragments of native sequence polypeptides and polypeptide variants (which are further defined herein), unless specified otherwise. STOP-1 proteins can be obtained from various species, e.g., humans, by using antibodies according to this invention or by recombinant or synthetic methods, including using deposited nucleic acid molecules. An oligomeric form of STOP-1 includes a human STOP-1 having only residues 94-243, or a part thereof. An oligomeric form according to this invention can include a dimer, a trimer and a hexamer of STOP-1. According to one preferred embodiment, the oligomeric form of STOP-1 is a trimer.

A "native sequence" polypeptide or "native" polypeptide is one which has the same amino acid sequence as a polypeptide (e.g., antibody) derived from nature. A "native sequence" polypeptide is one which has the same amino acid sequence as a polypeptide (e.g., antibody) derived from nature. Such native sequence polypeptides can be isolated from nature or can be produced by recombinant or synthetic means. Thus, a native sequence polypeptide can have the amino acid sequence of a naturally occurring human polypeptide, murine polypeptide, or polypeptide from any other mammalian species. A "native sequence" STOP-1 polypeptide or a "native" STOP-1 polypeptide comprises a polypeptide having the same amino acid sequence as the corresponding STOP-1 polypeptide derived from nature. For example, in one preferred embodiment, the nucleic acid sequence encoding a native sequence of human STOP-1 can be found in SEQ ID NO:2 and FIG. 2.

SEQ ID NO: 2
MRPQGPAASPQRLRGLLLLLLLQLPAPSSASEIPKGKQKAQLRQREVVDL

YNGMCLQGPAGVPGRDGSPGANVIPGTPGIPGRDGFKGEKGECLRESFEE

SWTPNYKQCSWSSLNYGIDLGKIAECTFTKMRSNSALRVLFSGSLRLKCR

NACCQRWYFTFNGAECSGPLPIEAIIYLDQGSPEMNSTINIHRTSSVEGL

CEGIGAGLVDVAIWVGTCSDYPKGDASTGWNSVSRIIIEELPK

Such STOP-1 polypeptides can be isolated from nature or can be produced by recombinant or synthetic means. The term "native sequence" or "native" STOP-1 polypeptide or protein specifically encompasses naturally-occurring truncated or secreted forms of the STOP-1 protein, naturally-occurring variant forms (e.g., alternatively spliced forms) and naturally-occurring allelic variants of the polypeptide. In certain embodiments of the invention, the native sequence STOP-1 polypeptides disclosed herein are mature or full-length native sequence polypeptides comprising the full-length amino acids sequences shown in the accompanying figures.

The approximate location of the "signal peptides" of the various STOP-1 polypeptides disclosed herein can be seen in the present specification and/or the accompanying figures. It is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"STOP-1 polypeptide variant" means a STOP-1 polypeptide having at least about 80% amino acid sequence identity with a full-length native sequence STOP-1 polypeptide sequence as disclosed herein, a STOP-1 polypeptide sequence lacking the signal peptide or triple helix domain as disclosed herein, or any other fragment of a full-length STOP-1 polypeptide sequence as disclosed herein (such as those encoded by a nucleic acid that represents only a portion of the complete coding sequence for a full-length STOP-1 polypeptide). Such STOP-1 polypeptide variants include, for instance, STOP-1 polypeptides wherein one or more amino acid residues are added, or deleted, at the N- or C-terminus of the full-length native amino acid sequence. Ordinarily, a STOP-1 polypeptide variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a full-length native sequence STOP-1 polypeptide sequence as disclosed herein, a STOP-1 polypeptide sequence lacking the signal peptide as disclosed herein, a triple helix domain of a STOP-1 polypeptide, with or without the signal peptide, as disclosed herein or any other specifically defined fragment of a full-length STOP-1 polypeptide sequence as disclosed herein. Ordinarily, STOP-1 variant polypeptides are at least about 10 amino acids in length, alternatively at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, STOP-1 variant polypeptides will have no more than one conservative amino acid substitution as compared to the native STOP-1 polypeptide sequence, alternatively no more than 2, 3, 4, 5, 6, 7, 8, 9, or 10 conservative amino acid substitution as compared to the native STOP-1 polypeptide sequence.

"Percent (%) amino acid sequence identity" with respect to the STOP-1 polypeptide sequences identified herein is defined as the percentage of amino acid residues in a candidate sequence that are identical with the amino acid residues in the specific STOP-1 polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or can be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "STOP-1", wherein "STOP-1" represents the amino acid sequence of a hypothetical STOP-1 polypeptide of interest, "Comparison Protein" represents the amino acid sequence of a polypeptide against which the "STOP-1" polypeptide of interest is being compared, and "X, "Y" and "Z" each represent different hypothetical amino acid residues. Unless specifically stated otherwise, all % amino acid sequence identity values used herein are obtained as described in the immediately preceding paragraph using the ALIGN-2 computer program.

"STOP-1 variant polynucleotide" or "STOP-1 variant nucleic acid sequence" means a nucleic acid molecule which encodes a STOP-1 polypeptide, preferably an active STOP-1 polypeptide, as defined herein and which has at least about 80% nucleic acid sequence identity with a nucleotide acid sequence encoding a full-length native sequence STOP-1 polypeptide sequence as disclosed herein, a full-length native sequence STOP-1 polypeptide sequence lacking the signal peptide as disclosed herein, the triple helix domain of a STOP-1 polypeptide, with or without the signal peptide, as disclosed herein or any other fragment of a full-length STOP-1 polypeptide sequence as disclosed herein (e.g., residues 94-243 of human STOP-1). Ordinarily, a STOP-1 variant polynucleotide will have at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% nucleic acid sequence identity with a nucleic acid sequence encoding a full-length native sequence STOP-1 polypeptide sequence as disclosed herein, a full-length native sequence STOP-1 polypeptide sequence lacking the signal peptide as disclosed herein, the triple helix domain of a STOP-1 polypeptide, with or without the signal sequence, as disclosed herein or any other fragment of a full-length STOP-1 polypeptide sequence as disclosed herein. Variants do not encompass the native nucleotide sequence.

Ordinarily, STOP-1 variant polynucleotides are at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

"Percent (%) nucleic acid sequence identity" with respect to STOP-1-encoding nucleic acid sequences identified herein is defined as the percentage of nucleotides in a candidate sequence that are identical with the nucleotides in the STOP-1 nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or can be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

$$100 \text{ times the fraction } W/Z$$

where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "STOP-1-DNA", wherein "STOP-1-DNA" represents a hypothetical STOP-1-encoding nucleic acid sequence of interest, "Comparison DNA" represents the nucleotide sequence of a nucleic acid molecule against which the "STOP-1-DNA" nucleic acid molecule of interest is being compared, and "N", "L" and "V" each represent different hypothetical nucleotides. Unless specifically stated otherwise, all % nucleic acid sequence identity values used herein are obtained as described in the immediately preceding paragraph using the ALIGN-2 computer program.

In other embodiments, STOP-1 variant polynucleotides are nucleic acid molecules that encode a STOP-1 polypeptide and which are capable of hybridizing, preferably under stringent hybridization and wash conditions, to nucleotide sequences encoding a full-length STOP-1 polypeptide as disclosed herein. STOP-1 variant polypeptides can be those that are encoded by a STOP-1 variant polynucleotide.

The term "full-length coding region" when used in reference to a nucleic acid encoding a STOP-1 polypeptide refers to the sequence of nucleotides which encode the full-length STOP-1 polypeptide of the invention (which is often shown between start and stop codons, inclusive thereof, in the accompanying figures). The term "full-length coding region" when used in reference to an ATCC deposited nucleic acid refers to the STOP-1 polypeptide-encoding portion of the cDNA that is inserted into the vector deposited with the ATCC (which is often shown between start and stop codons, inclusive thereof, in the accompanying figures).

"Isolated," when used to describe the various STOP-1 polypeptides disclosed herein, means polypeptide that has been identified and separated and/or recovered from a component of its natural environment. Contaminant components of its natural environment are materials that would typically interfere with diagnostic or therapeutic uses for the polypeptide, and can include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the STOP-1 polypeptide natural environment will not be present. Ordinarily, however, isolated polypeptide will be prepared by at least one purification step.

An "isolated" STOP-1 polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures.

Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, can be identified by those that: (1) employ low ionic strength and high temperature for washing, for example 0.015 M sodium chloride/0.0015 M sodium citrate/0.1% sodium dodecyl sulfate at 50 C; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42 C; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42 C, with a 10 minute wash at 42 C in 0.2×SSC (sodium chloride/sodium citrate) followed by a 10 minute high-stringency wash consisting of 0.1×SSC containing EDTA at 55 C.

"Moderately stringent conditions" can be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50 C. The skilled artisan will recognize how to adjust the temperature, ionic strength, etc. as necessary to accommodate factors such as probe length and the like.

The term "epitope tagged" when used herein refers to a chimeric polypeptide comprising a STOP-1 polypeptide or anti-STOP-1 antibody fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues). Polypeptides and antibodies of this invention that are epitope-tagged are contemplated.

"Biologically active" and "biological activity" and "biological characteristics" with respect to an STOP-1 means (1) having the ability to increase cell proliferation of at least one type of mammalian cell (e.g., 3T3) in vivo or ex vivo; (2) having the ability to specifically bind STOP-1; and/or (3) having the ability to otherwise modulate STOP-1 signaling or STOP-1 activity, except where specified otherwise.

"Biologically active" and "biological activity" and "biological characteristics" with respect to a modified STOP-1 polypeptide or a STOP-1 polypeptide (1) having the ability to partially or fully block, inhibit or neutralize a biological activity of a native STOP-1 (either in an antagonistic or blocking manner); (2) having the ability to specifically bind STOP-1; and/or (3) having the ability to modulate STOP-1 signaling or STOP-1 activity, except where specified otherwise.

"Biologically active" and "biological activity" and "biological characteristics" with respect to an anti-STOP-1 antibody of this invention means (1) having the ability to partially or fully block, inhibit or neutralize a biological activity of a native STOP-1 (either in an antagonistic or blocking manner); (2) having the ability to specifically bind STOP-1; and/or (3) having the ability to modulate STOP-1 signaling or STOP-1 activity, except where specified otherwise. In one preferred embodiment, an antibody of this invention binds to STOP-1 with an affinity of at least 1 uM or less, 100 nm or less, 50 nm or less, 10 nm or less, 5 nM or less, 1 nm or less. As used herein, "antibody variable domain" refers to the portions of the light and heavy chains of antibody molecules that include amino acid sequences of Complementary Determining Regions (CDRs; ie., CDR1, CDR2, and CDR3), and Framework Regions (FRs). $V_H$ refers to the variable domain of the heavy chain. $V_L$ refers to the variable domain of the light chain. According to the methods used in this invention, the amino acid positions assigned to CDRs and FRs are defined according to Kabat (Sequences of Proteins of Immunological Interest (National Institutes of Health, Bethesda, Md., 1987 and 1991)). Amino acid numbering of antibodies or antigen binding fragments is also according to that of Kabat.

As used herein, "codon set" refers to a set of different nucleotide triplet sequences used to encode desired variant amino acids. A set of oligonucleotides can be synthesized, for example, by solid phase synthesis, containing sequences that represent all possible combinations of nucleotide triplets provided by the codon set and that will encode the desired group of amino acids. A standard form of codon designation is that of the IUB code, which is known in the art and described herein. A "non-random codon set", as used herein, thus refers to a codon set that encodes select amino acids that fulfill partially, preferably completely, the criteria for amino acid selection as described herein. Synthesis of oligonucleotides with selected nucleotide "degeneracy" at certain positions is known in that art, for example the TRIM approach (Knappek et al.; J. Mol. Biol. (1999), 296:57-86); Garrard & Henner, Gene (1993), 128:103). Such sets of nucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can, but does not necessarily, include restriction enzyme sites useful for, for example, cloning purposes.

"Heterologous DNA" is any DNA that is introduced into a host cell. The DNA can be derived from a variety of sources including genomic DNA, cDNA, synthetic DNA and fusions or combinations of these. The DNA can include DNA from the same cell or cell type as the host or recipient cell or DNA from a different cell type, for example, from a mammal or plant. The DNA can, optionally, include marker or selection genes, for example, antibiotic resistance genes, temperature resistance genes, etc. Host cells encoding heterologous DNAs comprising the UNQ polypeptides and antibodies of this invention are contemplated as well as their use.

As used herein, "highly diverse position" refers to a position of an amino acid located in the variable regions of the light and heavy chains that have a number of different amino acid represented at the position when the amino acid sequences of known and/or naturally occurring antibodies or antigen binding fragments are compared. The highly diverse positions are typically in the CDR regions. In one aspect, the ability to determine highly diverse positions in known and/or naturally occurring antibodies is facilitated by the data provided by Kabat, Sequences of Proteins of Immunological Interest (National Institutes of Health, Bethesda, Md., 1987 and 1991). An internet-based database located at http://immuno.bme.nwu.edu provides an extensive collection and alignment of human light and heavy chain sequences and facilitates determination of highly diverse positions in these sequences. According to the invention, an amino acid position is highly diverse if it has preferably from about 2 to about 11, preferably from about 4 to about 9, and preferably from about 5 to about 7 different possible amino acid residue variations at that position. In some embodiments, an amino acid position is highly diverse if it has preferably at least about 2, preferably at least about 4, preferably at least about 6, and preferably at least about 8 different possible amino acid residue variations at that position.

As used herein, "library" refers to a plurality of antibody or antibody fragment sequences (for example, polypeptides of the invention), or the nucleic acids that encode these sequences, the sequences being different in the combination of variant amino acids that are introduced into these sequences according to the methods of the invention.

"Phage display" is a technique by which variant polypeptides are displayed as fusion proteins to a coat protein on the surface of phage, e.g., filamentous phage, particles. A utility of phage display lies in the fact that large libraries of randomized protein variants can be rapidly and efficiently sorted for those sequences that bind to a target molecule with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage. Wells and Lowman, *Curr. Opin. Struct. Biol.*, 3:355-362 (1992), and references cited therein. In monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations. Lowman and Wells, *Methods: A companion to Methods in Enzymology*, 3:205-0216 (1991).

A "phagemid" is a plasmid vector having a bacterial origin of replication, e.g., ColE1, and a copy of an intergenic region of a bacteriophage. The phagemid can be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid can form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle.

The term "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as an M13, f1, fd, Pf3 phage or a derivative thereof, or a lambdoid phage, such as lambda, 21, phi80, phi81, 82, 424, 434, etc., or a derivative thereof.

As used herein, "target amino acid" refers to an amino acid that belongs to the group of amino acids that are collectively the most commonly occurring amino acids found at a particular position of known and/or natural antibodies or antigen binding fragments. In some embodiments, the most commonly occurring amino acids" are those amino acids that are found in a particular position in preferably at least about 50%, preferably at least about 70%, preferably at least about 80%, preferably at least about 90%, preferably all of sequences of known and/or natural antibodies or antigen binding fragments. In some embodiments, the most commonly occurring amino acids" are those amino acids that are found in a particular position in preferably from about 50% to about 100%, preferably from about 60% to about 90%, preferably from about 70% to about 85%, preferably from about 80% to about 85% of the sequences of known and/or natural antibodies or antigen binding fragments. Known antibodies or antigen biding fragments are those whose sequences are available in the art, such as those available in publicly-accessible databases, such as the database of Kabat ("Sequence of Proteins of Immunological Interest, National Institutes of Health, Bethesda, Md., 1987 and 1991) and/or as located at http://immuno.bme.nwu.edu. The amino acid position is preferably a position in the CDR region. A target group of amino acids refers to a group of target amino acids for a particular position. Preferably, a target amino acid is not a cysteine residue. For positions in the light chain CDR1, CDR2, CDR3, and for heavy chain CDR1 and CDR2, typically, a target group of amino acids can include from preferably about two to about eleven, preferably from about 4 to about 9, preferably from about 5 to about 7, preferably about 6 amino acids at a particular highly diverse and solvent-accessible position of the source sequence.

The term "proteoglycan" refers to a molecule where at least one glycosaminoglycan side chain is covalently attached to the protein core of the molecule. A proteoglycan synthesis deficient cell line according to this invention includes a cell line that is deficient in galactosyltransferase I. According to one preferred embodiment, the cell line is a CHO-psbg cell line.

The term "antagonist" is any molecule that partially or fully blocks, inhibits, or neutralizes a biological activity of a native STOP-1 polypeptide and that specifically binds to a native STOP-1 polypeptide, wherein the binding of the antagonist (1) is to a native STOP-1 polypeptide in oligomeric form, (2) is to residues 94-243 of native human STOP-1 and/or (3) can be inhibited (e.g., as observed in a competitive ELISA assay using STOP-1 and 6B12) by a monoclonal antibody of this invention (e.g., a deposited antibody of this invention, etc.). According to one embodiment, the antagonist is a polypeptide. According to another embodiment, the 6B12 antibody can inhibit the binding of the antagonist to STOP-1. According to another embodiment, the antagonist binds to a residue within residues 33-52 or 33-53 of human STOP-1 or a non-human STOP-1 equivalent thereof.

The term "small molecule antagonist" refers to any molecule wherein the molecular weight is 1500 daltons or less and is an antagonist according to this invention. According to one embodiment the small molecule antagonist is below about 500 Daltons.

According to one preferred embodiment, the antagonist blocks, inhibits or neutralizes cell proliferation in cells expressing native STOP-1. In one embodiment, the antagonist or small molecule antagonist prevents migration of a cell to which STOP-1 binds. In one preferred embodiment, the antagonist or small molecule antagonist specifically binds to a trimeric form of STOP-1. Suitable antagonists include antibodies, amino acid sequence variants of native STOP-1 polypeptides, peptides, of this invention etc. Methods for dentifying antagonists of a STOP-1 polypeptide can comprise contacting a STOP-1 polypeptide with a candidate antagonist molecule and measuring a detectable change in one or more biological activities associated with the STOP-1 polypeptide.

The term "potentiator" refers to any molecule that enhances a biological activity of a native STOP-1 polypeptide and that specifically binds to a native STOP-1 polypeptide, wherein the potentiator can bind to an oligomeric form of a native STOP-1 polypeptide and has at least one additional activity selected from the group consisting of (1) is capable of binding to a residue in residues 94-243 of native human STOP-1, (2) is capable of aggregating STOP-1 on a cell; and (3) can be competed by a monoclonal antibody an S7 or S4 antibody of this invention (e.g., as observed in a competitive ELISA assay using STOP-1, S7 or S4 and the potentiator). According to one embodiment, the potentiator increases the binding of STOP-1 to a cell (e.g., HUVEC cells, HeLa cells, and HT1080 cells). In one preferred embodiment, the agonist binds to a trimeric form of STOP-1. Methods for identifying agonists of a STOP-1 polypeptide can comprise contacting a cell that binds STOP-1 with a STOP-1 polypeptide and the candidate agonist and measuring a detectable change in one or more biological activities associated with the STOP-1 polypeptide (e.g., increased binding of the STOP-1 polypeptide, cell proliferation or cell migration).

"Treating" or "treatment" or "alleviation" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. These terms indicate the therapeutic and prophylactic uses herein are successful if they ameliorate, lessen or decrease the symptoms, complications or other problems associated with a disease or ameliorate, lessen or decrease the chance of onset or frequency of the symptoms, complications or other problems associated with a disease.

A subject or mammal is successfully "treated" for a STOP-1 polypeptide-expressing cancer if, after receiving a therapeutic amount of an antagonist according to the methods of the present invention, the patient shows observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues. To the extent the anti-STOP-1 antibody or STOP-1 binding oligopeptide can prevent growth and/or kill existing cancer cells, it can be cytostatic and/or cytotoxic. Reduction of these signs or symptoms can also be felt by the patient.

A subject or mammal is successfully "treated" for abnormal angiogenesis if, after receiving a therapeutic amount of an antagonist or agonist according to the methods of the present invention, the patient shows observable and/or measurable [TO BE FILLED IN]; and/or relief to some extent, one or more of the symptoms associated with the abnormal angiogenesis; and improvement in quality of life issues.

The above parameters for assessing successful treatment and improvement in the disease are readily measurable by procedures familiar to a physician. For cancer therapy, efficacy can be measured, for example, by assessing the time to disease progression (TTP) and/or determining the response rate (RR). Metastasis can be determined by staging tests and by bone scan and tests for calcium level and other enzymes to determine spread to the bone. CT scans can also be done to look for spread to the pelvis and lymph nodes in the area. Chest X-rays and measurement of liver enzyme levels by known methods are used to look for metastasis to the lungs and liver, respectively. Other known methods for monitoring the disease include transrectal ultrasonography (TRUS) and transrectal needle biopsy (TRNB).

For bladder cancer, which is a more localized cancer, methods to determine progress of disease include urinary cytologic evaluation by cystoscopy, monitoring for presence of blood in the urine, visualization of the urothelial tract by sonography or an intravenous pyelogram, computed tomography (CT) and magnetic resonance imaging (MRI). The presence of distant metastases can be assessed by CT of the abdomen, chest x-rays, or radionuclide imaging of the skeleton.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of the treatment of, alleviating the symptoms of or diagnosis of a cancer refers to any animal classified as a mammal (aka "patient"), including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

By "solid phase" or "solid support" is meant a non-aqueous matrix to which an antibody, an antagonist or a polypeptide of the present invention can adhere or attach. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

As used herein, the term "immunoadhesin" designates antibody-like molecules that combine the binding specificity of a heterologous protein (an "adhesin") with the effector functions of immunoglobulin constant domains. Structurally, the immunoadhesins comprise a fusion of an amino acid sequence with the desired binding specificity that is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand—such as a portion of a native STOP-1 protein. The immunoglobulin constant domain sequence in the immunoadhesin can be obtained from any immunoglobulin, such as IgG-1, IgG-2, IgG-3, or IgG-4 subtypes, IgA (including IgA-1 and IgA-2), IgE, IgD, or IgM.

A "liposome" is a small vesicle composed of various types of lipids, phospholipids and/or surfactant which is useful for delivery of a drug (such as a STOP-1 polypeptide, an antibody thereto or a STOP-1 binding oligopeptide) to a mammal. The components of the liposome are commonly arranged in a bilayer formation, similar to the lipid arrangement of biological membranes.

A "small" molecule or "small" organic molecule is defined herein to have a molecular weight below about 500 Daltons.

An "effective amount" of a polypeptide, antibody, antagonist or composition as disclosed herein is an amount sufficient to carry out a specifically stated purpose. An "effective amount" can be determined empirically and by known methods relating to the stated purpose.

The term "therapeutically effective amount" refers to an amount of an antibody, polypeptide or antagonist of this invention effective to "treat" a disease or disorder in a mammal (aka patient). In the case of cancer, the therapeutically effective amount of the drug can reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See the definition herein of "treating". To the extent the drug can prevent growth and/or kill existing cancer cells, it can be cytostatic and/or cytotoxic.

A "growth inhibitory amount" of a polypeptide, antibody, antagonist or composition of this invention is an amount capable of inhibiting the growth of a cell, especially tumor, e.g., cancer cell, either in vitro or in vivo. A "growth inhibitory amount" of a polypeptide, antibody, antagonist or composition of this invention for purposes of inhibiting neoplastic cell growth can be determined empirically and by known methods or by examples provided herein.

A "cytotoxic amount" of a polypeptide, antibody, antagonist or composition of this invention is an amount capable of causing the destruction of a cell, especially tumor, e.g., cancer cell, either in vitro or in vivo. A "cytotoxic amount" of a polypeptide, antibody, antagonist or composition of this invention for purposes of inhibiting neoplastic cell growth can be determined empirically and by methods known in the art.

The term "antibody" is used in the broadest sense and specifically covers, for example, single anti-STOP-1 monoclonal antibodies (including agonist, antagonist, and neutralizing antibodies), anti-STOP-1 antibody compositions with polyepitopic specificity, polyclonal antibodies, single chain anti-STOP-1 antibodies, and fragments of anti-STOP-1 antibodies (see below) as long as they specifically bind a native STOP-1 polypeptide and/or exhibit a biological activity or immunological activity of this invention. According to one embodiment, the antibody binds to an oligomeric form of STOP-1, e.g., a trimeric form. In a further embodiment, the antibody specifically binds to human STOP-1 between residues 94-243. According to another embodiment, the antibody specifically binds to STOP-1, which binding can be inhibited by a monoclonal antibody of this invention (e.g., a deposited antibody of this invention, etc.). The phrase "functional fragment or analog" of an antibody is a compound having a qualitative biological activity in common with an antibody to which it is being referred. For example, a functional fragment or analog of an anti-STOP-1 antibody can be one which can specifically bind to a STOP-1 molecule. In one embodiment, the antibody can prevent or substantially reduce the ability of a STOP-1 molecule to induce cell proliferation. The term "immunoglobulin" (Ig) is used interchangeably with "antibody" herein. According to one embodiment, an antibody of this invention does not bind to a peptide having the amino acid sequence GWNSVSRIIIEELPK (SEQ ID NO:117).

An "isolated antibody" is one which has been identified and separated and/or recovered from a component of its natural environment. Contaminant components of its natural environment are materials which would interfere with diagnostic or therapeutic uses for the antibody, and can include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., *Basic and Clinical Immunology*, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and define specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (L1), 50-56 (L2) and 89-97 (L3) in the $V_L$, and around about 1-35 (H1), 50-65 (H2) and 95-102 (H3) in the $V_H$ (in one embodiment, H1 is around about 31-35); Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the $V_L$, and 26-32 (H1), 53-55 (H2) and 96-101 (H3) in the $V_H$; Chothia and Lesk *J. Mol. Biol.* 196:901-917 (1987)).

The term "monoclonal antibody" as used herein refers to an antibody obtained from a population of substantially homogeneous antibodies, i.e., the individual antibodies comprising the population are identical except for possible naturally occurring mutations that can be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they can be synthesized uncontaminated by other antibodies. The modifier "monoclonal" is not to be construed as requiring production of the antibody by any particular method. For example, the monoclonal antibodies useful in the present invention can be prepared by the hybridoma methodology first described by Kohler et al., *Nature*, 256:495 (1975), or can be made using recombinant DNA methods in bacterial, eukaryotic animal or plant cells (see, e.g., U.S. Pat. No. 4,816, 567). The "monoclonal antibodies" can also be isolated from phage antibody libraries using the techniques described in Clackson et al., *Nature*, 352:624-628 (1991), Marks et al., *J. Mol. Biol.*, 222:581-597 (1991), and the Examples below, for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit a biological activity of this invention (see U.S. Pat. No. 4,816,567; and Morrison et al., *Proc. Natl. Acad. Sci. USA*, 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

An "intact" antibody is one which comprises an antigen-binding site as well as a $C_L$ and at least heavy chain constant domains, $C_H1$, $C_H2$ and $C_H3$. The constant domains can be native sequence constant domains (e.g. human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al., *Protein Eng.* 8(10): 1057-1062 [1995]); single-chain antibody molecules; and multispecific antibodies formed from antibody fragments. The expression "linear antibodies" generally refers to the antibodies described in Zapata et al., Protein Eng., 8(10):1057-1062 (1995). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332: 323-329 (1988); and Presta, *Curr. Op. Struct. Biol.* 2:593-596 (1992).

A "species-dependent antibody," e.g., a mammalian anti-human IgE antibody, is an antibody which has a stronger binding affinity for an antigen from a first mammalian species than it has for a homologue of that antigen from a second mammalian species. Normally, the species-dependent antibody "bind specifically" to a human antigen (i.e., has a binding affinity (Kd) value of no more than about $1 \times 10^{-7}$ M, preferably no more than about $1 \times 10^{-8}$ and most preferably no more than about $1 \times 10^{-9}$ M) but has a binding affinity for a homologue of the antigen from a second non-human mammalian species which is at least about 50 fold, or at least about 500 fold, or at least about 1000 fold, weaker than its binding affinity for the human antigen. The species-dependent antibody can be of any of the various types of antibodies as defined above, but preferably is a humanized or human antibody.

A "STOP-1 binding oligopeptide" is an oligopeptide that binds, preferably specifically, to a STOP-1 polypeptide as described herein. STOP-1 binding oligopeptides can be chemically synthesized using known oligopeptide synthesis methodology or can be prepared and purified using recombinant technology. STOP-1 binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to a STOP-1 polypeptide as described herein. According to one embodiment, the STOP-1 binding oligopeptide binds to the same or overlapping region that the 6B12 antibody binds. STOP-1 binding oligopeptides can be identified without undue experimentation using known techniques. In this regard, it is noted that techniques for screening oligopeptide libraries for oligopeptides that are capable of specifically binding to a polypeptide target are known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., Proc. Natl. Acad. Sci. U.S.A., 81:3998-4002 (1984); Geysen et al., Proc. Natl. Acad. Sci. U.S.A., 82:178-182 (1985); Geysen et al., in Synthetic Peptides as Antigens, 130-149 (1986); Geysen et al., J. Immunol. Meth., 102:259-274 (1987); Schoofs et al., J. Immunol., 140:611-616 (1988), Cwirla, S. E. et al. (1990) Proc. Natl. Acad. Sci. USA, 87:6378; Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363, and Smith, G. P. (1991) Current Opin. Biotechnol., 2:668).

A polypeptide, antibody, antagonist or composition of this invention "which binds" an antigen of interest, e.g. a tumor-associated polypeptide antigen target such as STOP-1, is one that binds the antigen with sufficient affinity such that a polypeptide, antibody, antagonist or composition is useful as a diagnostic and/or therapeutic agent in targeting a cell or tissue expressing the antigen, and does not significantly cross-react with other proteins. In such embodiments, the extent of binding of the polypeptide, antibody, antagonist or composition to a "non-target" protein will be less than about 10% of the binding of the polypeptide, antibody, antagonist or composition to its particular target protein as determined by fluorescence activated cell sorting (FACS) analysis or radio-immunoprecipitation (RIA). With regard to the binding of a polypeptide, antibody, antagonist or composition to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific fox" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope (e.g., a non-STOP-1 protein). It is understood that an antibody that specifically binds to a human native STOP-1 polypeptide may also bind a non-human native STOP-1 polypeptide.

A polypeptide, antibody, antagonist or composition that "inhibits the growth" of tumor cells expressing a STOP-1 polypeptide or a "growth inhibitory" polypeptide, antibody, antagonist or composition is one which results in measurable growth inhibition of cancer cells expressing or overexpressing the appropriate STOP-1 polypeptide. Preferred growth inhibitory polypeptides, antibodies, antagonists or compositions inhibit growth of STOP-1-expressing tumor cells by greater than 20%, preferably from about 20% to about 50%, and even more preferably, by greater than 50% (e.g., from about 50% to about 100%) as compared to the appropriate control, the control typically being tumor cells not treated with the polypeptide, antibody, antagonist or composition being tested. In one embodiment, growth inhibition can be measured at an antibody concentration of about 0.1 to 30 μg/ml or about 0.5 nM to 200 nM in cell culture, where the growth inhibition is determined 1-10 days after exposure of the tumor cells to the antibody. Growth inhibition of tumor cells in vivo can be determined in various ways such as is described in the Experimental Examples section below. The antibody is growth inhibitory in vivo if administration of the anti-STOP-1 antibody at about 1 μg/kg to about 100 mg/kg body weight results in reduction in tumor size or tumor cell proliferation within about 5 days to 3 months from the first administration of the antibody, preferably within about 5 to 30 days.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-92 (1991). To assess ADCC activity of a molecule of interest, an in vitro ADCC assay, such as that described in U.S. Pat. No. 5,500,362 or 5,821,337 can be performed. Useful effector cells for such assays include peripheral blood mononuclear cells (PBMC) and Natural Killer (NK) cells. Alternatively, or additionally, ADCC activity of the molecule of interest can be assessed in vivo, e.g., in a animal model such as that disclosed in Clynes et al. (USA) 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, *Annu. Rev. Immunol.* 9:457-492 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells can be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202:163 (1996), can be performed.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain, as well as head and neck cancer, and associated metastases.

The terms "cell proliferative disorder" and "proliferative disorder" refer to disorders that are associated with some degree of abnormal cell proliferation. In one embodiment, the cell proliferative disorder is cancer. In one embodiment, the cell proliferative disorder is desmoplasia.

"Tumor", as used herein, refers to all neoplastic cell growth and proliferation, whether malignant or benign, and all pre-cancerous and cancerous cells and tissues.

The term abnormal angiogenesis according to this invention occurs when new blood vessels either grow excessively, insufficiently or inappropriately (e.g., the location, timing or onset of the angiogenesis being undesired from a medical standpoint) in a diseased state or such that it causes a diseased state. "Excessive, inappropriate or uncontrolled angiogenesis" occurs in a diseased state when there is new blood vessel growth that contributes to the worsening of the diseased state, such as in cancer, especially vascularized solid tumors and metastatic tumors (including colon, lung cancer (especially small-cell lung cancer), or prostate cancer), diseases caused by ocular neovascularisation, especially diabetic blindness, retinopathies, primarily diabetic retinopathy or age-induced macular degeneration and rubeosis; psoriasis, haemangioblastoma such as haemangioma; inflammatory renal diseases, such as glomerulonephritis, especially mesangioproliferative glomerulonephritis, haemolytic uremic syndrome, diabetic nephropathy or hypertensive nephrosclerosis; various inflammatory diseases, such as arthritis, especially rheumatoid arthritis, inflammatory bowel disease, psoriasis, sarcoidosis, arterial arteriosclerosis and diseases occurring after transplants, endometriosis or chronic asthma and more than 70 other conditions. The new blood vessels can feed the diseased tissues, destroy normal tissues, and in the case of cancer, the new vessels can allow tumor cells to escape into the circulation and lodge in other organs (tumor metastases). Insufficient angiogenesis occurs when there is inadequate blood vessels growth that contributes to the worsening of a diseased state, e.g., in diseases such as coronary artery disease, stroke, and delayed wound healing. Further, ulcers, strokes, and heart attacks can result from the absence of angiogenesis that normally required for natural healing. The present invention contemplates treating those patients that are at risk of developing the above-mentioned illnesses.

Other patients that are candidates for receiving the STOP-1 antagonists of this invention have, or are at risk for developing, abnormal proliferation of fibrovascular tissue, acne rosacea, acquired immune deficiency syndrome, artery occlusion, atopic keratitis, bacterial ulcers, Bechets disease, blood borne tumors, carotid obstructive disease, choroidal neovascularization, chronic inflammation, chronic retinal detachment, chronic uveitis, chronic vitritis, contact lens overwear, corneal graft rejection, corneal neovascularization, corneal graft neovascularization, Crohn's disease, Eales disease, epidemic keratoconjunctivitis, fungal ulcers, Herpes simplex infections, Herpes zoster infections, hyperviscosity syndromes, Kaposi's sarcoma, leukemia, lipid degeneration, Lyme's disease, marginal keratolysis, Mooren ulcer, Mycobacteria infections other than leprosy, myopia, ocular neovascular disease, optic pits, Osler-Weber syndrome (Osler-Weber-Rendu, osteoarthritis, Pagets disease, pars planitis, pemphigoid, phylectenulosis, polyarteritis, post-laser complications, protozoan infections, pseudoxanthoma elasticum, pterygium keratitis sicca, radial keratotomy, retinal neovascularization, retinopathy of prematurity, retrolental fibroplasias, sarcoid, scleritis, sickle cell anemia, Sjogrens syndrome, solid tumors, Stargarts disease, Steven's Johnson disease, superior limbic keratitis, syphilis, systemic lupus, Terrien's marginal degeneration, toxoplasmosis, trauma, tumors of Ewing sarcoma, tumors of neuroblastoma, tumors of osteosarcoma, tumors of retinoblastoma, tumors of rhabdomyosarcoma, ulcerative colitis, vein occlusion, Vitamin A deficiency and Wegeners sarcoidosis, undesired angiogenesis associated with diabetes, parasitic diseases, abnormal wound healing, hypertrophy following surgery, injury or trauma, inhibition of hair growth, inhibition of ovulation and corpus luteum formation, inhibition of implantation and inhibition of embryo development in the uterus.

Anti-angiogenesis therapies are useful in the general treatment of graft rejection, lung inflammation, nephrotic syndrome, preeclampsia, pericardial effusion, such as that associated with pericarditis, and pleural effusion, diseases and disorders characterized by undesirable vascular permeability, e.g., edema associated with brain tumors, ascites associated with malignancies, Meigs' syndrome, lung inflammation, nephrotic syndrome, pericardial effusion and pleural effusion and the like.

Other angiogenesis-dependent diseases that may be treated with the compositions of this invention include angiofibroma (abnormal blood of vessels which are prone to bleeding), neovascular glaucoma (abnormal growth of blood vessels in the eye), arteriovenous malformations (abnormal communication between arteries and veins), nonunion fractures (fractures that will not heal), atherosclerotic plaques (hardening of the arteries), pyogenic granuloma (common skin lesion composed of blood vessels), scleroderma (a form of connective tissue disease), hemangioma (tumor composed of blood vessels), trachoma (leading cause of blindness in the third world), hemophilic joints, vascular adhesions and hypertrophic scars (abnormal scar formation).

Since blood vessels play an important role in the regulation of bone turnover and growth, potentiators or agonists according to this invention may stimulate or enhance of bone and/or cartilage repair from disease or injury or by blocking inflammation or processes of tissue destruction (collagenase activity, osteoclast activity, etc.) mediated by inflammatory processes. Bone injuries or diseases to be treated with STOP-1 potentiators or agonists of this invention include periodontal diseases, other tooth-repair processes, osteoporosis and fractures.

A "stromal targeting agent" according to this invention is an agent that substantially recognizes and binds stromal tissue compared to other tissue. Stromal tissue is the connective tissue framework of an organ, gland, or other structure, as distinguished from the tissues performing the special function of the organ or part. Examples of stromal targeting agents include antibodies that specifically bind to FAP, fascin, HSP47, mesothelin and prostate stem antigen.

A polypeptide, antibody, antagonist or composition of this invention which "induces cell death" is one which causes a viable cell to become nonviable. The cell is one which expresses a STOP-1 polypeptide, preferably a cell that overexpresses a STOP-1 polypeptide as compared to a normal cell of the same tissue type. Preferably, the cell is a cancer cell, e.g., a breast, ovarian, stomach, endometrial, salivary gland, lung, kidney, colon, thyroid, pancreatic or bladder cell. Cell death in vitro can be determined in the absence of complement and immune effector cells to distinguish cell death induced by antibody-dependent cell-mediated cytotoxicity (ADCC) or complement dependent cytotoxicity (CDC). Thus, the assay for cell death can be performed using heat inactivated serum (i.e., in the absence of complement) and in the absence of immune effector cells. To determine whether a polypeptide, antibody, antagonist or composition of this invention is able to induce cell death, loss of membrane integrity as evaluated by uptake of propidium iodide (PI), trypan blue (see Moore et al. *Cytotechnology* 17:1-11 (1995)) or 7AAD can be assessed relative to untreated cells. Preferred cell death-inducing polypeptides, antibodies, antagonists or compositions are those which induce PI uptake in the PI uptake assay in BT474 cells.

A "STOP-1-expressing cell" is a cell which expresses an endogenous or transfected STOP-1 polypeptide either on the cell surface or in a secreted form. A "STOP-1-expressing cancer" is a cancer comprising cells that have a STOP-1 polypeptide present on the cell surface or that produce and secrete a STOP-1 polypeptide. In another embodiment, a "STOP-1-expressing cancer" optionally produces and secretes sufficient levels of STOP-1 polypeptide, such that a polypeptide, antibody, antagonist or composition of this invention can bind thereto and have a therapeutic effect with respect to the cancer. A cancer which "overexpresses" a STOP-1 polypeptide is one which has significantly higher levels of STOP-1 polypeptide at the cell surface thereof, or produces and secretes, compared to a noncancerous cell of the same tissue type. Such overexpression can be caused by gene amplification or by increased transcription or translation. STOP-1 polypeptide overexpression can be determined in a diagnostic or prognostic assay by evaluating increased levels of the STOP-1 protein present on the surface of a cell, or secreted by the cell (e.g., via an immunohistochemistry assay using anti-STOP-1 antibodies prepared against an isolated STOP-1 polypeptide which can be prepared using recombinant DNA technology from an isolated nucleic acid encoding the STOP-1 polypeptide; FACS analysis, etc.). Alternatively, or additionally, one can measure levels of STOP-1 polypeptide-encoding nucleic acid or mRNA in the cell, e.g., via fluorescent in situ hybridization using a nucleic acid based probe corresponding to a STOP-1-encoding nucleic acid or the complement thereof; (FISH; see WO98/45479 published October, 1998), Southern blotting, Northern blotting, or polymerase chain reaction (PCR) techniques, such as real time quantitative PCR (RT-PCR). One can also study STOP-1 polypeptide overexpression by measuring shed antigen in a biological fluid such as serum, e.g., using antibody-based assays (see also, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al., *J. Immunol. Methods* 132:73-80 (1990)). Aside from the above assays, various in vivo assays are available to the skilled practitioner. For example, one can expose cells within the body of the mammal to an antibody which is optionally labeled with a detectable label, e.g., a radioactive isotope, and binding of the antibody to cells in the mammal can be evaluated, e.g., by external scanning for radioactivity or by analyzing a biopsy taken from a mammal previously exposed to the antibody.

The word "label" when used herein refers to a detectable compound or composition which is conjugated directly or indirectly to the polypeptide, antibody, antagonist or composition so as to generate a "labeled" a polypeptide, antibody, antagonist or composition. The label can be detectable by itself (e.g. radioisotope labels or fluorescent labels) or, in the case of an enzymatic label, can catalyze chemical alteration of a substrate compound or composition which is detectable.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodepa, carboquone, meturedepa, and uredepa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON.toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

A "growth inhibitory agent" when used herein refers to a compound or composition which inhibits growth of a cell, especially a STOP-1-expressing cancer cell, either in vitro or in vivo. Thus, the growth inhibitory agent can be one which significantly reduces the percentage of STOP-1-expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3, 6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

The term "package insert" is used to refer to instructions customarily included in commercial packages of therapeutic products, that contain information about the indications, usage, dosage, administration, contraindications and/or warnings concerning the use of such therapeutic products.

TABLE 2

| STOP-1 | XXXXXXXXXXXXXXX | (Length = 15 amino acids) |
|---|---|---|
| Comparison Protein | XXXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the STOP-1 polypeptide) = 5 divided by 15 = 33.3%

TABLE 3

| STOP-1 | XXXXXXXXXX | (Length = 10 amino acids) |
|---|---|---|
| Comparison Protein | XXXXXYYYYYYZZYZ | (Length = 15 amino acids) |

% amino acid sequence identity = (the number of identically matching amino acid residues between the two polypeptide sequences as determined by ALIGN-2) divided by (the total number of amino acid residues of the STOP-1 polypeptide) = 5 divided by 10 = 50%

TABLE 4

| STOP-1-DNA | NNNNNNNNNNNNNN | (Length = 14 nucleotides) |
|---|---|---|
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 6 divided by 14 = 42.9%

TABLE 5

| STOP-1-DNA | NNNNNNNNNNNN | (Length = 12 nucleotides) |
|---|---|---|
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 4 divided by 12 = 33.3%

Compositions and Methods of the Invention
STOP-1 Polypeptide Variants

In addition to the full-length native sequence STOP-1 polypeptides described herein, it is contemplated that STOP-1 polypeptide variants can be prepared. STOP-1 polypeptide variants can be prepared by introducing appropriate nucleotide changes into the STOP-1 DNA, and/or by synthesis of the desired STOP-1 polypeptide. Those skilled in the art will appreciate that amino acid changes can alter post-translational processes of the STOP-1 polypeptide such as changing the number or position of glycosylation sites or altering the membrane anchoring characteristics.

Variations in the native full-length sequence STOP-1 polypeptide or in various domains of the STOP-1 polypeptide described herein, can be made, for example, using any of the techniques and guidelines for conservative and non-conservative mutations set forth, for instance, in U.S. Pat. No. 5,364, 934. Variations can be a substitution, deletion or insertion of one or more codons encoding the STOP-1 polypeptide that results in a change in the amino acid sequence of the STOP-1 polypeptide as compared with the native sequence STOP-1 polypeptide. Optionally the variation is by substitution of at least one amino acid with any other amino acid in one or more of the domains of the STOP-1 polypeptide. Guidance in determining which amino acid residue can be inserted, substituted or deleted without adversely affecting the desired activity can be found by comparing the sequence of the STOP-1 polypeptide with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions can optionally be in the range of about 1 to 5 amino acids. The variation allowed can be determined by systematically making insertions, deletions or substitutions of amino acids in the sequence and testing the resulting variants for activity exhibited by the full-length or mature native sequence.

In particular embodiments, conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are introduced and the products screened.

TABLE 6

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |

TABLE 6-continued

| Original Residue | Exemplary Substitutions | Preferred Substitutions |
|---|---|---|
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the STOP-1 polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic: trp, tyr, phe.

Non-conservative substitutions will entail exchanging a member of one of these classes for another class. Such substituted residues also can be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.,* 13:4331 (1986); Zoller et al., *Nucl. Acids Res.,* 10:6487 (1987)], cassette mutagenesis [Wells et al., *Gene* 34:315 (1985)], restriction selection mutagenesis [Wells et al., *Philos. Trans. R. Soc. London SerA,* 317:415 (1986)] or other known techniques can be performed on the cloned DNA to produce the STOP-1 variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science,* 244: 1081-1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.,* 150:1 (1976)]. If alanine substitution does not yield adequate amounts of variant, an isoteric amino acid can be used.

Modifications of STOP-1 Polypeptides

Covalent modifications of STOP-1 polypeptides are included within the scope of this invention. One type of covalent modification includes reacting targeted amino acid residues of a STOP-1 polypeptide with an organic derivatizing agent that is capable of reacting with selected side chains or the N- or C-terminal residues of the STOP-1 polypeptide. Derivatization with bifunctional agents is useful, for instance, for crosslinking the STOP-1 polypeptide to a water-insoluble support matrix or surface for use in the method for purifying anti-STOP-1 antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of the STOP-1 polypeptide included within the scope of this invention comprises altering the native glycosylation pattern of the polypeptide. "Altering the native glycosylation pattern" is intended for purposes herein to mean deleting one or more carbohydrate moieties found in the native sequence STOP-1 polypeptide (either by removing the underlying glycosylation site or by deleting the glycosylation by chemical and/or enzymatic means), and/or adding one or more glycosylation sites that are not present in the native sequence STOP-1 polypeptide. In addition, the phrase includes qualitative changes in the glycosylation of the native proteins, involving a change in the nature and proportions of the various carbohydrate moieties present.

Addition of glycosylation sites to the STOP-1 polypeptide can be accomplished by altering the amino acid sequence. The alteration can be made, for example, by the addition of, or substitution by, one or more serine or threonine residues to the native sequence STOP-1 polypeptide (for O-linked glycosylation sites). The STOP-1 amino acid sequence can optionally be altered through changes at the DNA level, particularly by mutating the DNA encoding the STOP-1 polypeptide at preselected bases such that codons are generated that will translate into the desired amino acids.

Another means of increasing the number of carbohydrate moieties on the STOP-1 polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem*., pp. 259-306 (1981).

Removal of carbohydrate moieties present on the STOP-1 polypeptide can be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.,* 259:52 (1987) and by Edge et al., *Anal. Biochem.,* 118:131 (1981). Enzymatic cleavage of carbohydrate moieties on polypeptides can be achieved by the use of a variety of endo- and exo-glycosidases as described by Thotakura et al., *Meth. Enzymol.,* 138:350 (1987).

Another type of covalent modification of the STOP-1 polypeptide comprises linking the STOP-1 polypeptide to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791,192 or 4,179,337.

The STOP-1 polypeptide of the present invention can also be modified in a way to form a chimeric molecule comprising the STOP-1 polypeptide fused to another, heterologous polypeptide or amino acid sequence.

In one embodiment, such a chimeric molecule comprises a fusion of the STOP-1 polypeptide with a protein transduction domain which targets the STOP-1 polypeptide for delivery to various tissues and more particularly across the brain blood barrier, using, for example, the protein transduction domain of human immunodeficiency virus TAT protein (Schwarze et al., 1999, Science 285: 1569-72).

In another embodiment, such a chimeric molecule comprises a fusion of the STOP-1 polypeptide with a tag polypeptide which provides an epitope to which an anti-tag antibody can selectively bind. The epitope tag is generally placed at the amino- or carboxyl-terminus of the STOP-1 polypeptide. The presence of such epitope-tagged forms of the STOP-1 polypeptide can be detected using an antibody against the tag polypeptide. Also, provision of the epitope tag enables the STOP-1 polypeptide to be readily purified by affinity purification using an anti-tag antibody or another type of affinity matrix that binds to the epitope tag. Various tag polypeptides and their respective antibodies are known in the art. Examples include poly-histidine (poly-His) or poly-histidine-glycine (poly-His-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

In an alternative embodiment, the chimeric molecule can comprise a fusion of the STOP-1 polypeptide with an immunoglobulin or a particular region of an immunoglobulin. For a bivalent form of the chimeric molecule (also referred to as an "immunoadhesin"), such a fusion could be to the Fc region of an IgG molecule. Ig fusions of this invention include polypeptides that comprise approximately or only residues 94-243, residues 33-53 or residues 33-52 of human STOP-1 in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also, U.S. Pat. No. 5,428,130 issued Jun. 27, 1995.

Preparation of the STOP-1 Polypeptide

The description below relates primarily to production of STOP-1 polypeptides by culturing cells transformed or transfected with a vector containing nucleic acid encoding STOP-1 polypeptides. It is, of course, contemplated that alternative methods that are known in the art can be employed to prepare the STOP-1 polypeptide. For instance, the STOP-1 polypeptide sequence, or portions thereof, can be produced by direct peptide synthesis using solid-phase techniques. See, e.g., Stewart et al., *Solid-Phase Peptide Synthesis* (W.H. Freeman Co.: San Francisco, Calif., 1969); Merrifield, *J. Am. Chem. Soc.*, 85: 2149-2154 (1963). In vitro protein synthesis can be performed using manual techniques or by automation. Automated synthesis can be accomplished, for instance, with an Applied Biosystems Peptide Synthesizer (Foster City, Calif.) using manufacturer's instructions. Various portions of the STOP-1 polypeptide can be chemically synthesized separately and combined using chemical or enzymatic methods to produce the full-length STOP-1 polypeptide.

Selection and Transformation of Host Cells

Host cells are transfected or transformed with expression or cloning vectors described herein for STOP-1 polypeptide production and cultured in conventional nutrient media modified as appropriate for inducing promoters, selecting transformants, or amplifying the genes encoding the desired sequences. The culture conditions, such as media, temperature, pH, and the like, can be selected by the skilled artisan without undue experimentation. In general, principles, protocols, and practical techniques for maximizing the productivity of cell cultures can be found in *Mammalian Cell Biotechnology: A Practical Approach*, M. Butler, ed. (IRL Press, 1991) and Sambrook et al., supra.

Methods of transfection are known to the ordinarily skilled artisan, for example, $CaPO_4$ treatment and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23: 315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transformations have been described in U.S. Pat. No. 4,399,216. Transformations into yeast are typically carried out according to the method of Van Solingen et al., *J. Bact.* 130: 946 (1977) and Hsiao et al., *Proc. Natl. Acad. Sci.* (*USA*), 76: 3829 (1979). However, other methods for introducing DNA into cells, such as by nuclear microinjection, electroporation, bacterial protoplast fusion with intact cells, or polycations, e.g., polybrene or polyornithine, can also be used. For various techniques for transforming mammalian cells, see, Keown et al., *Methods in Enzymology*, 185: 527-537 (1990) and Mansour et al., *Nature*, 336: 348-352 (1988).

Suitable host cells for cloning or expressing the DNA in the vectors herein include prokaryote, yeast, or higher eukaryote cells. Suitable prokaryotes include, but are not limited to, eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325); and K5 772 (ATCC 53,635). Other suitable prokaryotic host cells include Enterobacteriaceae such as *Escherichia*, e.g., *E. coli*, *Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 can be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for vectors encoding the STOP-1 polypeptide. *Saccharomyces cerevisiae* is a commonly used lower eukaryotic host microorganism. Others include *Schizosaccharomyces pombe* (Beach and Nurse, *Nature,* 290: 140 [1981]; EP 139,383 published 2 May 1985); *Kluyveromyces* hosts (U.S. Pat. No. 4,943,529; Fleer et al., *Bio/Technology,* 9: 968-975 (1991)) such as, e.g., *K. lactis* (MW98-8C, CBS683, CBS4574; Louvencourt et al., *J. Bacteriol.,* 737 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology,* 8: 135 (1990)), *K. thermotolerans*, and *K. marxianus; yarrowia* (P 402,226); *Pichia pastoris* (EP 183,070; Sreekrishna et al, *J. Basic Microbiol.,* 28: 265-278 [1988]); *Candida; Trichoderma reesia* (EP 244,234); *Neurospora crassa* (Case et al., *Proc. Natl. Acad. Sci. USA,* 76: 5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.,* 112: 284-289 [1983]; Tilburn et al., *Gene,* 26: 205-221 [1983]; Yelton et al., *Proc. Natl. Acad. Sci. USA,* 81: 1470-1474 [1984]) and *A. niger* (Kelly and Hynes, *EMBO J.,* 4: 475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts can be found in C. Anthony, *The Biochemistry of Methylotrophs,* 269 (1982).

Suitable host cells for the expression of nucleic acid encoding glycosylated STOP-1 polypeptides are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen. Virol.* 36: 59 (1977)); Chinese hamster ovary cells/–DHFR (CHO, Urlaub and Chasin, *Proc. Natl. Acad. Sci. USA,* 77:4216 (1980)); mouse sertoli cells (TM4, Mather, *Biol. Reprod.,* 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

Selection and Use of a Replicable Vector

The nucleic acid (e.g., cDNA or genomic DNA) encoding a polypeptide or antibody of this invention can be inserted into a replicable vector for cloning (amplification of the DNA) or for expression. Various vectors are publicly available. The vector can, for example, be in the form of a plasmid, cosmid, viral particle, or phage. The appropriate nucleic acid sequence can be inserted into the vector by a variety of procedures. In general, DNA is inserted into an appropriate restriction endonuclease site(s) using techniques known in the art. Vector components generally include, but are not limited to, one or more of a signal sequence if the sequence is to be secreted, an origin of replication, one or more marker genes, an enhancer element, a promoter, and a transcription termination sequence. Construction of suitable vectors containing one or more of these components employs standard ligation techniques that are known to the skilled artisan.

The polypeptide or antibody of this invention can be produced recombinantly not only directly, but also as a fusion polypeptide with a heterologous polypeptide, which can be a signal sequence or other polypeptide having a specific cleavage site at the N-terminus of the mature protein or polypeptide. In general, the signal sequence can be a component of the vector, or it can be a part of the DNA encoding the polypeptide or antibody that is inserted into the vector. The signal sequence can be a prokaryotic signal sequence selected, for example, from the group of the alkaline phosphatase, penicillinase, lpp, or heat-stable enterotoxin II leaders. For yeast secretion the signal sequence can be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences can be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV, or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the nucleic acid encoding the polypeptide or antibody such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77: 4216 (1980). A suitable selection gene for use in yeast is the trp1 gene present in the yeast plasmid YRp7. Stinchcomb et al., *Nature,* 282: 39 (1979); Kingsman et al., *Gene* 7: 141 (1979); Tschemper et al., *Gene* 10: 157 (1980). The trp1 gene provides a selection marker for a mutant strain of yeast lacking the ability to grow in tryptophan, for example, ATCC No. 44076 or PEP4-1. Jones, *Genetics*, 85: 12 (1977).

Expression and cloning vectors usually contain a promoter operably linked to the nucleic acid sequence encoding the polypeptide or antibody of this invention to direct mRNA synthesis. Promoters recognized by a variety of potential host cells are known. Promoters suitable for use with prokaryotic hosts include the β-lactamase and lactose promoter systems (Chang et al., *Nature*, 275: 615 (1978); Goeddel et al., *Nature*, 281: 544 (1979)), alkaline phosphatase, a tryptophan (trp) promoter system (Goeddel, *Nucleic Acids Res.*, 8: 4057 (1980); EP 36,776), and hybrid promoters such as the tac promoter (deBoer et al., *Proc. Natl. Acad. Sci. USA*, 80: 21-25 (1983)). Promoters for use in bacterial systems also will contain a Shine-Dalgarno (S.D.) sequence operably linked to the DNA encoding the polypeptide or antibody of this invention.

Examples of suitable promoting sequences for use with yeast hosts include the promoters for 3-phosphoglycerate kinase (Hitzeman et al., *J. Biol. Chem.*, 255: 2073 (1980)) or other glycolytic enzymes (Hess et al., *J. Adv. Enzyme Reg.*, 7: 149 (1968); Holland, *Biochemistry*, 17: 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters that are inducible promoters having the additional advantage of transcription controlled by growth conditions are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Nucleic acid transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus, and Simian Virus 40 (SV40); by heterologous mammalian promoters, e.g., the actin promoter or an immunoglobulin promoter; and by heat-shock promoters, provided such promoters are compatible with the host cell systems.

Transcription of a DNA encoding a polypeptide or antibody of this invention by higher eukaryotes can be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer can be spliced into the vector at a position 5' or 3' to the sequence coding for a polypeptide or antibody of this invention, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding polypeptide or antibody.

Still other methods, vectors, and host cells suitable for adaptation to the synthesis of the polypeptide or antibody of this invention in recombinant vertebrate cell culture are described in Gething et al., *Nature*, 293: 620-625 (1981); Mantei et al., *Nature* 281: 40-46 (1979); EP 117,060; and EP 117,058.

Detecting Gene Amplification/Expression

Gene amplification and/or expression can be measured in a sample directly, for example, by conventional Southern blotting, Northern blotting to quantitate the transcription of mRNA (Thomas, *Proc. Natl. Acad. Sci. USA*, 77:5201-5205 (1980)), dot blotting (DNA analysis), or in situ hybridization, using an appropriately labeled probe, based on the sequences provided herein. Alternatively, antibodies can be employed that can recognize specific duplexes, including DNA duplexes, RNA duplexes, and DNA-RNA hybrid duplexes or DNA-protein duplexes. The antibodies in turn can be labeled and the assay can be carried out where the duplex is bound to a surface, so that upon the formation of duplex on the surface, the presence of antibody bound to the duplex can be detected.

Gene expression, alternatively, can be measured by immunological methods, such as immunohistochemical staining of cells or tissue sections and assay of cell culture or body fluids, to quantitate directly the expression of gene product. Antibodies useful for immunohistochemical staining and/or assay of sample fluids can be either monoclonal or polyclonal, and can be prepared in any mammal or can be synthesized (e.g., the monoclonal antibodies of this invention). Conveniently, the antibodies can be prepared against a native-sequence STOP-1 polypeptide or against a synthetic peptide based on the DNA sequences provided herein or against exogenous sequence fused to DNA encoding the STOP-1 polypeptide and encoding a specific antibody epitope.

Purification of STOP-1 Polypeptides

Forms of STOP-1 polypeptides can be recovered from culture medium or from host cell lysates. If membrane-bound, it can be released from the membrane using a suitable detergent solution (e.g., TRITON-X™ 100) or by enzymatic cleavage. Cells employed in expression of nucleic acid encoding the STOP-1 polypeptide can be disrupted by various physical or chemical means, such as freeze-thaw cycling, sonication, mechanical disruption, or cell-lysing agents. According to one embodiment, it is desirable that the STOP-1 polypeptide is purified from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the STOP-1 polypeptide. Various methods of protein purification can be employed and such methods are known in the art and described, for example, in Deutscher, *Methods in Enzymology*, 182 (1990); Scopes, *Protein Purification: Principles and Practice* (Springer-Verlag: New York, 1982). The purification step(s) selected will depend, for example, on the nature of the production process used and the particular STOP-1 polypeptide produced.

According to one embodiment, the STOP-1 polypeptides are purified by affinity chromatography using an antibody of this invention.

Assaying Inhibition of Cell Proliferation

The inhibitory activity of antagonists of this invention can be measured using the assays of Examples 13-14 below and other assays known in the art.

Animal models of tumors and cancers (e.g., breast cancer, colon cancer, prostate cancer, lung cancer, etc.) include both non-recombinant and recombinant (transgenic) animals. Non-recombinant animal models include, for example, rodent, e.g., murine models. Such models can be generated by introducing tumor cells into syngeneic mice using standard techniques, e.g., subcutaneous injection, tail vein injection, spleen implantation, intraperitoneal implantation, implantation under the renal capsule, or orthopin implantation, e.g., colon cancer cells implanted in colonic tissue. See, e.g., PCT publication No. WO 97/33551, published Sep. 18, 1997. Probably the most often used animal species in oncological studies are immunodeficient mice and, in particular, nude mice. The observation that the nude mouse with thymic hypo/aplasia could successfully act as a host for human tumor xenografts has lead to its widespread use for this purpose. The autosomal recessive nu gene has been introduced into a very large number of distinct congenic strains of nude mouse, including, for example, ASW, A/He, AKR, BALB/c, B10.LP, C17, C3H, C57BL, C57, CBA, DBA, DDD, I/st, NC, NFR, NFS, NFS/N, NZB, NZC, NZW, P, RIII, and SJL. In addition, a wide variety of other animals with inherited immunological defects other than the nude mouse have been bred and used as recipients of tumor xenografts. For further details see, e.g., *The Nude Mouse in Oncology Research*, E. Boven and B. Winograd, eds. (CRC Press, Inc., 1991).

The cells introduced into such animals can be derived from known tumor/cancer cell lines, such as any of the above-listed tumor cell lines, and, for example, the B104-1-1 cell line (stable NIH-3T3 cell line transfected with the neu protooncogene); ras-transfected NIH-3T3 cells; Caco-2 (ATCC HTB-37); or a moderately well-differentiated grade II human colon adenocarcinoma cell line, HT-29 (ATCC HTB-38); or from tumors and cancers. Samples of tumor or cancer cells can be obtained from patients undergoing surgery, using standard conditions involving freezing and storing in liquid nitrogen. Karmali et al., *Br. J. Cancer*, 48: 689-696 (1983).

Tumor cells can be introduced into animals such as nude mice by a variety of procedures. The subcutaneous (s.c.) space in mice is very suitable for tumor implantation. Tumors can be transplanted s.c. as solid blocks, as needle biopsies by use of a trochar, or as cell suspensions. For solid-block or trochar implantation, tumor tissue fragments of suitable size are introduced into the s.c. space. Cell suspensions are freshly prepared from primary tumors or stable tumor cell lines, and injected subcutaneously. Tumor cells can also be injected as subdermal implants. In this location, the inoculum is deposited between the lower part of the dermal connective tissue and the s.c. tissue.

Animal models of breast cancer can be generated, for example, by implanting rat neuroblastoma cells (from which the neu oncogene was initially isolated), or neu-transformed NIH-3T3 cells into nude mice, essentially as described by Drebin et al. *Proc. Nat. Acad. Sci. USA*, 83: 9129-9133 (1986).

Similarly, animal models of colon cancer can be generated by passaging colon cancer cells in animals, e.g., nude mice, leading to the appearance of tumors in these animals. An orthotopic transplant model of human colon cancer in nude mice has been described, for example, by Wang et al., *Cancer Research*, 54: 4726-4728 (1994) and Too et al., *Cancer Research*, 55: 681-684 (1995). This model is based on the so-called "METAMOUSE™" sold by AntiCancer, Inc., (San Diego, Calif.).

Tumors that arise in animals can be removed and cultured in vitro. Cells from the in vitro cultures can then be passaged to animals. Such tumors can serve as targets for further testing or drug screening. Alternatively, the tumors resulting from the passage can be isolated and RNA from pre-passage cells and cells isolated after one or more rounds of passage analyzed for differential expression of genes of interest. Such passaging techniques can be performed with any known tumor or cancer cell lines.

For example, Meth A, CMS4, CMS5, CMS21, and WEHI-164 are chemically induced fibrosarcomas of BALB/c female mice (DeLeo et al., *J. Exp. Med.*, 146: 720 (1977)), which provide a highly controllable model system for studying the anti-tumor activities of various agents. Palladino et al., *J. Immunol.*, 138: 4023-4032 (1987). Briefly, tumor cells are propagated in vitro in cell culture. Prior to injection into the animals, the cell lines are washed and suspended in buffer, at a cell density of about $10 \times 10^6$ to $10 \times 10^7$ cells/ml. The animals are then infected subcutaneously with 10 to 100 ul of the cell suspension, allowing one to three weeks for a tumor to appear.

In addition, the Lewis lung (3LL) carcinoma of mice, which is one of the most thoroughly studied experimental tumors, can be used as an investigational tumor model. Efficacy in this tumor model has been correlated with beneficial effects in the treatment of human patients diagnosed with small-cell carcinoma of the lung (SCCL). This tumor can be introduced in normal mice upon injection of tumor fragments from an affected mouse or of cells maintained in culture. Zupi et al., *Br. J. Cancer*, 41: suppl. 4, 30 (1980). Evidence indicates that tumors can be started from injection of even a single cell and that a very high proportion of infected tumor cells survive. For further information about this tumor model see, Zacharski, *Haemostasis*, 16: 300-320 (1986).

One way of evaluating the efficacy of a test compound in an animal model with an implanted tumor is to measure the size of the tumor before and after treatment. Traditionally, the size of implanted tumors has been measured with a slide caliper in two or three dimensions. The measure limited to two dimensions does not accurately reflect the size of the tumor; therefore, it is usually converted into the corresponding volume by using a mathematical formula. However, the measurement of tumor size is very inaccurate. The therapeutic effects of a drug candidate can be better described as treatment-induced growth delay and specific growth delay. Another important variable in the description of tumor growth is the tumor volume doubling time. Computer programs for the calculation and description of tumor growth are also available, such as the program reported by Rygaard and Spang-Thomsen, *Proc. 6th Int. Workshop on Immune-Deficient Animals*, Wu and Sheng eds. (Basel, 1989), p. 301. It is noted, however, that necrosis and inflammatory responses following treatment can actually result in an increase in tumor size, at least initially. Therefore, these changes need to be carefully monitored, by a combination of a morphometric method and flow cytometric analysis.

Further, recombinant (transgenic) animal models can be engineered by introducing the coding portion of the STOP-1 gene identified herein into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g., baboons, chimpanzees and monkeys. Techniques known in the art to introduce a transgene into such animals include pronucleic microinjection (U.S. Pat. No. 4,873,191); retrovirus-mediated gene transfer into germ lines (e.g., Van der Putten et al., *Proc. Natl. Acad. Sci. USA*, 82: 6148-615 (1985)); gene targeting in embryonic stem cells (Thompson et al., *Cell*, 56: 313-321 (1989)); electroporation of embryos (Lo, *Mol. Cell. Biol.*, 3: 1803-1814 (1983)); and sperm-mediated gene transfer. Lavitrano et al, *Cell*, 57: 717-73 (1989). For a review, see for example, U.S. Pat. No. 4,736,866.

For the purpose of the present invention, transgenic animals include those that carry the transgene only in part of their cells ("mosaic animals"). The transgene can be integrated either as a single transgene, or in concatamers, e.g., head-to-head or head-to-tail tandems. Selective introduction of a transgene into a particular cell type is also possible by following, for example, the technique of Lasko et al., *Proc. Natl. Acad. Sci. USA*, 89: 6232-636 (1992). The expression of the transgene in transgenic animals can be monitored by standard techniques. For example, Southern blot analysis or PCR amplification can be used to verify the integration of the transgene. The level of mRNA expression can then be analyzed using techniques such as in situ hybridization, Northern blot analysis, PCR, or immunocytochemistry. The animals are further examined for signs of tumor or cancer development.

Alternatively, "knock-out" animals can be constructed that have a defective or altered gene encoding a STOP-1 polypeptide identified herein, as a result of homologous recombination between the endogenous gene encoding the STOP-1 polypeptide and altered genomic DNA encoding the same polypeptide introduced into an embryonic cell of the animal. For example, cDNA encoding a particular STOP-1 polypeptide can be used to clone genomic DNA encoding that polypeptide in accordance with established techniques. A portion of the genomic DNA encoding a particular STOP-1 polypeptide can be deleted or replaced with another gene, such as a gene encoding a selectable marker that can be used to monitor integration. Typically, several kilobases of unaltered flanking DNA (both at the 5' and 3' ends) are included in the vector. See, e.g., Thomas and Capecchi, *Cell*, 51: 503 (1987) for a description of homologous recombination vectors. The vector is introduced into an embryonic stem cell line (e.g., by electroporation) and cells in which the introduced DNA has homologously recombined with the endogenous DNA are selected. See, e.g., Li et al., *Cell* 69: 915 (1992). The selected cells are then injected into a blastocyst of an animal (e.g., a mouse or rat) to form aggregation chimeras. See, e.g., Bradley, in *Teratocarcinomas and Embryonic Stem Cells: A Practical Approach*, E. J. Robertson, ed. (IRL: Oxford, 1987), pp. 113-152. A chimeric embryo can then be implanted into a suitable pseudopregnant female foster animal and the embryo brought to term to create a "knock-out" animal. Progeny harboring the homologously recombined DNA in their germ cells can be identified by standard techniques and used to breed animals in which all cells of the animal contain the homologously recombined DNA. Knock-out animals can be characterized, for instance, by their ability to defend against certain pathological conditions and by their development of pathological conditions due to absence of the STOP-1 polypeptide.

The efficacy of antibodies specifically binding the STOP-1 polypeptides identified herein, and other drug candidates, can be tested also in the treatment of spontaneous animal tumors. A suitable target for such studies is the feline oral squamous cell carcinoma (SCC). Feline oral SCC is a highly invasive, malignant tumor that is the most common oral malignancy of cats, accounting for over 60% of the oral tumors reported in this species. It rarely metastasizes to distant sites, although this low incidence of metastasis can merely be a reflection of the short survival times for cats with this tumor. These tumors are usually not amenable to surgery, primarily because of the anatomy of the feline oral cavity. At present, there is no effective treatment for this tumor. Prior to entry into the study, each cat undergoes complete clinical examination and biopsy, and is scanned by computed tomography (CT). Cats diagnosed with sublingual oral squamous cell tumors are excluded from the study. The tongue can become paralyzed as a result of such tumor, and even if the treatment kills the tumor, the animals may not be able to feed themselves. Each cat is treated repeatedly, over a longer period of time. Photographs of the tumors will be taken daily during the treatment period, and at each subsequent recheck. After treatment, each cat undergoes another CT scan. CT scans and thoracic radiograms are evaluated every 8-weeks thereafter. The data are evaluated for differences in survival, response, and toxicity as compared to control groups. Positive response may require evidence of tumor regression, preferably with improvement of quality of life and/or increased life span.

In addition, other spontaneous animal tumors, such as fibrosarcoma, adenocarcinoma, lymphoma, chondroma, or leiomyosarcoma of dogs, cats, and baboons can also be tested. Of these, mammary adenocarcinoma in dogs and cats is a preferred model as its appearance and behavior are very similar to those in humans. However, the use of this model is limited by the rare occurrence of this type of tumor in animals.

Assays for Evaluating Angiogenic or Vasculogenic Activity

Assays that are useful for measuring the pro-angiogenic, antiangiogenic, pro-vasculogenic or anti-vasculogenic activity of the agonists, progenitors, antagonists of this invention include the assays of Examples 14 and 26 or other suitable assays known in the art such as those included below.

Assays for wound-healing activity include, for example, those described in Winter, Epidermal Wound Healing, Maibach, H I and Rovee, D T, eds. (Year Book Medical Publishers, Inc., Chicago), pp. 71-112, as modified by the article of Eaglstein and Mertz, J. Invest. Dermatol., 71: 382-384 (1978).

Assays for endothelial cell proliferation include, for example, those described in WO 02/00690 or United States Patent Publication No. 20010036955A1.

Assays for evaluating inhibition of angiogenesis include, for example, the assay described in United States Patent Publication No. 20010036955A1.

Assays for measuring inhibition of endothelial tube formation include, for example, the assay described in United States Patent Publication No. 20010036955A1.

Antibody Binding Studies

Antibody binding studies can be carried out using known assay methods, such as competitive binding assays, direct and indirect sandwich assays, and immunoprecipitation assays. Zola, *Monoclonal Antibodies: A Manual of Techniques* (CRC Press, Inc., 1987), pp. 147-158.

Competitive binding assays rely on the ability of a labeled standard to compete with the test sample analyte for binding with a limited amount of antibody. The amount of target protein in the test sample is inversely proportional to the amount of standard that becomes bound to the antibodies. To facilitate determining the amount of standard that becomes bound, the antibodies preferably are insolubilized before or after the competition, so that the standard and analyte that are bound to the antibodies can conveniently be separated from the standard and analyte that remain unbound.

Sandwich assays involve the use of two antibodies, each capable of binding to a different immunogenic portion, or epitope, of the protein to be detected. In a sandwich assay, the test sample analyte is bound by a first antibody that is immobilized on a solid support, and thereafter a second antibody binds to the analyte, thus forming an insoluble three-part complex. See, e.g., U.S. Pat. No. 4,376,110. The second antibody can itself be labeled with a detectable moiety (direct sandwich assays) or can be measured using an anti-immunoglobulin antibody that is labeled with a detectable moiety (indirect sandwich assay). For example, one type of sandwich assay is an ELISA assay, in which case the detectable moiety is an enzyme.

Competitive ELISA assays can be performed to screen polypeptides, antibodies or antagonists for those that specifically bind to STOP-1, which binding can be inhibited by a monoclonal antibody of this invention.

In one example, a competitive ELISA assay can be conducted following the methods described in the Examples (e.g., Example 22). A full length or short form of native STOP-1 protein (2 ug/ml in PBS) can be coated on a microtiter plate at 4° C. overnight or at room temperature for 2 hours. The wells can be blocked by adding 65 ul 1% BSA for 30 minutes followed by 40 ul 1% Tween20 for another 30 minutes. Next, the wells can be washed with PBS—0.05% Tween20 5 times. Various concentrations of S7, S16, S4, F15 or S9 antibody (in ELISA buffer) can be incubated in the wells for 30 minutes at room temperature. Then, polypeptides or antibodies to be tested can be added to different wells for 10 minutes at a concentration that would normally produce 90% binding capacity in the absence of the S7, S16, S4, F15 or S9 antibody. Next, the wells can be washed with PBS—0.05% Tween20 5 times. Binding can be quantified by methods known in the art.

For immunohistochemistry, the tissue sample can be fresh or frozen or can be embedded in paraffin and fixed with a preservative such as formalin, for example.

Cell-Based Tumor Assays

Cell-based assays and animal models for proliferative disorders, such as tumors, can be used to verify the inhibitory activity of the antagonists of this invention. Useful cell-based assays, animal models and methods include, for example, those set forth in the Examples below.

For example, cells of a cell type known to be involved in a proliferative disorder are transfected with STOP-1 cDNAs herein, and the ability of these cDNAs to induce excessive growth or inhibit growth is analyzed in the presence or absence of an antagonist. If the proliferative disorder is cancer, suitable tumor cells include, for example, stable tumor cell lines such as the B104-1-1 cell line (stable NIH-3T3 cell line transfected with the neu protooncogene) and ras-transfected NIH-3T3 cells, which can be transfected with the a STOP-1 sequence and monitored for tumorigenic growth. Such transfected cell lines can then be used to test the ability of poly- or monoclonal antibodies or antibody compositions to inhibit tumorigenic cell growth by exerting cytostatic or cytotoxic activity on the growth of the transformed cells, or by mediating antibody-dependent cellular cytotoxicity (ADCC).

In addition, primary cultures derived from tumors in transgenic animals (as described above) can be used in the cell-based assays herein, although stable cell lines are preferred. Techniques to derive continuous cell lines from transgenic animals are known in the art. See, e.g., Small et al., *Mol. Cell. Biol.*, 5: 642-648 (1985).

Gene Therapy

Described below are methods and compositions whereby disease symptoms can be ameliorated. The STOP-1 polypeptides (including STOP-1 polypeptide variants) described herein, antagonists and antibodies of this invention can be employed in accordance with the present invention by expression of each in vivo, which is often referred to as gene therapy. For example, STOP-1 polypeptide variants can be expressed in cells using these methods. According to one embodiment, the methods or the vectors used to express the STOP-1 polypeptides (including variants) involve the use of a stromal targeting agent to direct the vehicle containing the UNQ polypeptide or nucleic acid molecule to a desired stromal region.

There are two major approaches to getting the nucleic acid (optionally contained in a vector) into the mammal's cells: in vivo and ex vivo. For in vivo delivery the nucleic acid is injected directly into the mammal, usually at the sites where the STOP-1 polypeptide is required, i.e., the site of synthesis of the STOP-1 polypeptide, if known, and the site (e.g., wound) where biological activity of the STOP-1 polypeptide is needed. For ex vivo treatment, the mammal's cells are removed, the nucleic acid is introduced into these isolated cells, and the modified cells are administered to the mammal either directly or, for example, encapsulated within porous membranes that are implanted into the mammal (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or transferred in vivo in the cells of the intended host. Techniques suitable for the transfer of nucleic acid into mammalian cells in vitro include the use of liposomes, electroporation, microinjection, transduction, cell fusion, DEAE-dextran, the calcium phosphate precipitation method, etc. Transduction involves the association of a replication-defective, recombinant viral (preferably retroviral) particle with a cellular receptor, followed by introduction of the nucleic acids contained by the particle into the cell. A commonly used vector for ex vivo delivery of the gene is a retrovirus.

The currently preferred in vivo nucleic acid transfer techniques include transfection with viral or non-viral vectors (such as adenovirus, lentivirus, Herpes simplex I virus, or adeno-associated virus (AAV)) and lipid-based systems (useful lipids for lipid-mediated transfer of the gene are, for example, DOTMA, DOPE, and DC-Chol; see, e.g., Tonkinson et al., *Cancer Investigation*, 14(1): 54-65 (1996)). Such vectors are used to synthesize virus that can be used as vehicles for delivering agents, such as antagonists and nucleic acid molecules of this invention. The most preferred vectors for use in gene therapy are viruses, most preferably adenoviruses, AAV, lentiviruses, or retroviruses. A viral vector such as a retroviral vector includes at least one transcriptional promoter/enhancer or locus-defining element(s), or other elements that control gene expression by other means such as alternate splicing, nuclear RNA export, or post-translational modification of messenger. In addition, a viral vector such as a retroviral vector includes a nucleic acid molecule that, when transcribed in the presence of a gene encoding the STOP-1 polypeptide, is operably linked thereto and acts as a translation initiation sequence. Such vector constructs also include a packaging signal, long terminal repeats (LTRs) or portions thereof, and positive and negative strand primer binding sites appropriate to the virus used (if these are not already present in the viral vector). In addition, such vector typically includes a signal sequence for secretion of the STOP-1 polypeptide from a host cell in which it is placed. Preferably the signal sequence for this purpose is a mammalian signal sequence, most preferably the native signal sequence for the STOP-1 polypeptide. Optionally, the vector construct can also include a signal that directs polyadenylation, as well as one or more restriction sites and a translation termination sequence. By way of example, such vectors will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers. According to one embodiment, the vehicle has a stromal targeting agent.

In some situations, it is desirable to provide the nucleic acid source with an agent that targets the target cells, such as an antibody specific for a cell-surface membrane protein or the target cell, a ligand for a receptor on the target cell, etc. Where liposomes are employed, proteins that bind to a cell-surface membrane protein associated with endocytosis can be used for targeting and/or to facilitate uptake, e.g., capsid proteins or fragments thereof tropic for a particular cell type, antibodies for proteins that undergo internalization in cycling, and proteins that target intracellular localization and enhance intracellular half-life. The technique of receptor-mediated endocytosis is described, for example, by Wu et al., *J. Biol. Chem.,* 262: 4429-4432 (1987); and Wagner et al., *Proc. Natl. Acad. Sci. USA,* 87: 3410-3414 (1990). For a review of the currently known gene marking and gene therapy protocols, see, Anderson et al., *Science,* 256: 808-813 (1992). See also WO 93/25673 and the references cited therein.

Suitable gene therapy and methods for making retroviral particles and structural proteins can be found in, e.g., U.S. Pat. No. 5,681,746.

Detecting STOP-1 Mutations

This invention is also related to the use of the gene encoding the STOP-1 polypeptide as a diagnostic. Detection of a mutated form of the STOP-1 polypeptide can be indicative of a proclivity for developing a proliferative disorder. Detection of levels of the STOP-1 polypeptide in the tissue of a mammal over the levels of the same tissue in a normal mammal can also be indicative of proclivity of developing a proliferative disorder (below).

Individuals carrying mutations in the genes encoding a human STOP-1 polypeptide can be detected at the DNA level by a variety of techniques. Nucleic acids for diagnosis can be obtained from a mammal's cells, such as from blood, urine, saliva, tissue biopsy, and autopsy material. The genomic DNA can be used directly for detection or can be amplified enzymatically by using PCR (Saiki et al., *Nature,* 324: 163-166 (1986)) prior to analysis. RNA or cDNA can also be used for the same purpose. As an example, PCR primers complementary to the nucleic acid encoding the STOP-1 polypeptide can be used to identify and analyze the STOP-1 polypeptide mutations. For example, deletions and insertions can be detected by a change in size of the amplified product in comparison to the normal genotype. Point mutations can be identified by hybridizing amplified DNA to radiolabeled RNA encoding the STOP-1 polypeptide, or alternatively, radiolabeled antisense DNA sequences encoding the STOP-1 polypeptide. Perfectly matched sequences can be distinguished from mismatched duplexes by RNase A digestion or by differences in melting temperatures.

Genetic testing based on DNA sequence differences can be achieved by detection of alteration in electrophoretic mobility of DNA fragments in gels with or without denaturing agents. Small sequence deletions and insertions can be visualized by high resolution gel electrophoresis. DNA fragments of different sequences can be distinguished on denaturing formamidine gradient gels in which the mobilities of different DNA fragments are retarded in the gel at different positions according to their specific melting or partial melting temperatures. See, e.g., Myers et al., *Science,* 230: 1242 (1985).

Sequence changes at specific locations may also be revealed by nuclease protection assays, such as RNase and S1 protection or the chemical cleavage method, for example, Cotton et al., *Proc. Natl. Acad. Sci. USA,* 85: 4397-4401 (1985).

Thus, the detection of a specific DNA sequence can be achieved by methods such as hybridization, RNase protection, chemical cleavage, direct DNA sequencing, or the use of restriction enzymes, e.g., restriction fragment length polymorphisms (RFLP), and Southern blotting of genomic DNA.

In addition to more conventional gel-electrophoresis and DNA sequencing, mutations in the STOP-1 polypeptide can also be detected by in situ analysis.

Detecting STOP-1 Polypeptide or Nucleic Acid Levels

Levels of STOP-1 polypeptide or nucleic acid molecules can be detected, e.g., using the reagents disclosed herein in combination with methods known in the art, such as in situ hybridization, RT-PCR, northern blots, western blots, or by using the Examples and reagents provided herein.

A competition assay can be employed wherein antibodies specific to the STOP-1 polypeptide are attached to a solid support and labeled STOP-1 polypeptide and a sample derived from the host are passed over the solid support and the amount of label detected attached to the solid support can be correlated to a quantity of the STOP-1 polypeptide in the sample.

In one preferred embodiment, antibodies that specifically bind STOP-1 as described herein are used to monitor STOP-1 protein levels.

Screening Assays for Drug Candidates

This invention encompasses methods of screening compounds to identify those that mimic the STOP-1 polypeptide activity (agonists) or prevent the effect of the STOP-1 polypeptide (antagonists). Generally, the STOP-1 polypeptide is exposed to the drug candidate by incubation or contact under various conditions. Screening assays for antagonist drug candidates are designed to identify compounds that specifically bind or complex with the native STOP-1 polypeptide. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays in combination with the STOP-1 polypeptide, fragments thereof, or cells expressing the STOP-1 polypeptide or fragments thereof.

All assays for antagonists are common in that they call for contacting the drug candidate with a STOP-1 polypeptide encoded by a nucleic acid identified herein under conditions and for a time sufficient to allow these two components to interact.

In binding assays, the interaction is binding and the complex formed can be isolated or detected in the reaction mixture. For example, binding of STOP-1 polypeptide to a cancer cell or an endothelial cells in the absence or presence of the candidate antagonist can be performed in the assays described in the Examples below to evaluate whether the antagonist blocked binding of STOP-1 to the cells. In another embodiment, the STOP-1 polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the STOP-1 polypeptide and drying. Alternatively, an immobilized antibody, e.g., a monoclonal antibody, specific for the STOP-1 polypeptide to be immobilized can be used to anchor it to a solid surface. The assay is performed by adding the non-immobilized component, which can be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular STOP-1 polypeptide, its interaction with that polypeptide can be assayed by methods known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature* (*London*), 340: 245-246 (1989); Chien et al., *Proc. Natl. Acad. Sci. USA*, 88: 9578-9582 (1991)) as disclosed by Chevray and Nathans, *Proc. Natl. Acad. Sci. USA,* 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GALA, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with binding between a STOP-1 polypeptide and another protein, including another STOP-1 polypeptide can be tested as follows: usually a reaction mixture is prepared containing the STOP-1 polypeptide and other protein under conditions and for a time allowing for the interaction and binding of the two proteins. To test the ability of a candidate compound to inhibit binding, the reaction is run in the absence and in the presence of the test compound. In addition, a placebo can be added to a third reaction mixture, to serve as positive control. The binding (complex formation) between the test compound and the other polypeptide present in the mixture is monitored as described hereinabove. The formation of a complex in the control reaction(s) but not in the reaction mixture containing the test compound indicates that the test compound interferes with the interaction of the STOP-1 polypeptide and the other polypeptide.

In a proliferation assay, the STOP-1 polypeptide has the ability to stimulate the proliferation of endothelial cells in the presence of the co-mitogen ConA. Specifically, human umbilical vein endothelial cells can be obtained and cultured in 96-well flat-bottomed culture plates (Costar, Cambridge, Mass.) and supplemented with a reaction mixture appropriate for facilitating proliferation of the cells, the mixture containing Con-A (Calbiochem, La Jolla, Calif.). Con-A and the test inhibitory compound to be screened are added and after incubation at 37° C., cultures are pulsed with $^{3-}$H-thymidine and harvested onto glass fiber filters (phD; Cambridge Technology, Watertown, Mass.). Mean $^{3-}$H-thymidine incorporation (cpm) of triplicate cultures is determined using a liquid scintillation counter (Beckman Instruments, Irvine, Calif.). Significant $^{3-}$(H)-thymidine incorporation indicates stimulation of endothelial cell proliferation.

According to one embodiment, the assay described above or assays as described in the Examples below are performed to test antagonists of this invention. Alternatively, antagonists can be detected by combining the STOP-1 polypeptide and a potential antagonist with cold STOP-1 polypeptide under appropriate conditions for a competitive inhibition assay. The STOP-1 polypeptide can be labeled, such as by radioactivity or a colorimetric method, such that the number of STOP-1 polypeptide molecules bound can be used to determine the effectiveness of the potential antagonist. The STOP-1 polypeptide can be labeled by a variety of means including iodination or inclusion of a recognition site for a site-specific protein kinase. Following fixation and incubation, the slides are subjected to autoradiographic analysis Drug candidates include anti-STOP-1 antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a drug candidate can be a closely related protein, for example, a mutated form of the STOP-1 polypeptide that competitively inhibits the action of the STOP-1 polypeptide.

Administration Protocols, Schedules, Doses, and Formulations

The molecules herein and antagonists thereto are pharmaceutically useful as a prophylactic and therapeutic agent for various disorders and diseases as set forth above.

Therapeutic compositions of the polypeptides, antibodies or antagonists of this invention are prepared for storage by mixing the desired molecule having the appropriate degree of purity with optional pharmaceutically acceptable carriers, excipients, or stabilizers (*Remington's Pharmaceutical Sciences,* 16th edition, Osol, A. ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Additional examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Carriers for topical or gel-based forms of agonist or antagonist include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols. For all administrations, conventional depot forms are suitably used. Such forms include, for example, microcapsules, nano-capsules, liposomes, plasters, inhalation forms, nose sprays, sublingual tablets, and sustained-release preparations. The STOP-1 polypeptides or agonists or antagonists will typically be formulated in such vehicles at a concentration of about 0.1 mg/ml to 100 mg/ml.

Another formulation comprises incorporating a STOP-1 polypeptide or agonist or antagonist thereof into formed articles. Such articles can be used in modulating endothelial cell growth and angiogenesis. In addition, tumor invasion and metastasis can be modulated with these articles.

STOP-1 polypeptides or agonists or antagonists to be used for in vivo administration must be sterile. This is readily accomplished by filtration through sterile filtration membranes, prior to or following lyophilization and reconstitution. STOP-1 polypeptides ordinarily will be stored in lyophilized form or in solution if administered systemically. If in lyophilized form, the STOP-1 polypeptide or agonist or antagonist thereto is typically formulated in combination with other ingredients for reconstitution with an appropriate diluent at the time for use. An example of a liquid formulation of a STOP-1 polypeptide or agonist or antagonist is a sterile, clear, colorless unpreserved solution filled in a single-dose vial for subcutaneous injection. Preserved pharmaceutical compositions suitable for repeated use can contain, for example, depending mainly on the indication and type of polypeptide:

a. STOP-1 polypeptide or agonist or antagonist thereto;
 b. a buffer capable of maintaining the pH in a range of maximum stability of the polypeptide or other molecule in solution, preferably about 4-8;
 c. a detergent/surfactant primarily to stabilize the polypeptide or molecule against agitation-induced aggregation;
 d. an isotonifier;
 e. a preservative selected from the group of phenol, benzyl alcohol and a benzethonium halide, e.g., chloride; and
 f. water.

If the detergent employed is non-ionic, it can, for example, be polysorbates (e.g., POLYSORBATE™ (TWEEN™) 20, 80, etc.) or poloxamers (e.g., POLOXAMER™ 188). The use of non-ionic surfactants permits the formulation to be exposed to shear surface stresses without causing denaturation of the polypeptide. Further, such surfactant-containing formulations can be employed in aerosol devices such as those used in a pulmonary dosing, and needleless jet injector guns (see, e.g., EP 257,956).

An isotonifier can be present to ensure isotonicity of a liquid composition of the STOP-1 polypeptide or agonist or antagonist thereto, and includes polyhydric sugar alcohols, preferably trihydric or higher sugar alcohols, such as glycerin, erythritol, arabitol, xylitol, sorbitol, and mannitol. These sugar alcohols can be used alone or in combination. Alternatively, sodium chloride or other appropriate inorganic salts can be used to render the solutions isotonic.

The buffer can, for example, be an acetate, citrate, succinate, or phosphate buffer depending on the pH desired. The pH of one type of liquid formulation of this invention is buffered in the range of about 4 to 8, preferably about physiological pH.

The preservatives phenol, benzyl alcohol and benzethonium halides, e.g., chloride, are known antimicrobial agents that can be employed.

Therapeutic STOP-1 polypeptide or antibody compositions generally are placed into a container having a sterile access port, for example, an intravenous solution bag or vial having a stopper pierceable by a hypodermic injection needle. The formulations are preferably administered as repeated intravenous (i.v.), subcutaneous (s.c.), or intramuscular (i.m.) injections, or as aerosol formulations suitable for intranasal or intrapulmonary delivery (for intrapulmonary delivery see, e.g., EP 257,956).

STOP-1 polypeptides or antibodies can also be administered in the form of sustained-released preparations. Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater. Res.*, 15: 167-277 (1981) and Langer, *Chem. Tech.*, 12: 98-105 (1982) or poly(vinylalcohol)), polylactides (U.S. Pat. No. 3,773,919, EP 58,481), copolymers of L-glutamic acid and gamma ethyl-L-glutamate (Sidman et al., *Biopolymers*, 22: 547-556 (1983)), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(–)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they can denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions.

Sustained-release STOP-1 polypeptide and antibody compositions also include liposomally entrapped STOP-1 polypeptides. Liposomes containing the STOP-1 polypeptide are prepared by methods known per se: DE 3,218,121; Epstein et al., *Proc. Natl. Acad. Sci. USA*, 82: 3688-3692 (1985); Hwang et al., *Proc. Natl. Acad. Sci. USA*, 77: 4030-

4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200-800 Angstroms) unilamellar type in which the lipid content is greater than about 30 mol. % cholesterol, the selected proportion being adjusted for the optimal therapy.

The therapeutically effective dose of a STOP-1 polypeptide or antagonist thereto will, of course, vary depending on such factors as the proliferative disorder to be treated (including prevention), the method of administration, the type of compound being used for treatment, any co-therapy involved, the patient's age, weight, general medical condition, medical history, etc., and its determination is well within the skill of a practicing physician. Accordingly, it will be necessary for the therapist to titer the dosage and modify the route of administration as required to obtain the maximal therapeutic effect. The clinician will administer the STOP-1 polypeptide or antagonist until a dosage is reached that achieves the desired effect for treatment of the condition in question. For example, if the objective is the treatment of cancer, the amount would be one that inhibits the growth of the cancer.

With the above guidelines, the effective dose generally is within the range of from about 0.001 to about 1.0 mg/kg, more preferably about 0.01-1.0 mg/kg, most preferably about 0.01-0.1 mg/kg.

For non-oral use in treating proliferative disorders, it is advantageous to administer the STOP-1 polypeptide or antagonist thereto in the form of an injection at about 0.01 to 50 mg, preferably about 0.05 to 20 mg, most preferably 1 to 20 mg, per kg body weight, 1 to 3 times daily by intravenous injection. For oral administration, a molecule based on the STOP-1 polypeptide is preferably administered at about 5 mg to 1 g, preferably about 10 to 100 mg, per kg body weight, 1 to 3 times daily. It should be appreciated that endotoxin contamination should be kept minimally at a safe level, for example, less than 0.5 ng/mg protein. Moreover, for human administration, the formulations preferably meet sterility, pyrogenicity, general safety, and purity as required by FDA Office and Biologics standards.

The dosage regimen of a pharmaceutical composition containing the STOP-1 polypeptide to be used in tissue regeneration will be determined by the attending physician considering various factors that modify the action of the polypeptides, e.g., amount of tissue weight desired to be formed, the site of damage, the condition of the damaged tissue, the size of a wound, type of damaged tissue (e.g., bone), the patient's age, sex, and diet, the severity of any infection, time of administration, and other clinical factors. The dosage can vary with the type of matrix used in the reconstitution and with inclusion of other proteins in the pharmaceutical composition. For example, the addition of other known growth factors, such as IGF-I, to the final composition can also affect the dosage. Progress can be monitored by periodic assessment of tissue/bone growth and/or repair, for example, X-rays, histomorphometric determinations, and tetracycline labeling.

The route of STOP-1 polypeptide or antagonist or agonist administration is in accord with known methods, e.g., by injection or infusion by intravenous, intramuscular, intracerebral, intraperitoneal, intracerobrospinal, subcutaneous, intraocular, intraarticular, intrasynovial, intrathecal, oral, topical, or inhalation routes, or by sustained-release systems as noted below. The STOP-1 polypeptide or agonist or antagonists thereof also are suitably administered by intratumoral, peritumoral, intralesional, or perilesional routes, to exert local as well as systemic therapeutic effects. The intraperitoneal route is expected to be particularly useful, for example, in the treatment of ovarian tumors.

If a peptide or small molecule is employed as an antagonist or agonist, it is preferably administered orally or non-orally in the form of a liquid or solid to mammals.

Examples of pharmacologically acceptable salts of molecules that form salts and are useful hereunder include alkali metal salts (e.g., sodium salt, potassium salt), alkaline earth metal salts (e.g., calcium salt, magnesium salt), ammonium salts, organic base salts (e.g., pyridine salt, triethylamine salt), inorganic acid salts (e.g., hydrochloride, sulfate, nitrate), and salts of organic acid (e.g., acetate, oxalate, p-toluenesulfonate).

For compositions herein that are useful for bone, cartilage, tendon, or ligament regeneration, the therapeutic method includes administering the composition topically, systemically, or locally as an implant or device. When administered, the therapeutic composition for use is in a pyrogen-free, physiologically acceptable form. Further, the composition can desirably be encapsulated or injected in a viscous form for delivery to the site of bone, cartilage, or tissue damage. Topical administration can be suitable for wound healing and tissue repair. Preferably, for bone and/or cartilage formation, the composition would include a matrix capable of delivering the protein-containing composition to the site of bone and/or cartilage damage, providing a structure for the developing bone and cartilage and preferably capable of being resorbed into the body. Such matrices can be formed of materials presently in use for other implanted medical applications.

The choice of matrix material is based on biocompatibility, biodegradability, mechanical properties, cosmetic appearance, and interface properties. The particular application of the compositions will define the appropriate formulation. Potential matrices for the compositions can be biodegradable and chemically defined calcium sulfate, tricalcium phosphate, hydroxyapatite, polylactic acid, polyglycolic acid, and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices can be comprised of combinations of any of the above-mentioned types of material, such as polylactic acid and hydroxyapatite or collagen and tricalcium phosphate. The bioceramics can be altered in composition, such as in calcium-aluminate-phosphate and processing to alter pore size, particle size, particle shape, and biodegradability.

One specific embodiment is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the polypeptide compositions from disassociating from the matrix.

One suitable family of sequestering agents is cellulosic materials such as alkylcelluloses (including hydroxyalkylcelluloses), including methylcellulose, ethylcellulose, hydroxyethylcellulose, hydroxypropylcellulose, hydroxypropylmethylcellulose, and carboxymethylcellulose, one preferred being cationic salts of carboxymethylcellulose (CMC). Other preferred sequestering agents include hyaluronic acid, sodium alginate, poly(ethylene glycol), polyoxyethylene oxide, carboxyvinyl polymer, and poly(vinyl alcohol). The amount of sequestering agent useful herein is 0.5-20 wt %, preferably 1-10 wt %, based on total formulation weight, which represents the amount necessary to prevent desorption of the polypeptide (or its antagonist) from the polymer matrix and to provide appropriate handling of the composition, yet not so much that the progenitor cells are prevented from infiltrating the matrix, thereby providing the polypeptide (or its antagonist) the opportunity to assist the osteogenic activity of the progenitor cells.

Combination Therapies

The effectiveness of the STOP-1 polypeptide or an agonist or antagonist thereof in preventing or treating the disorder in question can be improved by administering the active agent serially or in combination with another agent that is effective for those purposes, either in the same composition or as separate compositions.

For example, for treatment of cell proliferative disorders, STOP-1 polypeptide antagonist therapy can be combined with the administration of other inhibitors of cell proliferation, such as cytotoxic agents.

In addition, STOP-1 polypeptide antagonists used to treat cancer can be combined with cytotoxic, chemotherapeutic, or growth-inhibitory agents as identified above. Also, for cancer treatment, the STOP-1 polypeptide antagonist thereof is suitably administered serially or in combination with radiological treatments, whether involving irradiation or administration of radioactive substances.

If the treating is for cancer, it may be desirable also to administer antibodies against other tumor-associated antigens, such as antibodies that bind to one or more of the ErbB2, EGFR, ErbB3, ErbB4, or VEGF receptor(s). Alternatively, or in addition, two or more antibodies binding the same or two or more different antigens disclosed herein may be co-administered to the patient. Sometimes, it may be beneficial also to administer one or more cytokines to the patient. In one preferred embodiment, the antagonist antibodies herein are co-administered with a growth-inhibitory agent. For example, the growth-inhibitory agent may be administered first, followed by an antagonist antibody of the present invention. However, simultaneous administration or administration of the antagonist antibody of the present invention first is also contemplated. Suitable dosages for the growth-inhibitory agent are those presently used and may be lowered due to the combined action (synergy) of the growth-inhibitory agent and the antibody herein.

In one embodiment, vascularization of tumors is attacked in combination therapy. The antagonist antibodies of this invention and another antibody (e.g., anti-VEGF) are administered to tumor-bearing patients at therapeutically effective doses as determined, for example, by observing necrosis of the tumor or its metastatic foci, if any. This therapy is continued until such time as no further beneficial effect is observed or clinical examination shows no trace of the tumor or any metastatic foci. Then TNF is administered, alone or in combination with an auxiliary agent such as alpha-, beta-, or gamma-interferon, anti-HER2 antibody, heregulin, anti-heregulin antibody, D-factor, interleukin-1 (IL-1), interleukin-2 (IL-2), granulocyte-macrophage colony stimulating factor (GM-CSF), or agents that promote microvascular coagulation in tumors, such as anti-protein C antibody, anti-protein S antibody, or C4b binding protein (see, WO 91/01753, published 21 Feb. 1991), or heat or radiation.

The effective amounts of the therapeutic agents administered in combination with the STOP-1 polypeptide or antagonist thereof will be at the physician's or veterinarian's discretion. Dosage administration and adjustment is done to achieve maximal management of the conditions to be treated. The dose will additionally depend on such factors as the type of the therapeutic agent to be used and the specific patient being treated. Typically, the amount employed will be the same dose as that used, if the given therapeutic agent is administered without the STOP-1 polypeptide.

Articles of Manufacture

An article of manufacture such as a kit containing the STOP-1 polypeptide or agonists or antagonists thereof useful for the diagnosis or treatment of the disorders described above comprises at least a container and a label. Suitable containers include, for example, bottles, vials, syringes, and test tubes. The containers can be formed from a variety of materials such as glass or plastic. The container holds a composition that is effective for diagnosing or treating the condition and can have a sterile access port (for example, the container can be an intravenous solution bag or a vial having a stopper pierceable by a hypodermic injection needle). The active agent in the composition is the STOP-1 polypeptide or an agonist or antagonist thereto. The label on, or associated with, the container indicates that the composition is used for diagnosing or treating the condition of choice. The article of manufacture can further comprise a second container comprising a pharmaceutically-acceptable buffer, such as phosphate-buffered saline, Ringer's solution, and dextrose solution. It can further include other materials desirable from a commercial and user standpoint, including other buffers, diluents, filters, needles, syringes, and package inserts with instructions for use. The article of manufacture can also comprise a second or third container with another active agent as described above.

Polyclonal Antibodies

Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent can include the STOP-1 polypeptide or a fusion protein thereof. It can be useful to conjugate the immunizing agent to a protein known to be immunogenic in the mammal being immunized. Examples of such immunogenic proteins include, but are not limited to, keyhole limpet hemocyanin, serum albumin, bovine thyroglobulin, and soybean trypsin inhibitor. Examples of adjuvants that can be employed include Freund's complete adjuvant and MPL-TDM adjuvant (monophosphoryl Lipid A or synthetic trehalose dicorynomycolate). The immunization protocol can be selected by one skilled in the art without undue experimentation.

Monoclonal Antibodies

Anti-STOP-1 antibodies can be monoclonal antibodies. Monoclonal antibodies can be prepared, e.g., using hybridoma methods, such as those described by Kohler and Milstein, *Nature*, 256:495 (1975) or can be made by recombinant DNA methods (U.S. Pat. No. 4,816,567) or can be produced by the methods described herein in the Example section. In a hybridoma method, a mouse, hamster, or other appropriate host animal is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the STOP-1 polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Goding, *Monoclonal Antibodies: Principles and Practice* (New York: Academic Press, 1986), pp. 59-103. Immortalized cell lines are usually transformed mammalian cells, particularly myeloma cells of rodent, bovine, and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high-level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. Kozbor, *J. Immunol.,* 133:3001 (1984); Brodeur et al., *Monoclonal Antibody Production Techniques and Applications* (Marcel Dekker, Inc.: New York, 1987) pp. 51-63.

The culture medium in which the hybridoma cells are cultured can then be assayed for the presence of monoclonal antibodies directed against the STOP-1 polypeptide. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones can be subcloned by limiting dilution procedures and grown by standard methods. Goding, supra. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy- and light-chain constant domains in place of the homologous murine sequences (U.S. Pat. No. 4,816,567; Morrison et al., supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies can be monovalent antibodies. Methods for preparing monovalent antibodies are known in the art. For example, one method involves recombinant expression of immunoglobulin light chain and modified heavy chain. The heavy chain is truncated generally at any point in the Fc region so as to prevent heavy-chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly Fab fragments, can be accomplished using techniques known in the art.

Human and Humanized Antibodies

The anti-STOP-1 antibodies can further comprise humanized antibodies or human antibodies. Humanized forms of non-human (e.g., murine) antibodies are chimeric immunoglobulins, immunoglobulin chains, or fragments thereof (such as Fv, Fab, Fab', F(ab')$_2$, or other antigen-binding subsequences of antibodies) that contain minimal sequence derived from non-human immunoglobulin. Humanized antibodies include human immunoglobulins (recipient antibody) in which residues from a CDR of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Humanized antibodies can also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin, and all or substantially all of the FR regions are those of a human immunoglobulin consensus sequence. The humanized antibody preferably also will comprise at least a portion of an immunoglobulin constant region (Fc), typically that of a human immunoglobulin. Jones et al., *Nature,* 321: 522-525 (1986); Riechmann et al., *Nature* 332: 323-329 (1988); Presta, *Curr. Op. Struct. Biol.,* 2:593-596 (1992).

Methods for humanizing non-human antibodies are known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., *Nature,* 321: 522-525 (1986); Riechmann et al., *Nature,* 332: 323-327 (1988); Verhoeyen et al., *Science,* 239: 1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); 5,545,807; and WO 97/17852. Alternatively, human antibodies can be made by introducing human immunoglobulin loci into transgenic animals, e.g., mice in which the endogenous immunoglobulin genes have been partially or completely inactivated. Upon challenge, human antibody production is observed that closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; and 5,661, 016, and in the following scientific publications: Marks et al., Bio/Technology, 10: 779-783 (1992); Lonberg et al., Nature, 368: 856-859 (1994); Morrison, Nature, 368: 812-813 (1994); Fishwild et al., Nature Biotechnology, 14: 845-851 (1996); Neuberger, Nature Biotechnology, 14: 826 (1996); Lonberg and Huszar, Intern. Rev. Immunol., 13: 65-93 (1995).

Alternatively, phage display technology (McCafferty et al., Nature 348:552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573, 905.

As discussed above, human antibodies may also be generated by in vitro activated B cells (see U.S. Pat. Nos. 5,567,610 and 5,229,275).

Human antibodies can also be produced using various techniques known in the art, including phage display libraries. Hoogenboom and Winter, J. Mol. Biol., 227: 381 (1991); Marks et al., J. Mol. Biol., 222: 581 (1991). The techniques of Cole et al. and Boerner et al. are also available for the preparation of human monoclonal antibodies. Cole et al., Monoclonal Antibodies and Cancer Therapy, Alan R. Liss, p. 77 (1985) and Boerner et al., J. Immunol., 147(1): 86-95 (1991).

Bispecific Anti-STOP-1 Antibodies

Bispecific antibodies are monoclonal, preferably human or humanized, antibodies that have binding specificities for at least two different antigens. In the present case, one of the binding specificities is for the STOP-1 polypeptide, the other one is for any other antigen, and preferably for a cell-surface protein or receptor or receptor subunit. For example, the cell-surface protein can be a natural killer (NK) cell receptor. Thus, according to one embodiment, a bispecific antibody of this invention can bind STOP-1 and bind a NK cell and, optionally, activate the NK cell. According to another embodiment, a bispecific antibody of this invention can bind STOP-1 and binds to a stromal tissue compared to other tissue (e.g., stromal targeting agent).

Methods for making bispecific antibodies are known in the art. Traditionally, the recombinant production of bispecific antibodies is based on the co-expression of two immunoglobulin heavy-chain/light-chain pairs, where the two heavy chains have different specificities. Milstein and Cuello, Nature, 305: 537-539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10: 3655-3659 (1991).

Antibody variable domains with the desired binding specificities (antibody-antigen combining sites) can be fused to immunoglobulin constant-domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies, see, for example, Suresh et al., Methods in Enzymology, 121: 210 (1986).

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991)

Heteroconjugate Antibodies

Heteroconjugate antibodies are composed of two covalently joined antibodies. Such antibodies have, for example, been proposed to target immune-system cells to unwanted cells (U.S. Pat. No. 4,676,980), and for treatment of HIV infection. WO 91/00360; WO 92/200373; EP 03089. It is contemplated that the antibodies can be prepared in vitro using known methods in synthetic protein chemistry, including those involving crosslinking agents. For example, immunotoxins can be constructed using a disulfide-exchange reaction or by forming a thioether bond. Examples of suitable reagents for this purpose include iminothiolate and methyl-4-mercaptobutyrimidate and those disclosed, for example, in U.S. Pat. No. 4,676,980.

Effector Function Engineering

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). See, Caron et al., *J. Exp. Med.*, 176: 1191-1195 (1992) and Shopes, *J. Immunol.*, 148: 2918-2922 (1992). Homodimeric antibodies with enhanced anti-tumor activity can also be prepared using heterobifunctional cross-linkers as described in Wolff et al., *Cancer Research*, 53: 2560-2565 (1993). Alternatively, an antibody can be engineered that has dual Fc regions and can thereby have enhanced complement lysis and ADCC capabilities. See, Stevenson et al., *Anti-Cancer Drug Design.* 3: 219-230 (1989).

Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See, WO94/11026.

In another embodiment, the antibody can be conjugated to a "receptor" (such as streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

Immunoliposomes

The antibodies disclosed herein can also be formulated as immunoliposomes. Liposomes containing the antibody are prepared by methods known in the art, such as described in Epstein et al., *Proc. Natl. Acad. Sci. USA*, 82: 3688 (1985); Hwang et al., *Proc. Natl. Acad. Sci. USA*, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.*, 257: 286-288 (1982) via a disulfide-interchange reaction. A chemotherapeutic agent (such as Doxorubicin) is optionally contained within the liposome. See, Gabizon et al., *J. National Cancer Inst.*, 81(19): 1484 (1989).

Pharmaceutical Compositions of Antibodies

Antibodies specifically binding a STOP-1 polypeptide identified herein, as well as other molecules identified by the screening assays disclosed hereinbefore, can be administered for the treatment of various disorders as noted above and below in the form of pharmaceutical compositions.

Lipofectins or liposomes can be used to deliver the polypeptides, nucleic acid molecules, antibodies, antagonists or composition of this invention into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA*, 90: 7889-7893 (1993).

The formulation herein can also contain more than one active compound as necessary for the particular indication being treated, preferably those with complementary activities that do not adversely affect each other. Alternatively, or in addition, the composition can comprise an agent that enhances its function, such as, for example, a cytotoxic agent, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's *Pharmaceutical Sciences*, supra.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they can denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions.

Methods of Treatment Using the Anti-STOP-1 Antibody

It is contemplated that the antibodies to a STOP-1 polypeptide can be used to treat various proliferative disorders and diseases complicated or related to angiogenesis as noted above.

The antibodies are administered to a mammal, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Intravenous administration of the antibody is preferred.

Other therapeutic regimens can be combined with the administration of the antibodies of the instant invention as noted above. For example, if the antibodies are to treat cancer, the patient to be treated with such antibodies can also receive radiation therapy. Alternatively, or in addition, a chemotherapeutic agent can be administered to the patient. Preparation and dosing schedules for such chemotherapeutic agents can be used according to manufacturers' instructions or as determined empirically by the skilled practitioner. Preparation and dosing schedules for such chemotherapy are also described in *Chemotherapy Service*, Ed., M. C. Perry (Williams & Wilkins: Baltimore, Md., 1992). The chemotherapeutic agent can precede, or follow administration of the antibody, or can be given simultaneously therewith. The antibody can be combined with an anti-estrogen compound such as tamoxifen or EVISTA™ or an anti-progesterone such as onapristone (see, EP 616812) in dosages known for such molecules.

If the antibodies are used for treating cancer, they can be, optionally, administer with antibodies against other tumor-associated antigens, such as antibodies that bind to one or more of the ErbB2, EGFR, ErbB3, ErbB4, or VEGF receptor(s). These also include the agents set forth above. Also, the antibody is suitably administered serially or in combination with radiological treatments, whether involving irradiation or administration of radioactive substances. Alternatively, or in addition, two or more antibodies binding the same or two or more different antigens disclosed herein can be co-administered to the patient. In a preferred embodiment, the antibodies herein are co-administered with a growth-inhibitory agent. For example, the growth-inhibitory agent can be administered first, followed by an antibody of the present invention. However, simultaneous administration or administration of the antibody of the present invention first is also contemplated. Suitable dosages for the growth-inhibitory agent are those presently used and can be lowered due to the combined action (synergy) of the growth-inhibitory agent and the antibody herein.

In one embodiment, vascularization of tumors is attacked in combination therapy. The anti-STOP-1 polypeptide antibody and another antibody (e.g., anti-VEGF) are administered to tumor-bearing patients at therapeutically effective doses as determined, for example, by observing necrosis of the tumor or its metastatic foci, if any. This therapy is continued until such time as no further beneficial effect is observed or clinical examination shows no trace of the tumor or any metastatic foci. Then TNF is administered, alone or in combination with an auxiliary agent such as alpha-, beta-, or gamma-interferon, anti-HER2 antibody, heregulin, anti-heregulin antibody, D-factor, interleukin-1 (IL-1), interleukin-2 (IL-2), granulocyte-macrophage colony stimulating factor (GM-CSF), or agents that promote microvascular coagulation in tumors, (such as anti-protein C antibody, anti-protein S antibody, or C4b binding protein, see, WO 91/01753, published 21 Feb. 1991), or heat or radiation.

Since the auxiliary agents will vary in their effectiveness, it can be desirable to compare their impact on the tumor by matrix screening in conventional fashion. The administration of anti-STOP-1 polypeptide antibody and TNF is repeated until the desired clinical effect is achieved. Alternatively, the anti-STOP-1 polypeptide antibody is administered together with TNF and, optionally, auxiliary agent(s). In instances where solid tumors are found in the limbs or in other locations susceptible to isolation from the general circulation, the therapeutic agents described herein are administered to the isolated tumor or organ. In other embodiments, a FGF or PDGF antagonist, such as an anti-FGF or an anti-PDGF neutralizing antibody, is administered to the patient in conjunction with the anti-STOP-1 polypeptide antibody. Treatment with anti-STOP-1 polypeptide antibodies preferably can be suspended during periods of wound healing or desirable neovascularization.

For the prevention or treatment of a proliferative disorder, the appropriate dosage of an antibody herein will depend on the type of disorder to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

For example, depending on the type and severity of the disorder, about 1 ug/kg to 50 mg/kg (e.g., 0.1-20 mg/kg) of antibody is an initial candidate dosage for administration to the patient, whether, for example, by one or more separate administrations, or by continuous infusion. A typical daily or weekly dosage might range from about 1 ug/kg to 100 mg/kg or more, depending on the factors mentioned above. For repeated administrations over several days or longer, depending on the condition, the treatment is repeated or sustained until a desired suppression of disorder symptoms occurs. However, other dosage regimens can be useful. The progress of this therapy is easily monitored by conventional techniques and assays, including, for example, radiographic tumor imaging.

Articles of Manufacture with Antibodies

An article of manufacture containing a container with the antibody and a label is also provided. Such articles are described above, wherein the active agent is an anti-STOP-1 antibody.

Diagnosis and Prognosis of Tumors using Antibodies

If the indication for which the antibodies are used is cancer, while cell-surface proteins, such as growth receptors over expressed in certain tumors, are excellent targets for drug candidates or tumor (e.g., cancer) treatment, the same proteins along with STOP-1 polypeptides find additional use in the diagnosis and prognosis of tumors. For example, antibodies directed against the STOP-1 polypeptides can be used as tumor diagnostics or prognostics.

For example, antibodies, including antibody fragments, can be used qualitatively or quantitatively to detect the expression of genes including the gene encoding the STOP-1 polypeptide. The antibody preferably is equipped with a detectable, e.g., fluorescent label, and binding can be monitored by light microscopy, flow cytometry, fluorimetry, or other techniques known in the art. Such binding assays are performed essentially as described above.

In situ detection of antibody binding to the marker gene products can be performed, for example, by immunofluorescence or immunoelectron microscopy. For this purpose, a histological specimen is removed from the patient, and a labeled antibody is applied to it, preferably by overlaying the antibody on a biological sample. This procedure also allows for determining the distribution of the marker gene product in the tissue examined. It will be apparent to those skilled in the art that a wide variety of histological methods are readily available for in situ detection.

All publications (including patents and patent applications) cited herein are hereby incorporated in their entirety by reference.

The deposits herein were made under the provisions of the Budapest Treaty on the International Recognition of the Deposit of Microorganisms for the Purpose of Patent Procedure and the Regulations thereunder (Budapest Treaty). This assures maintenance of a viable culture of the deposits for 30 years from the date of deposit. The deposits will be made available by ATCC under the terms of the Budapest Treaty, and subject to an agreement between Genentech, Inc. and ATCC, which assures permanent and unrestricted availability of the progeny of the culture of the deposits to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. 122 and the Commissioner's rules pursuant to thereto (including 37 C.F.R. 1.14 with particular reference to 886 OG 638).

The assignee of the present application has agreed that if a culture of the materials on deposits should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

Commercially available reagents referred to in the Examples were used according to manufacturer's instructions unless otherwise indicated. The source of those cells identified in the following Examples, and throughout the specification, by ATCC accession numbers is the American Type Culture Collection, Manassas, Va. Unless otherwise noted, the present invention uses standard procedures of recombinant DNA technology, such as those described hereinabove and in the following textbooks: Sambrook et al., supra; Ausubel et al., *Current Protocols in Molecular Biology* (Green Publishing Associates and Wiley Interscience, N.Y., 1989); Innis et al., *PCR Protocols: A Guide to Methods and Applications* (Academic Press, Inc.: N.Y., 1990); Harlow et al., *Antibodies: A Laboratory Manual* (Cold Spring Harbor Press: Cold Spring Harbor, 1988); Gait, *Oligonucleotide Synthesis* (IRL Press: Oxford, 1984); Freshney, *Animal Cell Culture*, 1987; Coligan et al., *Current Protocols in Immunology*, 1991.

Throughout this specification and claims, the word "comprise," or variations such as "comprises" or "comprising," will be understood to imply the inclusion of a stated integer or group of integers but not the exclusion of any other integer or group of integers.

The foregoing written description is considered to be sufficient to enable one skilled in the art to practice the invention. The following Examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXPERIMENTAL SECTION

EXAMPLE 1

STOP-1 is Conserved in Evolution

Nucleic acid molecules containing human, mouse and zebra fish STOP-1 were obtained by using PCR. Sequences with homology to human, mouse and zebra fish STOP-1 can be found in the Genebank database mouse EST: AK003674; chicken ESTs: A1585129, AL585130; rice fish ESTs: BJ490431, BJ498080, BJ510203, BJ504730; and zebra fish ESTs: AL727874, AW595388; and HGT AL844521. Amino acid sequences of human, mouse, rice fish, zebra fish and chicken STOP-1 are described in SEQ ID NOS: 3, 4, 5, 6, and 7, respectively, and FIG. 1. The cDNAs of human STOP-1 were deposited under the terms of the Budapest Treaty with the American Type Culture Collection (ATCC), 10801 University Blvd., Manassas, Va. 20110-2209, USA as described below:

| Species | Material | Deposit No. | Deposit Date |
|---|---|---|---|
| Human | 76393-1664 | 203323 | Oct. 6, 1998 |
| Human | h762HIP | PTA-5019 | Feb. 21, 2003 |

Amino acid alignment of STOP-1 among several higher vertebrate species (human, mouse, chicken, zebra and rice fishes) shows a high degree of conservation, in particular, parts of the C-terminal domain including the triple helix domain (FIG. 1). In the consensus sequence, an asterisk indicates residues conserved in all species. A blackened circle indicates residues that are conserved in most species.

FIG. 2 shows a human STOP-1 protein. The boxed sequence indicates the signal cleavage site. The Triple Helix Domain is underlined.

EXAMPLE 2

STOP-1 is Overexpressed in Tumors

A proprietary database containing gene expression information from microarrays (GeneExpress®, GeneLogic Inc., Gaithersburg, Md.) was analyzed for the expression of STOP-1 mRNA in various tumors (BLIST analysis, proprietary software written an developed at Genentech, Inc. for use with the GeneExpress® database). Some of the types of tissues analyzed included: adipose, adrenal, blood vessel, bone breast, cervix, CNS, colorectal endometrium, esophagus, gall bladder, head and neck, heart, hematopoetic, kidney, liver, lung, lymphoid, muscle, myometrium, euroendocrine, ovary, pancreas, prostate, skin, small intestine, soft tissue, stomach, testis, thymus, thyroid and urinary and normal tissues (breast, colon, lung, ovarian and kidney). STOP-1 mRNA levels were observed to be especially elevated in bone, breast, cervix, colorectal, endometrium, esophagus, glioma, head & neck, kidney, lung, euroendocrine, ovary, pancreas, skin, soft tissue, stomach, thyroid and urinary tumors.

RNA expression levels were also determined by reverse transcription (RT) and polymerase chain reaction (PCR) amplification of the specific target, STOP-1 (SEQ ID NO:1), in total RNA from a variety of tumors and normal tissues (breast, colon, lung, ovarian and kidney). Tissues were obtained by the Genentech pathology Department and RNA prepared by cesium chloride centrifugation.

One step RT-PCR amplification reactions consisted of 10× Buffer A (Applied Biosystems), 10 Units RNase inhibitor, 200 uM dATP, dCTP, dGTP, dTTP, 5 mM $MgC_{12}$, 1.25 Units Taq Gold Polymerase, 25 Units MULV reverse transcriptase (PE Biosystems), 50 ng total RNA, 200 nM gene-specific hybridization probe (FAM-CATCCAGTAGAAGCATCTC-CTTTTGGGTAA-TAMRA) (SEQ ID NO:23), 300 nM gene-specific forward primer (GGGTTGGCACTTGT-TCAGA) (SEQ ID NO:24) and 300 nM gene-specific reverse primer (CAATAATGATGCGAGAAACTGAAT) (SEQ ID NO:25) in water to a final volume of 50 uL. Thermal cycling conditions were as follows: 1) 48° C., 30 minutes; 2) 95° C., 10 minutes; and 3) 40 cycles of 95° C., 15 seconds and 60° C., 1 minute using an ABI 7700 Sequence Detection System. Transcript levels were normalized to the housekeeping genes GAPDH or RPL19.

Taqman analysis confirmed the overexpression of STOP-1 mRNA in these tumors, especially pancreas, kidney, breast, lung, ovarian, colorectal tumors, soft tissue, stomach thyroid and urinary tumors. Fourteen out of eighteen breast and colon tumor samples showed five to twenty-seven fold overexpression as compared with normal samples. Other tumor types also showed an increase although to a lesser degree. Those tumor types included adrenal, bone, cervical, endometrium, esophagus, head & neck, kidney, liver and euroendocrine.

EXAMPLE 3

In Situ Hybridization Studies (a) Probe Synthesis 12.0 µl (125 mCi) of [alpha-$^{33}$P]UTP (NEN/Perkin-Elmer NEG307H) was speed vac dried in a siliconized 1.5 µl microfuge (Eppendorf) tube. To each tube having dried $^{33}$P-UTP, the following reagents were added and incubated for 1 hour in a 37° C. water bath:

2.0 µl Transcription Optimized 5× Buffer (Promega, P1181)
2.0 µl SQ H2O
1.0 µl DTT, 100 mM (Promega, P1171)
2.0 µl rNTP mix, 2.5 mM [10 µl each of 10 mM rATP (Promega, P113B), rCTP (Promega, P114B) & GTP (Promega, P115B)+10 µl Nuclease-Free $H_2O$ (Promega, P1193)]
1.0 µl RNasin Ribonuclease Inhibitor (Promega, N2511)
1.0 µl DNA Template (1 ug of linear PCR-amplified DNA template encoding a portion of the human STOP-1 coding sequence flanked by the RNA polymerase promoter sequences of bacteriophage T7 on the upper strand for sense control probe transcription and of bacteriophage T3 on the bottom strand for antisense probe transcription)

The sequence in the transcription reaction with the sense and anti-sense probes was:

```
                                        (SEQ ID NO: 26)
5'-GGGAGCCATG CGACCCCAGG GCCCCGCCGC CTCCCCGCAG

CGGCTCCGCG GCCTCCTGCT GCTCCTGCTG CTGCAGCTGC

CCGCGCCGTC GAGCGCCTCT GAGATCCCCA AGGGGAAGCA

AAAGGCGCAG CTCCGGCAGA GGGAGGTGGT GGACCTGTAT

AATGGAATGT GCTTACAAGG GCCAGCAGGA GTGCCTGGTC

GAGACGGGAG CCCTGGGGCC AATGTTATTC CGGGTACACC

TGGGATCCCA GGTCGGGATG GATTCA - 3'
```

1.0 µl RNA Polymerase T3 (Promega, P2083) for antisense probes or 1.0 µl RNA Polymerase T7 (Promega, P2075) for sense probes.

Next, 1 µl of RQ1 RNase-Free DNase (Promega, M6101) was added to the Eppendorf tube containing the radioactively-labeled RNA probe and the reaction was further incubated for 15 minutes at 37° C. This step degraded the DNA template in the reaction. To stop the degradation reaction, 90 µl TE (10 mM Tris pH 7.6/1 mM EDTA pH 8.0) was added to the Eppendorf tube. Unincorporated nucleotides are removed using an RNeasy Mini Kit (Qiagen 74104, Germantown, Md.).

The probe yield was determined by pipetting onto separate rounds of DE81 ion exchange paper (Whatman, 3658 325) 1 µl prefiltered probe and 1 µl of probe following filtration. The samples are immersed in 6 ml of Biofluor (Packard, 6NEF-961) in scintillation vials (Wheaton Scientific, 986701) and counted on Beckman LS 6500.

Next, the probe was analyzed on a 6% Polyacrylamide TBE/Urea gel (Novex EC6865, Invitrogen, Carlsbad, Calif.) to confirm that the transcript was of the proper length. $1 \times 10^6$ cpm of probe or 2 μl of Novagen Perfect RNA marker 0.1-1 kb (Novagen 69924-1) was added to 3 μl TBE/Urea Sample Buffer (Novex, LC6876). The RNAs were denatured on 95° C. heat blocks for 3 minutes and then immediately chilled on ice. The samples were run at 180-250 volts for 45 minutes. The gel was exposed for 1 hour to Biomax MS film (Kodax, 829 4985) with an intensifying screen in −70° C. freezer.

(b) In Situ Hybridization

In situ hybridization analysis was performed initially on sections of normal and tumor tissues. The slides were hybridized to human STOP-1 sense and anti-sense RNA probes using the techniques described below. Further analysis was conducted on sections of tissue microarrays (TMAs) containing numerous normal and tumor tissue specimens. The TMA sections were hybridized exclusively with antisense RNA probes.

The slides were baked in an oven to adhere tissue to glass at 37° C. overnight followed by 65° C. for 30 minutes. The sections were deparaffinized in a Leica Autostainer XL (Leica, Deerfield, Ill.) by incubating 3 times for 5 minutes each in Xylenes (Richard Allen, Kalamazoo, Mich.) then rehydrating through a graded ethanol series to distilled water. Slides were then washed twice in 2×SSC (0.3 M NaCl, 0.030 M NaCitrate, pH 7.0) for 5 minutes each time. The slides were treated for 15 minutes in a 20 μg/ml Proteinase K (Roche Diagnostics, Indianapolis, Ind.) in 10 mM Tris pH 8.0/0.5 M NaCl solution at 37° C. and washed for 10 minutes in 0.5× SSC (0.075 M NaCl, 0.007 M NaCitrate, pH 7.0). The slides were dehydrated with an ethanol gradient (70%-95%-100%) and air-dried. The slides were covered with 100 μl hybridization buffer (50% formamide, 10% dextran sulfate, and 2×SSC) and prehybridized for 1-4 hours at 42° C. The [$^{33}$P]-labeled single-stranded STOP-1 probe (anti-sense orientation) referenced above at a concentration of $2 \times 10^6$ cpm was dissolved in 100 μl of hybridization buffer containing 1 mg/ml tRNA and added to the prehybridization buffer on one of the slides, mixed well, covered with coverslip, and allowed to hybridize overnight at 55° C. in a sealed humidified container.

The foregoing hybridization procedure was performed on another slide from the same tissue block using the same [$^{33}$P]-labeled single-stranded STOP-1 probe in the sense orientation.

After hybridization, the slides were washed twice for 10 minutes in 2×SSC containing 1 mM EDTA at room temperature, and then incubated for 30 minutes at 37° C. in 20 μg/mL RNase A in 10 mM Tris pH 8, 0.5 M NaCl. The slides were washed for 10 minutes in 2×SSC containing 1 mM EDTA at room temperature, then washed 4 times for 30 minutes each in 0.1×SSC containing 1 mM EDTA at 55° C., and then washed in 0.5×SSC for 10 minutes at room temperature. The slides were dehydrated for 2 minutes each in 50%, 70%, and 90% ethanol containing 0.3M ammonium acetate, and allowed to dry in the air.

Slides were apposed to X-ray film (Biomax MR Film, Kodax, 870 1302) for 16 hours to obtain a preliminary assessment of the success of the experiment. Slides were then dipped in NTB2 Emulsion (Kodax, 165 4433) [1:1 dilution with H$_2$0], allowed to dry overnight in complete darkness, transferred into light tight boxes with desiccant and allowed to expose for 4 weeks. After 4 weeks, slides were developed using D-19 developer [1:1 dilution with H$_2$0] for 3 minutes at 15° C., rinsed and fixed in GBX fixer for 6 minutes at 15° C. Slides were counterstained with hematoxylin and eosin prior to examination by a pathologist.

Table 7 shows the results of the in situ hybridization experiments:

TABLE 7

| TISSUE TYPE | NORMAL TISSUE (# of positive/total) | TUMOR TISSUE (# of positive/total) |
|---|---|---|
| Lung | 2/16 adult | 41/49 adenocarcinoma |
| | | 27/30 squamous cell carcinoma |
| | | 1/1 large cell carcinoma |
| | | 2/5 lung neuroendocrine tumor |
| | | Cell Lines - all tested negative |
| | | Calu-6 (lung carcinoma anaplastic) |
| | | SK-MES cell (squamous cell lung) |
| | | H322 |
| | | A549 (lung carcinoma) |
| | | H522 |
| Breast | 0/6 adult | 2/14 adult |
| Colon | 0/5 adult | 4/8 adult |
| Small Intestine | 1/5 adult | — |
| Pancreas | 0/2 adult | 3/5 adult |
| Heart | 0/2 fetal | — |
| | 0/4 adult | |
| Placenta | 0/5 adult | — |
| Aorta | 0/1 adult | — |
| Blood Vessel | 0/1 adult | — |
| Thymus | 0/1 adult | — |
| Trachea | 0/1 adult | — |
| Liver | 0/3 adult | 2/4 adult hepatocellular carcinoma |
| Thyroid | 1/3 adult | — |
| Skin | 1/1 adult in follicle and dermis | 4/4 adult melanoma |
| Stomach | 0/3 adult | — |
| Brain | 0/4 adult | — |
| Spleen | 0/4 adult | — |
| Lymph Node | 0/3 adult | 0/4 lymphomas adult |
| Prostate | 0/3 adult | 0/1 lymphomas adult |
| Ovary | 1/1 adult | 2/2 adult |
| Urinary Bladder | 0/1 adult | 3/3 transitional cell carcinomas |
| Gall Bladder | 0/1 adult | — |
| Kidney | 0/2 adult | 0/4 adult |
| Adrenal | 0/1 adult | — |
| Endometrium | — | 2/3 adult |
| Cartilage | — | 0/1 chondrosarcoma |
| Adipose | — | 0/1 liposarcoma |
| Fetal Tissues | 0/1 aorta, blood vessel, thymus, trachea, liver, lung | — |

The in situ hybridization experiments showed that most normal samples tested negative for STOP-1 mRNA. On the other hand, an astonishingly high number of lung tumors, colon tumors, pancreatic tumors, hepatocellular carcinomas, melanomas, ovarian cancers, endometrial cancers and urinary bladder transitional cell carcinomas showed significant STOP-1 mRNA expression. Furthermore, STOP-1 mRNA was mainly expressed in the stroma (e.g., lung squamous cell carcinomas, adenocarcinomas, breast carcinoma) and not the epithelial compartments of most tumors with the exception of the melanomas which expressed STOP-1 mRNA in the neoplastic cells. The few normal tissues that tested positive for STOP-1 mRNA showed expression in the stromal tissue, with the exception of the thyroid tissue, which expressed STOP-1 mRNA in its epithelial cells. "-" indicates that the tissues were not examined.

EXAMPLE 4

Northern Analysis of STOP-1 mRNA in Normal Tissues

Human and mouse STOP-1 cDNA probes (full length coding sequences) were radiolabeled with the random-prime kit (Perkin-Elmer) and applied for analysis of human multiple tissue and mouse embryo blots (Clontech) according to the instructions of the manufacturer. The results can be seen in FIGS. 3a and b.

Figure 3A:
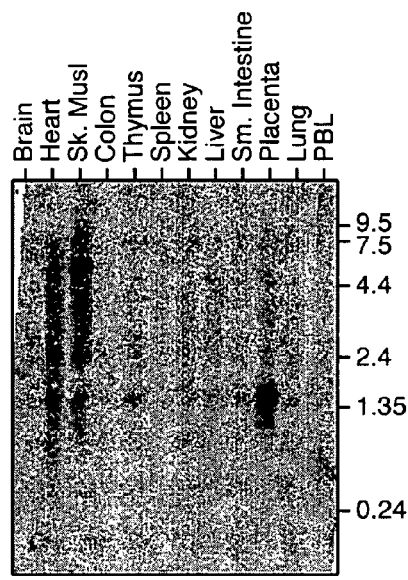
FIG. 3 shows (A) the presence of human STOP-1 mRNA in certain tissue types and (B) mouse STOP-1 mRNA from different stages of mouse development. Full length human or mouse STOP-1 DNAs were radiolabelled and used to probe northern blots of tissues from adult humans or developing mouse embryos.
Figure 3B:
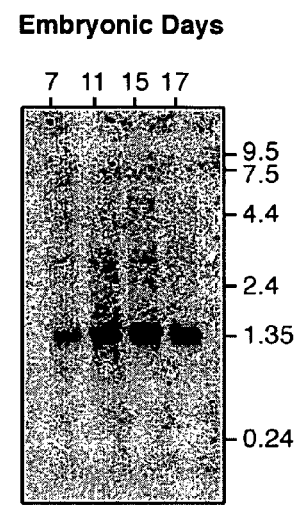

In normal adult human tissues, the highest STOP-1 mRNA expression was detected in placenta, heart and skeletal muscle (FIG. 3a). FIG. 3b shows a northern blot that indicates that strong STOP-1 mRNA expression in mouse embryos at 7, 11, 15 and 17 days of development.

EXAMPLE 5

STOP-1 DNA Constructs (a) Mammalian Cell Expression

All wild type and mutant human, mouse and zebrafish STOP-1 cDNA sequences were made by PCR and expressed in pIRESpuro2 vector (BD Biosciences) or pIRESpuro2 with synthetic 8×HIS tag coding sequence (HIP) for expression in mammalian cells. Human FAP cDNA were expressed in N-terminal pFLAG-CMV vector (Sigma).

TABLE 8

| Construct | Forward primer, 5'-3' | Reverse primer, 5'-3' | 5'/3' cloning sites | Cloning vector/ comments |
|---|---|---|---|---|
| HIP | GATCGCGGCCG CACACCACCAT CACCATCACCA TCACTAAGTGA (SEQ ID NO: 27) | GGCCTCACTTAG TGATGGTGATGG TGATGGTGGTGT GCGGCCGC (SEQ ID NO: 28) | BamHI/NotI | pIRESpuro2; HIP - modified original vector with C-terminal HIS, these are 2 adapter oligos |
| zf762HIP zebrafish construct | CTGCGCTAGCA CCATGATGGGT ACTAAACTGAC TCAACTTT (SEQ ID NO: 29) | GGAAGCGGCCGC TTTTGGAAGCTCT TCAATGATCA (SEQ ID NO: 30) | NheI/NotI | |
| m762pIRESpuro2 | GAAGCTAGCAC CATGCACCCC AAGGCCGCGCG GCCCCCCGCA GCTGCTGCTCG (SEQ ID NO: 31) | GAAGCGGCCGCT TATTTCGGTAGTT CTTCAATGATGA T (SEQ ID NO: 32) | NheI/NotI | pIRESpuro2 |
| h762pIRESpuro2 | CCAGCTAGCAC CATGCGACCCC AGGGCCCCGCC GCCT (SEQ ID NO: 33) | CAAGCGGCCGCT TATTTTGGTAGTT CTTCAATAATGA T (SEQ ID NO: 34) | NheI/NotI | pIRESpuro2 |
| h762HIP | CCAGCTAGCAC CATGCGACCCC AGGGCCCCGCC GCCT (SEQ ID NO: 33) | CAAGCGGCCGCT TTTGGTAGTTCTT CAATAATGAT (SEQ ID NO: 35) | NheI/NotI | HIP |
| ΔTHDh762HIP (1-54, 94-243, plus His) | CCAGCTAGCAC CATGCGACCCC AGGGCCCCGCC GCCT (SEQ ID NO: 33) | TCAAAGCTTTCC CTCAGCATTCCA TTATACAGGTCC ACCACCT (SEQ ID NO: 36) | NheI/HindIII | h762HIP |
| ΔΔTHDh762HIP (1-51, 94-243, plus His) | CCAGCTAGCAC CATGCGACCCC AGGGCCCCGCC GCCT (SEQ ID NO: 33) | CTCAAAGCTTTC CCTCAGATACAG GTCCACCACCTC CCTCTG (SEQ ID NO: 37) | NheI/HindIII | h762HIP |
| del-N-ter-HIP 1-32,54-243, plus His) | CCAGCTAGCAC CATGCGACCCC AGGGCCCCGCC GCCT (SEQ ID NO: 33) | GGGGAGCTCAGA GGCGCTCGACGG CGCGGGCA (SEQ ID NO: 38) | NheI/SacI | HIP |

TABLE 8-continued

| Construct | Forward primer, 5'-3' | Reverse primer, 5'-3' | 5'/3' cloning sites | Cloning vector/ comments |
|---|---|---|---|---|
| | GAAGAGCTCAG GGAAAGCTTTG AGGAGTCCTGG A (SEQ ID NO: 40) | CAAGCGGCCGCT TTTGGTAGTTCTT CAATAATGAT (SEQ ID NO: 35) | SacI/NotI | |
| h762G53AHIP | CCAGCTAGCAC CATGCGACCCC AGGGCCCCGCC GCCT (SEQ ID NO: 33) | ACAGGTCGACCA CCTCCCTCTGCCG GAGCT (SEQ ID NO: 39) | NheI/SalI | HIP |
| | GTGGTCGACCT GTATAATGCAA TGTGCTTACAA GGGCCAGCAGG A (SEQ ID NO: 41) | CAAGCGGCCGCT TTTGGTAGTTCTT CAATAATGAT (SEQ ID NO: 35) | SalI/NotI | |
| h762N186AHIP | CCAGCTAGCAC CATGCGACCCC AGGGCCCCGCC GCCT (SEQ ID NO: 33) | AATTGTCGACGC CATTTCAGGGCT TCCTTGGTCCAA (SEQ ID NO: 42) | NheI/SalI | HIP |
| | TGGCGTCGACA ATTAATATTCA TCGCACTT (SEQ ID NO: 43) | CAAGCGGCCGCT TTTGGTAGTTCTT CAATAATGAT (SEQ ID NO: 35) | SalI/NotI | |
| h762C55AHIP | CCAGCTAGCAC CATGCGACCCC AGGGCCCCGCC GCCT (SEQ ID NO: 33) | ACAGGTCGACCA CCTCCCTCTGCCG GAGCT (SEQ ID NO: 39) | NheI/SalI | HIP |
| | GTGGTCGACCT GTATAATGGAA TGGCCTTACAA GGGCCAGCAGG AGTGCCT (SEQ ID NO: 44) | CAAGCGGCCGCT TTTGGTAGTTCTT CAATAATGAT (SEQ ID NO: 35) | SalI/NotI | |
| h762C93AHIP | CCAGCTAGCAC CATGCGACCCC AGGGCCCCGCC GCCT (SEQ ID NO: 33) | CTCAAAGCTTTC CCTCAGAGCTTC CCCCTTTTCTCCT TTGAAT (SEQ ID NO: 45 | NheI/HindIII | h762HIP |
| h762C109AHIP | CCAGCTAGCAC CATGCGACCCC AGGGCCCCGCC GCCT (SEQ ID NO: 33) | CCATGAGGCCTG CTTGTAGTTGGG TGTC (SEQ ID NO: 46) | NheI/StuI | HIP |
| | AGCAGGCCTCA TGGAGTTCATT GAATTAT (SEQ ID NO: 47) | CAAGCGGCCGCT TTTGGTAGTTCTT CAATAATGAT (SEQ ID NO: 35) | StuI/NotIs | |
| h762C126AHIP | CCAGCTAGCAC CATGCGACCCC AGGGCCCCGCC GCCT (SEQ ID NO: 33) | TAAACGTTGCCT CCGCAATTTTCCC AAG (SEQ ID NO: 48) | NheI/AclI | HIP |
| | GGCAACGTTTA CAAAGATGCGT TCAAA (SEQ ID NO: 49) | CAAGCGGCCGCT TTTGGTAGTTCTT CAATAATGAT (SEQ ID NO: 35) | AclI/NotI | |
| h762C149AHIP | CCAGCTAGCAC CATGCGACCCC AGGGCCCCGCC GCCT (SEQ ID NO: 33) | GCATGCATTTCT GGCTTTTAGCCG AAGTGAGCCA (SEQ ID NO: 50) | NheI/NsiI | h762HIP |

TABLE 8-continued

| Construct | Forward primer, 5'-3' | Reverse primer, 5'-3' | 5'/3' cloning sites | Cloning vector/comments |
|---|---|---|---|---|
| h762C153AHIP | CCAGCTAGCACCATGCGACCCCAGGGCCCCGCCGCCT (SEQ ID NO: 33) | CTGGCATGCTGCATTTCTGCATTTTA (SEQ ID NO: 51) | NheI/SphI | HIP |
| | GCAGCATGCCAGCGTTGGTATTTCACATTCAA (SEQ ID NO: 52) | CAAGCGGCCGCTTTTGGTAGTTCTTCAATAATGAT (SEQ ID NO: 35) | SphI/NotI | |
| h762C154AHIP | AATGCATGCGCTCAGCGTTGGTATTTCACA (SEQ ID NO: 53) | CAAGCGGCCGCTTTTGGTAGTTCTTCAATAATGAT (SEQ ID NO: 35) | NsiI/NotI | h762HIP |
| h762C166AHIP | CCAGCTAGCACCATGCGACCCCAGGGCCCCGCCGCCT (SEQ ID NO: 33) | CCTGAGGCCTCAGCTCCATTGAATGTGAAA (SEQ ID NO: 54) | NheI/StuI | HIP |
| | CTGAGGCCTCAGGACCTCTTCCCATTGAA (SEQ ID NO: 55) | CAAGCGGCCGCTTTTGGTAGTTCTTCAATAATGAT (SEQ ID NO: 35) | StuI/NotI | |
| h762C201AHIP | CCAGCTAGCACCATGCGACCCCAGGGCCCCGCCGCCT (SEQ ID NO: 33) | TCCGGCGCCAATTCCTTCAGCAAGTCCTTCCACAGAAGAAGTGCGATGAA (SEQ ID NO: 56) | NheI/KasI | HIP |
| | ATTGGCGCCGGATTAGTGGATGTTGCTATCT (SEQ ID NO: 57) | CAAGCGGCCGCTTTTGGTAGTTCTTCAATAATGAT (SEQ ID NO: 35) | KasI/NotI | |
| h762C218AHIP | CCAGCTAGCACCATGCGACCCCAGGGCCCCGCCGCCT (SEQ ID NO: 33) | TGAAGCGGTACCAACCCAGATAGCAACATC (SEQ ID NO: 58) | NheI/KpnI | HIP |
| | GGCGGTACCGCTTCAGATTACCCAAAAGGAGA (SEQ ID NO: 59) | CAAGCGGCCGCTTTTGGTAGTTCTTCAATAATGAT (SEQ ID NO: 35) | KpnI/NotI | |
| h762N52AHIP | CCAGCTAGCACCATGCGACCCCAGGGCCCCGCCGCCT (SEQ ID NO: 33) | ACAGGTCGACCACCTCCCTCTGCCGGAGCT (SEQ ID NO: 39) | NheI/SalI | HIP |
| | GTGGTCGACCTGTATGCTGGAATGTGCTTACAAGGGCCAGCA (SEQ ID NO: 60) | CAAGCGGCCGCTTTTGGTAGTTCTTCAATAATGAT (SEQ ID NO: 35) | SalI/NotI | |
| h762G53AHIP | CCAGCTAGCACCATGCGACCCCAGGGCCCCGCCGCCT (SEQ ID NO: 33) | ACAGGTCGACCACCTCCCTCTGCCGGAGCT (SEQ ID NO: 39) Same as for h762N52AHIP | NheI/SalI | HIP |
| | GTGGTCGACCTGTATAATGCAATGTGCTTACAAGGGCCAGCAGGA (SEQ ID NO: 41) | CAAGCGGCCGCTTTTGGTAGTTCTTCAATAATGAT (SEQ ID NO: 35) | SalI/NotI | |

TABLE 8-continued

| Construct | Forward primer, 5'-3' | Reverse primer, 5'-3' | 5'/3' cloning sites | Cloning vector/ comments |
|---|---|---|---|---|
| h762M54AHIP | CCAGCTAGCACCATGCGACCCCAGGGCCCCGCCGCCT (SEQ ID NO: 33) | ACAGGTCGACCACCTCCCTCTGCCGGAGCT (SEQ ID NO: 39) Same as for h762N52AHIP | NheI/SalI | HIP |
|  | GTGGTCGACCTGTATAATGGAGCGTGCTTACAAGGGCCAGCAGGAGT (SEQ ID NO: 61) | CAAGCGGCCGCTTTTGGTAGTTCTTCAATAATGAT (SEQ ID NO: 35) | SalI/NotI |  |
| h762P63A, P69AHIP | CCAGCTAGCACCATGCGACCCCAGGGCCCCGCCGCCT (SEQ ID NO: 33) | TCGGCCGGCCACTCCTGCTGGCCCTTGTAA (SEQ ID NO: 62) | NheI/ NgoMIV | HIP |
|  | GTGGCCGGCCGAGACGGGAGCGCTGGGGCCAATGGCATTCCGGGTA (SEQ ID NO: 63 | CAAGCGGCCGCTTTTGGTAGTTCTTCAATAATGAT (SEQ ID NO: 35) | NgoMIV/ NotI |  |
| h762P75A, P78A, P81AHIP | CCAGCTAGCACCATGCGACCCCAGGGCCCCGCCGCCT (SEQ ID NO: 33) | TGTGCCGGCAATGCCATTGGCCCCAGG (SEQ ID NO: 64 | NheI/ NgoMIV | HIP |
|  | ATTGCCGGCACAGCTGGGATCGCAGGTCGGGATGGATTCAAAGGAGAAAA (SEQ ID NO: 65) | CAAGCGGCCGCTTTTGGTAGTTCTTCAATAATGAT (SEQ ID NO: 35) | NgoMIV/ NotI |  |
| h762K87A, K90AHIP | CCAGCTAGCACCATGCGACCCCAGGGCCCCGCCGCCT (SEQ ID NO: 33) | TTCGCCGGCGAATCCATCCCGACCTGGGAT (SEQ ID NO: 66) | NheI/ NgoMIV | HIP |
|  | TTCGCCGGCGAAGCGGGGGAATGTCTGAGGGAAAGCTTT (SEQ ID NO: 67) | CAAGCGGCCGCTTTTGGTAGTTCTTCAATAATGAT (SEQ ID NO: 35) | NgoMIV/ NotI |  |
| M762HIP | GAAGCTAGCACCATGCACCCCCAAGGCCGCGCGGCCCCCCCGCAGCTGCTGCTCG (SEQ ID NO: 31) | GAAGCGGCCGCTTTCGGTAGTTCTTCAATGAT (SEQ ID NO: 68) | NheI/NotI | HIP |
| hFAPCMV | GAAGCGGCCGCAAGACTTGGGTAAAAATCGTATTT (SEQ ID NO: 69) | GAAAGATCTCTAGTCTGACAAAGAGAAACACTGCTTTAGGA (SEQ ID NO: 70) | NotI/BglII | N-TER-PfLAG cmv |

(b) Baculovirus Expression

For expression in baculovirus, the following human STOP-1 constructs were made: S31humanSTOP-1-pAcGP67B encoding S31-K243, L94humanSTOP-1-pAcGP67B encoding L94-K243, and E89humanSTOP-1-pAcGP67B encoding E89-K243 of human STOP-1. S31humanSTOP-1-pAcGP67B was generated in a two step PCR approach. The 5' piece was generated from pAcGP67B using primers #161344 (GGATCGTCGGTTTTGTA-CAATATGT) (SEQ ID NO:71) and #161347 (GGGGATCT-CAGACGCAAAGGCAGAATGCGC) (SEQ ID NO:72). The 3' piece was generated from DNA #84694 using primers #161348 (TCTGCCTTTGCGTCTGAGATC-CCCAAGGGG) (SEQ ID NO:73) and #161732 (CCGTTCT- GCAGTTAATGATGATGATGATGATGATGATGG) (SEQ ID NO:74). The full length insert (which is then subcloned into pAcGP67B) was generated from a PCR reaction of equal parts 5' and 3' pieces using primers #161344 and #161732.

L94humanSTOP-1-pAcGP67B was generated in a two step PCR approach. The 5' piece was generated from pAcGP67B using primers #161344 and #161349 (GCTTTC-CCTCAGCGCAAAGGCAGAATGCGC) (SEQ ID NO:75). The 3' piece was generated from DNA #84694 using primers #161350 (TCTGCCTTTGCGCTGAGG-GAAAGCTTTGAGG) (SEQ ID NO:76) and #161346 (CCGGGATCCTTAATGATGATGATGATGATGAT) (SEQ ID NO:77). The full length insert (which is then subcloned into pAcGP67B) was generated from a PCR reaction of equal parts 5' and 3' pieces using primers #161344 and #161346.

DNA #84694 was amplified by PCR to generate two fragments containing S31-K243 and L94-K243 with C-terminal His tags. PCR fragments were subcloned into the baculovirus transfer vector pAcGP67B (PharMingen), which was then co-transfected with BaculoGold DNA (PharMingen) into Sf9 cells. Recombinant virus was isolated and amplified in Sf9 cells.

E89humanSTOP-1-pAcGP67B was generated in a two step PCR approach. The 5' piece was generated from pAcGP67B using primers #161344 (GGATCGTCG-GTTTTGTACAATATGT) (SEQ ID NO:71) and #161351 (ATTCCCCCTTTTCCGCAAAGGCAGAATGCGC) (SEQ ID NO:78). The 3' piece was generated from DNA #84694 using primers #161352 (TCTGCCTTTGCG-GAAAAGGGGGAATGTCTGAG) (SEQ ID NO:79) and #161346 (CCGGGATCCTTAATGATGATGATGAT-GATGAT) (SEQ ID NO:77). The full length insert (which is then subcloned into pAcGP67B) was generated from a PCR reaction of equal parts 5' and 3' pieces using primers #161344 and #161346.

EXAMPLE 6

Expression from STOP-1 DNA Constructs and Purification of Proteins

DNA encoding STOP-1 DNA constructs were transfected into CHO-DP12 cells, CHO-psgb cells (hamster galactosyltransferase I deficient epithelial pgsB-618 CHO cells) (ATCC #CRL-2241) or 293 cells (Roche) using calcium phosphate or fugene 6 transfection reagent according to the instructions of the manufacturer (Roche). The growth medias were supplemented with 1 mM NiCl, 5 mM CaCl2 and 50 mM Tris pH 7.6-8.0. Sixteen hours post transfection the serum containing the media was replaced with serum free media and protein was allowed to accumulate for 4-6 days. The secreted proteins were purified using Ni-NTA agarose beads.

Proteins from cell lysates were prepared by lysing the cells four days after transfection in buffer containing 50 mM HEPES (pH 7.5), 150 mM NaCl, 1% Triton X-100, 5 mM EDTA, 1× protease inhibitor cocktail (ROCHE, [lysis buffer]). Immunoprecipitation was performed by preclearing cell lysates (2 hr at 4° C.) with 25 µl of immobilized protein A/G-agarose beads (Pierce) followed by incubation (4 hr at 4° C.) of aliquots (0.5 ml) of lysates ($4 \times 10^5$ cells per aliquot) with anti-HIS epitope antibody (Qiagen) and with protein A/G-agarose beads. Immunoprecipitates were washed three times with lysis buffer and once with phosphate-buffered saline, fractionated by 10% SDS-PAGE, and transferred to a nitrocellulose membrane (Invitrogen). Western blot analysis was performed with mouse anti-HIS and the ECL kit (Amersham).

Figure 4A:
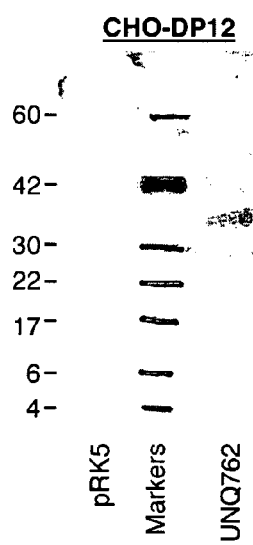
FIG. 4 shows coomassie-stained human STOP-1 proteins produced by (A) CHO-DP12 or (B) CHO-psgb (ATCC) cells and purified by nickel-NTA affinity chromatography. The vector, pRK5, was used as a control.
Figure 4B:
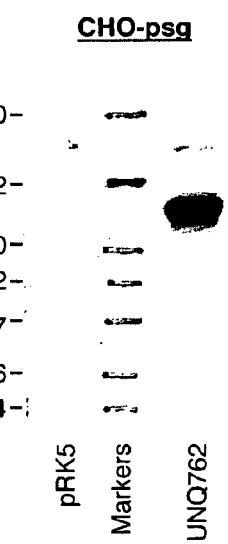
Figure 5A:
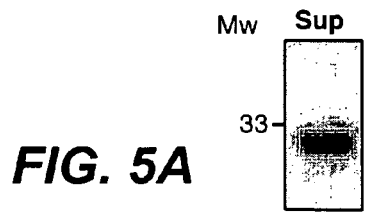
FIG. 5 shows a western blot of human histidine-tagged STOP-1 protein present in the (A) supernatant and (B) cell lysate of transient transfected CHO-psgb cells. The western blot was probed with anti-his antibody.
Figure 5B:
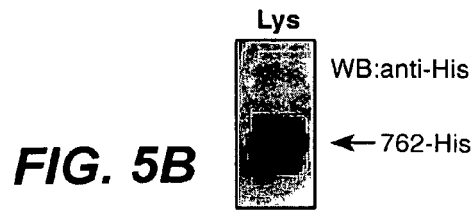

FIG. 4a shows that CHO-DP12 cells, used routinely for expression of recombinant proteins, produced little secreted STOP-1. In contrast, a CHO mutant cell deficient in proteoglycan synthesis, CHO-Psgb, produced much more secreted STOP-1 and yielded a better recovery of the secreted proteins in soluble form (FIG. 4b). pRK5 was transfected as a negative control. FIGS. 5a and b show that His-tagged protein can be detected with anti-His antibodies in cell supernatants and in cell lysates, respectively, of CHO-psgB transfected cells.

For protein production from baculovirus, Hi5 cells were infected with amplified baculovirus. After 3 days in culture at 27° C., the medium was harvested by centrifugation. The supernatant was supplemented with 50 mM Tris 8.0, 1 mM NiCl2, 5 mM CaCl2, and the pH was adjusted to 7.6. The medium was filtered and loaded onto a Ni-NTA agarose column (Qiagen). The column was washed with 50 mM Tris 8.0, 300 mM NaCl, 2 mM benzamidine, 0.5 mM PMSF, and 5 mM imidazole. Elution was performed in the same buffer with 300 mM imidazole. Fractions containing STOP-1 were pooled and concentrated. Protein was purified over a Superdex-75 column into 50 mM Tris 8.0, 100 mM NaCl, 0.5 mM PMSF, and 2 mM benzamidine. STOP-1 containing fractions were pooled, concentrated, and utilized for crystallography trials and other studies.

EXAMPLE 7

STOP-1 Oligomerization

Full length STOP-1-HIS proteins or various truncations thereof were expressed in SF9 baculovirus-infected cells or CHO cells as described above. The proteins were purified from the media by using Ni-NTA agarose beads as discussed above. The baculoviral-expressed proteins S31-K243-His, E89-K243-His, or L94-K243-His were loaded onto an 8 mm×300 mm Shodex KW802.5 size exclusion column and eluted with 100 mM NH4HCO3, 200 mM NH4Cl pH7.8 at a flow rate of 1 ml/ml. CHO-psgb expressed full length proteins were loaded onto an 8 mm×300 mm Shodex KW804 size exclusion column and eluted with 25 mM sodium phosphate, 500 mM NaCl at a flow rate of 1 ml/ml. CHO-psgb expressed proteins, M1-M54 fused to L94-K243-His, were loaded onto an 8 mm×300 mm Shodex KW802.5 size exclusion column and eluted with 25 mM sodium phosphate, 500 mM NaCl at a flow rate of 1 ml/ml.

The eluted protein was analyzed by an Agilent Model 1100 HPLC system with an Agilent multi wavelength detector (UV) connected to a Wyatt MiniDAWN laser light scattering (LS) instrument and a Wyatt Optilab differential refractometer (RI). The average molecular weight of the proteins or their aggregates in each peak was determined by selecting a peak and using the Zimm fitting method (Phillip J. Wyatt, (1993) Analytica Chimica Acta 272:1-40) with the Astra software package (Wyatt, USA). The percentage of aggregation was calculated from the integrated peak areas of the UV signal at 214 nm. See FIG. 6 and FIG. 7 for results.

Light scatter analysis indicates that the baculovirus S31-K243-His proteins primarily formed trimeric molecules (apparent molecular weight 74 kD, 95% of total integrated peak area) (FIG. 6A). The baculovirus E89-K243-His proteins formed complexes that were approximately 36% trimeric and 64% hexameric (i.e., apparent MW of 126 kD representing 36% of peak area, apparent MW of 61 kD representing 64% of peak area) (FIG. 6B). However, it is believed that the hexameric complexes formed by E89-K243-His are an anomaly due its odd number of cysteines. The baculovirus L94-243 protein, which lacks the triple helix domain, forms trimeric complexes (apparent MW of 59 kD representing 98% of peak area) (FIG. 6C). This indicates that the N-terminal domain of the protein and the triple helix domain are not required for trimerization. The L94-K243 region is sufficient. The THD can act to stabilize the trimers.

Proteins expressed in CHO-psgb also formed complexes (FIG. 7A-C). Light scatter analysis indicated that the full length-expressed protein (M1-K243-His) formed complexes that were approximately 58% hexameric and 42% trimeric (FIG. 7A). The complexes formed by delta-THD expression (M1-M54 and L94-L243-His) were in part trimeric (apparent MW of 66 kD representing 61% of peak area) and in part heterogeneous in mass (average MW of 627 kD) probably due to the varied glycosylation state of the proteins in CHO cells (FIG. 7B).

On SDS gels, purified full-length STOP-1 expressed in CHO-psgB cells migrated as a monomer under reducing conditions and as a dimer under non-reducing conditions (without DTT). See FIG. 7C. The results indicate that disulfide bonding can occur between two monomers.

EXAMPLE 8

Deletion and Point Mutational Analysis of STOP-1

Full-length STOP-1 (WT)-His, delta-THD-His, delta-delta-THD-His, delta-N-terminus and several point mutation mutants were expressed in CHO-psgb cells as described above. Whole cell extract extracts were prepared. Aliquots from the whole cell extracts or the media in which the cells were cultured were run on an SDS gel under reducing and non-reducing conditions and western blotted with anti-His antibody (ECL detection kit, Amersham).

Figure 8A:
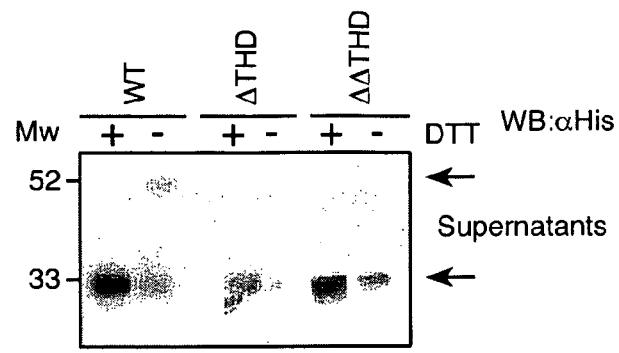
FIG. 8 shows western blots of (A) cell culture media and (B) whole cell lysates from CHO-psgb cells expressing human his-tagged STOP-1 WT, delta-THD, and delta-delta-THD STOP-1 (residues 1-51, 94-243, plus histidine tag) and subjected to reducing or non-reducing conditions. The western blots were probed with anti-his antibody.
Figure 8B:
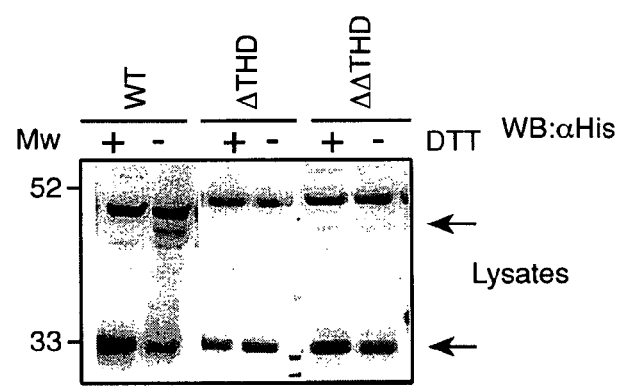

FIGS. 8A and B indicates that a disulfide bond can form between two monomers in the THD region in extracts from supernatants and lysates, respectively. Each deletion mutants lacking the THD, which includes cysteine 55 failed to form dimers under non-reducing conditions. Homodimers were present in the supernatant and lysates of cells expressing full length protein under non-reducing conditions, but not under reducing conditions. Table 9 summarizes the results as follows:

TABLE 9

| Construct | Secretion | Dimerization |
| --- | --- | --- |
| WT | + | + |
| delta-THD | + | − |
| delta-delta-THD | + | − |
| delta-N-ter | + | + |

"+" indicates that the level of secretion or dimerization was the same as wild-type STOP-1.
"−" indicates that dimerization was not detectable in this assay.

Figure 9A:
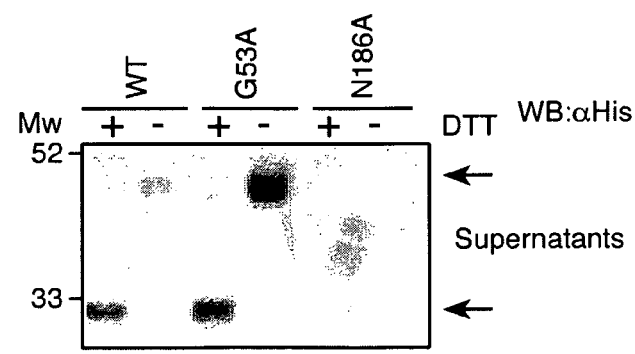
FIG. 9 shows western blots of (A) cell culture media and (B) whole cell lysates from CHO-psgb cells expressing his-tagged WT, G53A and N186A STOP-1 constructs and subjected to reducing or non-reducing conditions. The western blots were probed with anti-his antibody.
Figure 9B:
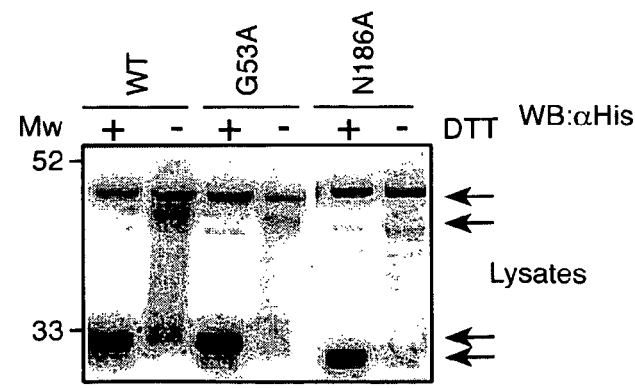

Point mutants of human STOP-1 were tested for the ability to secrete and dimerize. FIGS. 9A and B shows that wild-type STOP-1 protein and a G53A mutant were secreted and that homodimers are observed in the in supernatants and lysates. However, a mutant at 186 ("N" mutated to "A"), a potential glycosylation site, was not present in the culture media and did not homodimerize. Many other mutants were also tested. Table 10 summarizes the results as follows:

TABLE 10

| Construct | Secretion | Dimerization |
| --- | --- | --- |
| WT | + | + |
| N52A | + | + |
| G53A | ++ | + |
| M54A | + | + |
| P63A, P69A | + | + |
| P75A, P78A, P81A | + | + |
| K87A, K90A | + | + |
| N186A | − | − |

"+" indicates that the level of secretion or dimerization was the same or better ("++") than wild-type STOP-1.
"−" indicates that secretion or dimerization was not detectable in this assay.
All these mutants except N186A were secreted and ran similar to WT on SDS gels.

Figure 10A:
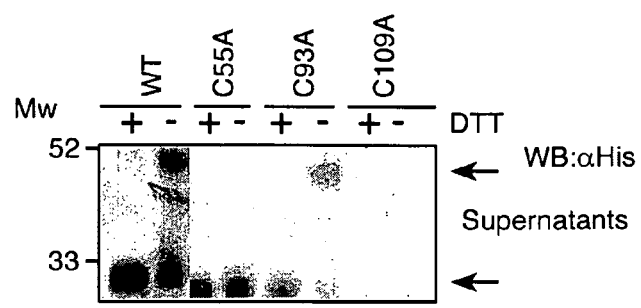
FIG. 10 shows western blots of (A) cell culture media and (B) whole cell lysates from CHO-psgb cells expressing his-tagged WT, C55A, C93A and C109A STOP-1 constructs and subjected to reducing or non-reducing conditions. The western blots were probed with anti-his antibody.
Figure 10B:
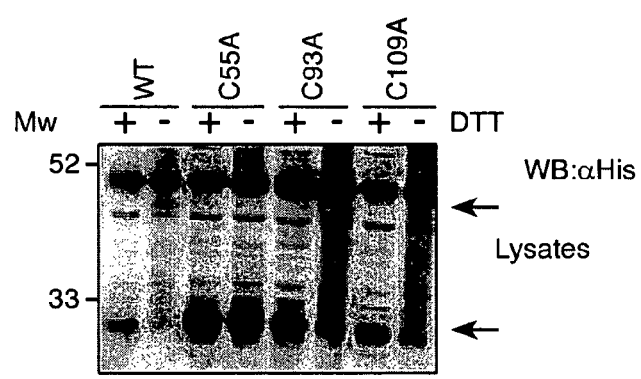

FIGS. 10A and B show the state of the a human STOP-1 protein having point mutations at cysteine residues 55, 93 and 109. Point mutations were also made at other cysteines throughout the protein. Table 11 summarizes the results as follows:

TABLE 11

| Construct | Secretion | Dimerization |
| --- | --- | --- |
| WT | + | + |
| C55A | + | − |
| C93A | + | + |
| C109A | − | |
| C126A | − | |
| C153A | − | |
| C154A | − | |
| C153A, C154A | −/+ | −/+ |
| C166A | − | |
| C201A | − | |
| C218A | − | |

"+" indicates that the level of secretion or dimerization was the same as wild-type STOP-1.
"−" indicates that dimerization was not visibly detectable in this assay.
"−/+" indicates that secretion or dimerization was weakly detectable in this assay.

All of the mutants were expressed, but only two were secreted—C55A and C93A. C93A was secreted and formed dimers in contrast to C55A, which was secreted but did not form dimers indicating that C55 is required for intra-subunit disulfide bonding.

EXAMPLE 9

Wnt Pathway Upregulates STOP-1 mRNA

The STOP-1 gene is located on human chromosome 8 between 8q22 and 8q23. The gene is located close to genes encoding proteins important in the Wnt signalling pathway such as the FZD6 gene (frizzled homolog 8 (drosophila)), the WISP-1 gene (WNT1 inducible secreted protein 1). There are at least three regulatory genes in the Wnt pathway that are mutated in primary human cancers and experimental tumors of other species.

MMTV-Wnt-1 transgenic mice were prepared by Genentech, Inc. These mice overexpress the Wnt-1 protein under the control of the MMTV promoter. The C57Mg cells do not overexpress Wnt-1. Breast tumors in these mice were removed. mRNA was extracted from the breast tumors or from C57Mg mammary epithelial cells. A reverse transcriptase reaction was performed with an oligo(dT) primer, the avian myeloblastosis virus reverse transcriptase (Promega) and the extracted mRNA according to manufacturer's instructions (Promega). PCR on the reverse transcribed products was carried out with Ex-taq polymerase (Takara) using mRLP19 primers and mouse STOP-1 primers:

mRPL19:
5'-ATCGCCAATGCCAACTCCCGTCA-3'    (SEQ ID NO: 80)
and

5'-GCTTGCGTGCTTCCTTGGTCTTA-3'.   (SEQ ID NO: 81)

mRLP19 is the murine mitochondrial ribosomal protein L19 (RPL19), a housekeeping protein. PCR using primers against mRLP19 was used as a control for the extraction and PCR of mRNA.

mSTOP-1:
5-TGCTGCTGCAGCTGCCCGCGCCGTCGAG-3   (SEQ ID NO: 82)
and

5-TCCAGTAGAAGCATCTCCTTTTGGGTAA-3.  (SEQ ID NO: 83)

Figure 11:
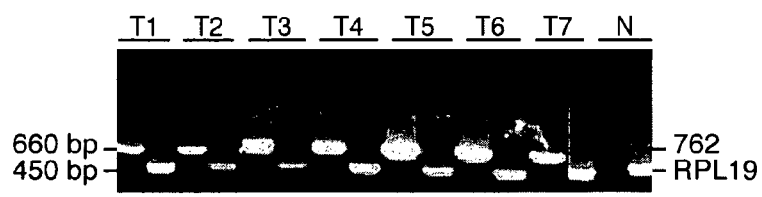
FIG. 11 shows that murine STOP-1 mRNA (mSTOP-1 mRNA) is expressed in breast tumors derived from MMTV-WNT1 transgenic mice but not in normal mammary epithelial cells. RNA samples were taken from breast tumor cells (marked "T1"-"T7") or C57Mg mouse normal mammary epithelial cells (marked, "N"), subjected to RT-PCR with mSTOP-1 primers and mRLP19 primers. The PCR products were separated on an agarose gel.

The results show that mSTOP-1 mRNA is expressed in the breast tumors of MMTV-Wnt-1 transgenic mice (FIG. 11, lanes T1-T7), whereas it is not expressed in C57Mg normal mouse mammary epithelial cells ("N"). Thus, a connection is suggested between the Wnt signalling pathway and STOP-1 expression.

EXAMPLE 10

Coexpression of STOP-1 with Other Genes

A proprietary database containing gene expression information (GeneExpress®, GeneLogic Inc., Gaithersburg, Md.) was analyzed for genes that are expressed in the same tissues as STOP-1 (BLIST analysis, proprietary software written an developed at Genentech, Inc. for use with the GeneExpress® database). By this method, several genes having significant correlation of expression in breast and colon tumors were identified. Genes that were coexpressed in breast and colon tumors included, Wisp-1 (a WNT target gene), SFRP2 (a soluble WNT receptor), fibroblast activation protein (FAP), a cell surface serine protease that has been implicated in ion cancer), collagen type 1 alpha 2 chain, collagen type V alpha 2 chain, Thrombospondin 2 (THBS2) (ECM), ADAM12 (a MMP enzyme), OB-Cadherin and OSF-2 (TCI protein). The later genes suggest involvement of STOP-1 in formation and/or modulation of the extracellular matrix.

EXAMPLE 11

STOP-1 is cleaved by MMP-7 and MMP-9 In Vitro

Materials: Human his-tagged STOP-1 protein was produced using a baculovirus expression system. Matrix metalloproteases (MMPs)-1, -2, -3, -7, and -9 were purchased from Enzyme Systems Products. Trypsin was obtained from Sigma.

Proteolytic Digestion of STOP-1: Prior to reaction with STOP-1, MMPs were activated with 1 mM p-aminomercuric acetate for 1 h at 37 degrees Celsius. STOP-1 (3 µg) was digested with proteases (50 or 250 nM) in a final volume of 20 µl for 4 hours at 37 degrees Celsius. Buffer A (50 mM Tris, pH 87.5, 10 mM $CaCl_2$, 10 µM $ZnCl_2$ and 100 mM NaCl) was the buffer used for the MMP cleavage reaction. Buffer A lacking $ZnCl_2$ was the buffer used for the trypsin cleavage reactions. The MMP reactions were terminated by addition of EDTA (15 mM). The trypsin reaction was terminated by addition of PMSF (1 mM). Samples were then analyzed by SDS-PAGE and Coomassie staining.

FIG. 23 shows the cleavage of baculoviral expressed human STOP-1 protein by various proteases in vitro. MMP-7 also cleaved human STOP-1 in vitro, whereas MMP-1, -2 and -3 produced minimal or no cleavage products (data not shown). MMP-7 produced STOP-1 cleavage products of about 23 and 21 kDa. In contrast, MMP-9 produced STOP-1 cleavage products of about 22 and 18 kDa. Trypsin produced 20 and 22 kDa fragments (data not shown). These data suggest that STOP-1 activity may be regulated by proteolysis. This can be particularly relevant with tumor stromal-associated proteases such as MMP-7 and MMP-9.

EXAMPLE 12

STOP-1 Expression Promotes 3T3 Proliferation (a) Cell Culture and Generation of 3T3 STOP-1 Stable Cell Lines 3T3 cells were maintained in DMEM supplemented with 10% FCS. Mouse and human, STOP-1-expressing cell lines were established by transfection of 3T3 cells with m762pIRESpuro2 and h762pIRESpuro2 vectors using FuGENE 6 transfection reagent (Roche) according to the instructions of the manufacturer. STOP-1 clones were established by selecting transfected cells with puromycin (4 g/ml).

(b) In Vitro Proliferation Assay

Figure 12A:
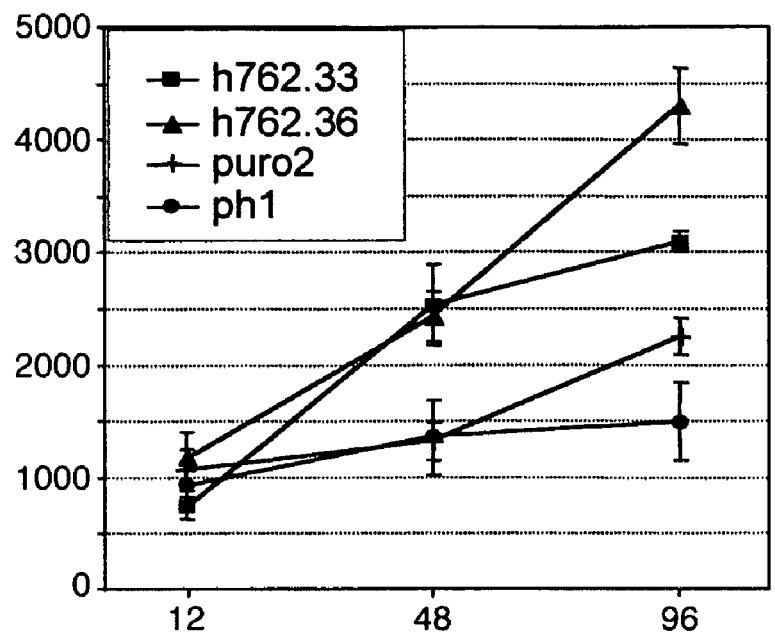
FIG. 12A shows the amount of $^3$H-thymidine incorporation (counts per minute (cpm)) in 3T3 cells at 12, 28 and 96 hours after addition of $^3$H-thymidine.
Figure 12B:
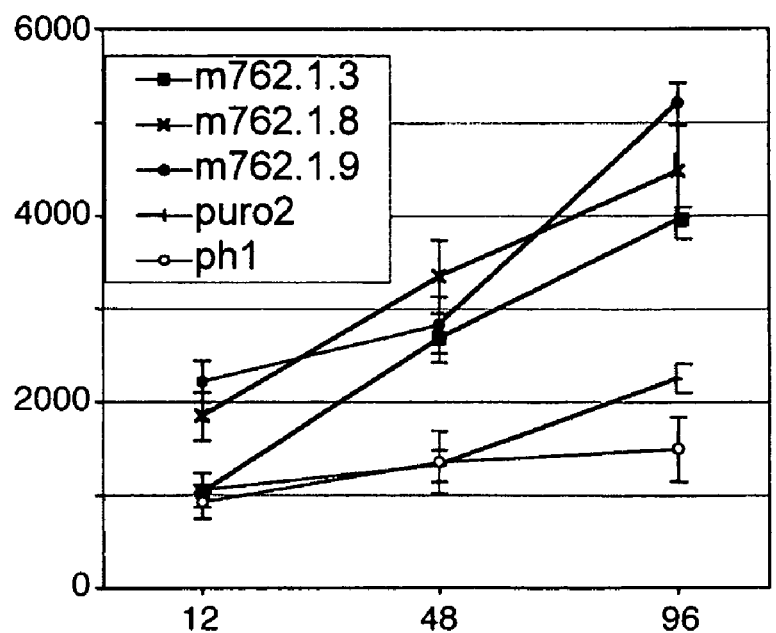
FIG. 12B shows the amount of $^3$H-thymidine incorporation (counts per minute (cpm)) in 3T3 cells at 12, 28 and 96 hours after addition of $^3$H-thymidine. Controls: transfections with vector alone (puro2 and ph1).

3T3 cells were transfected with mouse STOP-1, human STOP-1 or vector alone as described above and were plated in 96-well plates at $1.5 \times 10^3$ cells in DMEM with 10% FCS. Twelve hours later the media was change to DMEM with 1.5% FCS and 10 uCi/ml [$^3$H]-thymidine. After 12 hours, 48 hours and 96 hours, the cells were harvested onto a GF/C filter using Packard's 96-well Filtermate 196, washed and counted on a top count, microplate scintillation counter (Packard). The results show that clones expressing STOP-1 demonstrated increased proliferation as compared with vector alone-transfected clones (puro2 and ph1). See FIGS. 12A and B.

(c) Retroviral Expression in 3T3 Cell Lines

Figure 13A:
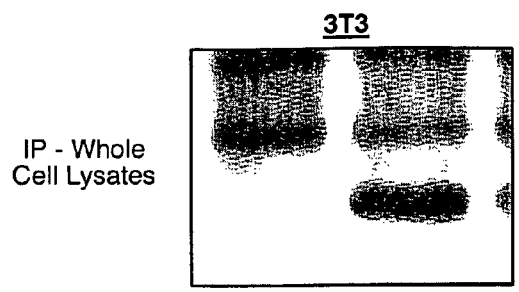
FIGS. 13A and B are western blots of human STOP-1 proteins expressed from 3T3 cells or 293, respectively, infected with a retrovirus encoding a control vector (Babe) or human STOP-1. STOP-1 was immunoprecipitated from whole cell lysates using the S7-IgG antibody. Western blots were probed with polyclonal anti-human STOP-1 antibodies.
Figure 13B:
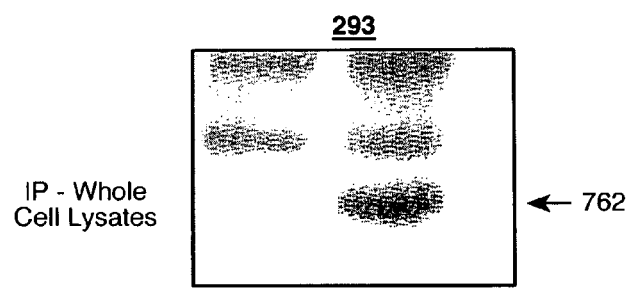
FIG. 13 shows the proliferation of 3T3 or 293 cells after infection with retrovirus encoding human STOP-1.
FIG. 13C shows the level of cell proliferation observed for the infected cell populations as detected by a colorimetric Cell Titer Assay.
Figure 13C:
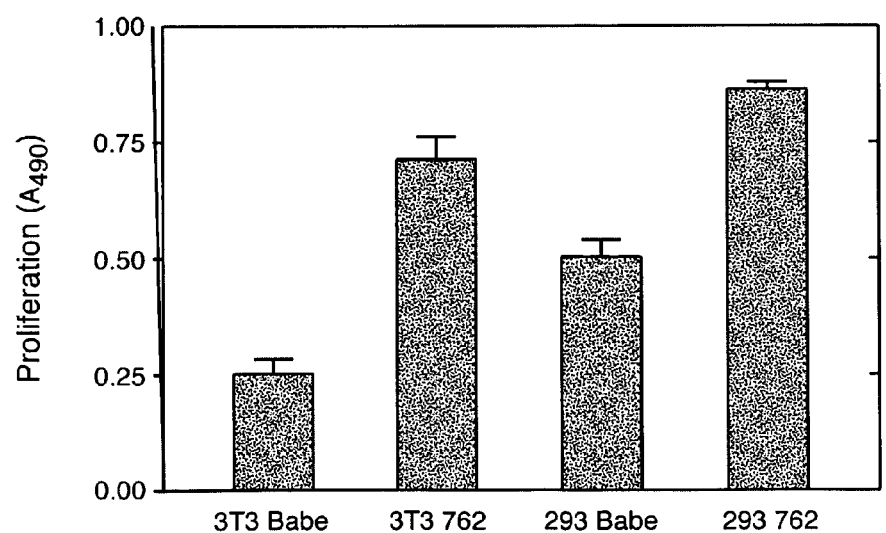

A human full-length STOP-1 cDNA was cloned from H762pirespuro2 into the pMSCV1 (puro) vector (Clontech) and introduced into 3T3 fibroblasts and 293 cells by retroviral infection using the method described by Maecker et al., (Maeker H. L., et al., Cancer Cell 2, 139-148, 2002). Briefly, 5000 cells/well were plated in 96 well plates and switched to low serum media (0.25% fetal calf serum) the following day. The retrovirally infected cells were selected in puromycin (3 ug/ml). After 24 hours, cell proliferation was measured using the Cell Titer Kit (Promega). FIG. 13C shows that infection with STOP-1 retrovirus promotes proliferation of both 3T3 and 293 cells, respectively, as compared to 3T3 or 293 cells infected with a control.

For detection of STOP-1 protein, whole cell lysates of cell pellets (~$2 \times 10^6$ cells) were prepared and incubated with antibody S7-IgG (1 µg) described below and subsequently immunoprecipitated with protein A/G. Immunoprecipitates were then denatured and transferred to nitrocellulose membranes. STOP-1 was then detected using rabbit polyclonal anti-STOP-1 antibodies. FIGS. 13A and B show expression of STOP-1 in 3T3 and 293 cells in whole cell lysates following infection with STOP-1 retrovirus as compared to a vector control, Babe.

EXAMPLE 13

STOP-1 Expression Causes Tumorigenesis in Mice

Female athymic nu/nu mice (Charles River Laboratory, [5 animals per group]) were inoculated subcutaneously with $1 \times 10^6$ 3T3 cells stably transfected with mouse or human STOP-1, RAS cDNA (Hudziak R M, Lewis G D, Shalaby M R, Eessalu T E, Aggarwal B B, Ullrich A, Shepard H M. (1988) Proc Natl Acad. Sci. 85(14), pp.: 5102-6) or an empty puro2 vector (p2). Tumor growth was measured 1 time per week. The stably 3T3 cell lines were also evaluated for STOP-1 expression by preparing whole cell lysates of pelleted cells, performing SDS-PAGE on aliquots of the lysates or cell culture media, and western blotting the gels and probing them with rabbit anti-STOP-1 antibody. Cells transfected with RAS cDNA served as positive controls. See FIG. 14A-C.

Figure 14A:
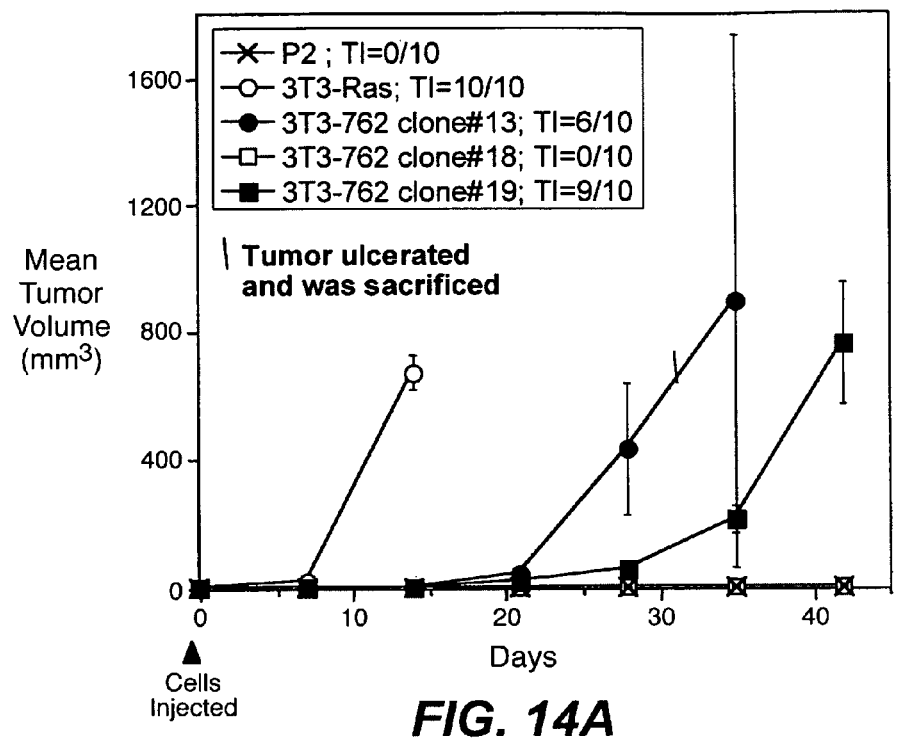
FIG. 14A shows the mean volume of tumors in mice implanted with 3T3 fibroblasts transfected with vector alone (p2 vector) or DNA encoding mouse STOP-1 or RAS protein. The transfected cells were implanted into nude mice or tested for protein expression.
Figures 14B, 14C:
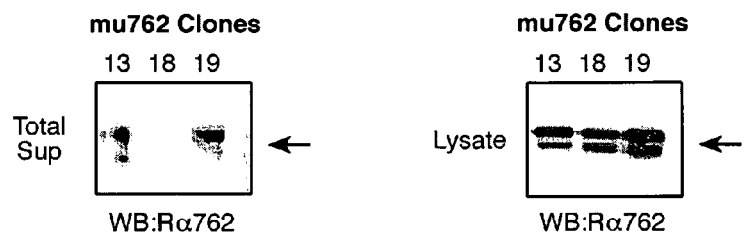
FIGS. 14B and C show western blots of aliquots of the supernatants and lysates, respectively, of the transfected cells. The western blot was probed with rabbit anti-STOP-1 polyclonal antibodies. "TI" refers to the tumor incident ratio.

The results show that murine STOP-1 was present in the lysates of all of the NIH 3T3 clones, but was only present in the cell culture media of two of the three NIH 3T3 clones (FIGS. 14B and C, respectively). In other words, clone 18 expressed the protein intracellularly but was defective at secreting the murine STOP-1 protein. See FIG. 14B. Further, the two clones that secreted STOP-1 produced tumors in nude mice whereas the clone that was deficient in secretion did not (FIG. 14A). These results suggest that secreted murine STOP-1 by itself can be tumorigenic whereas intracellularly expressed STOP-1 is not.

Figure 15:
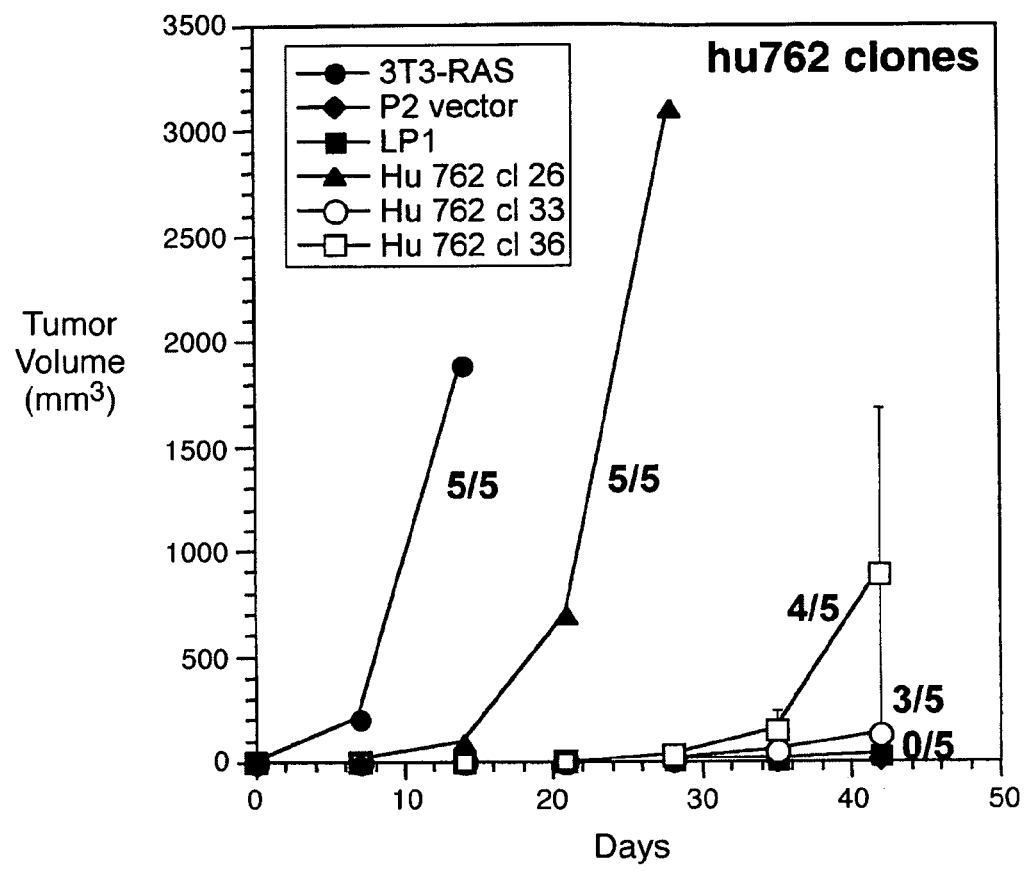
FIG. 15 shows that human STOP-1 promotes tumorigenesis by 3T3 fibroblasts in a xenograft mouse model.
Figure 16A:
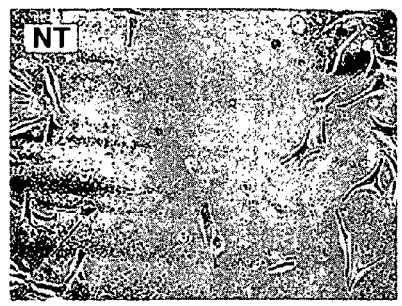
FIG. 16 shows that recombinant STOP-1 protein potentiates SK-Mel-31 cells wound healing and motility. SK-Mel-31 cells were treated with (A) NT—no exogenous ligand treatment, (13) b762—baculoviral produced human STOP-1 protein, (C) hrEGF—(50 ng/ml), (D) hrEGF and b762 or (E) CHO mammalian produced human STOP-1 protein.
Figure 16C:
Figure 16B:
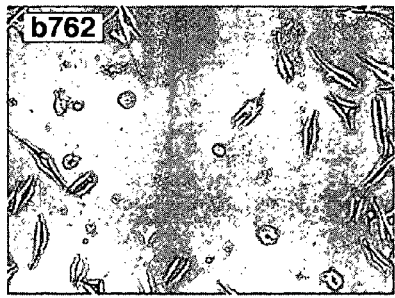
Figure 16D:
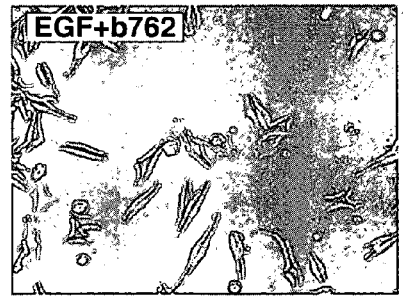
Figure 16E:
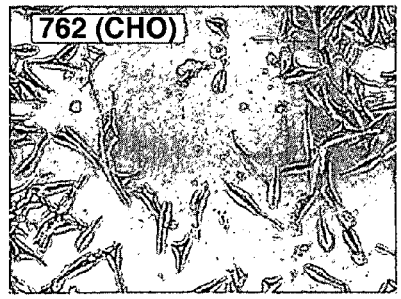

The results also show that human STOP-1 can drive tumorigenesis in mice. See FIG. 15. Tumors grew in several mice that expressed the human STOP-1 protein and in the RAS control, but not in the mice treated with cells transfected with vector alone. Like the mouse STOP-1, these results suggest that secreted human STOP-1 by itself can be tumorigenic.

EXAMPLE 14

STOP-1 Promotes Wound Healing

Malignant melanoma SK-MEL-31 cells were maintained in DMEM supplemented with 10% FCS. SK-Mel-31 cells were cultured in 6 well dishes (Corning) until they reached subconfluency, then starved for 8 hours in DMEM with 2% heat-inactivated FCS. The cells were then treated for 2 hours in FCS-free DMEM with 10 µg/ml mitomycin C (Sigma) and subjected to the following in vitro wound closure assay.

A cell-free area was introduced by scraping the SK-MEL-31 cell monolayer with a yellow pipette tip. Cell migration to the cell-free area for 48 hours after scraping was evaluated while the cells were maintained in DMEM supplemented with 2% heat-inactivated FCS in the absence or presence of 30 ng/ml EGF (Roche), 1 g/ml of full length baculovirus expressed human STOP-1 protein, both or none. FIGS. 16A-E are phase-contrast photographs of the scraped area 48 hours after scraping.

The results show that cells migrated to the scraped area when treated with EGF or STOP-1, especially STOP-1 expressed from CHO-psgB cells. The results indicate that STOP-1 promotes cell migration. Cell migration occurs in tumor growth as it invades surrounding tissue. The data further supports the tumor promoting properties of STOP-1.

EXAMPLE 15

Monoclonal Antibody Development

Ten BALB/c mice (Charles River Laboratories, Wilmington, Del.) were hyperimmunized with recombinant polyhistidine-tagged (HIS8) human STOP-1 (a.k.a. DNA 145960) transiently expressed in PSGB chinese hamster ovary cells (Genentech, Inc., South San Francisco, Calif.) in Ribi adjuvant (Ribi Immunochem Research, Inc., Hamilton, Mo.). B-cells from five mice demonstrating anti-STOP-1 antibody titers were fused with mouse myeloma cells (X63.Ag8.653; American Type Culture Collection, Rockville, Md.) using a modified protocol analogous to one previously described (Kohler, G. and Milstein, C. (1975) Nature 256: 495-497; Hongo, J. S., et al., (1995) Hybridoma 14:253-260).

After 10-14 days, the supernatants were harvested and screened for antibody production by direct enzyme-linked immunosorbent assay (ELISA). One positive clone (6B12.1.7), showing the highest immunobinding after the second round of subcloning by limiting dilution, was injected into Pristane-primed mice (Freund Y R and Blair P B (1982) J Immunol 129:2826-2830) for in vivo production of MAb. The ascites fluid was pooled and purified by Protein A affinity chromatography (Pharmacia fast protein liquid chromatography [FPLC]; Pharmacia, Uppsala, Sweden) as previously described (Hongo et al., 1995, supra). The purified antibody preparation was sterile filtered (0.2-µm pore size; Nalgene, Rochester N.Y.) and stored at 4° C. in phosphate buffered saline (PBS). The hybridoma clone producing the 6B12 antibody was deposited under the terms of the Budapest Treaty with the American Type Culture Collection (ATCC), 10801 University Blvd., Manassas, Va. 20110-2209, USA on Mar. 28, 2003 as "6B12.1.7".

The binding site for the 6B12 antibody was mapped to an N-terminal region of human STOP-1. The His-tagged constructs encoding the human full length protein, the delta-THD protein, the delta-delta-THD protein, the delta-N-terminal protein and the zebrafish full length protein were expressed in CHO-psgB cells. Aliquots of transfected cell extracts were run on SDS-PAGE, western blotted and probed with either anti-His antibody or 6B12 antibody.

Figure 17A:
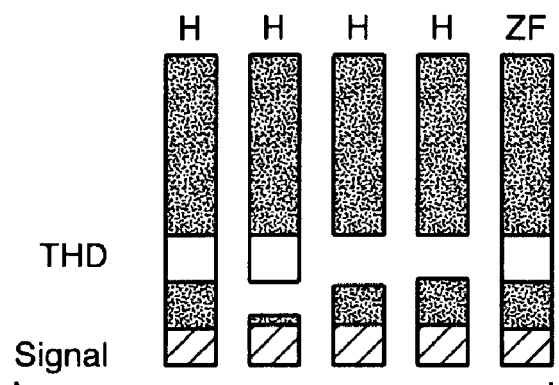
FIG. 17A is a schematic of the his-tagged human and full length zebrafish STOP-1 proteins used in the epitope location studies of FIGS. 18B and C.
Figure 17B:
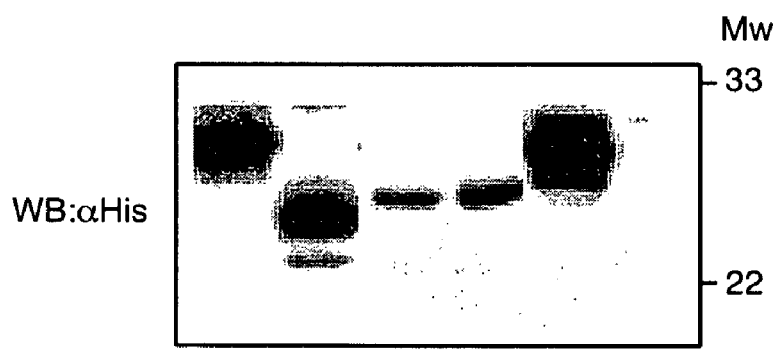
FIGS. 17B and C show western blots probed with anti-his antibody and 6B12 antibody, respectively, of extracts from cells that recombinantly expressed the proteins of FIG. 17A.
Figure 17C:
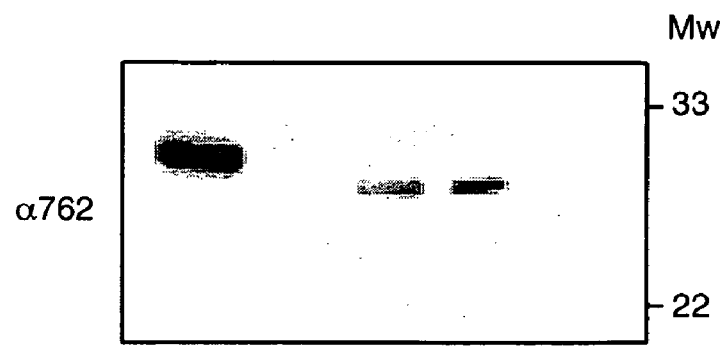
FIG. 17 shows that anti-human STOP-1 antibody, 6B12, binds to the N-terminal sequence of human STOP-1 between the signal sequence and triple helix domains.

The 6B12 monoclonal antibody worked well on westerns. See FIG. 17C. It bound to all of the human proteins expressed as described above except for the delta-N-terminal protein. Therefore, the binding epitope of the 6B12 antibody maps to the N-terminal amino acids #33-52 of human STOP-1. The 6B12 antibody did not recognize the zebrafish STOP-1 protein on a western blot.

EXAMPLE 16

Phage-Derived Antibodies Against STOP-1

Overview: Phage-derived antibodies against STOP-1 were made using, in part, materials and methods described in U.S. Provisional Application No. 60/385,338 ("the '338 application"), filed Jun. 3, 2002. In this study, phagemids were further modified and the resultant antibodies were screened based on binding to oligomerized STOP-1.

Construction of Anti-Her2 Fab and F(ab)'$_2$ phagemid: The phagemid vector, pS0643 (also known as phGHam-g3, e.g., U.S. Pat. No. 5,688,666, Example 8), contains pBR322 and f1 origins of replication, an ampicillin resistant gene, an *E. coli* alkaline phosphatase (phoA) promoter (Bass et al., (1990) *Proteins* 8:309-314), and a sequence encoding a stII secretion signal sequence fused to residues 1-191 of human growth hormone (hGH) and a sequence encoding the C-terminal residues 267-421 of protein III of M13 phage (hereinafter, cP3). The pS0643 phagemid also contains an XbaI site and amber stop codon following residue 191 of hGH. The stII secretion signal sequence can export a protein to the periplasm of a bacteria cell (e.g., a light chain region (LC) of an antibody). In this study, the sequence encoding the human growth hormone (hGH) was removed from the pS0643 vector and replaced with a NsiI/XbaI nucleic acid fragment encoding a humanized anti-Her2 Fab fragment ("h4D5" sequence) ligated in frame with the stII secretion signal (humAb4D5-8, see Carter et al., (1992) PNAS 89:4285-4289, Table 1 and FIG. 1 therein or U.S. Pat. No. 5,821,337, for sequence).

The h4D5 antibody is a humanized antibody that specifically recognizes a cancer-associated antigen known as Her-2 (erbB2). In this study, the h4d5 was obtained by polymerase chain reaction using the humAb4D5 version 8 ("humAb4D5-8") sequence and primers engineered to give rise to a 5' NsiI site and a 3' XbaI site in the PCR product (Carter et al., (1992) PNAS 89:4285-4289). The PCR product was cleaved with NsiI and XbaI and ligated into the pS0643 phagemid vector. The h4D5 nucleic sequence encodes modified CDR regions from a mouse monoclonal antibody specific for Her-2 in a mostly human consensus sequence Fab framework. Specifically, the sequence contains a kappa light chain (LC region) upstream of $V_H$ and $C_H1$ domains (HC region). The method of making the anti-Her-2 antibody and the identity of the variable domain sequences are provided in U.S. Pat. Nos. 5,821,337 and 6,054,297.

The pS0643 plasmid containing humanized 4D5 (version 8) was still further modified. For example, a herpes simplex virus type 1 glycoprotein D epitope tag (gD tag) was added in frame to the c-terminus of the LC using site-directed mutagenesis. Following the stop codon downstream of the LC, a ribosome binding site and nucleic acid molecule encoding a stII signal sequence were ligated to the N-terminus of the HC sequence. Consequently, the HC sequence is in frame with the C-terminal domain of the p3 (cP3), a minor coat protein of M13 phage. Thus, a Fab displayed on phage can be produced from one construct. This Fab phagemid vector is referred to as pV0350-2b (FIGS. 25A-H) and can be schematically illustrated as FIG. 24A.

To generate F(ab)'$_2$ displayed on phage, the pV0350-2b vector was further modified by inserting a dimerizable leucine zipper GCN4 sequence (GRMKQLEDKVEELL-SKNYHLENEVARLKKLVGERG) (SEQ ID NO:84) between the HC and cP3 sequences by cassette mutagenesis. The GCN4 leucine zipper brings two sets of LC/HC-cP3 fusion polypeptides together in the *E. coli* periplasm and presents the dimer on the surface of phage. This F(ab)'$_2$ phagemid vector is referred to as pV0350-4 (FIGS. 26A-H) and can be schematically illustrated as FIG. 24B.

Generating F(ab) Libraries with H1/H2/H3 Diversity for Use in STOP-1 Selection:

A diversified library for finding anti-STOP-1 antibodies was created by mutating the sequences encoding the HC variable regions in the pV0350-2b and pV0350-4 vector using Kunkel mutagenesis and screening the phage containing them based on binding to human STOP-1 by ELISA assay. The screening method is described in greater detail below. Other antibodies having greater specificity or affinity to STOP-1 can be obtained by, e.g., further mutagenizing the Fab and F(ab)'$_2$ sequences (e.g., by Kunkel mutagenesis, (Kunkel et al., (1987) Methods Enzymol. 154:367-382)) in their LC CDR regions and screening them by binding to STOP-1.

Expression of phage: *E. coli* strain SS320 was transformed with the mutagenized DNA described above by electroporation. The size of the libraries was approximately $10^9$. Transformed bacterial cells were grown up overnight in the presence of helper phage K07 to produce displaying phage that could still infect other bacterial cells. Next, *E. coli* strain XL-1 Blue (Strategene, San Diego, Calif.) was infected with F(ab) or F(ab)'$_2$ phage and then K07 helper phage (Strategene, San Diego, Calif.) were grown in 2YT media at 37° C. for 20 hours and phage was harvested as described (Sidhu et al., Methods Enzymol. (2000), 328:333-363). Briefly, phage was purified by first precipitating them from the overnight culture media with polyethylene glycol, and resuspended in PBS. Phage were quantitated by spectrophotometer with its reading at 268 nm (1 OD=1.13×10$^{13}$/ml).

Phage sorting: The phage libraries were subjected to four rounds of sorting. 96-well Nunc Maxisorp plates were coated with 100 ul/well of target antigen (CHO-psgb-expressed human his-tagged STOP-1 full length or baculovirally-expressed human his-tagged #94-243 amino acids ("short form")) (5 ug/ml) in PBS at 4° C. overnight or room temperature for 2 hours. The plates were blocked with 65 ul 1% blocking protein for 30 min and 40 ul 1% Tween20 for another 30 min (blocking protein: 1$^{st}$ round—bovine serum albumin (BSA), 2$^{nd}$ round—ovalbumin, 3$^{rd}$ round—casein, 4$^{th}$ round—ovalbumin). Next, the library phage was diluted to 3~5 O.D/ml with 1% BSA with 0.1% Tween 20 (1 O.D=1.13×10$^{13}$ phage/ml). In general, the phage input was 1$^{st}$ round 3-5 O.D/ml, 2$^{nd}$ round 3 O.D/ml, 3$^{rd}$ round 0.5~1 O.D/ml and 4$^{th}$ round input 0.1~0.5 O.D/ml. The diluted phage was incubated for 30 minutes at room temperature. The wells were washed at least five times continuously with PBS and 0.05% Tween 20. The blocked library phage was added 100 ul/well to 8 target antigen-coated wells and 2 uncoated wells at room temperature for 1 hour. The plates were washed continuously at least 10 times with PBS and 0.05% Tween 20. The phages were eluted with 100 ul/well of 100 mM HCl at room temperature for 20 minutes. The eluted phages (from coated wells) and background phage (from uncoated wells) were collected in separate tubes. The eluted collections were neutralized by adding 1/10 volume 1M Tris pH 11.0 to both tubes. BSA was added to a final 0.1% into the tube of eluted phage. The eluted phage was heated at 62 C for 20 minutes. To titer the phage, 90 ul of log phase XL-1 (OD 600 nm~0.1-0.3) was infected with 10 ul eluted phage or background phage at 37° C. for 30 minutes. Next, the infected cells were serially diluted in 10 fold increments with 90 ul 2YT. 10 ul aliquots of the infected cells were plated per carbenicillin plate.

To propagate the phage, approximately 400 ul of eluted phage was used to infect ~4 ml log phase XL-1soup (OD 600 nm~0.1-0.3) at 37° C. for 30-45 minutes. Helper phage, K07, and carbenicillin were added to the infection at a final concentration of 1×10$^{10}$ pfu/ml K07 and 50 ug/ml carbenicillin at 37° C. for another hour. The culture was grown in 50:50 2YT/CRAP media with carbenicillin 50 ug/ml and 50 ug/ml kanamycin to final volumes of 20~25 ml at 37° C. overnight (or at least 17 hours). The next day, the culture was grown at 30 C for another 2 hours to increase the phage yield.

The phage was purified by spinning down the cells at 8000 rpm for 10 minutes. The supernatant was collected. 20% PEG/2.5M NaCl was added at 1/5 of the supernatant volume, mixed and allowed to sit on ice for 5 minutes. The phage was spun down into a pellet at 12000 rpm for 15 minutes. The supernatant was collected and spun again for 5 minutes at 5000 rpm. The pellets were resuspended in 1 ml PBS and spun down at 12000 rpm for 15 minutes to clear debris. The steps starting with the PEG/NaCl addition were repeated on the resuspended pellet. The OD of the resuspended phage pellet was read at 270 nm.

The second, third and fourth rounds of phage sorting were completed by repeating the phage sorting steps as described above. The phage antibodies that were selected based on binding to the short form were designated as "S#" (e.g., S4, S9, S7 and S16). The phage antibodies that were selected based on binding to the full length form were designated as "F#" (e.g., F5, F6, F13 and F47).

ELISA Screening Assay: Clones from the sorts 2 to 4 were screened for specificity and affinity by ELISA assay. Positive clones (binders) were clones that had above background binding to the target antigens and not to other non-relevant protein, such as bovine serum albumin and insulin-like growth factor-1 (IGF-1).

First, the wells of a 384-well microtiter plate were coated with either full length or "short form" (#93aa-243aa) his-tagged human STOP-1, IGF-1, Her-2 or anti-gD at 20 ul per well (2 µg/ml in PBS) at 4° C. overnight or room temperature for 2 hours.

| HER2 | STOP-1 |
|---|---|
| Anti-gD | IGF-1 |

In another 96 well plate, colonies from sorts 2-4 were grown overnight at 37° C. in 150 ul 50:50 2YT/CRAP media with 50 ug/ml carbenicillin and helper phage K07. The plate was spun down at 2500 rpm for 20 minutes. 50 ul of the supernatant was mixed with 120 ul of ELISA buffer (PBS—0.5% BSA and 0.05% Tween20). 30 ul of the mixture was added to each quadrant of the 384-well coating plate and incubated at room temperature for 1 hour. Binding was quantified by adding 75 ul/well of horse radish peroxidase (HRP)-conjugated anti-M13 antibody in PBS plus 0.5% BSA and 0.05% Tween20 at room temperature for 30 minutes (Sidhu et al., supra). The wells were washed with PBS—0.05% Tween20 at least five times. Next, 100 ul/well of a 1:1 ratio of 3,3',5,5'-tetramethylbenzidine (TMB) Peroxidase substrate and Peroxidase Solution B ($H_2O_2$) ((Kirkegaard-Perry Laboratories (Gaithersburg, Md.)) was added to the well and incubated for 5 minutes at room temperature. The reaction was stopped by adding 100 ul 1M Phosphoric Acid ($H_3PO_4$) ((Kirkegaard-Perry Laboratories (Gaithersburg, Md.)) to each well. The OD of the yellow color in each well was determined using a standard ELISA plate reader at 450 nm. The F(ab) or F(ab)$'_2$ phage concentration that resulted in about 90% of maximum binding to the coated plate was used in the solution binding competition ELISAs. F(ab) and F(ab)$'_2$ phage having 34 fold greater binding than BSA, IGF-1, Her2 and anti-gD were considered to have better specificity. Those binders were sequenced.

FIG. 18 shows a partial amino acid sequence of several of the binders that had higher affinity and specificity (e.g., S7, S16, F5, S4, F13, F47 and S9). Three clones share identical CDR sequences —F13, F47 and S4. S7 and S16 also share some sequence homology. Based on the sequence homology between F13, F47, S4, S7, S9 and S16 in their $V_H$-CDR1, $V_H$-CDR2 and $V_H$-CDR3 regions, consensus sequences for the commonly recognized epitope were derived. Amino acid and nucleic acid sequences coding for a phage display S4-Fab, a phage display S9-Fab, a phage display S7-F(ab)'2, a phage display S16-F(ab)'2, a phage display F5-F(ab)'2 can be found in FIGS. 27A-C, FIGS. 28A-C, FIGS. 29A-C, FIGS. 30A-C and FIGS. 31A-C, respectively. S7 has SEQ ID NOS: 8-10. S16 has SEQ ID NOS: 11-13. F5 has SEQ ID NOS: 14-16. S4, F13 and F47 have SEQ ID NOS: 17-19. S9 has SEQ ID NOS: 20-22.

The following vectors have been deposited under the terms of the Budapest Treaty with the American Type Culture Collection (ATCC), 10801 University Blvd., Manassas, Va. 20110-2209, USA as described below:

| Material | Deposit No. | Deposit Date |
|---|---|---|
| V0350-4-S7 | PTA-5090 | Mar. 25, 2003 |
| V0350-4-S16 | PTA-5089 | Mar. 25, 2003 |
| V0350-2b-S4 | PTA-5086 | Mar. 25, 2003 |
| V0350-2b-S9 | PTA-5087 | Mar. 25, 2003 |
| V0350-4-F5 | PTA-5088 | Mar. 25, 2003 |

EXAMPLE 17

Solution Binding Competition ELISA

To determine a binding affinity for selected F(ab) and F(ab)$'_2$ phage, competition ELISAs were performed.

First, the phage were propagated and purified. Ten uls of XL-1 bacteria infected with one of the clones for 30 minutes at 37° C. was plated on a carbenicillin plate. A colony was picked and grown in 2 mls (2YT and 50 ug/ml carbenicillin) at 37° C. for 3-4 hours. Helper phage, K07, was added to the culture at a final concentration of $10^{10}$ pfu/ml for another 1 hour at 37° C. Twenty mls of media (2YT/CRAP 50:50 with 50 ug/ml carbenicillin was added to the culture for growth overnight at 37° C. The phage was purified as described above.

Second, the concentration of purified phage that would be optimal for use in the following competition ELISA assay was determined (i.e., approximately 90% of maximal binding capacity on the coated plate). 96-well Nunc Maxisorp plates were coated with full length or short form human STOP-1 (2 ug/ml in PBS) at 4° C. overnight or at room temperature for 2 hours. The wells were blocked by adding 65 ul 1% BSA for 30 minutes followed by 40 ul 1% Tween20 for another 30 minutes. Next, the wells were washed with PBS—0.05% Tween20 5 times. Various dilutions of F(ab) or F(ab)$'_2$ phage down to 0.1 O.D./ml in ELISA buffer (PBS—0.1% BSA and 0.05% Tween20) were added to the wells for 15 minutes at room temperature. The wells were then washed with PBS—0.05% Tween20 at least three times. 75 ul of HRP-conjugated anti-M13 antibody (Amersham, 1/5000 dilution with ELISA buffer) per well was added and incubated at room temperature for 30 minutes. The wells were washed again with PBS—0.05% Tween20 at least five times. Next, 100 ul/well of a 1:1 ratio of 3,3',5,5'-tetramethylbenzidine (TMB) Peroxidase substrate and Peroxidase Solution B ($H_2O_2$) ((Kirkegaard-Perry Laboratories (Gaithersburg, Md.)) was added to the well and incubated for 5 minutes at room temperature. The reaction was stopped by adding 100 ul 1M Phosphoric Acid ($H_3PO_4$) ((Kirkegaard-Perry Laboratories (Gaithersburg, Md.)) to each well. The optical density of the color in each well was determined using a standard ELISA plate reader at 450 nm. The dilutions of phage were plotted against the O.D. readings.

Third, a competition ELISA was performed. 96-well Nunc Maxisorp plates were coated with full length or short form human STOP-1 (2 ug/ml in PBS) at 4° C. overnight or at room temperature for 2 hours. The wells were blocked by adding 65 ul 1% BSA for 30 minutes followed by 40 ul 1% Tween20 for another 30 minutes. The wells were washed with PBS—0.05% Tween20 5 times. Based on the binding assay above, 50 ul of the dilution of phage that resulted in about 90% of maximum binding to the coated plate was incubated with 50 ul of various concentrations of full length or short form human STOP-1 (0.1 to 500 nM) in ELISA buffer solution for 1 hour at room temperature in a well. The unbound phage was assayed by transferring 75 ul of the well mixture to second 96-well plate pre-coated with full length or short form human STOP-1 and incubating at room temperature for 15 minutes. The wells of the second plate were washed with PBS—0.5% Tween20 at least three times. 75 ul of HRP-conjugated anti-M13 antibody (⅕₀₀₀ dilution with ELISA buffer) per well was added and incubated at room temperature for 30 minutes. The wells were washed again with PBS—0.05% Tween20 at least five times. Next, 100 ul/well of a 1:1 ratio of 3,3',5,5'-tetramethylbenzidine (TMB) Peroxidase substrate and Peroxidase Solution B ($H_2O_2$) ((Kirkegaard-Perry Laboratories (Gaithersburg, Md.)) was added to the well and incubated for 5 minutes at room temperature. The reaction was stopped by adding 100 ul 1M Phosphoric Acid ($H_3PO_4$) ((Kirkegaard-Perry Laboratories (Gaithersburg, Md.)) to each well. The optical density of the color in each well was determined using a standard ELISA plate reader at 450 nm. The concentrations of competitor STOP-1 were plotted against the O.D. readings. The $IC_{50}$, the concentration of STOP-1 that inhibits 50% of the F(ab)-phage or F(ab)'₂-phage, represents the affinity. See Table 12.

Table 12 shows that F5 binds the N-terminus of full length STOP-1, not the short form. S7, S16, S9 and S4 (and therefore F13 and F47) bind to the short form (#94-243) of human STOP-1. In Table 2, the term "762 S/S" indicates that the wells of the microtiter plate were coated with the short form of human STOP-1 and that the F(ab)-phage or F(ab)'₂-phage were competed with the short form of human STOP-1. The term "762 S/F" indicates that the wells of the microtiter plate were coated with the short form of human STOP-1 and that the F(ab)-phage or F(ab)'₂-phage were competed with the full length form of human STOP-1. The term "762 F/F" indicates that the wells of the microtiter plate were coated with the full length form of human STOP-1 and that the F(ab)-phage or F(ab)'₂-phage were competed with the full length form of human STOP-1. "ND" indicates that the result was not detectable. "N/A" indicates that the result was not available.

TABLE 12

| | 762 S/S | 762 S/F | 762 F/F | STOP-1 binding |
|---|---|---|---|---|
| F(ab)'₂ | | | | |
| S7 | 35 nM | 4.7 nM | 2.7 nM | Short form |
| S16 | 114 nM | n/a | 32 nM | Short form |
| F5 | ND | 1 uM | N/A | Full length |
| Fab | | | | |
| S4 | 3 nM | 719 nM | 0.9 nM | Short form |
| S9 | >1 uM | 331 nM | N/A | Short form |
| F13 | 3.8 nM | 795 nM | n/a | Short form |
| F47 | 3.8 nM | 795 nM | n/a | Short form |

These antibodies also recognized human STOP-1 in immunoprecipitations.

EXAMPLE 18

6B12 Blocking Assay

The binding location of certain F(ab)'₂-phage was also explored. It is known that the monoclonal anti-human STOP-1 antibody, 6B12, binds to an N-terminal region of human STOP-1 protein. Therefore, it was tested whether 6B12 could block binding of certain F(ab)'₂-phage to STOP-1.

The 6B12 blocking assay was conducted as follows: 96-well Nunc Maxisorp plates were coated with full length human STOP-1 (2 ug/ml in PBS) at 4° C. overnight or at room temperature for 2 hours. The wells were blocked by adding 65 ul 1% BSA at room temperature for 30 minutes followed by 40 ul 1% Tween20 for another 30 minutes. Next, the wells were washed with PBS—0.05% Tween20 5 times. Various concentrations of 6B12 antibody (in ELISA buffer) were incubated in the wells for 30 minutes at room temperature. Then, S7-F(ab)'₂-phage, S16-F(ab)'₂-phage or F5-F(ab)'₂-phage were added to each well for 10 minutes at a concentration that would normally produce 90% binding capacity in the absence of the 6B12 antibody. The wells were washed with PBS—0.05% Tween20 5 times.

Binding was quantified by adding 75 ul/well of horse radish peroxidase (HRP)-conjugated anti-M13 antibody in PBS plus 0.5% BSA and 0.05% Tween20 at room temperature for 30 minutes (Sidhu et al., supra). The wells were washed with PBS—0.05% Tween20 at least five times. Next, 100 ul/well of a 1:1 ratio of 3,3',5,5'-tetramethylbenzidine (TMB) Peroxidase substrate and Peroxidase Solution B ($H_2O_2$) ((Kirkegaard-Perry Laboratories (Gaithersburg, Md.)) was added to the well. The reaction was stopped by adding 100 ul 1M Phosphoric Acid ($H_3PO_4$) ((Kirkegaard-Perry Laboratories (Gaithersburg, Md.)) to each well and allowed to incubate for 5 minutes at room temperature. The OD of the yellow color in each well was determined using a standard ELISA plate reader at 450 nm.

TABLE 13

| F(ab)'₂ | 6B12 blocking |
|---|---|
| S7 | − |
| S16 | − |
| F5 | + |

Table 13 shows the 6B12 antibody was able to block F(ab)'₂-F5 phage but not F(ab)'₂-S7 phage or F(ab)'₂-S16 phage. Therefore, F5 binds to human STOP-1 in the same N-terminal region as 6B12 whereas S7 and S16 do not.

EXAMPLE 19

F(ab) and IgG Protein Constructs and Protein Expression

F(ab) Constructs for Expression in Bacterial Cells: V0350-2b-S4 and V0350-2b-S7 phagemids were modified by removing the viral cP3 sequences, replacing them with a terminator sequence containing 5'-GCTCGGTTGCCGC-CGGGCGTTTTTTATG-3' (SEQ ID NO:85), and removing the sequences encoding the leucine zipper and gD tags (hereinafter, pv0120-S4 and pV0120-S7, respectively). FIG. 24C is a schematic of this vector. The pv0120 vectors were transformed into *E coli* 34B8 cells. Single colonies were picked and grown in complete CRAP medium with 25 ug/ml carbenicillin at 30° C. for at least 22 hours. The expressed proteins were purified through a Protein G high trap column (Amersham Pharmacia).

Amino acid and nucleic acid sequences coding for an S4-Fab are illustrated in FIGS. 32A-G.

IgG Constructs for Expression in Mammalian Cells:

Generally, IgG1 constructs were made by swapping the light chain encoded in the LPG3 vector with the light chain of S4 or S7 and by swapping the $V_H$ and $C_H1$ region encoded in the LPG4 vector with the $V_H$ and $C_H1$ region of S4 or S7. FIG. 24D is a schematic of the LPG3 and LPG4 vectors encoding the light and heavy chains, respectively, of an IgG protein.

The LPG3 vector encodes a humanized MaE11 E27 light chain. The LPG4 vector encodes a humanized MaE11 E27 heavy chain. Together, they encode a full-length human IgG1 version of humanized MaE11 E27 (an anti-IgE antibody). See, U.S. Pat. No. 6,172,213 (Lowman) for more information about humanized MaE11 E27. The LPG3 and LPG4 vectors were pRK vectors (Gorman, C M et al., (1990) *DNA Protein Eng. Tech.* 2:3) that were modified by, among other things, inserting the full-length light chain and heavy chain, respectively, of a humanized MaE11 E27. The LPG3 and LPG4 vectors were obtained from Yan Wu at Genentech, Inc., South San Francisco, Calif.

The LPG4 vector was digested with BsiwI and ApaI to remove the heavy chain variable regions of the humanized MaE11 E27 antibody. The removed sequences were replaced with a BsiwI-ApaI fragment from the pv0120-S4 or the pv0120-S7 vectors. The LPG3 vector was digested with EcorRV and KpnI to remove the light chain variable regions of the humanized MaE11 E27 antibody. The removed sequences were replaced with an EcorRV-KpnI fragment from the pv0120-S4 or the pv0120-S7 vectors encoding the light chain variable regions of S4 and S7. The resulting vectors, LPG3-humankappaG6 and LPG4-humanHC-S4, are described in FIGS. 35 and 36 (SEQ ID NO:110 and SEQ ID NO:112, respectively). The sequence of LPG4-humanHC-S7 is the same as the sequence of LPG4-humanHC-S4, except that the sequence between the BsiwI-ApaI sites is the same as the sequence between the BsiwI-ApaI sites of the pv0120-S7 vector.

LPG3-humankappaG6, LPG4-humanHC-S4 and LPG4-humanHC-S7 dsDNA were prepared for transfection. DP12 DHFR+CHO cells (ATCC) were seeded at $1.5 \times 10^6$ cells/ml in tissue culture media containing 1× Tris EDTA (TE), 2 mg/L insulin, 1% dFBS, 0.15 g/L gentamycin sulfate. The cells were incubated at 37° C. for one to two hours before transfecting. Next, 3.5 L of warm tissue culture media was added to the culture together with 20 mg DNA, 20 ml of DMRIE-C reagent (1,2-dimyristyloxypropyl-3-dimethyl-hydroxylethyl ammonium bromide, Genentech, Inc.) and incubated for at least more 20 minutes at 37° C. The culture was added to a bioreactor, and 250 ml/L of warm tissue culture media was added. The cell culture temperature was shifted to 33° C. After 7-12 days, the cells were centrifuged at 1000 rpm for 5 minutes and then the supernatant was filtered through a 0.2 um filter. The proteins in the supernatant were purified through a Protein G high trap column (Amersham Pharmacia).

Amino acid and nucleic acid sequences coding for an S4 IgG protein are illustrated in FIGS. 33A-F and FIGS. 24A-G.

EXAMPLE 20

Affinity Measurement of S4 and S7 Fab and IgG

ELISA assays were performed to determine the affinity of S4 and S7 Fab and IgG for human STOP-1. First, the concentration of purified Fab and IgG that would be optimal for use in a competition ELISA assay was determined (i.e., approximately 90% of maximal binding capacity on the coated plate). 96-well Nunc Maxisorp plates were coated with full length or short form human STOP-1 (2 ug/ml in PBS) at 4° C. overnight or at room temperature for 2 hours. The wells were blocked by adding 65 ul 1% BSA for 30 minutes followed by 40 ul 1% Tween20 for another 30 minutes. Next, the wells were washed with PBS—0.05% Tween20 5 times. Concentrations of F(ab) or IgG from 0.1 nM to 100 nM diluted in ELISA buffer (PBS—0.5% BSA and 0.05% Tween20) were added to the wells for 15 minutes at room temperature. The wells were then washed with PBS—0.05% Tween20 at least three times. 75 ul of HRP-conjugated Protein G antibody (Amersham, 1/5000 dilution with ELISA buffer) per well was added and incubated at room temperature for 30 minutes. The wells were washed again with PBS—0.05% Tween20 at least five times. Next, 100 ul/well of a 1:1 ratio of 3,3',5,5'-tetramethylbenzidine (TMB) Peroxidase substrate and Peroxidase Solution B ($H_2O_2$) ((Kirkegaard-Perry Laboratories (Gaithersburg, Md.)) was added to the well. The reaction was stopped by adding 100 ul 1M Phosphoric Acid ($H_3PO_4$) ((Kirkegaard-Perry Laboratories (Gaithersburg, Md.)) to each well and allowed to incubate for 5 minutes at room temperature. The optical density of the color in each well was determined using a standard ELISA plate reader at 450 nm. The dilutions of Fab or IgG were plotted against the O.D. readings.

FIG. 19 shows an example of a ELISA assay used to determine the optimal concentration of Fab or IgG in a competition assay. "S coated" refers to a short form (#94-243) of STOP-1 coated on a microtiter plate. "F coated" refers to a full-length form of human STOP-1 coated on a microtiter plate. Approximately 90% of maximal binding was considered to be optimal for use in a competitive ELISA assay.

Next, a competition ELISA was performed using the optimal concentration of Fab and IgG determined above. 96-well Nunc Maxisorp plates were coated with full length or short form human STOP-1 (2 ug/ml in PBS) at 4° C. overnight or at room temperature for 2 hours. The wells were blocked by adding 65 ul 1% BSA for 30 minutes followed by 40 ul 1% Tween20 for another 30 minutes. The wells were washed with PBS—0.05% Tween20 5 times. Based on the binding assay above, 50 ul of the dilution of Fab or IgG that resulted in about 90% of maximum binding to the coated plate was incubated with 50 ul of various concentrations of full length or short form human STOP-1 (0.1 to 500 nM) in ELISA buffer solution for 1 hour at room temperature in a well. The unbound Fab or IgG was assayed by transferring 75 ul of the well mixture to second 96-well plate pre-coated with full length or short form human STOP-1 and incubating at room temperature for 15 minutes. The wells of the second plate were washed with PBS—0.5% Tween20 at least three times. 75 ul of HRP-conjugated Protein G (1/5000 dilution with ELISA buffer) per well was added and incubated at room temperature for 30 minutes. The wells were washed again with PBS—0.05% Tween20 at least five times. Next, 100 ul/well of a 1:1 ratio of 3,3',5,5'-tetramethylbenzidine (TMB) Peroxidase substrate and Peroxidase Solution B ($H_2O_2$) ((Kirkegaard-Perry Laboratories (Gaithersburg, Md.)) was added to the well. The reaction was stopped by adding 100 ul 1M Phosphoric Acid ($H_3PO_4$) ((Kirkegaard-Perry Laboratories (Gaithersburg, Md.)) to each well and allowed to incubate for 5 minutes at room temperature. The optical density of the color in each well was determined using a standard ELISA plate reader at 450 nm. The concentrations of the added competitor STOP-1 were plotted against the O.D. readings. The $IC_{50}$ is the concentration of STOP-1 that inhibited 50% of the Fab or IgG binding. See FIGS. 20A and B. The binding affinities are indicated in the parentheticals.

FIG. 21 is a summary of the binding affinities of several phage-derived antibodies against STOP-1. "S/S" refers to an ELISA in which the microtiter plate was coated with a short form of STOP-1 and competed with a short form of STOP-1. "F/S" refers to an ELISA in which the microtiter plate was coated with a full-length form of human STOP-1 and competed with a short form of human STOP-1. "F/F" refers to an ELISA in which the microtiter plate was coated with a full-length form of STOP-1 and competed with a full-length form of STOP-1. The phage used in these studies were the S4-Fab phage and the S7-F(ab)'$_2$ phage.

EXAMPLE 21

S4 Blocking Assay

S4 IgG was used in a competitive ELISA assay to see if it could block S4 (Fab)-phage, S7 (F(ab)'$_2$)-phage, S9 (Fab)-phage, S16 (F(ab)'$_2$)-phage or F5 (F(ab)'$_2$)-phage binding to a short form or a full-length form of human STOP-1.

First, 96-well Nunc Maxisorp plates were coated with full length human STOP-1 (2 ug/ml in PBS) at 4° C. overnight or at room temperature for 2 hours. The wells were blocked by adding 65 ul 1% BSA for 30 minutes followed by 40 ul 1% Tween20 for another 30 minutes. Next, the wells were washed with PBS—0.05% Tween20 5 times. Various concentrations of S4 IgG (in ELISA buffer) were incubated in the wells for 30 minutes at room temperature. Then, S4 (Fab)-phage, S7 (F(ab)'$_2$)-phage, S9 (Fab)-phage, S16 (F(ab)'$_2$)-phage or F5 (F(ab)'$_2$)-phage were added to different wells for 10 minutes at a concentration that would normally produce 90% binding capacity in the absence of the S4 IgG antibody. The wells were washed with PBS—0.05% Tween20 5 times.

Binding was quantified by adding 75 ul/well of horse radish peroxidase (HRP)-conjugated anti-M13 antibody in PBS plus 0.5% BSA and 0.05% Tween20 at room temperature for 30 minutes (Sidhu et al., supra). The wells were washed with PBS—0.05% Tween20 at least five times. Next, 100 ul/well of a 1:1 ratio of 3,3',5,5'-tetramethylbenzidine (TMB) Peroxidase substrate and Peroxidase Solution B ($H_2O_2$) ((Kirkegaard-Perry Laboratories (Gaithersburg, Md.)) was added to the well. The reaction was stopped by adding 100 ul 1M Phosphoric Acid ($H_3PO_4$) ((Kirkegaard-Perry Laboratories (Gaithersburg, Md.)) to each well. The OD of the yellow color in each well was determined using a standard ELISA plate reader at 450 nm.

FIG. 22 shows that most of the phage-derived antibodies, except F5, bound a similar region on STOP-1 as the S4 phage-derived antibody. The Y axis refers to percentage unblocked as calculated by dividing the OD450 nm value of the well that blocked S4 IgG by the OD450 nm value of a well without S4 IgG. The phage tested were S4 (Fab) phage, S7 (F(ab)'$_2$) phage, S9 (Fab) phage, S16 (F(ab)'$_2$) phage and F5 (F(ab)'$_2$) phage. A lower % means the more blocking by S4 IgG.

EXAMPLE 23

Optimizing Binding by Altering the Light Chain Sequence

Binding of the antibodies can be further optimized by, inter alia, by altering the sequence of the light chain. Optimization can be carried out by methods known in the art, including known phage display methods. Additionally, the sequence of the light chain CDR's can be changed by site-directed mutagenesis and screened by ELISA assays similar to the methods described in Example 16 above, except that the diversity is generated in the light chain variable region as described in U.S. Provisional Patent No. 60/385,388, filed Jun. 3, 2002. See also below.

According to one example, the libraries of antibody variable light chain domains are optimized to maximize diversity in the CDR regions while minimizing structural perturbations in the antibody variable domains. Structural perturbations in antibody variable domains are generally associated with improperly folded antibody domains resulting in low yield, for example when produced in bacterial cells. Low yields decrease the number of binders detected in screening. Diversity in the light chain CDR regions can be generated by identifying solvent accessible and highly diverse positions in each CDR for CDRs L1, L2, L3, and designing an oligonucleotide comprising at least one tailored (i.e., non-random) codon set encoding variant amino acids for the amino acid position corresponding to the position of at least one solvent accessible residue at a highly diverse position in at least one CDR region. A tailored codon set is a degenerate nucleic acid sequence that preferably encodes the most commonly occurring amino acids at the corresponding positions of the solvent accessible residues in known, natural antibodies.

Solvent accessible residues in the CDRs can be identified in the antibody variable domain template molecule by analyzing the crystal structure of the template molecule. Humanized antibody 4D5 is efficiently produced and properly folded when produced in a variety of host cells, including bacterial cell culture. The crystal structure for the humanized antibody 4D5 variable region is known and publicly available at http://www.rcsb.org (accession code IFVC).

The solvent accessible positions in the CDRs of the light chain have been identified using the Insight II program (Accelrys, San Diego, Calif.).

CDR residues were also analyzed to determine which positions in the CDRs were highly diverse. Highly diverse positions in the CDR regions for the heavy and light chains were identified by examining the sequences of known, naturally occurring antibodies in the Kabat database (Kabat, E. A., et al., (1991) Sequences of Proteins of Immunological Interest, Fifth Edition, NIH Publication No. 91-3242). The Kabat database is also available through http://www.bioinf.org.uk/abs/. In the Kabat database, there were about 1540 sequences of the human light chain and 3600 sequences for the human heavy chain. The CDR sites were aligned and numbered as described by Kabat (see http://www.bioinf.org.uk/abs/du). Highly diverse amino acid positions were identified by lining up and ranking the amino acid usage, from most frequently used to less frequently used for each CDR residue. For example, L3-91 (i.e., residue 91 of the light chain CDR3) was found to be Y (tyrosine) in 849 out of 1582 antibody sequences in the Kabat database, and it is the amino acid found most frequently at this position. Next on the list of frequency serine (occurring in 196 sequences), followed by arginine (169 sequences), alanine (118 sequences), glycine (61 sequences), histidine (41 sequences), with the remaining 35 sequences being one of the remaining amino acids. The frequency of amino acids in human antibody light chain sequences from the Kabat database (including illustrative diverse sites, with corresponding diversity list of amino acids) is shown in FIG. 35.

Amino acid residues found in a particular position that collectively constitute the most frequently occurring amino acids among the known, natural antibody sequences can be selected as the basis for library design. The most frequently occurring amino acids were deemed to be those that most commonly found in the top 90% of the list of diverse amino acids (this group of amino acids is referred to herein as "target group of amino acids"). However, as described herein, the percent cutoff for a target group of amino acids can be varied, as described above, according to the circumstances and purpose of the diversity library that is to be achieved.

For humanized antibody 4D5, the positions identified as solvent accessible and highly diverse were:

| Light Chain | |
|---|---|
| CDR1 | 28, 29, 30, 31, 32 |
| CDR2 | 50, 53 |
| CDR3 | 91, 92, 93, 94, 96 |
| Heavy Chain | |
| CDR 1 | 28, 30, 31, 32, 33 |
| CDR2 | 50, 52, 53, 54, 56, 58 |

Examples of amino acids that occur at high frequency in natural diversity (i.e., among known, natural antibody sequences) (referred to as "target group" or "natural diversity" in FIG. 3), and the designed diversity of amino acids by DNA codons ("Diversity<DNA codon>") for each of these positions is shown in FIG. 36.

Codon sets encoding a specific group of amino acids (Diversity) have been designed to include at least a certain percentage of the amino acids in the known, natural sequences (designated as "% covering" in FIG. 36). Of the amino acids encoded by a codon set, at least about 40% of the amino acid can target amino acids identified for a particular solvent accessible and highly diverse position (designated as "% good" in FIG. 36; amino acids encoded by a codon set that are target amino acids are shown in bold in column 3 of FIG. 36). However, as described herein, the % good value can be varied according to circumstance and objectives. The codon sets were selected such that they preferably encoded the amino acids with the highest occurrences at a particular position. The number of non-target amino acids coded by a codon set for a particular position was minimized. Effectiveness of codon set selection/design was evaluated in part based on the "% good" value. A high percentage meant very low non-target amino acids; a high value of "% good" was deemed more important than having more target amino acids among the amino acids coded by a particular codon set. Redundancy was included in calculating the "% good" value. For evaluation purposes, the "% covering" value was also calculated. This value represents the percentage of natural diversity covered by the "good" amino acids (of the amino acids encoded by a particular codon set). For example, for L3-91, when codon set KMT is used, the "good" amino acids are YSA, which is 75% of the YSAD amino acids encoded by the codon. YSA are amino acids that cover 1190 out of 1580 known, natural antibody sequences at this amino acid position. 1190/1580 equals 75%, which is the "% covering" value. Thus, in one design using KMT at L3-91, 75% of the library covers 75% of the natural diversity in CDRL3 at position 91.

The codon sets were also designed to exclude, when possible, cysteine and stop codons. The presence of cysteine residues tends to cause folding problems and stop codons can decrease the effective library size. In the design of the codon sets, it was also deemed desirable to minimize the number of nontarget amino acids.

The codon sets designed for each solvent accessible and highly diverse residue of humanized antibody 4D5 are shown in FIG. 36. At any particular residue, one or more codon set(s) could be used depending on the target amino acids that are identified. For example, two L1 oligonucleotides can be combined—one containing codon YKG and the other containing TWT at L3-96, or one containing codon DGG and the other containing DHT at H2-50.

The various codon sets could be used to generate diverse libraries with diversity in one or more CDR regions, including CDR L1, CDR L2, CDR L3. For example, FIGS. 37-40 show various illustrative versions of codon set designs that can be used to generate diversity. FIG. 36 provides a summary of the amino acid coverage of these designs. In general, it is preferable, but not necessary, that the designs narrow the diversity to cover more of the natural diversity and exclude as much as possible the "non-target" amino acids. In some embodiments, a design that does not score the highest based on these criteria can be used to obtain good binders for a STOP-1.

EXAMPLE 24

STOP-1 Binds to the Cell Surface of Cells

HT1080 cells were incubated with recombinant purified full length human His-tagged STOP-1 (10 ug/ml, A; 0.5 million cells per sample) in the presence of 10 ug/ml of S7 or 6b12 monoclonal antibodies in FACS buffer (20 mM HEPES, pH 7.5, 140 mM NaCl, 1 mM CaCl2, 1 mM MgCl2, 2% FBS) at 4° C. for 1 hour. Protein binding was detected by treating the cells with FACS with anti-His monoclonal antibodies (5 mg/ml) or anti-Flag (5 mg/ml, as a negative control) and followed by FITC-conjugated goat anti-mouse antibodies.

FIG. 41 shows that STOP-1 binds specifically to the surface of human HeLa cells, human HT1080 fibroblast cells and human umbilical vein endothelial cells (HUVEC) cells, but not human embryonic kidney 293 cells. It is believed that a receptor for STOP-1 exists on HeLa, HT1080 and HUVEC cells.

EXAMPLE 25

S7 Monoclonal Antibody Promotes STOP-1 Binding to Cells

HT1080 cells were incubated with recombinant purified full length human His-tagged STOP-1 (10 ug/ml, A; 0.5 million cells per sample) in presence of 100 ug/ml of S7 or 6b12 monoclonal antibodies in FACS buffer (20 mM HEPES, pH 7.5, 140 mM NaCl, 1 mM CaCl2, 1 mM MgCl2, 2% FBS) at 4° C. for 1 hour. Protein binding was detected by FACS treatment with anti-His monoclonal antibodies (5 mg/ml) or anti-Flag (5 mg/ml, as a control) followed by treatment with FITC-conjugated goat anti-mouse antibodies.

FIG. 42 shows that the S7 antibody potentiated STOP-1 binding to the cell surface of HT1080 cells whereas 6B12 did not. The S4 antibody was also tested in the same assay and found to potentiate STOP-1 binding to HT1080 cells. Because the S7 antibodies and S4 antibodies were able to bind to STOP-1 bound to cells, the binding of S7 antibody or S4 antibody to STOP-1 does not appear to interfere with the binding of the STOP-1 receptor to STOP-1. Thus, the epitope that the S7 antibody binds to on STOP-1 does not appear to be required for STOP-1 binding to its receptor.

EXAMPLE 26

STOP-1 Promotes Endothelial Cell Migration

Directional cell migration was measured using a modified Boyden chemotaxis chamber (Transwells™, Corning, Inc.).

Polycarbonate filters with 8 micron pores were incubated with a 0.1% solution of collagen I from Collaborative Sciences overnight at 4° C. This process coated the undersurface of the filters with collagen, an extracellular matrix protein necessary for cell attachment. The next day, the filters were rinsed in PBS and blocked for 1 hr at room temperature with a blocking medium (200 microliters in each lower chamber) that consisted of basic endothelial cell medium (Clonetics) with 1% bovine serum albumin (BSA).

HUVEC cells (from Clonetics, grown in complete medium) were harvested using a cell dissociation solution (0.25% EDTA) and resuspended in a migration medium (endothelial cell basic medium having 0.1% BSA, but no growth factors). The resuspended cells were placed in the upper chamber of the modified Boyden chamber (10,000 cells/ml, 150 microliters/well). The migration medium containing bFGF (1 ng/ml or 10 ng/ml, final concentration) or STOP-1 (1 ug/ml or 10 ug/ml, final concentration) were added to the lower chamber of the modified Boyden chamber (300 microliters/well). Migration medium alone (without bFGF or STOP-1) was added to the lower chambers as controls. Each condition was done in triplicate. The modified Boyden chemotaxis chambers were placed in an incubator at 37° C. (5% CO2) for 3 hours.

Afterwards, cells that had not migrated (located on the top of the filters facing the upper chamber) were gently removed using cotton swabs. The filters were fixed in a 4% paraformaldehyde solution (10 min, RT) and stained with a 0.2% crystal violet solution (5 min, RT), to visualize the cells. The cells located on the undersurface of the filters (i.e., that migrated) were then counted using a Nikon inverted microscope. The filters were randomized ("blinding" the investigator to the conditions). The cells in six random fields (40x) per filter were counted, 3 filters per condition. The data in FIG. 44 represents the mean number of cells from one representative experiment (out of 3).

FIG. 43 indicates that STOP-1 is chemotactic (i.e., induces directional migration) to HUVEC cells. This effect is comparable in magnitude to that of bFGF (a growth factor which has been previously shown to induce HUVEC migration and to act overall as a pro-angiogenic molecule). Treatment with both bFGF and STOP-1 did not show an additive effect. Nor did treatment with bFGF or STOP-1 potentiate each other's effects. This preliminary data suggests that STOP-1 acts as a pro-angiogenenic or pro-vasculogenic molecule. Work to further confirm this effect will include the repetition of the same or similar experiment using an antibody that blocks of the interaction of STOP-1 with HUVEC cells.

EXAMPLE 27

STOP-1 Binds to MDA435 Cells

MDA-MB-435 human mammary carcinoma cells were removed from culture flasks with 10 mM EDTA and resuspended in cold PBS containing 2% fetal bovine serum. The cell number was adjusted to 1,000,000 cells/ml, and 0.5 ml of the suspension was dispensed into tubes with 10 mg/ml flag-tagged full length human STOP-1 and 100 mg/ml of specific (6B12) or control (4B7) antibodies. The mixture was incubated for 1 hour on ice and washed with cold suspension buffer. The mixture was then incubated with anti-flag M2-FITC for 1 hour on ice. Cells were washed in suspension buffer and fluorescence was measured by flow cytometry.

FIG. 44 graphically depicts the flow cytometry analysis. The geometric mean value of the signal intensity produced by cells treated with detection antibody alone (anti-flag M2-FITC antibody without STOP-1) was approximately 7.99. The geometric mean values of the signal intensities produced by the cells treated with STOP-1 alone, STOP-1 with 6B12 and STOP-1 with 4B7 were approximately 13.24, 8.3 and 11.39, respectively. The results show that STOP-1 binds to MDA-MB-435 breast carcinoma cells and that 6B12, a monoclonal antibody specific to STOP-1, blocks STOP-1 binding to those cells. The isotype control, 4B7 antibody, showed no appreciable activity. S4 and S7 antibodies were also used in this assay. Both antibodies did not block STOP-1 from binding to MDA-MB-435 cells, their presence in the assay resulted in an increase in the STOP-1 binding to the cells.

EXAMPLE 28

STOP-1 mRNA Expression is Upregulated by TNFalpha and Cellular Stress

Previous studies have shown that conditions of low oxygen (hypoxia) or cellular stress promote tumorigenesis and angiogenesis. TNFalpha is often used to stimulate cellular responses associated with stress and has been implicated in promoting angiogenesis and tumorigenesis. To test whether STOP-1 expression was influenced by tumorigenic and angiogenic triggers, HUVEC cells were subjected to treatment with TNFalpha and hypoxic conditions.

HUVEC cells were incubated for 3, 8 or 24 hours with 100 ng/ml of human recombinant TNFalpha (Genentech, Inc.) under hypoxic conditions (95% air, 5% CO2) or normoxic conditions (approximately, 95% air, 5% CO2). The mRNA from the treated cells was extracted and subjected to TaqMan RT-PCR reactions using the primers and conditions described in Example 2. The fold change in expression of STOP-1 mRNA at the end of each time period was calculated by comparing it to its level of expression after three hours of incubation under normoxic conditions (without 100 ng/ml TNFalpha).

Figure 45A:
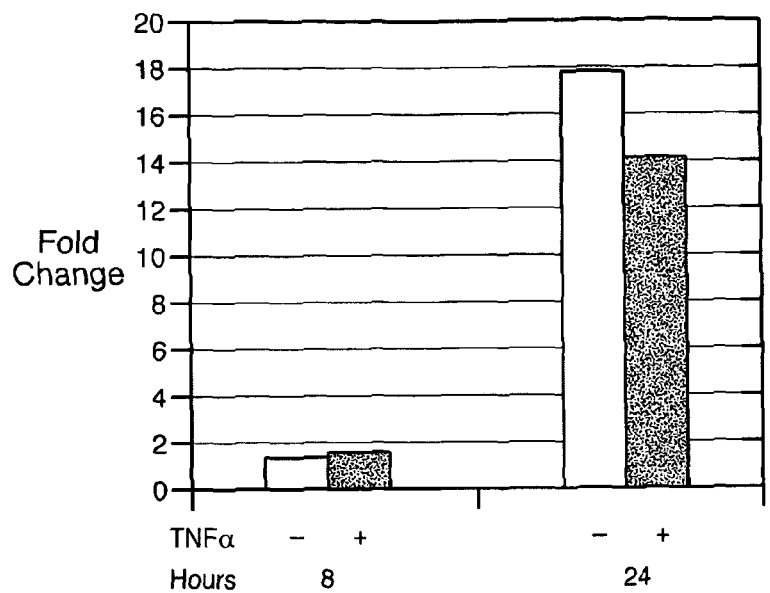
Figure 45B:
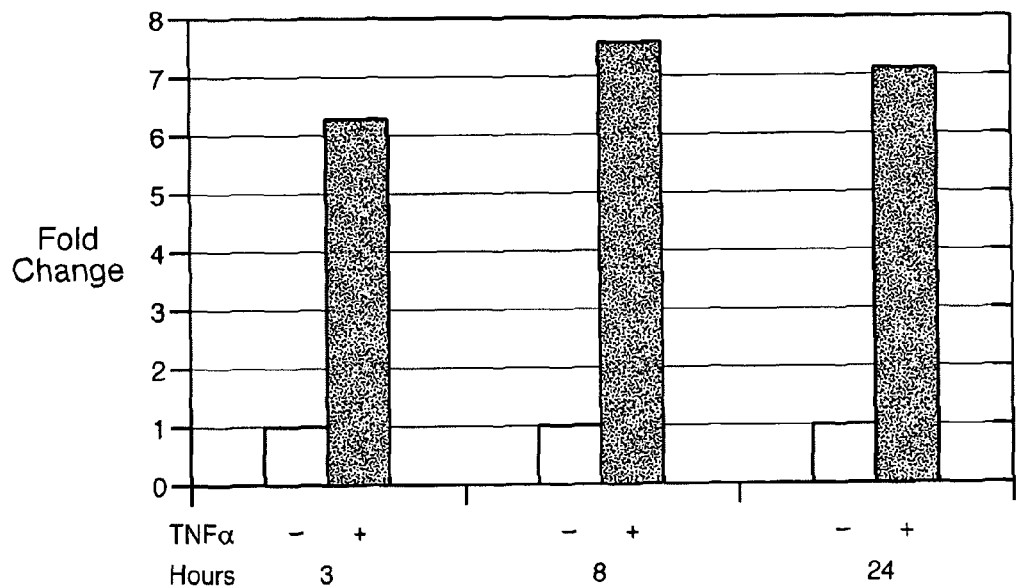

FIG. 45B shows that STOP-1 mRNA expression is significantly upregulated upon treatment with TNFalpha under normoxic conditions. The expression levels did not appear to change substantially at the 3, 8 and 34 hour time points. FIG. 45A, on the other hand, shows that TNFalpha has little or no effect on STOP-1 mRNA levels in cells incubated under hypoxic conditions. Interestingly, in absence of TNFalpha, STOP-1 expression was significantly upregulated after 34 hours of treatment under hypoxic conditions, but not after 3 hours of treatment. These results indicate that STOP-1 expression in HUVEC cells is responsive to treatment with TNFalpha and hypoxic conditions, but the response is not additive or synergistic, possibly indicating similar pathways of action.

| SEQUENCE LISTING KEY | |
|---|---|
| SEQ ID | Description |
| 1 | DNA76393-1664 |
| 2 | amino acid sequence of DNA76393-1664 |
| 3 | alternative STOP-1 amino acid sequence |
| 4 | mouse STOP-1 amino acid sequence |
| 5 | rice fish STOP-1 amino acid sequence |
| 6 | zebra fish STOP-1 amino acid sequence |
| 7 | chicken STOP-1 amino acid sequence |
| 8 | S7 - first amino acid sequence |
| 9 | S7 - second amino acid sequence |
| 10 | S7 - third amino acid sequence |
| 11 | S16 - first amino acid sequence |
| 12 | S16 - second amino acid sequence |
| 13 | S16 - third amino acid sequence |
| 14 | F5 - first amino acid sequence |
| 15 | F5 - second amino acid sequence |
| 16 | F5 - third amino acid sequence |
| 17 | S4 - first amino acid sequence |
| 18 | S4 - second amino acid sequence |
| 19 | S4 - third amino acid sequence |
| 20 | S9 - first amino acid sequence |
| 21 | S9 - second amino acid sequence |
| 22 | S9 - third amino acid sequence |
| 23 | RT-PCR hybridization probe |
| 24 | RT-PCR forward primer |
| 25 | RT-PCR reverse primer |
| 26 | Template sequence |
| 27 | Primer sequence |
| 28 | Primer sequence |
| 29 | Primer sequence |
| 30 | Primer sequence |
| 31 | Primer sequence |
| 32 | Primer sequence |
| 33 | Primer sequence |
| 34 | Primer sequence |
| 35 | Primer sequence |
| 36 | Primer sequence |
| 37 | Primer sequence |
| 38 | Primer sequence |
| 39 | Primer sequence |
| 40 | Primer sequence |
| 41 | Primer sequence |
| 42 | Primer sequence |
| 43 | Primer sequence |
| 44 | Primer sequence |
| 45 | Primer sequence |
| 46 | Primer sequence |
| 47 | Primer sequence |
| 48 | Primer sequence |
| 49 | Primer sequence |
| 50 | Primer sequence |
| 51 | Primer sequence |
| 52 | Primer sequence |
| 53 | Primer sequence |
| 54 | Primer sequence |
| 55 | Primer sequence |
| 56 | Primer sequence |
| 57 | Primer sequence |
| 58 | Primer sequence |
| 59 | Primer sequence |
| 60 | Primer sequence |
| 61 | Primer sequence |
| 62 | Primer sequence |
| 63 | Primer sequence |
| 64 | Primer sequence |
| 65 | Primer sequence |
| 66 | Primer sequence |
| 67 | Primer sequence |
| 68 | Primer sequence |
| 69 | Primer sequence |
| 70 | Primer sequence |
| 71 | Primer sequence |
| 72 | Primer sequence |
| 73 | Primer sequence |
| 74 | Primer sequence |
| 75 | Primer sequence |

-continued

SEQUENCE LISTING KEY

| SEQ ID | Description |
|---|---|
| 76 | Primer sequence |
| 77 | Primer sequence |
| 78 | Primer sequence |
| 79 | Primer sequence |
| 80 | Primer sequence |
| 81 | Primer sequence |
| 82 | Primer sequence |
| 83 | Primer sequence |
| 84 | GCN4 leucine zipper |
| 85 | Oligo containing terminator sequence |
| 86 | an amino acid sequence comprising an anti-Her-2 Fab light chain |
| 87 | an amino acid sequence comprising an anti-Her-2 Fab heavy chain region |
| 88 | a nucleic acid sequence of a phagemid encoding SEQ ID NOs: 86 and 87 (pv0350-2b) |
| 89 | an amino acid sequence comprising an anti-Her-2 F(ab)'$_2$ light chain |
| 90 | an amino acid sequence comprising an anti-Her-2 F(ab)'$_2$ heavy chain region |
| 91 | a nucleic acid sequence of a phagemid encoding the amino acid sequences of SEQ ID NOs: 89 and 90 (pv0350-4) |
| 92 | an amino acid sequence comprising an S4-Fab light chain |
| 93 | an amino acid sequence comprising an S4-Fab heavy chain region |
| 94 | a nucleic acid sequence encoding the amino acid sequences of SEQ ID NOs: 92 and 93 |
| 95 | an amino acid sequence comprising an S9-Fab light chain |
| 96 | an amino acid sequence comprising an S9-Fab heavy chain region |
| 97 | a nucleic acid sequence encoding the amino acid sequences of SEQ ID NOs: 95 and 96 |
| 98 | an amino acid sequence comprising an S7-F(ab)'$_2$ light chain |
| 99 | an amino acid sequence comprising an S7-F(ab)'$_2$ heavy chain region |
| 100 | a nucleic acid sequence encoding the amino acid sequences of SEQ ID NOs: 98 and 99 |
| 101 | an amino acid sequence comprising an S16-F(ab)'$_2$ light chain |
| 102 | an amino acid sequence comprising an S16-F(ab)'$_2$ heavy chain region |
| 103 | a nucleic acid sequence encoding the amino acid sequences of SEQ ID NOs: 101 and 102 |
| 104 | an amino acid sequence comprising a F5-F(ab)'$_2$ light chain |
| 105 | an amino acid sequence comprising an F5-F(ab)'$_2$ heavy chain region |
| 106 | a nucleic acid sequence encoding the amino acid sequences of SEQ ID NOs: 104 and 105 |
| 107 | an amino acid sequence comprising an S4-Fab light chain |
| 108 | an amino acid sequence comprising an S4-Fab heavy chain region |
| 109 | a nucleic acid sequence of a vector encoding the amino acid sequence if SEQ ID NOs: 107 and 108 (pv0120-S4) |
| 110 | an amino acid sequence comprising an S4 IgG Light Chain |
| 111 | a nucleic acid sequence of a vector encoding the amino acid sequence of SEQ ID NO: 110 (LPG3.HumanKappaG6) |
| 112 | an amino acid sequence comprising an S4 IgG Heavy Chain |
| 113 | nucleic acid sequence of a vector encoding the amino acid sequence of SEQ ID NO: 112 (LPG4.HumanHC-S4) |
| 114 | Consensus Amino Acid Sequence of FIG. 1 |
| 115 | An H2 consensus sequence |
| 116 | An H3 consensus sequence |
| 117 | Polypeptide sequence |

All patent, applications and publications recited herein are hereby incorporated by reference.

What is claimed:

1. A monoclonal antibody that specifically binds to amino acids 33-52 or 33-53 of human STOP-1.

2. The monoclonal antibody according to claim 1, wherein the antibody blocks STOP-1 binding to cells.

3. The monoclonal antibody according to claim 1, wherein the monoclonal antibody binds to an oligomeric form of human STOP-1.

4. A monoclonal antibody that specifically binds to human STOP-1 and that is selected from the group consisting of:
(i) a monoclonal antibody comprising (a) a $V_H$-CDR1 comprising the amino acid sequence of TINNYD (SEQ ID NO:14); (b) a $V_H$-CDR2 comprising the amino acid sequence of GYISPPSGATY (SEQ ID NO:15); and (c) a $V_H$-CDR3 comprising the amino acid sequence CAR-MVGMRRGVMDY (SEQ ID NO:16); and
(ii) a monoclonal antibody produced by the hybridoma cell line deposited with ATCC under accession number 6B12.1.7.

5. A monoclonal antibody that specifically binds to human STOP-1 and that comprises the amino acid sequence of the heavy chain of FIG. 31 (amino acids 21-251 of SEQ ID NO:105).

6. The monoclonal antibody according to claim 5, further comprising the amino acid sequence of:
(a) the light chain of FIG. 27 (amino acids 24-239 of SEQ ID NO:92); or (b) the light chain of FIG. 33 (amino acids 20-233 of SEQ ID NO:110).

7. A monoclonal antibody having a biological characteristic of 6B12 produced by the hybridoma cell line deposited on Mar. 28, 2003 as designation 6B12.1.7 in the American Type Culture Collection (ATCC), wherein the biological characteristic is the ability to block STOP-1 binding to cells.

8. A monoclonal antibody that specifically binds to STOP-1, wherein the binding of the antibody to STOP-1 can be inhibited by a second monoclonal antibody selected from the group consisting of F5 encoded by the nucleic acid molecule deposited with ATCC as designation V0350-4-F5 and 6B12 produced by the hybridoma cell line deposited with the ATCC as designation 6B12.1.7.

9. A monoclonal antibody that specifically binds to STOP-1, wherein the antibody comprises the light and heavy chain sequences of an antibody selected from the group consisting of F5 encoded by the nucleic acid molecule deposited with ATCC as designation V0350-4-F5, and 6B12 produced by the hybridoma cell line deposited with the ATCC as designation 6B12.1.7.

10. The antibody according to any one of claims 1-2, 3, 4, 5-6, 7, 8, and 9, wherein the antibody is a chimeric antibody, humanized antibody, antibody fragment, or bispecific antibody.

11. The antibody according to any one of claims 1-2, 3, 4, 5-6, 7, 8, and 9, wherein the antibody is conjugated to an agent selected from the group consisting of a growth inhibitory agent, a cytotoxic agent, a detection agent, an agent that improves the bioavailability of the antibody, and an agent that improves the half-life of the antibody.

12. The antibody according to claim 11, wherein said cytotoxic agent is selected from the group consisting of a toxin, an antibiotic and a radioactive isotope.

13. A composition comprising the monoclonal antibody according to any one of claims 1-2, 3, 4, 5-6, 7, 8, and 9.

14. The composition according to claim 13, further comprising a stromal targeting agent.

15. The composition according to claim 14, wherein the stromal targeting agent is covalently linked to the monoclonal antibody.

16. The composition according to claim 14, wherein the stromal targeting agent recognizes a stromal cell of a tumor.

17. A monoclonal antibody comprising (a) a $V_H$ comprising the CDR1, CDR2, and CDR3 of the $V_H$ of the monoclonal antibody produced by the hybridoma cell line deposited with ATCC under accession number 6B12.1.7 and (b) a $V_L$ comprising the CDR1, CDR2, and CDR3 of the $V_L$ of the monoclonal antibody produced by the hybridoma cell line deposited with ATCC under accession number 6B12.1.7.

18. The monoclonal antibody of claim 4, wherein the monoclonal antibody is produced by the hybridoma cell line deposited with ATCC under accession number 6B12.1.7.

19. A humanized form of the monoclonal antibody of claim 18.

* * * * *

```
                        SEQUENCE LISTING

<160> NUMBER OF SEQ ID NOS: 117

<210> SEQ ID NO 1
<211> LENGTH: 1257
<212> TYPE: DNA
<213> ORGANISM: Homo sapiens
```

<400> SEQUENCE: 1

```
ggagagaggc gcgcgggtga aaggcgcatt gatgcagcct gcggcggcct          50
cggagcgcgg cggagccaga cgctgaccac gttcctctcc tcggtctcct         100
ccgcctccag ctccgcgctg cccggcagcc gggagccatg cgaccccagg         150
gccccgccgc ctccccgcag cggctccgcg gcctcctgct gctcctgctg         200
ctgcagctgc ccgcgccgtc gagcgcctct gagatcccca aggggaagca         250
aaaggcgcag ctccggcaga gggaggtggt ggacctgtat aatggaatgt         300
gcttacaagg gccagcagga gtgcctggtc gagacgggag ccctggggcc         350
aatgttattc cgggtacacc tgggatccca ggtcgggatg gattcaaagg         400
agaaaagggg gaatgtctga gggaaagctt tgaggagtcc tggacaccca         450
actacaagca gtgttcatgg agttcattga attatggcat agatcttggg         500
aaaattgcgg agtgtacatt tacaaagatg cgttcaaata gtgctctaag         550
agttttgttc agtggctcac ttcggctaaa atgcagaaat gcatgctgtc         600
agcgttggta tttcacattc aatggagctg aatgttcagg acctcttccc         650
attgaagcta taatttattt ggaccaagga agccctgaaa tgaattcaac         700
aattaatatt catcgcactt cttctgtgga aggactttgt gaaggaattg         750
gtgctggatt agtggatgtt gctatctggg ttggcacttg ttcagattac         800
ccaaaaggag atgcttctac tggatggaat tcagtttctc gcatcattat         850
tgaagaacta ccaaaataaa tgctttaatt ttcatttgct acctcttttt         900
ttattatgcc ttggaatggt tcacttaaat gacattttaa ataagtttat         950
gtatacatct gaatgaaaag caaagctaaa tatgtttaca gaccaaagtg        1000
tgatttcaca ctgtttttaa atctagcatt attcattttg cttcaatcaa        1050
aagtggtttc aatattttt ttagttggtt agaatacttt cttcatagtc        1100
acattctctc aacctataat ttggaatatt gttgtggtct tttgtttttt        1150
ctcttagtat agcattttta aaaaaatata aaagctacca atctttgtac        1200
aatttgtaaa tgttaagaat ttttttttata tctgttaaat aaaaattatt        1250
tccaaca                                                       1257
```

<210> SEQ ID NO 2
<211> LENGTH: 243
<212> TYPE: PRT
<213> ORGANISM: Homo sapiens

<400> SEQUENCE: 2

```
Met Arg Pro Gln Gly Pro Ala Ala Ser Pro Gln Arg Leu Arg Gly
  1               5                  10                  15
Leu Leu Leu Leu Leu Leu Leu Gln Leu Pro Ala Pro Ser Ser Ala
                 20                  25                  30
Ser Glu Ile Pro Lys Gly Lys Gln Lys Ala Gln Leu Arg Gln Arg
                 35                  40                  45
Glu Val Val Asp Leu Tyr Asn Gly Met Cys Leu Gln Gly Pro Ala
                 50                  55                  60
Gly Val Pro Gly Arg Asp Gly Ser Pro Gly Ala Asn Val Ile Pro
                 65                  70                  75
Gly Thr Pro Gly Ile Pro Gly Arg Asp Gly Phe Lys Gly Glu Lys
```

```
                    80                  85                  90
Gly Glu Cys Leu Arg Glu Ser Phe Glu Ser Trp Thr Pro Asn
                95                  100                 105
Tyr Lys Gln Cys Ser Trp Ser Ser Leu Asn Tyr Gly Ile Asp Leu
                110                 115                 120
Gly Lys Ile Ala Glu Cys Thr Phe Thr Lys Met Arg Ser Asn Ser
                125                 130                 135
Ala Leu Arg Val Leu Phe Ser Gly Ser Leu Arg Leu Lys Cys Arg
                140                 145                 150
Asn Ala Cys Cys Gln Arg Trp Tyr Phe Thr Phe Asn Gly Ala Glu
                155                 160                 165
Cys Ser Gly Pro Leu Pro Ile Glu Ala Ile Ile Tyr Leu Asp Gln
                170                 175                 180
Gly Ser Pro Glu Met Asn Ser Thr Ile Asn Ile His Arg Thr Ser
                185                 190                 195
Ser Val Glu Gly Leu Cys Glu Gly Ile Gly Ala Gly Leu Val Asp
                200                 205                 210
Val Ala Ile Trp Val Gly Thr Cys Ser Asp Tyr Pro Lys Gly Asp
                215                 220                 225
Ala Ser Thr Gly Trp Asn Ser Val Ser Arg Ile Ile Ile Glu Glu
                230                 235                 240
Leu Pro Lys

<210> SEQ ID NO 3
<211> LENGTH: 243
<212> TYPE: PRT
<213> ORGANISM: Homo sapiens

<400> SEQUENCE: 3

Met Arg Pro Gln Gly Pro Ala Ala Ser Pro Gln Arg Leu Arg Gly
  1               5                  10                  15
Leu Leu Leu Leu Leu Leu Leu Gln Leu Pro Ala Pro Ser Ser Ala
                20                  25                  30
Ser Glu Ile Pro Lys Gly Lys Gln Lys Ala Gln Leu Arg Gln Arg
                35                  40                  45
Glu Val Val Asp Leu Tyr Asn Gly Met Cys Leu Gln Gly Pro Ala
                50                  55                  60
Gly Val Pro Gly Arg Asp Gly Ser Pro Gly Ala Asn Gly Ile Pro
                65                  70                  75
Gly Thr Pro Gly Ile Pro Gly Arg Asp Gly Phe Lys Gly Glu Lys
                80                  85                  90
Gly Glu Cys Leu Arg Glu Ser Phe Glu Ser Trp Thr Pro Asn
                95                  100                 105
Tyr Lys Gln Cys Ser Trp Ser Ser Leu Asn Tyr Gly Ile Asp Leu
                110                 115                 120
Gly Lys Ile Ala Glu Cys Thr Phe Thr Lys Met Arg Ser Asn Ser
                125                 130                 135
Ala Leu Arg Val Leu Phe Ser Gly Ser Leu Arg Leu Lys Cys Arg
                140                 145                 150
Asn Ala Cys Cys Gln Arg Trp Tyr Phe Thr Phe Asn Gly Ala Glu
                155                 160                 165
Cys Ser Gly Pro Leu Pro Ile Glu Ala Ile Ile Tyr Leu Asp Gln
                170                 175                 180
Gly Ser Pro Glu Met Asn Ser Thr Ile Asn Ile His Arg Thr Ser
```

```
                    185                 190                 195
Ser Val Glu Gly Leu Cys Glu Gly Ile Gly Ala Gly Leu Val Asp
                200                 205                 210

Val Ala Ile Trp Val Gly Thr Cys Ser Asp Tyr Pro Lys Gly Asp
                215                 220                 225

Ala Ser Thr Gly Trp Asn Ser Val Ser Arg Ile Ile Ile Glu Glu
                230                 235                 240

Leu Pro Lys

<210> SEQ ID NO 4
<211> LENGTH: 245
<212> TYPE: PRT
<213> ORGANISM: Mus musculus

<400> SEQUENCE: 4

Met His Pro Gln Gly Arg Ala Ala Pro Pro Gln Leu Leu Leu Gly
  1               5                  10                  15

Leu Phe Leu Val Leu Leu Leu Leu Gln Leu Ser Ala Pro Ser
                 20                  25                  30

Ser Ala Ser Glu Asn Pro Lys Val Lys Gln Lys Ala Leu Ile Arg
                 35                  40                  45

Gln Arg Glu Val Val Asp Leu Tyr Asn Gly Met Cys Leu Gln Gly
                 50                  55                  60

Pro Ala Gly Val Pro Gly Arg Asp Gly Ser Pro Gly Ala Asn Gly
                 65                  70                  75

Ile Pro Gly Thr Pro Gly Ile Pro Gly Arg Asp Gly Phe Lys Gly
                 80                  85                  90

Glu Lys Gly Glu Cys Leu Arg Glu Ser Phe Glu Glu Ser Trp Thr
                 95                 100                 105

Pro Asn Tyr Lys Gln Cys Ser Trp Ser Ser Leu Asn Tyr Gly Ile
                110                 115                 120

Asp Leu Gly Lys Ile Ala Glu Cys Thr Phe Thr Lys Met Arg Ser
                125                 130                 135

Asn Ser Ala Leu Arg Val Leu Phe Ser Gly Ser Leu Arg Leu Lys
                140                 145                 150

Cys Arg Asn Ala Cys Cys Gln Arg Trp Tyr Phe Thr Phe Asn Gly
                155                 160                 165

Ala Glu Cys Ser Gly Pro Leu Pro Ile Glu Ala Ile Ile Tyr Leu
                170                 175                 180

Asp Gln Gly Ser Pro Glu Leu Asn Ser Thr Ile Asn Ile His Arg
                185                 190                 195

Thr Ser Ser Val Glu Gly Leu Cys Glu Gly Ile Gly Ala Gly Leu
                200                 205                 210

Val Asp Val Ala Ile Trp Val Gly Thr Cys Ser Asp Tyr Pro Lys
                215                 220                 225

Gly Asp Ala Ser Thr Gly Trp Asn Ser Val Ser Arg Ile Ile Ile
                230                 235                 240

Glu Glu Leu Pro Lys
                245

<210> SEQ ID NO 5
<211> LENGTH: 229
<212> TYPE: PRT
<213> ORGANISM: Oryzias latipes

<400> SEQUENCE: 5
```

```
Met Thr Pro Leu Ser Pro Arg Leu Leu Ile Leu Leu Cys Leu Ala
  1               5                  10                  15

Leu Pro Leu His Gly Gln Glu Lys Gly Arg Ser Arg Gly Tyr Arg
             20                  25                  30

Lys Asp Pro Asp Ala Asp Lys Phe Gly Ser Cys Leu Gln Gly Pro
             35                  40                  45

Ala Gly Thr Pro Gly Arg Asp Gly Asn Pro Gly Ala Asn Gly Ile
             50                  55                  60

Pro Gly Thr Pro Gly Ile Pro Gly Arg Asp Gly Leu Lys Gly Glu
             65                  70                  75

Lys Gly Glu Cys Val Ser Glu Val Phe Glu Glu Pro Trp Lys Pro
             80                  85                  90

Asn Tyr Lys Gln Cys Ala Trp Asn Ser Leu Asn Tyr Gly Ile Asp
             95                 100                 105

Leu Gly Lys Ile Ala Asp Cys Thr Phe Thr Lys Leu Arg Ser Glu
            110                 115                 120

Ser Ala Leu Arg Val Leu Phe Thr Gly Ser Leu Arg Leu Lys Cys
            125                 130                 135

Lys Glu Ala Cys Cys Gln Arg Trp Tyr Phe Thr Phe Asp Gly Ala
            140                 145                 150

Glu Cys Thr Gly Pro Leu Pro Val Glu Ser Ile Ile Tyr Leu Asn
            155                 160                 165

Gln Gly Ser Pro Glu Leu Asn Ser Thr Ile Asn Ile His Arg Thr
            170                 175                 180

Ser Ser Val Glu Gly Leu Cys Glu Gly Ile Lys Ala Gly Leu Val
            185                 190                 195

Asp Val Ala Leu Trp Val Gly Thr Cys Ala Asp Tyr Pro Arg Gly
            200                 205                 210

Asp Ala Ser Thr Gly Trp Asn Ser Val Ser Arg Ile Ile Ile Glu
            215                 220                 225

Glu Leu Pro Lys

<210> SEQ ID NO 6
<211> LENGTH: 231
<212> TYPE: PRT
<213> ORGANISM: Danio rerio

<400> SEQUENCE: 6

Met Gly Thr Lys Leu Thr Gln Leu Leu Ile Cys Phe Trp Ile Ser
  1               5                  10                  15

Leu Pro Phe Cys Val Thr Gln Lys Ala Lys Glu Arg Ile Pro Arg
             20                  25                  30

Gln Arg Asp Ala Glu Phe Thr Asp Lys Tyr Gln Ala Cys Val Gln
             35                  40                  45

Gly Val Pro Gly Val Gln Gly Arg Asp Gly Asn Pro Gly Ile Asn
             50                  55                  60

Gly Ile Pro Gly Thr Pro Gly Ile Pro Gly Arg Asp Gly Leu Lys
             65                  70                  75

Gly Glu Lys Gly Glu Cys Val Ser Glu Arg Phe Glu Glu Pro Trp
             80                  85                  90

Lys Pro Asn Phe Lys Gln Cys Ala Trp Asn Ser Leu Asn Tyr Gly
             95                 100                 105

Ile Asp Leu Gly Lys Ile Ala Glu Cys Thr Phe Thr Lys Gln Arg
            110                 115                 120
```

```
Ser Asp Ser Ala Leu Arg Val Leu Phe Ser Gly Ser Leu Arg Leu
            125                 130                 135

Lys Cys Lys Thr Ala Cys Cys Gln Arg Trp Tyr Phe Thr Phe Asn
            140                 145                 150

Gly Ala Glu Cys Thr Gly Pro Leu Pro Ile Glu Ser Ile Val Tyr
            155                 160                 165

Leu Asp Gln Gly Ser Pro Glu Leu Asn Ser Thr Ile Asn Ile His
            170                 175                 180

Arg Thr Ser Thr Val Glu Gly Leu Cys Glu Gly Ile His Ala Gly
            185                 190                 195

Leu Val Asp Val Gly Ile Trp Val Gly Thr Cys Ala Asp Tyr Pro
            200                 205                 210

Arg Gly Asp Ala Ser Thr Gly Trp Asn Ser Val Ser Arg Val Ile
            215                 220                 225

Ile Glu Glu Leu Pro Lys
            230

<210> SEQ ID NO 7
<211> LENGTH: 201
<212> TYPE: PRT
<213> ORGANISM: Gallus gallus

<400> SEQUENCE: 7

Arg Pro Arg Glu Val Leu Glu Ala Tyr Asn Gly Val Cys Leu Gln
  1               5                  10                  15

Gly Pro Ser Gly Val Pro Gly Arg Asp Gly Asn Pro Gly Thr Asn
             20                  25                  30

Gly Ile Pro Gly Thr Pro Gly Ile Pro Gly Arg Asp Gly Pro Lys
             35                  40                  45

Gly Glu Lys Gly Glu Cys Leu Arg Glu Ser Ile Glu Glu Ser Trp
             50                  55                  60

Thr Pro Asn Phe Lys Gln Cys Ser Trp Ser Ala Leu Asn Tyr Gly
             65                  70                  75

Ile Asp Leu Gly Lys Ile Ala Glu Cys Thr Phe Thr Lys Met Arg
             80                  85                  90

Ser Asn Ser Ala Leu Arg Val Leu Phe Ser Gly Ser Leu Arg Leu
             95                 100                 105

Lys Cys Arg Ser Ala Cys Cys Gln Arg Trp Tyr Phe Thr Phe Asn
            110                 115                 120

Gly Ala Glu Cys Ala Gly Pro Leu Pro Ile Glu Ala Ile Ile Tyr
            125                 130                 135

Leu Asp Gln Gly Ser Pro Glu Leu Asn Ser Thr Ile Asn Ile His
            140                 145                 150

Arg Thr Ser Ser Val Glu Gly Leu Cys Glu Gly Ile Asn Ala Gly
            155                 160                 165

Leu Val Asp Ile Ala Ile Trp Val Gly Thr Cys Ser Asp Tyr Pro
            170                 175                 180

Arg Gly Asp Ala Ser Thr Gly Trp Asn Ser Val Ser Arg Ile Ile
            185                 190                 195

Ile Glu Glu Leu Pro Lys
            200

<210> SEQ ID NO 8
<211> LENGTH: 6
<212> TYPE: PRT
```

```
<213> ORGANISM: Artificial sequence
<220> FEATURE:
<223> OTHER INFORMATION: sequence is synthesized

<400> SEQUENCE: 8

Thr Ile Ser Gly Ser Asp
                5

<210> SEQ ID NO 9
<211> LENGTH: 11
<212> TYPE: PRT
<213> ORGANISM: Artificial sequence
<220> FEATURE:
<223> OTHER INFORMATION: sequence is synthesized

<400> SEQUENCE: 9

Gly Arg Ile Ser Pro Tyr Gly Gly Asn Thr Asn
                5                   10

<210> SEQ ID NO 10
<211> LENGTH: 13
<212> TYPE: PRT
<213> ORGANISM: Artificial sequence
<220> FEATURE:
<223> OTHER INFORMATION: sequence is synthesized

<400> SEQUENCE: 10

Cys Ala Arg Val Gly Gly Leu Lys Leu Leu Phe Asp Tyr
                5                   10

<210> SEQ ID NO 11
<211> LENGTH: 6
<212> TYPE: PRT
<213> ORGANISM: Artificial sequence
<220> FEATURE:
<223> OTHER INFORMATION: sequence is synthesized

<400> SEQUENCE: 11

Thr Ile Thr Asn Ser Asp
                5

<210> SEQ ID NO 12
<211> LENGTH: 11
<212> TYPE: PRT
<213> ORGANISM: Artificial sequence
<220> FEATURE:
<223> OTHER INFORMATION: sequence is synthesized

<400> SEQUENCE: 12

Ala Thr Ile Tyr Pro Tyr Gly Gly Tyr Thr Tyr
                5                   10

<210> SEQ ID NO 13
<211> LENGTH: 14
<212> TYPE: PRT
<213> ORGANISM: Artificial sequence
<220> FEATURE:
<223> OTHER INFORMATION: sequence is synthesized

<400> SEQUENCE: 13

Cys Ala Arg Gly Gly Gly Met Asp Gly Tyr Val Met Asp Tyr
                5                   10

<210> SEQ ID NO 14
<211> LENGTH: 6
<212> TYPE: PRT
<213> ORGANISM: Artificial sequence
```

```
<220> FEATURE:
<223> OTHER INFORMATION: sequence is synthesized

<400> SEQUENCE: 14

Thr Ile Asn Asn Tyr Asp
                    5

<210> SEQ ID NO 15
<211> LENGTH: 11
<212> TYPE: PRT
<213> ORGANISM: Artificial sequence
<220> FEATURE:
<223> OTHER INFORMATION: sequence is synthesized

<400> SEQUENCE: 15

Gly Tyr Ile Ser Pro Ser Gly Ala Thr Tyr
                    5                   10

<210> SEQ ID NO 16
<211> LENGTH: 14
<212> TYPE: PRT
<213> ORGANISM: Artificial sequence
<220> FEATURE:
<223> OTHER INFORMATION: sequence is synthesized

<400> SEQUENCE: 16

Cys Ala Arg Met Val Gly Met Arg Arg Gly Val Met Asp Tyr
                    5                   10

<210> SEQ ID NO 17
<211> LENGTH: 6
<212> TYPE: PRT
<213> ORGANISM: Artificial sequence
<220> FEATURE:
<223> OTHER INFORMATION: sequence is synthesized

<400> SEQUENCE: 17

Thr Ile Ser Gly Ser Trp
                    5

<210> SEQ ID NO 18
<211> LENGTH: 11
<212> TYPE: PRT
<213> ORGANISM: Artificial sequence
<220> FEATURE:
<223> OTHER INFORMATION: sequence is synthesized

<400> SEQUENCE: 18

Ala Trp Ile Ala Pro Tyr Ser Gly Ala Thr Asp
                    5                   10

<210> SEQ ID NO 19
<211> LENGTH: 13
<212> TYPE: PRT
<213> ORGANISM: Artificial sequence
<220> FEATURE:
<223> OTHER INFORMATION: sequence is synthesized

<400> SEQUENCE: 19

Cys Ala Arg Glu Gly Gly Leu Tyr Trp Val Phe Asp Tyr
                    5                   10

<210> SEQ ID NO 20
<211> LENGTH: 6
<212> TYPE: PRT
<213> ORGANISM: Artificial sequence
<220> FEATURE:
```

-continued

<223> OTHER INFORMATION: sequence is synthesized

<400> SEQUENCE: 20

Thr Ile Ser Asn Tyr Gly
                5

<210> SEQ ID NO 21
<211> LENGTH: 11
<212> TYPE: PRT
<213> ORGANISM: Artificial sequence
<220> FEATURE:
<223> OTHER INFORMATION: sequence is synthesized

<400> SEQUENCE: 21

Gly Arg Ile Ser Pro Ser Asn Gly Ser Thr Tyr
                5                   10

<210> SEQ ID NO 22
<211> LENGTH: 10
<212> TYPE: PRT
<213> ORGANISM: Artificial sequence
<220> FEATURE:
<223> OTHER INFORMATION: sequence is synthesized

<400> SEQUENCE: 22

Cys Ala Lys Cys Ser Val Arg Phe Ala Tyr
                5                   10

<210> SEQ ID NO 23
<211> LENGTH: 30
<212> TYPE: DNA
<213> ORGANISM: Artificial sequence
<220> FEATURE:
<223> OTHER INFORMATION: sequence is synthesized

<400> SEQUENCE: 23
catccagtag aagcatctcc ttttgggtaa                                30

<210> SEQ ID NO 24
<211> LENGTH: 19
<212> TYPE: DNA
<213> ORGANISM: Artificial sequence
<220> FEATURE:
<223> OTHER INFORMATION: sequence is synthesized

<400> SEQUENCE: 24
gggttggcac ttgttcaga                                            19

<210> SEQ ID NO 25
<211> LENGTH: 24
<212> TYPE: DNA
<213> ORGANISM: Artificial sequence
<220> FEATURE:
<223> OTHER INFORMATION: sequence is synthesized

<400> SEQUENCE: 25
caataatgat gcgagaaact gaat                                      24

<210> SEQ ID NO 26
<211> LENGTH: 266
<212> TYPE: DNA
<213> ORGANISM: Artificial sequence
<220> FEATURE:
<223> OTHER INFORMATION: sequence is synthesized

<400> SEQUENCE: 26

```
gggagccatg cgaccccagg gccccgccgc ctccccgcag cggctccgcg        50
gcctcctgct gctcctgctg ctgcagctgc ccgcgccgtc gagcgcctct       100
gagatcccca aggggaagca aaaggcgcag ctccggcaga gggaggtggt       150
ggacctgtat aatggaatgt gcttacaagg gccagcagga gtgcctggtc       200
gagacgggag ccctggggcc aatgttattc cgggtacacc tgggatccca       250
ggtcgggatg gattca                                            266
```

<210> SEQ ID NO 27
<211> LENGTH: 44
<212> TYPE: DNA
<213> ORGANISM: Artificial sequence
<220> FEATURE:
<223> OTHER INFORMATION: sequence is synthesized

<400> SEQUENCE: 27

```
gatcgcggcc gcacaccacc atcaccatca ccatcactaa  gtga            44
```

<210> SEQ ID NO 28
<211> LENGTH: 44
<212> TYPE: DNA
<213> ORGANISM: Artificial sequence
<220> FEATURE:
<223> OTHER INFORMATION: sequence is synthesized

<400> SEQUENCE: 28

```
ggcctcactt agtgatggtg atggtgatgg tggtgtgcgg  ccgc            44
```

<210> SEQ ID NO 29
<211> LENGTH: 41
<212> TYPE: DNA
<213> ORGANISM: Artificial sequence
<220> FEATURE:
<223> OTHER INFORMATION: sequence is synthesized

<400> SEQUENCE: 29

```
ctgcgctagc accatgatgg gtactaaact gactcaactt  t               41
```

<210> SEQ ID NO 30
<211> LENGTH: 35
<212> TYPE: DNA
<213> ORGANISM: Artificial sequence
<220> FEATURE:
<223> OTHER INFORMATION: sequence is synthesized

<400> SEQUENCE: 30

```
ggaagcggcc gcttttggaa gctcttcaat  gatca                      35
```

<210> SEQ ID NO 31
<211> LENGTH: 55
<212> TYPE: DNA
<213> ORGANISM: Artificial sequence
<220> FEATURE:
<223> OTHER INFORMATION: sequence is synthesized

<400> SEQUENCE: 31

```
gaagctagca ccatgcaccc ccaaggccgc gcggcccccc cgcagctgct        50
gctcg                                                        55
```

<210> SEQ ID NO 32
<211> LENGTH: 38
<212> TYPE: DNA
<213> ORGANISM: Artificial sequence

```
<220> FEATURE:
<223> OTHER INFORMATION: sequence is synthesized

<400> SEQUENCE: 32
gaagcggccg cttatttcgg tagttcttca  atgatgat                              38

<210> SEQ ID NO 33
<211> LENGTH: 37
<212> TYPE: DNA
<213> ORGANISM: Artificial sequence
<220> FEATURE:
<223> OTHER INFORMATION: sequence is synthesized

<400> SEQUENCE: 33
ccagctagca ccatgcgacc ccagggcccc  gccgcct                               37

<210> SEQ ID NO 34
<211> LENGTH: 38
<212> TYPE: DNA
<213> ORGANISM: Artificial sequence
<220> FEATURE:
<223> OTHER INFORMATION: sequence is synthesized

<400> SEQUENCE: 34
caagcggccg cttattttgg tagttcttca  ataatgat                              38

<210> SEQ ID NO 35
<211> LENGTH: 35
<212> TYPE: DNA
<213> ORGANISM: Artificial sequence
<220> FEATURE:
<223> OTHER INFORMATION: sequence is synthesized

<400> SEQUENCE: 35
caagcggccg cttttggtag ttcttcaata  atgat                                 35

<210> SEQ ID NO 36
<211> LENGTH: 43
<212> TYPE: DNA
<213> ORGANISM: Artificial sequence
<220> FEATURE:
<223> OTHER INFORMATION: sequence is synthesized

<400> SEQUENCE: 36
tcaaagcttt ccctcagcat tccattatac aggtccacca  cct                       43

<210> SEQ ID NO 37
<211> LENGTH: 42
<212> TYPE: DNA
<213> ORGANISM: Artificial sequence
<220> FEATURE:
<223> OTHER INFORMATION: sequence is synthesized

<400> SEQUENCE: 37
ctcaaagctt tccctcagat acaggtccac cacctccctc  tg                        42

<210> SEQ ID NO 38
<211> LENGTH: 32
<212> TYPE: DNA
<213> ORGANISM: Artificial sequence
<220> FEATURE:
<223> OTHER INFORMATION: sequence is synthesized

<400> SEQUENCE: 38
ggggagctca gaggcgctcg acggcgcggg  ca                                   32
```

<210> SEQ ID NO 39
<211> LENGTH: 30
<212> TYPE: DNA
<213> ORGANISM: Artificial sequence
<220> FEATURE:
<223> OTHER INFORMATION: sequence is synthesized

<400> SEQUENCE: 39
acaggtcgac cacctccctc tgccggagct                              30

<210> SEQ ID NO 40
<211> LENGTH: 34
<212> TYPE: DNA
<213> ORGANISM: Artificial sequence
<220> FEATURE:
<223> OTHER INFORMATION: sequence is synthesized

<400> SEQUENCE: 40
gaagagctca gggaaagctt tgaggagtcc tgga                         34

<210> SEQ ID NO 41
<211> LENGTH: 45
<212> TYPE: DNA
<213> ORGANISM: Artificial sequence
<220> FEATURE:
<223> OTHER INFORMATION: sequence is synthesized

<400> SEQUENCE: 41
gtggtcgacc tgtataatgc aatgtgctta caagggccag cagga             45

<210> SEQ ID NO 42
<211> LENGTH: 36
<212> TYPE: DNA
<213> ORGANISM: Artificial sequence
<220> FEATURE:
<223> OTHER INFORMATION: sequence is synthesized

<400> SEQUENCE: 42
aattgtcgac gccatttcag ggcttccttg gtccaa                       36

<210> SEQ ID NO 43
<211> LENGTH: 30
<212> TYPE: DNA
<213> ORGANISM: Artificial sequence
<220> FEATURE:
<223> OTHER INFORMATION: sequence is synthesized

<400> SEQUENCE: 43
tggcgtcgac aattaatatt catcgcactt                              30

<210> SEQ ID NO 44
<211> LENGTH: 51
<212> TYPE: DNA
<213> ORGANISM: Artificial sequence
<220> FEATURE:
<223> OTHER INFORMATION: sequence is synthesized

<400> SEQUENCE: 44
gtggtcgacc tgtataatgg aatggcctta caagggccag caggagtgcc        50
t                                                             51

<210> SEQ ID NO 45
<211> LENGTH: 43
<212> TYPE: DNA
<213> ORGANISM: Artificial sequence

```
<220> FEATURE:
<223> OTHER INFORMATION: sequence is synthesized

<400> SEQUENCE: 45
ctcaaagctt tccctcagag cttcccccatt ttctcctttg  aat                    43

<210> SEQ ID NO 46
<211> LENGTH: 28
<212> TYPE: DNA
<213> ORGANISM: Artificial sequence
<220> FEATURE:
<223> OTHER INFORMATION: sequence is synthesized

<400> SEQUENCE: 46
ccatgaggcc tgcttgtagt  tgggtgtc                                       28

<210> SEQ ID NO 47
<211> LENGTH: 29
<212> TYPE: DNA
<213> ORGANISM: Artificial sequence
<220> FEATURE:
<223> OTHER INFORMATION: sequence is synthesized

<400> SEQUENCE: 47
agcaggcctc atggagttca  ttgaattat                                      29

<210> SEQ ID NO 48
<211> LENGTH: 28
<212> TYPE: DNA
<213> ORGANISM: Artificial sequence
<220> FEATURE:
<223> OTHER INFORMATION: sequence is synthesized

<400> SEQUENCE: 48
taaacgttgc ctccgcaatt  ttcccaag                                       28

<210> SEQ ID NO 49
<211> LENGTH: 27
<212> TYPE: DNA
<213> ORGANISM: Artificial sequence
<220> FEATURE:
<223> OTHER INFORMATION: sequence is synthesized

<400> SEQUENCE: 49
ggcaacgttt acaaagatgc  gttcaaa                                        27

<210> SEQ ID NO 50
<211> LENGTH: 34
<212> TYPE: DNA
<213> ORGANISM: Artificial sequence
<220> FEATURE:
<223> OTHER INFORMATION: sequence is synthesized

<400> SEQUENCE: 50
gcatgcattt ctggctttta gccgaagtga  gcca                                34

<210> SEQ ID NO 51
<211> LENGTH: 26
<212> TYPE: DNA
<213> ORGANISM: Artificial sequence
<220> FEATURE:
<223> OTHER INFORMATION: sequence is synthesized

<400> SEQUENCE: 51
ctggcatgct gcatttctgc  atttta                                         26
```

<210> SEQ ID NO 52
<211> LENGTH: 32
<212> TYPE: DNA
<213> ORGANISM: Artificial sequence
<220> FEATURE:
<223> OTHER INFORMATION: sequence is synthesized

<400> SEQUENCE: 52
gcagcatgcc agcgttggta tttcacattc aa                      32

<210> SEQ ID NO 53
<211> LENGTH: 30
<212> TYPE: DNA
<213> ORGANISM: Artificial sequence
<220> FEATURE:
<223> OTHER INFORMATION: sequence is synthesized

<400> SEQUENCE: 53
aatgcatgcg ctcagcgttg gtatttcaca                         30

<210> SEQ ID NO 54
<211> LENGTH: 30
<212> TYPE: DNA
<213> ORGANISM: Artificial sequence
<220> FEATURE:
<223> OTHER INFORMATION: sequence is synthesized

<400> SEQUENCE: 54
cctgaggcct cagctccatt gaatgtgaaa                         30

<210> SEQ ID NO 55
<211> LENGTH: 29
<212> TYPE: DNA
<213> ORGANISM: Artificial sequence
<220> FEATURE:
<223> OTHER INFORMATION: sequence is synthesized

<400> SEQUENCE: 55
ctgaggcctc aggacctctt cccattgaa                          29

<210> SEQ ID NO 56
<211> LENGTH: 50
<212> TYPE: DNA
<213> ORGANISM: Artificial sequence
<220> FEATURE:
<223> OTHER INFORMATION: sequence is synthesized

<400> SEQUENCE: 56
tccggcgcca attccttcag caagtccttc cacagaagaa gtgcgatgaa   50

<210> SEQ ID NO 57
<211> LENGTH: 31
<212> TYPE: DNA
<213> ORGANISM: Artificial sequence
<220> FEATURE:
<223> OTHER INFORMATION: sequence is synthesized

<400> SEQUENCE: 57
attggcgccg gattagtgga tgttgctatc t                       31

<210> SEQ ID NO 58
<211> LENGTH: 30
<212> TYPE: DNA
<213> ORGANISM: Artificial sequence
<220> FEATURE:
<223> OTHER INFORMATION: sequence is synthesized

```
<400> SEQUENCE: 58
tgaagcggta ccaacccaga tagcaacatc                                  30

<210> SEQ ID NO 59
<211> LENGTH: 32
<212> TYPE: DNA
<213> ORGANISM: Artificial sequence
<220> FEATURE:
<223> OTHER INFORMATION: sequence is synthesized

<400> SEQUENCE: 59
ggcggtaccg cttcagatta cccaaaagga ga                               32

<210> SEQ ID NO 60
<211> LENGTH: 42
<212> TYPE: DNA
<213> ORGANISM: Artificial sequence
<220> FEATURE:
<223> OTHER INFORMATION: sequence is synthesized

<400> SEQUENCE: 60
gtggtcgacc tgtatgctgg aatgtgctta caagggccag ca                    42

<210> SEQ ID NO 61
<211> LENGTH: 47
<212> TYPE: DNA
<213> ORGANISM: Artificial sequence
<220> FEATURE:
<223> OTHER INFORMATION: sequence is synthesized

<400> SEQUENCE: 61
gtggtcgacc tgtataatgg agcgtgctta caagggccag caggagt               47

<210> SEQ ID NO 62
<211> LENGTH: 30
<212> TYPE: DNA
<213> ORGANISM: Artificial sequence
<220> FEATURE:
<223> OTHER INFORMATION: sequence is synthesized

<400> SEQUENCE: 62
tcggccggcc actcctgctg gcccttgtaa                                  30

<210> SEQ ID NO 63
<211> LENGTH: 46
<212> TYPE: DNA
<213> ORGANISM: Artificial sequence
<220> FEATURE:
<223> OTHER INFORMATION: sequence is synthesized

<400> SEQUENCE: 63
gtggccggcc gagacgggag cgctggggcc aatggcattc cgggta                46

<210> SEQ ID NO 64
<211> LENGTH: 27
<212> TYPE: DNA
<213> ORGANISM: Artificial sequence
<220> FEATURE:
<223> OTHER INFORMATION: sequence is synthesized

<400> SEQUENCE: 64
tgtgccggca atgccattgg ccccagg                                     27

<210> SEQ ID NO 65
```

<211> LENGTH: 50
<212> TYPE: DNA
<213> ORGANISM: Artificial sequence
<220> FEATURE:
<223> OTHER INFORMATION: sequence is synthesized

<400> SEQUENCE: 65
attgccggca cagctgggat cgcaggtcgg gatggattca aaggagaaaa          50

<210> SEQ ID NO 66
<211> LENGTH: 30
<212> TYPE: DNA
<213> ORGANISM: Artificial sequence
<220> FEATURE:
<223> OTHER INFORMATION: sequence is synthesized

<400> SEQUENCE: 66
ttcgccggcg aatccatccc gacctgggat          30

<210> SEQ ID NO 67
<211> LENGTH: 39
<212> TYPE: DNA
<213> ORGANISM: Artificial sequence
<220> FEATURE:
<223> OTHER INFORMATION: sequence is synthesized

<400> SEQUENCE: 67
ttcgccggcg aagcggggga atgtctgagg gaaagcttt          39

<210> SEQ ID NO 68
<211> LENGTH: 32
<212> TYPE: DNA
<213> ORGANISM: Artificial sequence
<220> FEATURE:
<223> OTHER INFORMATION: sequence is synthesized

<400> SEQUENCE: 68
gaagcggccg ctttcggtag ttcttcaatg at          32

<210> SEQ ID NO 69
<211> LENGTH: 35
<212> TYPE: DNA
<213> ORGANISM: Artificial sequence
<220> FEATURE:
<223> OTHER INFORMATION: sequence is synthesized

<400> SEQUENCE: 69
gaagcggccg caagacttgg gtaaaaatcg tattt          35

<210> SEQ ID NO 70
<211> LENGTH: 41
<212> TYPE: DNA
<213> ORGANISM: Artificial sequence
<220> FEATURE:
<223> OTHER INFORMATION: sequence is synthesized

<400> SEQUENCE: 70
gaaagatctc tagtctgaca aagagaaaca ctgctttagg a          41

<210> SEQ ID NO 71
<211> LENGTH: 25
<212> TYPE: DNA
<213> ORGANISM: Artificial sequence
<220> FEATURE:
<223> OTHER INFORMATION: sequence is synthesized

<400> SEQUENCE: 71

```
ggatcgtcgg ttttgtacaa tatgt                                    25

<210> SEQ ID NO 72
<211> LENGTH: 30
<212> TYPE: DNA
<213> ORGANISM: Artificial sequence
<220> FEATURE:
<223> OTHER INFORMATION: sequence is synthesized

<400> SEQUENCE: 72
ggggatctca gacgcaaagg cagaatgcgc                               30

<210> SEQ ID NO 73
<211> LENGTH: 30
<212> TYPE: DNA
<213> ORGANISM: Artificial sequence
<220> FEATURE:
<223> OTHER INFORMATION: sequence is synthesized

<400> SEQUENCE: 73
tctgcctttg cgtctgagat ccccaagggg                               30

<210> SEQ ID NO 74
<211> LENGTH: 39
<212> TYPE: DNA
<213> ORGANISM: Artificial sequence
<220> FEATURE:
<223> OTHER INFORMATION: sequence is synthesized

<400> SEQUENCE: 74
ccgttctgca gttaatgatg atgatgatga tgatgatgg                     39

<210> SEQ ID NO 75
<211> LENGTH: 30
<212> TYPE: DNA
<213> ORGANISM: Artificial sequence
<220> FEATURE:
<223> OTHER INFORMATION: sequence is synthesized

<400> SEQUENCE: 75
gctttccctc agcgcaaagg cagaatgcgc                               30

<210> SEQ ID NO 76
<211> LENGTH: 31
<212> TYPE: DNA
<213> ORGANISM: Artificial sequence
<220> FEATURE:
<223> OTHER INFORMATION: sequence is synthesized

<400> SEQUENCE: 76
tctgcctttg cgctgaggga aagctttgag g                             31

<210> SEQ ID NO 77
<211> LENGTH: 32
<212> TYPE: DNA
<213> ORGANISM: Artificial sequence
<220> FEATURE:
<223> OTHER INFORMATION: sequence is synthesized

<400> SEQUENCE: 77
ccgggatcct taatgatgat gatgatgatg at                            32

<210> SEQ ID NO 78
<211> LENGTH: 31
<212> TYPE: DNA
```

```
<213> ORGANISM: Artificial sequence
<220> FEATURE:
<223> OTHER INFORMATION: sequence is synthesized

<400> SEQUENCE: 78
attccccctt ttccgcaaag gcagaatgcg c                                31

<210> SEQ ID NO 79
<211> LENGTH: 32
<212> TYPE: DNA
<213> ORGANISM: Artificial sequence
<220> FEATURE:
<223> OTHER INFORMATION: sequence is synthesized

<400> SEQUENCE: 79
tctgcctttg cggaaaaggg ggaatgtctg ag                               32

<210> SEQ ID NO 80
<211> LENGTH: 23
<212> TYPE: DNA
<213> ORGANISM: Artificial sequence
<220> FEATURE:
<223> OTHER INFORMATION: sequence is synthesized

<400> SEQUENCE: 80
atcgccaatg ccaactcccg tca                                         23

<210> SEQ ID NO 81
<211> LENGTH: 23
<212> TYPE: DNA
<213> ORGANISM: Artificial sequence
<220> FEATURE:
<223> OTHER INFORMATION: sequence is synthesized

<400> SEQUENCE: 81
gcttgcgtgc ttccttggtc tta                                         23

<210> SEQ ID NO 82
<211> LENGTH: 28
<212> TYPE: DNA
<213> ORGANISM: Artificial sequence
<220> FEATURE:
<223> OTHER INFORMATION: sequence is synthesized

<400> SEQUENCE: 82
tgctgctgca gctgcccgcg ccgtcgag                                    28

<210> SEQ ID NO 83
<211> LENGTH: 28
<212> TYPE: DNA
<213> ORGANISM: Artificial sequence
<220> FEATURE:
<223> OTHER INFORMATION: sequence is synthesized

<400> SEQUENCE: 83
tccagtagaa gcatctcctt ttgggtaa                                    28

<210> SEQ ID NO 84
<211> LENGTH: 35
<212> TYPE: PRT
<213> ORGANISM: Saccharomyces cerevisiae

<400> SEQUENCE: 84

Gly Arg Met Lys Gln Leu Glu Asp Lys Val Glu Glu Leu Leu Ser
 1               5                  10                  15
```

Lys Asn Tyr His Leu Glu Asn Glu Val Ala Arg Leu Lys Lys Leu
                20                  25                  30

Val Gly Glu Arg Gly
                35

<210> SEQ ID NO 85
<211> LENGTH: 28
<212> TYPE: DNA
<213> ORGANISM: Artificial sequence
<220> FEATURE:
<223> OTHER INFORMATION: sequence is synthesized

<400> SEQUENCE: 85
gctcggttgc cgccgggcgt ttttatg                                          28

<210> SEQ ID NO 86
<211> LENGTH: 255
<212> TYPE: PRT
<213> ORGANISM: Artificial sequence
<220> FEATURE:
<223> OTHER INFORMATION: sequence is synthesized

<400> SEQUENCE: 86

Met Lys Lys Asn Ile Ala Phe Leu Leu Ala Ser Met Phe Val Phe
  1               5                  10                  15

Ser Ile Ala Thr Asn Ala Tyr Ala Asp Ile Gln Met Thr Gln Ser
                 20                  25                  30

Pro Ser Ser Leu Ser Ala Ser Val Gly Asp Arg Val Thr Ile Thr
                 35                  40                  45

Cys Arg Ala Ser Gln Asp Val Ser Thr Ala Val Ala Trp Tyr Gln
                 50                  55                  60

Gln Lys Pro Gly Lys Ala Pro Lys Leu Leu Ile Tyr Ser Ala Ser
                 65                  70                  75

Phe Leu Tyr Ser Gly Val Pro Ser Arg Phe Ser Gly Ser Gly Ser
                 80                  85                  90

Gly Thr Asp Phe Thr Leu Thr Ile Ser Ser Leu Gln Pro Glu Asp
                 95                 100                 105

Phe Ala Thr Tyr Tyr Cys Gln Gln Ser Tyr Thr Thr Pro Pro Thr
                110                 115                 120

Phe Gly Gln Gly Thr Lys Val Glu Ile Lys Arg Thr Val Ala Ala
                125                 130                 135

Pro Ser Val Phe Ile Phe Pro Pro Ser Asp Glu Gln Leu Lys Ser
                140                 145                 150

Gly Thr Ala Ser Val Val Cys Leu Leu Asn Asn Phe Tyr Pro Arg
                155                 160                 165

Glu Ala Lys Val Gln Trp Lys Val Asp Asn Ala Leu Gln Ser Gly
                170                 175                 180

Asn Ser Gln Glu Ser Val Thr Glu Gln Asp Ser Lys Asp Ser Thr
                185                 190                 195

Tyr Ser Leu Ser Ser Thr Leu Thr Leu Ser Lys Ala Asp Tyr Glu
                200                 205                 210

Lys His Lys Val Tyr Ala Cys Glu Val Thr His Gln Gly Leu Ser
                215                 220                 225

Ser Pro Val Thr Lys Ser Phe Asn Arg Gly Glu Cys Gly Ala Ser
                230                 235                 240

Ser Gly Met Ala Asp Pro Asn Arg Phe Arg Gly Lys Asp Leu Ala
                245                 250                 255

-continued

```
<210> SEQ ID NO 87
<211> LENGTH: 409
<212> TYPE: PRT
<213> ORGANISM: Artificial sequence
<220> FEATURE:
<223> OTHER INFORMATION: sequence is synthesized

<400> SEQUENCE: 87
```

Met Lys Lys Asn Ile Ala Phe Leu Leu Ala Ser Met Phe Val Phe
 1               5                  10                  15

Ser Ile Ala Thr Asn Ala Tyr Ala Glu Val Gln Leu Val Glu Ser
             20                  25                  30

Gly Gly Gly Leu Val Gln Pro Gly Gly Ser Leu Arg Leu Ser Cys
             35                  40                  45

Ala Ala Ser Gly Phe Asn Ile Lys Asp Thr Tyr Ile His Trp Val
             50                  55                  60

Arg Gln Ala Pro Gly Lys Gly Leu Glu Trp Val Ala Arg Ile Tyr
             65                  70                  75

Pro Thr Asn Gly Tyr Thr Arg Tyr Ala Asp Ser Val Lys Gly Arg
             80                  85                  90

Phe Thr Ile Ser Ala Asp Thr Ser Lys Asn Thr Ala Tyr Leu Gln
             95                 100                 105

Met Asn Ser Leu Arg Ala Glu Asp Thr Ala Val Tyr Tyr Cys Ser
            110                 115                 120

Arg Trp Gly Gly Asp Gly Phe Tyr Ala Met Asp Tyr Trp Gly Gln
            125                 130                 135

Gly Thr Leu Val Thr Val Ser Ser Ala Ser Thr Lys Gly Pro Ser
            140                 145                 150

Val Phe Pro Leu Ala Pro Ser Ser Lys Ser Thr Ser Gly Gly Thr
            155                 160                 165

Ala Ala Leu Gly Cys Leu Val Lys Asp Tyr Phe Pro Glu Pro Val
            170                 175                 180

Thr Val Ser Trp Asn Ser Gly Ala Leu Thr Ser Gly Val His Thr
            185                 190                 195

Phe Pro Ala Val Leu Gln Ser Ser Gly Leu Tyr Ser Leu Ser Ser
            200                 205                 210

Val Val Thr Val Pro Ser Ser Ser Leu Gly Thr Gln Thr Tyr Ile
            215                 220                 225

Cys Asn Val Asn His Lys Pro Ser Asn Thr Lys Val Asp Lys Lys
            230                 235                 240

Val Glu Pro Lys Ser Cys Asp Lys Thr His Leu Ser Gly Gly Gly
            245                 250                 255

Ser Gly Ser Gly Asp Phe Asp Tyr Glu Lys Met Ala Asn Ala Asn
            260                 265                 270

Lys Gly Ala Met Thr Glu Asn Ala Asp Glu Asn Ala Leu Gln Ser
            275                 280                 285

Asp Ala Lys Gly Lys Leu Asp Ser Val Ala Thr Asp Tyr Gly Ala
            290                 295                 300

Ala Ile Asp Gly Phe Ile Gly Asp Val Ser Gly Leu Ala Asn Gly
            305                 310                 315

Asn Gly Ala Thr Gly Asp Phe Ala Gly Ser Asn Ser Gln Met Ala
            320                 325                 330

Gln Val Gly Asp Gly Asp Asn Ser Pro Leu Met Asn Asn Phe Arg
            335                 340                 345

```
Gln Tyr Leu Pro Ser Leu Pro Gln Ser Val Glu Cys Arg Pro Phe
                350                 355                 360

Val Phe Ser Ala Gly Lys Pro Tyr Glu Phe Ser Ile Asp Cys Asp
            365                 370                 375

Lys Ile Asn Leu Phe Arg Gly Val Phe Ala Phe Leu Leu Tyr Val
            380                 385                 390

Ala Thr Phe Met Tyr Val Phe Ser Thr Phe Ala Asn Ile Leu Arg
            395                 400                 405

Asn Lys Glu Ser

<210> SEQ ID NO 88
<211> LENGTH: 7060
<212> TYPE: DNA
<213> ORGANISM: Artificial sequence
<220> FEATURE:
<223> OTHER INFORMATION: sequence is synthesized

<400> SEQUENCE: 88
```

| | | | | |
|---|---|---|---|---|
| gaattcaact | tctccatact | ttggataagg | aaatacagac | atgaaaaatc | 50 |
| tcattgctga | gttgttattt | aagcttgccc | aaaaagaaga | agagtcgaat | 100 |
| gaactgtgtg | cgcaggtaga | agctttggag | attatcgtca | ctgcaatgct | 150 |
| tcgcaatatg | gcgcaaaatg | accaacagcg | gttgattgat | caggtagagg | 200 |
| gggcgctgta | cgaggtaaag | cccgatgcca | gcattcctga | cgacgatacg | 250 |
| gagctgctgc | gcgattacgt | aaagaagtta | ttgaagcatc | ctcgtcagta | 300 |
| aaaagttaat | cttttcaaca | gctgtcataa | agttgtcacg | gccgagactt | 350 |
| atagtcgctt | tgttttattt | ttttaatgta | tttgtaacta | gtacgcaagt | 400 |
| tcacgtaaaa | agggtatgta | gaggttgagg | tgattttatg | aaaaagaata | 450 |
| tcgcatttct | tcttgcatct | atgttcgttt | tttctattgc | tacaaatgcc | 500 |
| tatgcagata | tccagatgac | ccagtccccg | agctccctgt | ccgcctctgt | 550 |
| gggcgatagg | gtcaccatca | cctgccgtgc | cagtcaggat | gtgtccactg | 600 |
| ctgtagcctg | gtatcaacag | aaaccaggaa | aagctccgaa | gcttctgatt | 650 |
| tactcggcat | ccttcctcta | ctctggagtc | ccttctcgct | tctctggtag | 700 |
| cggttccggg | acggatttca | ctctgaccat | cagcagtctg | cagccggaag | 750 |
| acttcgcaac | ttattactgt | cagcaatctt | atactactcc | tcccacgttc | 800 |
| ggacagggta | ccaaggtgga | gatcaaacga | actgtggctg | caccatctgt | 850 |
| cttcatcttc | ccgccatctg | atgagcagtt | gaaatctgga | actgcctctg | 900 |
| ttgtgtgcct | gctgaataac | ttctatccca | gagaggccaa | agtacagtgg | 950 |
| aaggtggata | acgccctcca | atcgggtaac | tcccaggaga | gtgtcacaga | 1000 |
| gcaggacagc | aaggacagca | cctacagcct | cagcagcacc | ctgacgctga | 1050 |
| gcaaagcaga | ctacgagaaa | cacaaagtct | acgcctgcga | agtcacccat | 1100 |
| cagggcctga | gctcgcccgt | cacaaagagc | ttcaacaggg | gagagtgtgg | 1150 |
| tgccagctcc | ggtatggctg | atccgaaccg | tttccgcggt | aaggacctgg | 1200 |
| cataactcga | ggctgatcct | ctacgccgga | cgcatcgtgg | ccctagtacg | 1250 |
| caagttcacg | taaaaagggt | aactagaggt | tgaggtgatt | ttatgaaaaa | 1300 |
| gaatatcgca | tttcttcttg | catctatgtt | cgttttttct | attgctacaa | 1350 |
| acgcgtacgc | tgaggttcag | ctggtggagt | ctggcggtgg | cctggtgcag | 1400 |

-continued

```
ccaggggct  cactccgttt  gtcctgtgca  gcttctggct  tcaacattaa        1450
agacacctat  atacactggg  tgcgtcaggc  cccgggtaag  ggcctggaat        1500
gggttgcaag  gatttatcct  acgaatggtt  atactagata  tgccgatagc        1550
gtcaagggcc  gtttcactat  aagcgcagac  acatccaaaa  acacagccta        1600
cctacaaatg  aacagcttaa  gagctgagga  cactgccgtc  tattattgta        1650
gccgctgggg  aggggacggc  ttctatgcta  tggactactg  gggtcaagga        1700
acactagtca  ccgtctcctc  ggcctccacc  aagggcccat  cggtcttccc        1750
cctggcaccc  tcctccaaga  gcacctctgg  gggcacagcg  gccctgggct        1800
gcctggtcaa  ggactacttc  cccgaaccgg  tgacggtgtc  gtggaactca        1850
ggcgccctga  ccagcggcgt  gcacaccttc  ccggctgtcc  tacagtcctc        1900
aggactctac  tccctcagca  gcgtggtgac  cgtgccctcc  agcagcttgg        1950
gcacccagac  ctacatctgc  aacgtgaatc  acaagcccag  caacaccaag        2000
gtcgacaaga  aagttgagcc  caaatcttgt  gacaaaactc  acctcagtgg        2050
cggtggctct  ggttccggtg  attttgatta  tgaaaagatg  gcaaacgcta        2100 ataaggggc   tatgaccgaa  aatgccgatg  aaaacgcgct  acagtctgac        2150
gctaaaggca  aacttgattc  tgtcgctact  gattacggtg  ctgctatcga        2200
tggtttcatt  ggtgacgttt  ccggccttgc  taatggtaat  ggtgctactg        2250
gtgattttgc  tggctctaat  tcccaaatgg  ctcaagtcgg  tgacggtgat        2300
aattcacctt  taatgaataa  tttccgtcaa  tatttacctt  ccctccctca        2350
atcggttgaa  tgtcgccctt  tgtctttag   cgctggtaaa  ccatatgaat        2400
tttctattga  ttgtgacaaa  ataaacttat  ccgtggtgt   ctttgcgttt        2450 cttttatatg  ttgccacctt  tatgtatgta  ttttctacgt  ttgctaacat        2500
actgcgtaat  aaggagtctt  aatcatgcca  gttcttttgg  ctagcgccgc        2550
cctataccct  gtctgcctcc  ccgcgttgcg  tcgcggtgca  tggagccggg        2600
ccacctcgac  ctgaatggaa  gccggcggca  cctcgctaac  ggattcacca        2650
ctccaagaat  tggagccaat  caattcttgc  ggagaactgt  gaatgcgcaa        2700 accaacccctt gcagaacat  atccatcgcg  tccgccatct  ccagcagccg        2750
cacgcggcgc  atctcgggca  gcgttgggtc  ctggccacgg  gtgcgcatga        2800
tcgtgctcct  gtcgttgagg  acccggctag  gctggcgggg  ttgccttact        2850
ggttagcaga  atgaatcacc  gatacgcgag  cgaacgtgaa  gcgactgctg        2900
ctgcaaaacg  tctgcgacct  gagcaacaac  atgaatggtc  ttcggtttcc        2950
gtgtttcgta  aagtctggaa  acgcggaagt  cagcgccctg  caccattatg        3000
ttccggatct  gcatcgcagg  atgctgctgg  ctaccctgtg  aacacctac         3050 atctgtatta  acgaagcgct  ggcattgacc  ctgagtgatt  tttctctggt        3100
cccgccgcat  ccataccgcc  agttgtttac  cctcacaacg  ttccagtaac        3150
cgggcatgtt  catcatcagt  aacccgtatc  gtgagcatcc  tctctcgttt        3200
catcggtatc  attacccccca tgaacagaaa  ttccccctta  cacggaggca        3250
tcaagtgacc  aaacaggaaa  aaaccgccct  taacatggcc  cgctttatca        3300
gaagccagac  attaacgctt  ctggagaaac  tcaacgagct  ggacgcggat        3350
```

| | |
|---|---|
| gaacaggcag acatctgtga atcgcttcac gaccacgctg atgagcttta | 3400 |
| ccgcaggatc cggaaattgt aaacgttaat attttgttaa aattcgcgtt | 3450 |
| aaattttgt taaatcagct catttttaa ccaataggcc gaaatcggca | 3500 |
| aaatcccta taaatcaaaa gaatagaccg atagggtt gagtgttgtt | 3550 |
| ccagtttgga acaagagtcc actattaaag aacgtggact ccaacgtcaa | 3600 |
| agggcgaaaa accgtctatc agggctatgg cccactacgt gaaccatcac | 3650 |
| cctaatcaag tttttgggg tcgaggtgcc gtaaagcact aaatcggaac | 3700 |
| cctaaaggga gcccccgatt tagagcttga cggggaaagc cggcgaacgt | 3750 |
| ggcgagaaag gaagggaaga aagcgaaagg agcgggcgct agggcgctgg | 3800 |
| caagtgtagc ggtcacgctg cgcgtaacca ccacacccgc cgcgcttaat | 3850 |
| gcgccgctac agggcgcgtc cggatcctgc ctcgcgcgtt tcggtgatga | 3900 |
| cggtgaaaac ctctgacaca tgcagctccc ggagacggtc acagcttgtc | 3950 |
| tgtaagcgga tgccgggagc agacaagccc gtcagggcgc gtcagcgggt | 4000 |
| gttggcgggt gtcggggcgc agccatgacc cagtcacgta gcgatagcgg | 4050 |
| agtgtatact ggcttaacta tgcggcatca gagcagattg tactgagagt | 4100 |
| gcaccatatg cggtgtgaaa taccgcacag atgcgtaagg agaaaatacc | 4150 |
| gcatcaggcg ctcttccgct tcctcgctca ctgactcgct gcgctcggtc | 4200 |
| gttcggctgc ggcgagcggt atcagctcac tcaaaggcgg taatacggtt | 4250 |
| atccacagaa tcaggggata acgcaggaaa gaacatgtga gcaaaaggcc | 4300 |
| agcaaaaggc caggaaccgt aaaaaggccg cgttgctggc gttttccat | 4350 |
| aggctccgcc cccctgacga gcatcacaaa aatcgacgct caagtcagag | 4400 |
| gtggcgaaac ccgacaggac tataaagata ccaggcgttt cccctggaa | 4450 |
| gctccctcgt gcgctctcct gttccgaccc tgccgcttac cggatacctg | 4500 |
| tccgcctttc tcccttcggg aagcgtggcg ctttctcata gctcacgctg | 4550 |
| taggtatctc agttcggtgt aggtcgttcg ctccaagctg ggctgtgtgc | 4600 |
| acgaaccccc cgttcagccc gaccgctgcg ccttatccgg taactatcgt | 4650 |
| cttgagtcca acccggtaag acacgactta tcgccactgg cagcagccac | 4700 |
| tggtaacagg attagcagag cgaggtatgt aggcggtgct acagagttct | 4750 |
| tgaagtggtg gcctaactac ggctacacta gaaggacagt atttggtatc | 4800 |
| tgcgctctgc tgaagccagt taccttcgga aaaagagttg gtagctcttg | 4850 |
| atccggcaaa caaaccaccg ctggtagcgg tggtttttt gtttgcaagc | 4900 |
| agcagattac gcgcagaaaa aaaggatctc aagaagatcc tttgatcttt | 4950 |
| tctacggggt ctgacgctca gtggaacgaa aactcacgtt aagggatttt | 5000 |
| ggtcatgaga ttatcaaaaa ggatcttcac ctagatcctt ttaaattaaa | 5050 |
| aatgaagttt taaatcaatc taagtatat atgagtaaac ttggtctgac | 5100 |
| agttaccaat gcttaatcag tgaggcacct atctcagcga tctgtctatt | 5150 |
| tcgttcatcc atagttgcct gactcccgt cgtgtagata actacgatac | 5200 |
| gggagggctt accatctggc cccagtgctg caatgatacc gcgagaccca | 5250 |
| cgctcaccgg ctccagattt atcagcaata aaccagccag ccggaagggc | 5300 |
| cgagcgcaga agtggtcctg caactttatc cgcctccatc cagtctatta | 5350 |

```
attgttgccg ggaagctaga gtaagtagtt cgccagttaa tagtttgcgc      5400
aacgttgttg ccattgctgc aggcatcgtg gtgtcacgct cgtcgtttgg      5450
tatggcttca ttcagctccg gttcccaacg atcaaggcga gttacatgat      5500
cccccatgtt gtgcaaaaaa gcggttagct ccttcggtcc tccgatcgtt      5550
gtcagaagta agttggccgc agtgttatca ctcatggtta tggcagcact      5600
gcataattct cttactgtca tgccatccgt aagatgcttt tctgtgactg      5650
gtgagtactc aaccaagtca ttctgagaat agtgtatgcg cgaccgagt       5700 tgctcttgcc cggcgtcaac acgggataat accgcgccac atagcagaac      5750
tttaaaagtg ctcatcattg gaaaacgttc ttcggggcga aaactctcaa      5800
ggatcttacc gctgttgaga tccagttcga tgtaacccac tcgtgcaccc      5850
aactgatctt cagcatcttt tactttcacc agcgtttctg ggtgagcaaa      5900
aacaggaagg caaaatgccg caaaaaaggg aataagggcg acacggaaat      5950
gttgaatact catactcttc cttttcaat attattgaag catttatcag       6000
ggttattgtc tcatgagcgg atacatattt gaatgtattt agaaaaataa      6050 acaaatacggg gttccgcgca catttccccg aaaagtgcca cctgacgtct     6100
aagaaaccat tattatcatg acattaacct ataaaaatag gcgtatcacg      6150
aggccctttc gtcttcaata caggtagacc tttcgtagag atgtacagtg      6200
aaatccccga aattatacac atgactgaag gaagggagct cgtcattccc      6250
tgccgggtta cgtcacctaa catcactgtt actttaaaaa agtttccact      6300
tgacactttg atccctgatg gaaaacgcat aatctgggac agtagaaagg      6350
gcttcatcat atcaaatgca acgtacaaag aaatagggct tctgacctgt      6400
gaagcaacag tcaatgggca tttgtataag acaaactatc tcacacatcg      6450
acaaaccaat acaatacagg tagacctttc gtagagatgt acagtgaaat      6500
ccccgaaatt atacacatga ctgaaggaag ggagctcgtc attccctgcc      6550
gggttacgtc acctaacatc actgttactt taaaaaagtt tccacttgac      6600
actttgatcc ctgatggaaa acgcataatc tgggacagta gaaagggctt      6650
catcatatca aatgcaacgt acaaagaaat agggcttctg acctgtgaag      6700
caacagtcaa tgggcatttg tataagacaa actatctcac acatcgacaa      6750
accaatacaa tctacaggta gacctttcgt agagatgtac agtgaaatcc      6800
ccgaaattat acacatgact gaaggaaggg agctcgtcat tccctgccgg      6850
gttacgtcac ctaacatcac tgttacttta aaaagtttc cacttgacac       6900 tttgatccct gatggaaaac gcataatctg gacagtaga aagggcttca       6950 tcatatcaaa tgcaacgtac aaagaaatag ggcttctgac ctgtgaagca      7000
acagtcaatg gcatttgta taagacaaac tatctcacac atcgacaaac       7050
caatacaatc                                                  7060
```

<210> SEQ ID NO 89
<211> LENGTH: 256
<212> TYPE: PRT
<213> ORGANISM: Artificial sequence
<220> FEATURE:
<223> OTHER INFORMATION: sequence is synthesized

<400> SEQUENCE: 89

```
Met Lys Lys Asn Ile Ala Phe Leu Leu Ala Ser Met Phe Val Phe
  1               5                  10                  15

Ser Ile Ala Thr Asn Ala Tyr Ala Ser Asp Ile Gln Met Thr Gln
                 20                  25                  30

Ser Pro Ser Ser Leu Ser Ala Ser Val Gly Asp Arg Val Thr Ile
                 35                  40                  45

Thr Cys Arg Ala Ser Gln Asp Val Ser Thr Ala Val Ala Trp Tyr
                 50                  55                  60

Gln Gln Lys Pro Gly Lys Ala Pro Lys Leu Leu Ile Tyr Ser Ala
                 65                  70                  75

Ser Phe Leu Tyr Ser Gly Val Pro Ser Arg Phe Ser Gly Ser Gly
                 80                  85                  90

Ser Gly Thr Asp Phe Thr Leu Thr Ile Ser Ser Leu Gln Pro Glu
                 95                 100                 105

Asp Phe Ala Thr Tyr Tyr Cys Gln Gln Ser Tyr Thr Thr Pro Pro
                110                 115                 120

Thr Phe Gly Gln Gly Thr Lys Val Glu Ile Lys Arg Thr Val Ala
                125                 130                 135

Ala Pro Ser Val Phe Ile Phe Pro Pro Ser Asp Glu Gln Leu Lys
                140                 145                 150

Ser Gly Thr Ala Ser Val Val Cys Leu Leu Asn Asn Phe Tyr Pro
                155                 160                 165

Arg Glu Ala Lys Val Gln Trp Lys Val Asp Asn Ala Leu Gln Ser
                170                 175                 180

Gly Asn Ser Gln Glu Ser Val Thr Glu Gln Asp Ser Lys Asp Ser
                185                 190                 195

Thr Tyr Ser Leu Ser Ser Thr Leu Thr Leu Ser Lys Ala Asp Tyr
                200                 205                 210

Glu Lys His Lys Val Tyr Ala Cys Glu Val Thr His Gln Gly Leu
                215                 220                 225

Ser Ser Pro Val Thr Lys Ser Phe Asn Arg Gly Glu Cys Gly Ala
                230                 235                 240

Ser Ser Gly Met Ala Asp Pro Asn Arg Phe Arg Gly Lys Asp Leu
                245                 250                 255

Ala
```

<210> SEQ ID NO 90
<211> LENGTH: 445
<212> TYPE: PRT
<213> ORGANISM: Artificial sequence
<220> FEATURE:
<223> OTHER INFORMATION: sequence is synthesized

<400> SEQUENCE: 90

```
Met Lys Lys Asn Ile Ala Phe Leu Leu Ala Ser Met Phe Val Phe
  1               5                  10                  15

Ser Ile Ala Thr Asn Ala Tyr Ala Glu Val Gln Leu Val Glu Ser
                 20                  25                  30

Gly Gly Gly Leu Val Gln Pro Gly Gly Ser Leu Arg Leu Ser Cys
                 35                  40                  45

Ala Ala Ser Gly Phe Asn Ile Lys Asp Thr Tyr Ile His Trp Val
                 50                  55                  60

Arg Gln Ala Pro Gly Lys Gly Leu Glu Trp Val Ala Arg Ile Tyr
                 65                  70                  75
```

-continued

```
Pro Thr Asn Gly Tyr Thr Arg Tyr Ala Asp Ser Val Lys Gly Arg
                80                  85                  90

Phe Thr Ile Ser Ala Asp Thr Ser Lys Asn Thr Ala Tyr Leu Gln
                95                 100                 105

Met Asn Ser Leu Arg Ala Glu Asp Thr Ala Val Tyr Tyr Cys Ser
               110                 115                 120

Arg Trp Gly Gly Asp Gly Phe Tyr Ala Met Asp Tyr Trp Gly Gln
               125                 130                 135

Gly Thr Leu Val Thr Val Ser Ser Ala Ser Thr Lys Gly Pro Ser
               140                 145                 150

Val Phe Pro Leu Ala Pro Ser Ser Lys Ser Thr Ser Gly Gly Thr
               155                 160                 165

Ala Ala Leu Gly Cys Leu Val Lys Asp Tyr Phe Pro Glu Pro Val
               170                 175                 180

Thr Val Ser Trp Asn Ser Gly Ala Leu Thr Ser Gly Val His Thr
               185                 190                 195

Phe Pro Ala Val Leu Gln Ser Ser Gly Leu Tyr Ser Leu Ser Ser
               200                 205                 210

Val Val Thr Val Pro Ser Ser Ser Leu Gly Thr Gln Thr Tyr Ile
               215                 220                 225

Cys Asn Val Asn His Lys Pro Ser Asn Thr Lys Val Asp Lys Lys
               230                 235                 240

Val Glu Pro Lys Ser Cys Asp Lys Thr His Gly Arg Met Lys Gln
               245                 250                 255

Leu Glu Asp Lys Val Glu Glu Leu Leu Ser Lys Asn Tyr His Leu
               260                 265                 270

Glu Asn Glu Val Ala Arg Leu Lys Lys Leu Val Gly Glu Arg Gly
               275                 280                 285

Lys Leu Ser Gly Gly Gly Ser Gly Ser Gly Asp Phe Asp Tyr Glu
               290                 295                 300

Lys Met Ala Asn Ala Asn Lys Gly Ala Met Thr Glu Asn Ala Asp
               305                 310                 315

Glu Asn Ala Leu Gln Ser Asp Ala Lys Gly Lys Leu Asp Ser Val
               320                 325                 330

Ala Thr Asp Tyr Gly Ala Ala Ile Asp Gly Phe Ile Gly Asp Val
               335                 340                 345

Ser Gly Leu Ala Asn Gly Asn Gly Ala Thr Gly Asp Phe Ala Gly
               350                 355                 360

Ser Asn Ser Gln Met Ala Gln Val Gly Asp Gly Asp Asn Ser Pro
               365                 370                 375

Leu Met Asn Asn Phe Arg Gln Tyr Leu Pro Ser Leu Pro Gln Ser
               380                 385                 390

Val Glu Cys Arg Pro Phe Val Phe Ser Ala Gly Lys Pro Tyr Glu
               395                 400                 405

Phe Ser Ile Asp Cys Asp Lys Ile Asn Leu Phe Arg Gly Val Phe
               410                 415                 420

Ala Phe Leu Leu Tyr Val Ala Thr Phe Met Tyr Val Phe Ser Thr
               425                 430                 435

Phe Ala Asn Ile Leu Arg Asn Lys Glu Ser
               440                 445
```

<210> SEQ ID NO 91
<211> LENGTH: 7171

```
<212> TYPE: DNA
<213> ORGANISM: Artificial sequence
<220> FEATURE:
<223> OTHER INFORMATION: sequence is synthesized

<400> SEQUENCE: 91
gaattcaact tctccatact ttggataagg aaatacagac atgaaaaatc          50
tcattgctga gttgttattt aagcttgccc aaaaagaaga agagtcgaat         100
gaactgtgtg cgcaggtaga agctttggag attatcgtca ctgcaatgct         150
tcgcaatatg gcgcaaaatg accaacagcg gttgattgat caggtagagg         200
gggcgctgta cgaggtaaag cccgatgcca gcattcctga cgacgatacg         250
gagctgctgc gcgattacgt aaagaagtta ttgaagcatc ctcgtcagta         300
aaaagttaat cttttcaaca gctgtcataa agttgtcacg gccgagactt         350
atagtcgctt tgttttatt ttttaatgta tttgtaacta gtacgcaagt          400
tcacgtaaaa agggtatgta gaggttgagg tgattttatg aaaaagaata         450
tcgcatttct tcttgcatct atgttcgttt tttctattgc tacaaatgcc         500
tatgcatccg atatccagat gacccagtcc ccgagctccc tgtccgcctc         550
tgtgggcgat agggtcacca tcacctgccg tgccagtcag gatgtgtcca         600
ctgctgtagc ctggtatcaa cagaaaccag gaaaagctcc gaagcttctg         650
atttactcgg catccttcct ctactctgga gtcccttctc gcttctctgg         700
tagcggttcc gggacggatt tcactctgac catcagcagt ctgcagccgg         750
aagacttcgc aacttattac tgtcagcaat cttatactac tcctcccacg         800
ttcggacagg gtaccaaggt ggagatcaaa cgaactgtgg ctgcaccatc         850
tgtcttcatc ttcccgccat ctgatgagca gttgaaatct ggaactgcct         900
ctgttgtgtg cctgctgaat aacttctatc ccagagaggc caaagtacag         950
tggaaggtgg ataacgccct ccaatcgggt aactcccagg agagtgtcac        1000
agagcaggac agcaaggaca gcacctacag cctcagcagc accctgacgc        1050
tgagcaaagc agactacgag aaacacaaag tctacgcctg cgaagtcacc        1100
catcagggcc tgagctcgcc cgtcacaaag agcttcaaca ggggagagtg        1150
tggtgccagc tccggtatgg ctgatccgaa ccgtttccgc ggtaaggacc        1200
tggcataact cgaggctgat cctctacgcc ggacgcatcg tggccctagt        1250
acgcaagttc acgtaaaaag ggtaactaga ggttgaggtg attttatgaa        1300
aaagaatatc gcatttcttc ttgcatctat gttcgttttt tctattgcta        1350
caaacgcgta cgctgaggtt cagctggtgg agtctggcgg tggcctggtg        1400
cagccagggg gctcactccg tttgtcctgt gcagcttctg gcttcaacat        1450
taaagacacc tatatacact gggtgcgtca ggccccgggt aagggcctgg        1500
aatgggttgc aaggatttat cctacgaatg gttatactag atatgccgat        1550
agcgtcaagg gccgtttcac tataagcgca gacacatcca aaaacacagc        1600
ctacctacaa atgaacagct aagagctgag gacactgcc gtctattatt         1650
gtagccgctg ggagggggac ggcttctatg ctatggacta ctggggtcaa        1700
ggaacactag tcaccgtctc ctcggcctcc accaagggcc catcggtctt        1750
cccccctggca ccctcctcca agagcacctc tgggggcaca gcggccctgg       1800
```

```
gctgcctggt caaggactac ttccccgaac cggtgacggt gtcgtggaac        1850
tcaggcgccc tgaccagcgg cgtgcacacc ttcccggctg tcctacagtc        1900
ctcaggactc tactccctca gcagcgtggt gaccgtgccc tccagcagct        1950
tgggcaccca gacctacatc tgcaacgtga atcacaagcc cagcaacacc        2000
aaggtcgaca agaaagttga gcccaaatct tgtgacaaaa ctcacggccg        2050
catgaaacag ctagaggaca aggtcgaaga gctactctcc aagaactacc        2100
acctagagaa tgaagtggca agactcaaaa aacttgtcgg ggagcgcgga        2150
aagcttagtg gcggtggctc tggttccggt gattttgatt atgaaaagat        2200
ggcaaacgct aataagggg ctatgaccga aaatgccgat gaaaacgcgc         2250
tacagtctga cgctaaaggc aaacttgatt ctgtcgctac tgattacggt        2300
gctgctatcg atggtttcat tggtgacgtt ccggccttg ctaatggtaa         2350 tggtgctact ggtgattttg ctggctctaa ttcccaaatg gctcaagtcg        2400
gtgacggtga taattcacct ttaatgaata atttccgtca atatttacct        2450
tccctccctc aatcggttga atgtcgccct tttgtcttta gcgctggtaa        2500
accatatgaa ttttctattg attgtgacaa aataaactta ttccgtggtg        2550
tctttgcgtt tcttttatat gttgccacct ttatgtatgt attttctacg        2600
tttgctaaca tactgcgtaa taaggagtct taatcatgcc agttcttttg        2650
gctagcgccg ccctatacct tgtctgcctc cccgcgttgc gtcgcggtgc        2700
atggagccgg gccacctcga cctgaatgga agccggcggc acctcgctaa        2750
cggattcacc actccaagaa ttggagccaa tcaattcttg cggagaactg        2800
tgaatgcgca aaccaaccct tggcagaaca tatccatcgc gtccgccatc        2850
tccagcagcc gcacgcggcg catctcgggc agcgttgggt cctggccacg        2900
ggtgcgcatg atcgtgctcc tgtcgttgag dacccggcta ggctggcggg       2950
gttgccttac tggttagcag aatgaatcac cgatacgcga cgaacgtga         3000 agcgactgct gctgcaaaac gtctgcgacc tgagcaacaa catgaatggt        3050
cttcggtttc cgtgtttcgt aaagtctgga acgcggaag tcagcgccct         3100 gcaccattat gttccggatc tgcatcgcag gatgctgctg gctaccctgt        3150
ggaacaccta catctgtatt aacgaagcgc tggcattgac cctgagtgat        3200
ttttctctgg tcccgccgca tccataccgc cagttgttta ccctcacaac        3250
gttccagtaa ccgggcatgt tcatcatcag taacccgtat cgtgagcatc        3300
ctctctcgtt tcatcggtat cattacccc atgaacagaa attccccctt         3350
acacggaggc atcaagtgac caaacaggaa aaaaccgccc ttaacatggc        3400
ccgctttatc agaagccaga cattaacgct tctggagaaa ctcaacgagc        3450
tggacgcgga tgaacaggca gacatctgtg aatcgcttca cgaccacgct        3500
gatgagcttt accgcaggat ccggaaattg taaacgttaa tattttgtta        3550
aaattcgcgt taaatttttg ttaaatcagc tcatttttta accaataggc        3600
cgaaatcgga aaatcccctt ataaatcaaa agaatagacc gagatagggt        3650
tgagtgttgt tccagtttgg aacaagagtc cactattaaa gaacgtggac        3700
tccaacgtca aagggcgaaa aaccgtctat cagggctatg gcccactacg        3750
tgaaccatca ccctaatcaa gttttttggg gtcgaggtgc cgtaaagcac        3800
```

```
taaatcggaa ccctaaaggg agcccccgat ttagagcttg acggggaaag      3850
ccggcgaacg tggcgagaaa ggaagggaag aaagcgaaag gagcgggcgc      3900
tagggcgctg gcaagtgtag cggtcacgct gcgcgtaacc accacacccg      3950
ccgcgcttaa tgcgccgcta cagggcgcgt ccggatcctg cctcgcgcgt      4000
ttcggtgatg acggtgaaaa cctctgacac atgcagctcc cggagacggt      4050
cacagcttgt ctgtaagcgg atgccgggag cagacaagcc cgtcagggcg      4100
cgtcagcggg tgttggcggg tgtcggggcg cagccatgac ccagtcacgt      4150
agcgatagcg gagtgtatac tggcttaact atgcggcatc agagcagatt      4200
gtactgagag tgcaccatat gcggtgtgaa ataccgcaca gatgcgtaag      4250
gagaaaatac cgcatcaggc gctcttccgc ttcctcgctc actgactcgc      4300 tgcgctcgt cgttcggctg cggcgagcgg tatcagctca ctcaaaggcg      4350
gtaatacggt tatccacaga atcagggat aacgcaggaa agaacatgtg      4400
agcaaaaggc cagcaaaagg ccaggaaccg taaaaaggcc gcgttgctgg      4450
cgttttccca taggctccgc cccctgacg agcatcacaa aaatcgacgc      4500
tcaagtcaga ggtggcgaaa cccgacagga ctataaagat accaggcgtt      4550
tccccctgga agctccctcg tgcgctctcc tgttccgacc ctgccgctta      4600
ccggatacct gtccgccttt ctcccttcgg aagcgtggc gctttctcat      4650 agctcacgct gtaggtatct cagttcggtg taggtcgttc gctccaagct      4700
gggctgtgtg cacgaacccc ccgttcagcc cgaccgctgc gccttatccg      4750
gtaactatcg tcttgagtcc aacccggtaa gacacgactt atcgccactg      4800
gcagcagcca ctggtaacag gattagcaga gcgaggtatg taggcggtgc      4850
tacagagttc ttgaagtggt ggcctaacta cggctacact agaaggacag      4900
tatttggtat ctgcgctctg ctgaagccag ttaccttcgg aaaaagagtt      4950
ggtagctctt gatccggcaa acaaaccacc gctggtagcg gtggtttttt      5000
tgtttgcaag cagcagatta cgcgcagaaa aaaaggatct caagaagatc      5050
ctttgatctt ttctacgggg tctgacgctc agtggaacga aaactcacgt      5100
taagggattt tggtcatgag attatcaaaa aggatcttca cctagatcct      5150
tttaaattaa aaatgaagtt ttaaatcaat ctaaagtata tatgagtaaa      5200
cttggtctga cagttaccaa tgcttaatca gtgaggcacc tatctcagcg      5250
atctgtctat ttcgttcatc catagttgcc tgactccccg tcgtgtagat      5300
aactacgata cgggagggct taccatctgg ccccagtgct gcaatgatac      5350
cgcgagaccc acgctcaccg gctccagatt tatcagcaat aaaccagcca      5400
gccggaaggg ccgagcgcag aagtggtcct gcaactttat ccgcctccat      5450
ccagtctatt aattgttgcc gggaagctag agtaagtagt tcgccagtta      5500
atagtttgcg caacgttgtt gccattgctg caggcatcgt ggtgtcacgc      5550
tcgtcgtttg gtatggcttc attcagctcc ggttcccaac gatcaaggcg      5600
agttacatga tcccccatgt tgtgcaaaaa agcggttagc tccttcggtc      5650
ctccgatcgt tgtcagaagt aagttggccg cagtgttatc actcatggtt      5700
atggcagcac tgcataattc tcttactgtc atgccatccg taagatgctt      5750
```

| | |
|---|---|
| ttctgtgact ggtgagtact caaccaagtc attctgagaa tagtgtatgc | 5800 |
| ggcgaccgag ttgctcttgc ccggcgtcaa cacgggataa taccgcgcca | 5850 |
| catagcagaa ctttaaaagt gctcatcatt ggaaaacgtt cttcggggcg | 5900 |
| aaaactctca aggatcttac cgctgttgag atccagttcg atgtaaccca | 5950 |
| ctcgtgcacc caactgatct tcagcatctt ttactttcac cagcgtttct | 6000 |
| gggtgagcaa aaacaggaag gcaaaatgcc gcaaaaaagg gaataagggc | 6050 |
| gacacggaaa tgttgaatac tcatactctt ccttttcaa tattattgaa | 6100 |
| gcatttatca gggttattgt ctcatgagcg gatacatatt tgaatgtatt | 6150 |
| tagaaaaata aacaaatagg ggttccgcgc acatttcccc gaaaagtgcc | 6200 |
| acctgacgtc taagaaacca ttattatcat gacattaacc tataaaaata | 6250 |
| ggcgtatcac gaggcccttt cgtcttcaat acaggtagac ctttcgtaga | 6300 |
| gatgtacagt gaaatccccg aaattataca catgactgaa ggaagggagc | 6350 |
| tcgtcattcc ctgccgggtt acgtcaccta acatcactgt tactttaaaa | 6400 |
| aagtttccac ttgacacttt gatccctgat ggaaaacgca taatctggga | 6450 |
| cagtagaaag ggcttcatca tatcaaatgc aacgtacaaa gaaatagggc | 6500 |
| ttctgacctg tgaagcaaca gtcaatgggc atttgtataa gacaaactat | 6550 |
| ctcacacatc gacaaaccaa tacaatacag gtagaccttt cgtagagatg | 6600 |
| tacagtgaaa tccccgaaat tatacacatg actgaaggaa gggagctcgt | 6650 |
| cattccctgc cgggttacgt cacctaacat cactgttact ttaaaaagt | 6700 |
| ttccacttga cactttgatc cctgatggaa aacgcataat ctgggacagt | 6750 |
| agaaagggct tcatcatatc aaatgcaacg tacaagaaa tagggcttct | 6800 |
| gacctgtgaa gcaacagtca atgggcattt gtataagaca aactatctca | 6850 |
| cacatcgaca aaccaataca atctacaggt agacctttcg tagagatgta | 6900 |
| cagtgaaatc cccgaaatta tacacatgac tgaaggaagg gagctcgtca | 6950 |
| ttccctgccg ggttacgtca cctaacatca ctgttacttt aaaaaagttt | 7000 |
| ccacttgaca ctttgatccc tgatggaaaa cgcataatct gggacagtag | 7050 |
| aaagggcttc atcatatcaa atgcaacgta caaagaaata gggcttctga | 7100 |
| cctgtgaagc aacagtcaat gggcatttgt ataagacaaa ctatctcaca | 7150 |
| catcgacaaa ccaatacaat c | 7171 |

<210> SEQ ID NO 92
<211> LENGTH: 255
<212> TYPE: PRT
<213> ORGANISM: Artificial sequence
<220> FEATURE:
<223> OTHER INFORMATION: sequence is synthesized

<400> SEQUENCE: 92

```
Met Lys Lys Asn Ile Ala Phe Leu Leu Ala Ser Met Phe Val Phe
  1               5                  10                  15

Ser Ile Ala Thr Asn Ala Tyr Ala Asp Ile Gln Met Thr Gln Ser
                 20                  25                  30

Pro Ser Leu Ser Ala Ser Val Gly Asp Arg Val Thr Ile Thr
             35                  40                  45

Cys Arg Ala Ser Gln Asp Val Ser Thr Ala Val Ala Trp Tyr Gln
         50                  55                  60
```

```
Gln Lys Pro Gly Lys Ala Pro Lys Leu Leu Ile Tyr Ser Ala Ser
             65                  70                  75

Phe Leu Tyr Ser Gly Val Pro Ser Arg Phe Ser Gly Ser Gly Ser
             80                  85                  90

Gly Thr Asp Phe Thr Leu Thr Ile Ser Ser Leu Gln Pro Glu Asp
             95                 100                 105

Phe Ala Thr Tyr Tyr Cys Gln Gln His Tyr Thr Thr Pro Pro Thr
            110                 115                 120

Phe Gly Gln Gly Thr Lys Val Glu Ile Lys Arg Thr Val Ala Ala
            125                 130                 135

Pro Ser Val Phe Ile Phe Pro Pro Ser Asp Glu Gln Leu Lys Ser
            140                 145                 150

Gly Thr Ala Ser Val Val Cys Leu Leu Asn Asn Phe Tyr Pro Arg
            155                 160                 165

Glu Ala Lys Val Gln Trp Lys Val Asp Asn Ala Leu Gln Ser Gly
            170                 175                 180

Asn Ser Gln Glu Ser Val Thr Glu Gln Asp Ser Lys Asp Ser Thr
            185                 190                 195

Tyr Ser Leu Ser Ser Thr Leu Thr Leu Ser Lys Ala Asp Tyr Glu
            200                 205                 210

Lys His Lys Val Tyr Ala Cys Glu Val Thr His Gln Gly Leu Ser
            215                 220                 225

Ser Pro Val Thr Lys Ser Phe Asn Arg Gly Glu Cys Gly Ala Ser
            230                 235                 240

Ser Gly Met Ala Asp Pro Asn Arg Phe Arg Gly Lys Asp Leu Ala
            245                 250                 255

<210> SEQ ID NO 93
<211> LENGTH: 408
<212> TYPE: PRT
<213> ORGANISM: Artificial sequence
<220> FEATURE:
<223> OTHER INFORMATION: sequence is synthesized

<400> SEQUENCE: 93

Met Lys Lys Asn Ile Ala Phe Leu Leu Ala Ser Met Phe Val Phe
  1               5                  10                  15

Ser Ile Ala Thr Asn Ala Tyr Ala Glu Val Gln Leu Val Glu Ser
             20                  25                  30

Gly Gly Gly Leu Val Gln Pro Gly Gly Ser Leu Arg Leu Ser Cys
             35                  40                  45

Ala Ala Ser Gly Phe Thr Ile Ser Gly Ser Trp Ile His Trp Val
             50                  55                  60

Arg Gln Ala Pro Gly Lys Gly Leu Glu Trp Val Ala Trp Ile Ala
             65                  70                  75

Pro Tyr Ser Gly Ala Thr Asp Tyr Ala Asp Ser Val Lys Gly Arg
             80                  85                  90

Phe Thr Ile Ser Ala Asp Thr Ser Lys Asn Thr Ala Tyr Leu Gln
             95                 100                 105

Met Asn Ser Leu Arg Ala Glu Asp Thr Ala Val Tyr Tyr Cys Ala
            110                 115                 120

Arg Glu Gly Gly Leu Tyr Trp Val Phe Asp Tyr Trp Gly Gln Gly
            125                 130                 135

Thr Leu Val Thr Val Ser Ser Ala Ser Thr Lys Gly Pro Ser Val
            140                 145                 150
```

```
Phe Pro Leu Ala Pro Ser Ser Lys Ser Thr Ser Gly Gly Thr Ala
                155                 160                 165
Ala Leu Gly Cys Leu Val Lys Asp Tyr Phe Pro Glu Pro Val Thr
            170                 175                 180
Val Ser Trp Asn Ser Gly Ala Leu Thr Ser Gly Val His Thr Phe
        185                 190                 195
Pro Ala Val Leu Gln Ser Ser Gly Leu Tyr Ser Leu Ser Ser Val
    200                 205                 210
Val Thr Val Pro Ser Ser Ser Leu Gly Thr Gln Thr Tyr Ile Cys
215                 220                 225
Asn Val Asn His Lys Pro Ser Asn Thr Lys Val Asp Lys Lys Val
                230                 235                 240
Glu Pro Lys Ser Cys Asp Lys Thr His Leu Ser Gly Gly Gly Ser
            245                 250                 255
Gly Ser Gly Asp Phe Asp Tyr Glu Lys Met Ala Asn Ala Asn Lys
        260                 265                 270
Gly Ala Met Thr Glu Asn Ala Asp Glu Asn Ala Leu Gln Ser Asp
    275                 280                 285
Ala Lys Gly Lys Leu Asp Ser Val Ala Thr Asp Tyr Gly Ala Ala
290                 295                 300
Ile Asp Gly Phe Ile Gly Asp Val Ser Gly Leu Ala Asn Gly Asn
                305                 310                 315
Gly Ala Thr Gly Asp Phe Ala Gly Ser Asn Ser Gln Met Ala Gln
            320                 325                 330
Val Gly Asp Gly Asp Asn Ser Pro Leu Met Asn Asn Phe Arg Gln
        335                 340                 345
Tyr Leu Pro Ser Leu Pro Gln Ser Val Glu Cys Arg Pro Phe Val
    350                 355                 360
Phe Ser Ala Gly Lys Pro Tyr Glu Phe Ser Ile Asp Cys Asp Lys
365                 370                 375
Ile Asn Leu Phe Arg Gly Val Phe Ala Phe Leu Leu Tyr Val Ala
                380                 385                 390
Thr Phe Met Tyr Val Phe Ser Thr Phe Ala Asn Ile Leu Arg Asn
            395                 400                 405
Lys Glu Ser

<210> SEQ ID NO 94
<211> LENGTH: 2082
<212> TYPE: DNA
<213> ORGANISM: Artificial sequence
<220> FEATURE:
<223> OTHER INFORMATION: sequence is synthesized

<400> SEQUENCE: 94
atgaaaaaga atatcgcatt tcttcttgca tctatgttcg tttttttctat          50 tgctacaaat gcctatgcag atatccagat gacccagtcc ccgagctccc         100
tgtccgcctc tgtgggcgat agggtcacca tcacctgccg tgccagtcag         150
gatgtgtcca ctgctgtagc ctggtatcaa cagaaaccag gaaaagctcc         200
gaagcttctg atttactcgg catccttcct ctactctgga gtcccttctc         250
gcttctctgg tagcggttcc gggacggatt tcactctgac catcagcagt         300
ctgcagccgg aagacttcgc aacttattac tgtcagcaac attatactac         350
tcctcccacg ttcggacagg gtaccaaggt ggagatcaaa cgaactgtgg         400
```

```
ctgcaccatc tgtcttcatc ttcccgccat ctgatgagca gttgaaatct        450
ggaactgcct ctgttgtgtg cctgctgaat aacttctatc ccagagaggc        500
caaagtacag tggaaggtgg ataacgccct ccaatcgggt aactcccagg        550
agagtgtcac agagcaggac agcaaggaca gcacctacag cctcagcagc        600
accctgacgc tgagcaaagc agactacgag aaacacaaag tctacgcctg        650
cgaagtcacc catcagggcc tgagctcgcc cgtcacaaag agcttcaaca        700
ggggagagtg tggtgccagc tccggtatgg ctgatccgaa ccgtttccgc        750
ggtaaggacc tggcataact cgaggctgat cctctacgcc ggacgcatcg        800
tggccctagt acgcaagttc acgtaaaaag ggtaactaga ggttgaggtg        850
attttatgaa aaagaatatc gcatttcttc ttgcatctat gttcgttttt        900
tctattgcta caaacgcgta cgctgaggtt cagctggtgg agtctggcgg        950
tggcctggtg cagccagggg gctcactccg tttgtcctgt gcagcttctg       1000
gcttcaccat tagtggttct tggatacact gggtgcgtca ggccccgggt       1050
aagggcctgg aatgggttgc ttggattgct ccttatagcg gcgctactga       1100
ctatgccgat agcgtcaagg gccgtttcac tataagcgca gacacatcca       1150
aaaacacagc ctacctacaa atgaacagct taagagctga ggacactgcc       1200
gtctattatt gtgcaagaga gggggcttg tactgggtgt tcgactactg       1250
gggtcaagga acactagtca ccgtctcctc ggcctccacc aagggcccat       1300
cggtcttccc cctggcaccc tcctccaaga gcacctctgg gggcacagcg       1350
gccctgggct gcctggtcaa ggactacttc cccgaaccgg tgacggtgtc       1400
gtggaactca ggcgccctga ccagcggcgt gcacaccttc ccggctgtcc       1450
tacagtcctc aggactctac tccctcagca gcgtggtgac cgtgccctcc       1500
agcagcttgg gcacccagac ctacatctgc aacgtgaatc acaagcccag       1550
caacaccaag gtcgacaaga agttgagcc caaatcttgt gacaaaactc       1600
acctcagtgg cggtggctct ggttccggtg attttgatta tgaaaagatg       1650
gcaaacgcta ataaggggc tatgaccgaa aatgccgatg aaaacgcgct       1700
acagtctgac gctaaaggca aacttgattc tgtcgctact gattacggtg       1750
ctgctatcga tggtttcatt ggtgacgttt ccggccttgc taatggtaat       1800
ggtgctactg gtgattttgc tggctctaat tcccaaatgg ctcaagtcgg       1850
tgacggtgat aattcacctt taatgaataa tttccgtcaa tatttacctt       1900
ccctccctca atcggttgaa tgtcgccctt tgtctttag cgctggtaaa       1950
ccatatgaat tttctattga ttgtgacaaa ataaacttat tccgtggtgt       2000
cttttgcgttt ctttatatg ttgccacctt tatgtatgta ttttctacgt       2050
ttgctaacat actgcgtaat aaggagtctt aa                          2082
```

<210> SEQ ID NO 95
<211> LENGTH: 255
<212> TYPE: PRT
<213> ORGANISM: Artificial sequence
<220> FEATURE:
<223> OTHER INFORMATION: sequence is synthesized

<400> SEQUENCE: 95

```
Met Lys Lys Asn Ile Ala Phe Leu Leu Ala Ser Met Phe Val Phe
  1               5                  10                  15

Ser Ile Ala Thr Asn Ala Tyr Ala Asp Ile Gln Met Thr Gln Ser
                 20                  25                  30

Pro Ser Ser Leu Ser Ala Ser Val Gly Asp Arg Val Thr Ile Thr
                 35                  40                  45

Cys Arg Ala Ser Gln Asp Val Ser Thr Ala Val Ala Trp Tyr Gln
                 50                  55                  60

Gln Lys Pro Gly Lys Ala Pro Lys Leu Leu Ile Tyr Ser Ala Ser
                 65                  70                  75

Phe Leu Tyr Ser Gly Val Pro Ser Arg Phe Ser Gly Ser Gly Ser
                 80                  85                  90

Gly Thr Asp Phe Thr Leu Thr Ile Ser Ser Leu Gln Pro Glu Asp
                 95                 100                 105

Phe Ala Thr Tyr Tyr Cys Gln Gln His Tyr Thr Thr Pro Pro Thr
                110                 115                 120

Phe Gly Gln Gly Thr Lys Val Glu Ile Lys Arg Thr Val Ala Ala
                125                 130                 135

Pro Ser Val Phe Ile Phe Pro Pro Ser Asp Glu Gln Leu Lys Ser
                140                 145                 150

Gly Thr Ala Ser Val Val Cys Leu Leu Asn Asn Phe Tyr Pro Arg
                155                 160                 165

Glu Ala Lys Val Gln Trp Lys Val Asp Asn Ala Leu Gln Ser Gly
                170                 175                 180

Asn Ser Gln Glu Ser Val Thr Glu Gln Asp Ser Lys Asp Ser Thr
                185                 190                 195

Tyr Ser Leu Ser Ser Thr Leu Thr Leu Ser Lys Ala Asp Tyr Glu
                200                 205                 210

Lys His Lys Val Tyr Ala Cys Glu Val Thr His Gln Gly Leu Ser
                215                 220                 225

Ser Pro Val Thr Lys Ser Phe Asn Arg Gly Glu Cys Gly Ala Ser
                230                 235                 240

Ser Gly Met Ala Asp Pro Asn Arg Phe Arg Gly Lys Asp Leu Ala
                245                 250                 255

<210> SEQ ID NO 96
<211> LENGTH: 405
<212> TYPE: PRT
<213> ORGANISM: Artificial sequence
<220> FEATURE:
<223> OTHER INFORMATION: sequence is synthesized

<400> SEQUENCE: 96

Met Lys Lys Asn Ile Ala Phe Leu Leu Ala Ser Met Phe Val Phe
  1               5                  10                  15

Ser Ile Ala Thr Asn Ala Tyr Ala Glu Val Gln Leu Val Glu Ser
                 20                  25                  30

Gly Gly Gly Leu Val Gln Pro Gly Gly Ser Leu Arg Leu Ser Cys
                 35                  40                  45

Ala Ala Ser Gly Phe Thr Ile Ser Asn Tyr Gly Ile His Trp Val
                 50                  55                  60

Arg Gln Ala Pro Gly Lys Gly Leu Glu Trp Val Gly Arg Ile Ser
                 65                  70                  75

Pro Ser Asn Gly Ser Thr Tyr Tyr Ala Asp Ser Val Lys Gly Arg
                 80                  85                  90
```

```
Phe Thr Ile Ser Ala Asp Thr Ser Lys Asn Thr Ala Tyr Leu Gln
                    95                  100                 105

Met Asn Ser Leu Arg Ala Glu Asp Thr Ala Val Tyr Tyr Cys Ala
            110                 115                 120

Lys Cys Ser Val Arg Phe Ala Tyr Trp Gly Gln Gly Thr Leu Val
            125                 130                 135

Thr Val Ser Ser Ala Ser Thr Lys Gly Pro Ser Val Phe Pro Leu
            140                 145                 150

Ala Pro Ser Ser Lys Ser Thr Ser Gly Gly Thr Ala Ala Leu Gly
            155                 160                 165

Cys Leu Val Lys Asp Tyr Phe Pro Glu Pro Val Thr Val Ser Trp
            170                 175                 180

Asn Ser Gly Ala Leu Thr Ser Gly Val His Thr Phe Pro Ala Val
            185                 190                 195

Leu Gln Ser Ser Gly Leu Tyr Ser Leu Ser Ser Val Val Thr Val
            200                 205                 210

Pro Ser Ser Ser Leu Gly Thr Gln Thr Tyr Ile Cys Asn Val Asn
            215                 220                 225

His Lys Pro Ser Asn Thr Lys Val Asp Lys Val Glu Pro Lys
            230                 235                 240

Ser Cys Asp Lys Thr His Leu Ser Gly Gly Ser Gly Ser Gly
            245                 250                 255

Asp Phe Asp Tyr Glu Lys Met Ala Asn Ala Asn Lys Gly Ala Met
            260                 265                 270

Thr Glu Asn Ala Asp Glu Asn Ala Leu Gln Ser Asp Ala Lys Gly
            275                 280                 285

Lys Leu Asp Ser Val Ala Thr Asp Tyr Gly Ala Ala Ile Asp Gly
            290                 295                 300

Phe Ile Gly Asp Val Ser Gly Leu Ala Asn Gly Asn Gly Ala Thr
            305                 310                 315

Gly Asp Phe Ala Gly Ser Asn Ser Gln Met Ala Gln Val Gly Asp
            320                 325                 330

Gly Asp Asn Ser Pro Leu Met Asn Asn Phe Arg Gln Tyr Leu Pro
            335                 340                 345

Ser Leu Pro Gln Ser Val Glu Cys Arg Pro Phe Val Phe Ser Ala
            350                 355                 360

Gly Lys Pro Tyr Glu Phe Ser Ile Asp Cys Asp Lys Ile Asn Leu
            365                 370                 375

Phe Arg Gly Val Phe Ala Phe Leu Leu Tyr Val Ala Thr Phe Met
            380                 385                 390

Tyr Val Phe Ser Thr Phe Ala Asn Ile Leu Arg Asn Lys Glu Ser
            395                 400                 405

<210> SEQ ID NO 97
<211> LENGTH: 2073
<212> TYPE: DNA
<213> ORGANISM: Artificial sequence
<220> FEATURE:
<223> OTHER INFORMATION: sequence is synthesized

<400> SEQUENCE: 97
atgaaaaaga atatcgcatt tcttcttgca tctatgttcg tttttttctat        50 tgctacaaat gcctatgcag atatccagat gacccagtcc ccgagctccc       100
tgtccgcctc tgtgggcgat agggtcacca tcacctgccg tgccagtcag       150
```

| | |
|---|---|
| gatgtgtcca ctgctgtagc ctggtatcaa cagaaaccag gaaaagctcc | 200 |
| gaagcttctg atttactcgg catccttcct ctactctgga gtcccttctc | 250 |
| gcttctctgg tagcggttcc gggacggatt tcactctgac catcagcagt | 300 |
| ctgcagccgg aagacttcgc aacttattac tgtcagcaac attatactac | 350 |
| tcctcccacg ttcggacagg gtaccaaggt ggagatcaaa cgaactgtgg | 400 |
| ctgcaccatc tgtcttcatc ttcccgccat ctgatgagca gttgaaatct | 450 |
| ggaactgcct ctgttgtgtg cctgctgaat aacttctatc ccagagaggc | 500 |
| caaagtacag tggaaggtgg ataacgccct ccaatcgggt aactcccagg | 550 |
| agagtgtcac agagcaggac agcaaggaca gcacctacag cctcagcagc | 600 |
| accctgacgc tgagcaaagc agactacgag aaacacaaag tctacgcctg | 650 |
| cgaagtcacc catcagggcc tgagctcgcc cgtcacaaag agcttcaaca | 700 |
| ggggagagtg tggtgccagc tccggtatgg ctgatccgaa ccgtttccgc | 750 |
| ggtaaggacc tggcataact cgaggctgat cctctacgcc ggacgcatcg | 800 |
| tggccctagt acgcaagttc acgtaaaaag ggtaactaga ggttgaggtg | 850 |
| attttatgaa aaagaatatc gcatttcttc ttgcatctat gttcgttttt | 900 |
| tctattgcta caaacgcgta cgctgaggtt cagctggtgg agtctggcgg | 950 |
| tggcctggtg cagccagggg gctcactccg tttgtcctgt gcagcttctg | 1000 |
| gcttcaccat tagtaattat gggatacact gggtgcgtca ggccccgggt | 1050 |
| aagggcctgg aatgggttgg taggatttct ccttctaacg gctctactta | 1100 |
| ctatgccgat agcgtcaagg gccgtttcac tataagcgca gacacatcca | 1150 |
| aaaacacagc ctacctacaa atgaacagct taagagctga ggacactgcc | 1200 |
| gtctattatt gtgcaaaatg ctcggtcagg ttcgcttact ggggtcaagg | 1250 |
| aacactagtc accgtctcct cggcctccac caagggccca tcggtcttcc | 1300 |
| ccctggcacc ctcctccaag agcacctctg ggggcacagc ggccctgggc | 1350 |
| tgcctggtca aggactactt ccccgaaccg gtgacggtgt cgtggaactc | 1400 |
| aggcgccctg accagcggcg tgcacacctt cccggctgtc ctacagtcct | 1450 |
| caggactcta ctccctcagc agcgtggtga ccgtgccctc cagcagcttg | 1500 |
| ggcacccaga cctacatctg caacgtgaat cacaagccca gcaacaccaa | 1550 |
| ggtcgacaag aaagttgagc ccaaatcttg tgacaaaact cacctcagtg | 1600 |
| gcggtggctc tggttccggt gattttgatt atgaaaagat ggcaaacgct | 1650 |
| aataagggggg ctatgaccga aaatgccgat gaaaacgcgc tacagtctga | 1700 |
| cgctaaaggc aaacttgatt ctgtcgctac tgattacggt gctgctatcg | 1750 |
| atggtttcat tggtgacgtt tccggccttg ctaatggtaa tggtgctact | 1800 |
| ggtgattttg ctggctctaa ttcccaaatg gctcaagtcg gtgacggtga | 1850 |
| taattcacct ttaatgaata atttccgtca atatttacct tccctccctc | 1900 |
| aatcggttga atgtcgccct tttgtctttta gcgctggtaa accatatgaa | 1950 |
| ttttctattg attgtgacaa aataaactta ttccgtggtg tctttgcgtt | 2000 |
| tcttttatat gttgccacct ttatgtatgt atttttctacg tttgctaaca | 2050 |
| tactgcgtaa taaggagtct taa | 2073 |

<210> SEQ ID NO 98
<211> LENGTH: 256
<212> TYPE: PRT
<213> ORGANISM: Artificial sequence
<220> FEATURE:
<223> OTHER INFORMATION: sequence is synthesized

<400> SEQUENCE: 98

Met Lys Lys Asn Ile Ala Phe Leu Leu Ala Ser Met Phe Val Phe
1               5                   10                  15

Ser Ile Ala Thr Asn Ala Tyr Ala Ser Asp Ile Gln Met Thr Gln
                20                  25                  30

Ser Pro Ser Ser Leu Ser Ala Ser Val Gly Asp Arg Val Thr Ile
                35                  40                  45

Thr Cys Arg Ala Ser Gln Asp Val Ser Thr Ala Val Ala Trp Tyr
            50                  55                  60

Gln Gln Lys Pro Gly Lys Ala Pro Lys Leu Leu Ile Tyr Ser Ala
65                  70                  75

Ser Phe Leu Tyr Ser Gly Val Pro Ser Arg Phe Ser Gly Ser Gly
                80                  85                  90

Ser Gly Thr Asp Phe Thr Leu Thr Ile Ser Ser Leu Gln Pro Glu
                95                  100                 105

Asp Phe Ala Thr Tyr Tyr Cys Gln Gln Ser Tyr Thr Thr Pro Pro
                110                 115                 120

Thr Phe Gly Gln Gly Thr Lys Val Glu Ile Lys Arg Thr Val Ala
                125                 130                 135

Ala Pro Ser Val Phe Ile Phe Pro Pro Ser Asp Glu Gln Leu Lys
                140                 145                 150

Ser Gly Thr Ala Ser Val Val Cys Leu Leu Asn Asn Phe Tyr Pro
                155                 160                 165

Arg Glu Ala Lys Val Gln Trp Lys Val Asp Asn Ala Leu Gln Ser
                170                 175                 180

Gly Asn Ser Gln Glu Ser Val Thr Glu Gln Asp Ser Lys Asp Ser
                185                 190                 195

Thr Tyr Ser Leu Ser Ser Thr Leu Thr Leu Ser Lys Ala Asp Tyr
                200                 205                 210

Glu Lys His Lys Val Tyr Ala Cys Glu Val Thr His Gln Gly Leu
                215                 220                 225

Ser Ser Pro Val Thr Lys Ser Phe Asn Arg Gly Glu Cys Gly Ala
                230                 235                 240

Ser Ser Gly Met Ala Asp Pro Asn Arg Phe Arg Gly Lys Asp Leu
                245                 250                 255

Ala

<210> SEQ ID NO 99
<211> LENGTH: 444
<212> TYPE: PRT
<213> ORGANISM: Artificial sequence
<220> FEATURE:
<223> OTHER INFORMATION: sequence is synthesized

<400> SEQUENCE: 99

Met Lys Lys Asn Ile Ala Phe Leu Leu Ala Ser Met Phe Val Phe
1               5                   10                  15

Ser Ile Ala Thr Asn Ala Tyr Ala Glu Val Gln Leu Val Glu Ser
                20                  25                  30

Gly Gly Gly Leu Val Gln Pro Gly Gly Ser Leu Arg Leu Ser Cys

-continued

|  | 35 |  |  |  | 40 |  |  |  | 45 |  |
|---|---|---|---|---|---|---|---|---|---|---|
| Ala | Ala | Ser | Gly | Phe | Thr | Ile | Ser | Gly | Ser | Asp | Ile | His | Trp | Val |

Ala Ala Ser Gly Phe Thr Ile Ser Gly Ser Asp Ile His Trp Val
                    50                      55                      60

Arg Gln Ala Pro Gly Lys Gly Leu Glu Trp Val Gly Arg Ile Ser
                    65                      70                      75

Pro Tyr Gly Gly Asn Thr Asn Tyr Ala Asp Ser Val Lys Gly Arg
                    80                      85                      90

Phe Thr Ile Ser Ala Asp Thr Ser Lys Asn Thr Ala Tyr Leu Gln
                    95                     100                     105

Met Asn Ser Leu Arg Ala Glu Asp Thr Ala Val Tyr Tyr Cys Ala
                   110                     115                     120

Arg Val Gly Gly Leu Lys Leu Leu Phe Asp Tyr Trp Gly Gln Gly
                   125                     130                     135

Thr Leu Val Thr Val Ser Ser Ala Ser Thr Lys Gly Pro Ser Val
                   140                     145                     150

Phe Pro Leu Ala Pro Ser Ser Lys Ser Thr Ser Gly Gly Thr Ala
                   155                     160                     165

Ala Leu Gly Cys Leu Val Lys Asp Tyr Phe Pro Glu Pro Val Thr
                   170                     175                     180

Val Ser Trp Asn Ser Gly Ala Leu Thr Ser Gly Val His Thr Phe
                   185                     190                     195

Pro Ala Val Leu Gln Ser Ser Gly Leu Tyr Ser Leu Ser Ser Val
                   200                     205                     210

Val Thr Val Pro Ser Ser Ser Leu Gly Thr Gln Thr Tyr Ile Cys
                   215                     220                     225

Asn Val Asn His Lys Pro Ser Asn Thr Lys Val Asp Lys Lys Val
                   230                     235                     240

Glu Pro Lys Ser Cys Asp Lys Thr His Gly Arg Met Lys Gln Leu
                   245                     250                     255

Glu Asp Lys Val Glu Glu Leu Leu Ser Lys Asn Tyr His Leu Glu
                   260                     265                     270

Asn Glu Val Ala Arg Leu Lys Lys Leu Val Gly Glu Arg Gly Lys
                   275                     280                     285

Leu Ser Gly Gly Gly Ser Gly Ser Gly Asp Phe Asp Tyr Glu Lys
                   290                     295                     300

Met Ala Asn Ala Asn Lys Gly Ala Met Thr Glu Asn Ala Asp Glu
                   305                     310                     315

Asn Ala Leu Gln Ser Asp Ala Lys Gly Lys Leu Asp Ser Val Ala
                   320                     325                     330

Thr Asp Tyr Gly Ala Ala Ile Asp Gly Phe Ile Gly Asp Val Ser
                   335                     340                     345

Gly Leu Ala Asn Gly Asn Gly Ala Thr Gly Asp Phe Ala Gly Ser
                   350                     355                     360

Asn Ser Gln Met Ala Gln Val Gly Asp Gly Asp Asn Ser Pro Leu
                   365                     370                     375

Met Asn Asn Phe Arg Gln Tyr Leu Pro Ser Leu Pro Gln Ser Val
                   380                     385                     390

Glu Cys Arg Pro Phe Val Phe Ser Ala Gly Lys Pro Tyr Glu Phe
                   395                     400                     405

Ser Ile Asp Cys Asp Lys Ile Asn Leu Phe Arg Gly Val Phe Ala
                   410                     415                     420

Phe Leu Leu Tyr Val Ala Thr Phe Met Tyr Val Phe Ser Thr Phe
                   425                     430                     435

Ala Asn Ile Leu Arg Asn Lys Glu Ser
            440

<210> SEQ ID NO 100
<211> LENGTH: 2193
<212> TYPE: DNA
<213> ORGANISM: Artificial sequence
<220> FEATURE:
<223> OTHER INFORMATION: sequence is synthesized

<400> SEQUENCE: 100

| | |
|---|---|
| atgaaaaaga atatcgcatt tcttcttgca tctatgttcg ttttttctat | 50 |
| tgctacaaat gcctatgcat ccgatatcca gatgacccag tccccgagct | 100 |
| ccctgtccgc ctctgtgggc gatagggtca ccatcacctg ccgtgccagt | 150 |
| caggatgtgt ccactgctgt agcctggtat aacagaaac aggaaaagc | 200 |
| tccgaagctt ctgatttact cggcatcctt cctctactct ggagtccctt | 250 |
| ctcgcttctc tggtagcggt tccgggacgg atttcactct gaccatcagc | 300 |
| agtctgcagc cggaagactt cgcaacttat tactgtcagc aatcttatac | 350 |
| tactcctccc acgttcggac agggtaccaa ggtggagatc aaacgaactg | 400 |
| tggctgcacc atctgtcttc atcttcccgc catctgatga gcagttgaaa | 450 |
| tctggaactg cctctgttgt gtgcctgctg aataacttct atcccagaga | 500 |
| ggccaaagta cagtggaagg tggataacgc cctccaatcg ggtaactccc | 550 |
| aggagagtgt cacagagcag gacagcaagg acagcaccta cagcctcagc | 600 |
| agcaccctga cgctgagcaa agcagactac gagaaacaca agtctacgc | 650 |
| ctgcgaagtc acccatcagg gcctgagctc gcccgtcaca aagagcttca | 700 |
| acaggggaga gtgtggtgcc agctccggta tggctgatcc gaaccgtttc | 750 |
| cgcggtaagg acctggcata actcgaggct gatcctctac gccggacgca | 800 |
| tcgtggccct agtacgcaag ttcacgtaaa aagggtaact agaggttgag | 850 |
| gtgattttat gaaaaagaat atcgcatttc ttcttgcatc tatgttcgtt | 900 |
| ttttctattg ctacaaacgc gtacgctgag gttcagctgg tggagtctgg | 950 |
| cggtggcctg gtgcagccag ggggctcact ccgtttgtcc tgtgcagctt | 1000 |
| ctggcttcac cattagtggt tctgatatac actgggtgcg tcaggccccg | 1050 |
| ggtaagggcc tggaatgggt tggtaggatt ctccttatg gcggcaatac | 1100 |
| taactatgcc gatagcgtca agggccgttt cactataagc gcagacacat | 1150 |
| ccaaaaacac agcctaccta caaatgaaca gcttaagagc tgaggacact | 1200 |
| gccgtctatt attgtgcaag agtcggcggc ctcaagttgc tgttcgacta | 1250 |
| ctggggtcaa ggaacactag tcaccgtctc ctcggcctcc accaagggcc | 1300 |
| catcggtctt ccccctggca cctcctcca agagcacctc tgggggcaca | 1350 |
| gcggccctgg gctgcctggt caaggactac ttccccgaac cggtgacggt | 1400 |
| gtcgtggaac tcaggcgccc tgaccagcgg cgtgcacacc ttcccggctg | 1450 |
| tcctacagtc ctcaggactc tactccctca gcagcgtggt gaccgtgccc | 1500 |
| tccagcagct gggcaccca gacctacatc tgcaacgtga atcacaagcc | 1550 |
| cagcaacacc aaggtcgaca agaaagttga gcccaaatct tgtgacaaaa | 1600 |
| ctcacggccg catgaaacag ctagaggaca aggtcgaaga gctactctcc | 1650 |

|  |  |
|---|---|
| aagaactacc acctagagaa tgaagtggca agactcaaaa aacttgtcgg | 1700 |
| ggagcgcgga aagcttagtg gcggtggctc tggttccggt gattttgatt | 1750 |
| atgaaaagat ggcaaacgct aataagggggg ctatgaccga aaatgccgat | 1800 |
| gaaaacgcgc tacagtctga cgctaaaggc aaacttgatt ctgtcgctac | 1850 |
| tgattacggt gctgctatcg atggtttcat tggtgacgtt ccggccttg | 1900 |
| ctaatggtaa tggtgctact ggtgattttg ctggctctaa ttcccaaatg | 1950 |
| gctcaagtcg gtgacggtga taattcacct ttaatgaata atttccgtca | 2000 |
| atatttacct tccctccctc aatcggttga atgtcgccct tttgtcttta | 2050 |
| gcgctggtaa accatatgaa ttttctattg attgtgacaa ataaactta | 2100 |
| ttccgtggtg tctttgcgtt tctttttatat gttgccacct ttatgtatgt | 2150 |
| attttctacg tttgctaaca tactgcgtaa taaggagtct taa | 2193 |

<210> SEQ ID NO 101
<211> LENGTH: 256
<212> TYPE: PRT
<213> ORGANISM: Artificial sequence
<220> FEATURE:
<223> OTHER INFORMATION: sequence is synthesized

<400> SEQUENCE: 101

```
Met Lys Lys Asn Ile Ala Phe Leu Leu Ala Ser Met Phe Val Phe
 1               5                  10                  15

Ser Ile Ala Thr Asn Ala Tyr Ala Ser Asp Ile Gln Met Thr Gln
                20                  25                  30

Ser Pro Ser Ser Leu Ser Ala Ser Val Gly Asp Arg Val Thr Ile
                35                  40                  45

Thr Cys Arg Ala Ser Gln Asp Val Ser Thr Ala Val Ala Trp Tyr
                50                  55                  60

Gln Gln Lys Pro Gly Lys Ala Pro Lys Leu Leu Ile Tyr Ser Ala
                65                  70                  75

Ser Phe Leu Tyr Ser Gly Val Pro Ser Arg Phe Ser Gly Ser Gly
                80                  85                  90

Ser Gly Thr Asp Phe Thr Leu Thr Ile Ser Ser Leu Gln Pro Glu
                95                 100                 105

Asp Phe Ala Thr Tyr Tyr Cys Gln Gln Ser Tyr Thr Thr Pro Pro
               110                 115                 120

Thr Phe Gly Gln Gly Thr Lys Val Glu Ile Lys Arg Thr Val Ala
               125                 130                 135

Ala Pro Ser Val Phe Ile Phe Pro Pro Ser Asp Glu Gln Leu Lys
               140                 145                 150

Ser Gly Thr Ala Ser Val Val Cys Leu Leu Asn Asn Phe Tyr Pro
               155                 160                 165

Arg Glu Ala Lys Val Gln Trp Lys Val Asp Asn Ala Leu Gln Ser
               170                 175                 180

Gly Asn Ser Gln Glu Ser Val Thr Glu Gln Asp Ser Lys Asp Ser
               185                 190                 195

Thr Tyr Ser Leu Ser Ser Thr Leu Thr Leu Ser Lys Ala Asp Tyr
               200                 205                 210

Glu Lys His Lys Val Tyr Ala Cys Glu Val Thr His Gln Gly Leu
               215                 220                 225

Ser Ser Pro Val Thr Lys Ser Phe Asn Arg Gly Glu Cys Gly Ala
```

```
                      230                 235                 240
Ser Ser Gly Met Ala Asp Pro Asn Arg Phe Arg Gly Lys Asp Leu
                          245                 250                 255

Ala

<210> SEQ ID NO 102
<211> LENGTH: 445
<212> TYPE: PRT
<213> ORGANISM: Artificial sequence
<220> FEATURE:
<223> OTHER INFORMATION: sequence is synthesized

<400> SEQUENCE: 102

Met Lys Lys Asn Ile Ala Phe Leu Leu Ala Ser Met Phe Val Phe
  1               5                  10                  15

Ser Ile Ala Thr Asn Ala Tyr Ala Glu Val Gln Leu Val Glu Ser
                 20                  25                  30

Gly Gly Gly Leu Val Gln Pro Gly Gly Ser Leu Arg Leu Ser Cys
                 35                  40                  45

Ala Ala Ser Gly Phe Thr Ile Thr Asn Ser Asp Ile His Trp Val
                 50                  55                  60

Arg Gln Ala Pro Gly Lys Gly Leu Glu Trp Val Ala Thr Ile Tyr
                 65                  70                  75

Pro Tyr Gly Gly Tyr Thr Tyr Tyr Ala Asp Ser Val Lys Gly Arg
                 80                  85                  90

Phe Thr Ile Ser Ala Asp Thr Ser Lys Asn Thr Ala Tyr Leu Gln
                 95                 100                 105

Met Asn Ser Leu Arg Ala Glu Asp Thr Ala Val Tyr Tyr Cys Ala
                110                 115                 120

Arg Gly Gly Gly Met Asp Gly Tyr Val Met Asp Tyr Trp Gly Gln
                125                 130                 135

Gly Thr Leu Val Thr Val Ser Ser Ala Ser Thr Lys Gly Pro Ser
                140                 145                 150

Val Phe Pro Leu Ala Pro Ser Ser Lys Ser Thr Ser Gly Gly Thr
                155                 160                 165

Ala Ala Leu Gly Cys Leu Val Lys Asp Tyr Phe Pro Glu Pro Val
                170                 175                 180

Thr Val Ser Trp Asn Ser Gly Ala Leu Thr Ser Gly Val His Thr
                185                 190                 195

Phe Pro Ala Val Leu Gln Ser Ser Gly Leu Tyr Ser Leu Ser Ser
                200                 205                 210

Val Val Thr Val Pro Ser Ser Ser Leu Gly Thr Gln Thr Tyr Ile
                215                 220                 225

Cys Asn Val Asn His Lys Pro Ser Asn Thr Lys Val Asp Lys Lys
                230                 235                 240

Val Glu Pro Lys Ser Cys Asp Lys Thr His Gly Arg Met Lys Gln
                245                 250                 255

Leu Glu Asp Lys Val Glu Glu Leu Leu Ser Lys Asn Tyr His Leu
                260                 265                 270

Glu Asn Glu Val Ala Arg Leu Lys Lys Leu Val Gly Glu Arg Gly
                275                 280                 285

Lys Leu Ser Gly Gly Gly Ser Gly Ser Gly Asp Phe Asp Tyr Glu
                290                 295                 300

Lys Met Ala Asn Ala Asn Lys Gly Ala Met Thr Glu Asn Ala Asp
                305                 310                 315
```

```
Glu Asn Ala Leu Gln Ser Asp Ala Lys Gly Lys Leu Asp Ser Val
                320                 325                 330

Ala Thr Asp Tyr Gly Ala Ala Ile Asp Gly Phe Ile Gly Asp Val
            335                 340                 345

Ser Gly Leu Ala Asn Gly Asn Gly Ala Thr Gly Asp Phe Ala Gly
        350                 355                 360

Ser Asn Ser Gln Met Ala Gln Val Gly Asp Gly Asp Asn Ser Pro
    365                 370                 375

Leu Met Asn Asn Phe Arg Gln Tyr Leu Pro Ser Leu Pro Gln Ser
                380                 385                 390

Val Glu Cys Arg Pro Phe Val Phe Ser Ala Gly Lys Pro Tyr Glu
            395                 400                 405

Phe Ser Ile Asp Cys Asp Lys Ile Asn Leu Phe Arg Gly Val Phe
        410                 415                 420

Ala Phe Leu Leu Tyr Val Ala Thr Phe Met Tyr Val Phe Ser Thr
    425                 430                 435

Phe Ala Asn Ile Leu Arg Asn Lys Glu Ser
                440                 445

<210> SEQ ID NO 103
<211> LENGTH: 2196
<212> TYPE: DNA
<213> ORGANISM: Artificial sequence
<220> FEATURE:
<223> OTHER INFORMATION: sequence is synthesized

<400> SEQUENCE: 103
atgaaaaaga atatcgcatt tcttcttgca tctatgttcg ttttttctat          50
tgctacaaat gcctatgcat ccgatatcca gatgacccag tccccgagct         100
ccctgtccgc ctctgtgggc gatagggtca ccatcacctg ccgtgccagt         150
caggatgtgt ccactgctgt agcctggtat caacagaaac aggaaaaagc         200
tccgaagctt ctgatttact cggcatcctt cctctactct ggagtccctt         250
ctcgcttctc tggtagcggt tccgggacgg atttcactct gaccatcagc         300
agtctgcagc cggaagactt cgcaacttat tactgtcagc aatcttatac         350
tactcctccc acgttcggac agggtaccaa ggtggagatc aaacgaactg         400
tggctgcacc atctgtcttc atcttcccgc catctgatga gcagttgaaa         450
tctggaactg cctctgttgt gtgcctgctg aataacttct atcccagaga         500
ggccaaagta cagtggaagg tggataacgc cctccaatcg ggtaactccc         550
aggagagtgt cacagagcag gacagcaagg acagcaccta cagcctcagc         600
agcaccctga cgctgagcaa agcagactac gagaaacaca agtctacgc          650 ctgcgaagtc acccatcagg gcctgagctc gcccgtcaca aagagcttca         700
acaggggaga gtgtggtgcc agctccggta tggctgatcc gaaccgtttc         750
cgcggtaagg acctggcata actcgaggct gatcctctac gccggacgca         800
tcgtggccct agtacgcaag ttcacgtaaa aagggtaact agaggttgag         850
gtgattttat gaaaagaat atcgcatttc ttcttgcatc tatgttcgtt          900
ttttctattg ctacaaacgc gtacgctgag gttcagctgg tggagtctgg         950
cggtggcctg gtgcagccag ggggctcact ccgtttgtcc tgtgcagctt        1000
ctggcttcac cattactaat tccgatatac actgggtgcg tcaggccccg        1050
```

```
ggtaagggcc tggaatgggt tgctactatt tatccttatg gcggctatac      1100
ttactatgcc gatagcgtca agggccgttt cactataagc gcagacacat      1150
ccaaaaacac agcctaccta caaatgaaca gcttaagagc tgaggacact      1200
gccgtctatt attgtgcaag agggggcggg atggacggct acgttatgga      1250
ctactgggggc aaggaacac tagtcaccgt ctcctcggcc tccaccaagg      1300
gcccatcggt cttccccctg caccctcct ccaagagcac ctctgggggc       1350
acagcggccc tgggctgcct ggtcaaggac tacttccccg aaccggtgac      1400
ggtgtcgtgg aactcaggcg ccctgaccag cggcgtgcac accttcccgg      1450
ctgtcctaca gtcctcagga ctctactccc tcagcagcgt ggtgaccgtg      1500
ccctccagca gcttgggcac ccagacctac atctgcaacg tgaatcacaa      1550
gcccagcaac accaaggtcg acaagaaagt tgagcccaaa tcttgtgaca      1600
aaactcacgg ccgcatgaaa cagctagagg acaaggtcga agagctactc      1650
tccaagaact accacctaga gaatgaagtg caagactca aaaaacttgt       1700
cggggagcgc ggaaagctta gtggcggtgg ctctggttcc ggtgattttg      1750
attatgaaaa gatggcaaac gctaataagg gggctatgac cgaaaatgcc      1800
gatgaaaacg cgctacagtc tgacgctaaa ggcaaacttg attctgtcgc      1850
tactgattac ggtgctgcta tcgatggttt cattggtgac gtttccggcc      1900
ttgctaatgg taatggtgct actggtgatt ttgctggctc taattcccaa      1950
atggctcaag tcggtgacgg tgataattca cctttaatga ataatttccg      2000
tcaatattta ccttccctcc ctcaatcggt tgaatgtcgc ccttttgtct      2050
ttagcgctgg taaaccatat gaattttcta ttgattgtga caaataaac       2100
ttattccgtg gtgtctttgc gtttctttta tatgttgcca cctttatgta      2150
tgtattttct acgtttgcta acatactgcg taataaggag tcttaa          2196
```

<210> SEQ ID NO 104
<211> LENGTH: 256
<212> TYPE: PRT
<213> ORGANISM: Artificial sequence
<220> FEATURE:
<223> OTHER INFORMATION: sequence is synthesized

<400> SEQUENCE: 104

```
Met Lys Lys Asn Ile Ala Phe Leu Leu Ala Ser Met Phe Val Phe
 1               5                  10                  15

Ser Ile Ala Thr Asn Ala Tyr Ala Ser Asp Ile Gln Met Thr Gln
                20                  25                  30

Ser Pro Ser Ser Leu Ser Ala Ser Val Gly Asp Arg Val Thr Ile
                35                  40                  45

Thr Cys Arg Ala Ser Gln Asp Val Ser Thr Ala Val Ala Trp Tyr
                50                  55                  60

Gln Gln Lys Pro Gly Lys Ala Pro Lys Leu Leu Ile Tyr Ser Ala
                65                  70                  75

Ser Phe Leu Tyr Ser Gly Val Pro Ser Arg Phe Ser Gly Ser Gly
                80                  85                  90

Ser Gly Thr Asp Phe Thr Leu Thr Ile Ser Ser Leu Gln Pro Glu
                95                 100                 105

Asp Phe Ala Thr Tyr Tyr Cys Gln Gln Ser Tyr Thr Thr Pro Pro
```

```
                       110                 115                 120
Thr Phe Gly Gln Gly Thr Lys Val Glu Ile Lys Arg Thr Val Ala
                   125                 130                 135

Ala Pro Ser Val Phe Ile Phe Pro Pro Ser Asp Glu Gln Leu Lys
                   140                 145                 150

Ser Gly Thr Ala Ser Val Val Cys Leu Leu Asn Asn Phe Tyr Pro
                   155                 160                 165

Arg Glu Ala Lys Val Gln Trp Lys Val Asp Asn Ala Leu Gln Ser
                   170                 175                 180

Gly Asn Ser Gln Glu Ser Val Thr Glu Gln Asp Ser Lys Asp Ser
                   185                 190                 195

Thr Tyr Ser Leu Ser Ser Thr Leu Thr Leu Ser Lys Ala Asp Tyr
                   200                 205                 210

Glu Lys His Lys Val Tyr Ala Cys Glu Val Thr His Gln Gly Leu
                   215                 220                 225

Ser Ser Pro Val Thr Lys Ser Phe Asn Arg Gly Glu Cys Gly Ala
                   230                 235                 240

Ser Ser Gly Met Ala Asp Pro Asn Arg Phe Arg Gly Lys Asp Leu
                   245                 250                 255

Ala

<210> SEQ ID NO 105
<211> LENGTH: 445
<212> TYPE: PRT
<213> ORGANISM: Artificial sequence
<220> FEATURE:
<223> OTHER INFORMATION: sequence is synthesized

<400> SEQUENCE: 105

Met Lys Lys Asn Ile Ala Phe Leu Leu Ala Ser Met Phe Val Phe
  1               5                  10                  15

Ser Ile Ala Thr Asn Ala Tyr Ala Glu Val Gln Leu Val Glu Ser
                 20                  25                  30

Gly Gly Gly Leu Val Gln Pro Gly Gly Ser Leu Arg Leu Ser Cys
                 35                  40                  45

Ala Ala Ser Gly Phe Thr Ile Asn Asn Tyr Asp Ile His Trp Val
                 50                  55                  60

Arg Gln Ala Pro Gly Lys Gly Leu Glu Trp Val Gly Tyr Ile Ser
                 65                  70                  75

Pro Pro Ser Gly Ala Thr Tyr Tyr Ala Asp Ser Val Lys Gly Arg
                 80                  85                  90

Phe Thr Ile Ser Ala Asp Thr Ser Lys Asn Thr Ala Tyr Leu Gln
                 95                 100                 105

Met Asn Ser Leu Arg Ala Glu Asp Thr Ala Val Tyr Tyr Cys Ala
                110                 115                 120

Arg Met Val Gly Met Arg Arg Gly Val Met Asp Tyr Trp Gly Gln
                125                 130                 135

Gly Thr Leu Val Thr Val Ser Ser Ala Ser Thr Lys Gly Pro Ser
                140                 145                 150

Val Phe Pro Leu Ala Pro Ser Ser Lys Ser Thr Ser Gly Gly Thr
                155                 160                 165

Ala Ala Leu Gly Cys Leu Val Lys Asp Tyr Phe Pro Glu Pro Val
                170                 175                 180

Thr Val Ser Trp Asn Ser Gly Ala Leu Thr Ser Gly Val His Thr
                185                 190                 195
```

```
Phe Pro Ala Val Leu Gln Ser Ser Gly Leu Tyr Ser Leu Ser Ser
                200                 205                 210
Val Val Thr Val Pro Ser Ser Ser Leu Gly Thr Gln Thr Tyr Ile
            215                 220                 225
Cys Asn Val Asn His Lys Pro Ser Asn Thr Lys Val Asp Lys Lys
        230                 235                 240
Val Glu Pro Lys Ser Cys Asp Lys Thr His Gly Arg Met Lys Gln
    245                 250                 255
Leu Glu Asp Lys Val Glu Glu Leu Leu Ser Lys Asn Tyr His Leu
260                 265                 270
Glu Asn Glu Val Ala Arg Leu Lys Lys Leu Val Gly Glu Arg Gly
                275                 280                 285
Lys Leu Ser Gly Gly Gly Ser Gly Ser Gly Asp Phe Asp Tyr Glu
            290                 295                 300
Lys Met Ala Asn Ala Asn Lys Gly Ala Met Thr Glu Asn Ala Asp
        305                 310                 315
Glu Asn Ala Leu Gln Ser Asp Ala Lys Gly Lys Leu Asp Ser Val
    320                 325                 330
Ala Thr Asp Tyr Gly Ala Ala Ile Asp Gly Phe Ile Gly Asp Val
335                 340                 345
Ser Gly Leu Ala Asn Gly Asn Gly Ala Thr Gly Asp Phe Ala Gly
                350                 355                 360
Ser Asn Ser Gln Met Ala Gln Val Gly Asp Gly Asp Asn Ser Pro
            365                 370                 375
Leu Met Asn Asn Phe Arg Gln Tyr Leu Pro Ser Leu Pro Gln Ser
        380                 385                 390
Val Glu Cys Arg Pro Phe Val Phe Ser Ala Gly Lys Pro Tyr Glu
    395                 400                 405
Phe Ser Ile Asp Cys Asp Lys Ile Asn Leu Phe Arg Gly Val Phe
410                 415                 420
Ala Phe Leu Leu Tyr Val Ala Thr Phe Met Tyr Val Phe Ser Thr
                425                 430                 435
Phe Ala Asn Ile Leu Arg Asn Lys Glu Ser
            440                 445

<210> SEQ ID NO 106
<211> LENGTH: 2196
<212> TYPE: DNA
<213> ORGANISM: Artificial sequence
<220> FEATURE:
<223> OTHER INFORMATION: sequence is synthesized

<400> SEQUENCE: 106
atgaaaaaga atatcgcatt tcttcttgca tctatgttcg tttttttctat         50 tgctacaaat gcctatgcat ccgatatcca gatgacccag tccccgagct        100
ccctgtccgc ctctgtgggc gatagggtca ccatcacctg ccgtgccagt        150
caggatgtgt ccactgctgt agcctggtat aacagaaac caggaaaagc         200 tccgaagctt ctgatttact cggcatcctt cctctactct ggagtccctt        250
ctcgcttctc tggtagcggt tccgggacgg atttcactct gaccatcagc        300
agtctgcagc cggaagactt cgcaacttat tactgtcagc aatcttatac        350
tactcctccc acgttcggac agggtaccaa ggtggagatc aaacgaactg        400
tggctgcacc atctgtcttc atcttcccgc catctgatga gcagttgaaa        450
```

-continued

```
tctggaactg cctctgttgt gtgcctgctg aataacttct atcccagaga      500
ggccaaagta cagtggaagg tggataacgc cctccaatcg ggtaactccc      550
aggagagtgt cacagagcag gacagcaagg acagcaccta cagcctcagc      600
agcaccctga cgctgagcaa agcagactac gagaaacaca aagtctacgc      650
ctgcgaagtc acccatcagg gcctgagctc gcccgtcaca aagagcttca      700
acaggggaga gtgtggtgcc agctccggta tggctgatcc gaaccgtttc      750
cgcggtaagg acctggcata actcgaggct gatcctctac gccggacgca      800
tcgtggccct agtacgcaag ttcacgtaaa aagggtaact agaggttgag      850
gtgattttat gaaaaagaat atcgcatttc ttcttgcatc tatgttcgtt      900
ttttctattg ctacaaacgc gtacgctgag gttcagctgg tggagtctgg      950
cggtggcctg gtgcagccag ggggctcact ccgtttgtcc tgtgcagctt     1000
ctggcttcac cattaataat tatgatatac actgggtgcg tcaggccccg     1050
ggtaagggcc tggaatgggt tggttatatt tctcctccta gcggcgctac     1100
ttactatgcc gatagcgtca agggccgttt cactataagc gcagacacat     1150
ccaaaaacac agcctaccta caaatgaaca gcttaagagc tgaggacact     1200
gccgtctatt attgtgcaag aatggtcggc atgcggaggg gggttatgga     1250
ctactggggt caaggaacac tagtcaccgt ctcctcggcc tccaccaagg     1300
gcccatcggt cttccccctg gcaccctcct ccaagagcac ctctggggc      1350 acagcggccc tgggctgcct ggtcaaggac tacttccccg aaccggtgac     1400
ggtgtcgtgg aactcaggcg ccctgaccag cggcgtgcac accttcccgg     1450
ctgtcctaca gtcctcagga ctctactccc tcagcagcgt ggtgaccgtg     1500
ccctccagca gcttgggcac ccagacctac atctgcaacg tgaatcacaa     1550
gcccagcaac accaaggtcg acaagaaagt tgagcccaaa tcttgtgaca     1600
aaactcacgg ccgcatgaaa cagctagagg acaaggtcga agagctactc     1650
tccaagaact accacctaga gaatgaagtg gcaagactca aaaaacttgt     1700
cggggagcgc ggaaagctta gtggcggtgg ctctggttcc ggtgattttg     1750
attatgaaaa gatggcaaac gctaataagg gggctatgac cgaaaatgcc     1800
gatgaaaacg cgctacagtc tgacgctaaa ggcaaacttg attctgtcgc     1850
tactgattac ggtgctgcta tcgatggttt cattggtgac gtttccggcc     1900
ttgctaatgg taatggtgct actggtgatt ttgctggctc taattcccaa     1950
atggctcaag tcggtgacgg tgataattca cctttaatga ataatttccg     2000
tcaatattta ccttccctcc ctcaatcggt tgaatgtcgc ccttttgtct     2050
ttagcgctgg taaaccatat gaattttcta ttgattgtga caaaataaac     2100
ttattccgtg gtgtctttgc gtttcttttta tatgttgcca cctttatgta     2150 tgtatttct acgtttgcta acatactgcg taataaggag tcttaa        2196
```

<210> SEQ ID NO 107
<211> LENGTH: 255
<212> TYPE: PRT
<213> ORGANISM: Artificial sequence
<220> FEATURE:
<223> OTHER INFORMATION: sequence is synthesized

```
<400> SEQUENCE: 107

Met Lys Lys Asn Ile Ala Phe Leu Leu Ala Ser Met Phe Val Phe
 1               5                  10                  15

Ser Ile Ala Thr Asn Ala Tyr Ala Asp Ile Gln Met Thr Gln Ser
                20                  25                  30

Pro Ser Ser Leu Ser Ala Ser Val Gly Asp Arg Val Thr Ile Thr
                35                  40                  45

Cys Arg Ala Ser Gln Asp Val Ser Thr Ala Val Ala Trp Tyr Gln
                50                  55                  60

Gln Lys Pro Gly Lys Ala Pro Lys Leu Leu Ile Tyr Ser Ala Ser
                65                  70                  75

Phe Leu Tyr Ser Gly Val Pro Ser Arg Phe Ser Gly Ser Gly Ser
                80                  85                  90

Gly Thr Asp Phe Thr Leu Thr Ile Ser Ser Leu Gln Pro Glu Asp
                95                  100                 105

Phe Ala Thr Tyr Tyr Cys Gln Gln Ser Tyr Thr Thr Pro Pro Thr
                110                 115                 120

Phe Gly Gln Gly Thr Lys Val Glu Ile Lys Arg Thr Val Ala Ala
                125                 130                 135

Pro Ser Val Phe Ile Phe Pro Pro Ser Asp Glu Gln Leu Lys Ser
                140                 145                 150

Gly Thr Ala Ser Val Val Cys Leu Leu Asn Asn Phe Tyr Pro Arg
                155                 160                 165

Glu Ala Lys Val Gln Trp Lys Val Asp Asn Ala Leu Gln Ser Gly
                170                 175                 180

Asn Ser Gln Glu Ser Val Thr Glu Gln Asp Ser Lys Asp Ser Thr
                185                 190                 195

Tyr Ser Leu Ser Ser Thr Leu Thr Leu Ser Lys Ala Asp Tyr Glu
                200                 205                 210

Lys His Lys Val Tyr Ala Cys Glu Val Thr His Gln Gly Leu Ser
                215                 220                 225

Ser Pro Val Thr Lys Ser Phe Asn Arg Gly Glu Cys Gly Ala Ser
                230                 235                 240

Ser Gly Met Ala Asp Pro Asn Arg Phe Arg Gly Lys Asp Leu Ala
                245                 250                 255

<210> SEQ ID NO 108
<211> LENGTH: 250
<212> TYPE: PRT
<213> ORGANISM: Artificial sequence
<220> FEATURE:
<223> OTHER INFORMATION: sequence is synthesized

<400> SEQUENCE: 108

Met Lys Lys Asn Ile Ala Phe Leu Leu Ala Ser Met Phe Val Phe
 1               5                  10                  15

Ser Ile Ala Thr Asn Ala Tyr Ala Glu Val Gln Leu Val Glu Ser
                20                  25                  30

Gly Gly Gly Leu Val Gln Pro Gly Gly Ser Leu Arg Leu Ser Cys
                35                  40                  45

Ala Ala Ser Gly Phe Thr Ile Ser Gly Ser Trp Ile His Trp Val
                50                  55                  60

Arg Gln Ala Pro Gly Lys Gly Leu Glu Trp Val Ala Trp Ile Ala
                65                  70                  75

Pro Tyr Ser Gly Ala Thr Asp Tyr Ala Asp Ser Val Lys Gly Arg
```

```
                    80                  85                  90
Phe Thr Ile Ser Ala Asp Thr Ser Lys Asn Thr Ala Tyr Leu Gln
                95                 100                 105
Met Asn Ser Leu Arg Ala Glu Asp Thr Ala Val Tyr Tyr Cys Ala
               110                 115                 120
Arg Glu Gly Gly Leu Tyr Trp Val Phe Asp Tyr Trp Gly Gln Gly
               125                 130                 135
Thr Leu Val Thr Val Ser Ser Ala Ser Thr Lys Gly Pro Ser Val
               140                 145                 150
Phe Pro Leu Ala Pro Ser Ser Lys Ser Thr Ser Gly Gly Thr Ala
               155                 160                 165
Ala Leu Gly Cys Leu Val Lys Asp Tyr Phe Pro Glu Pro Val Thr
               170                 175                 180
Val Ser Trp Asn Ser Gly Ala Leu Thr Ser Gly Val His Thr Phe
               185                 190                 195
Pro Ala Val Leu Gln Ser Ser Gly Leu Tyr Ser Leu Ser Ser Val
               200                 205                 210
Val Thr Val Pro Ser Ser Ser Leu Gly Thr Gln Thr Tyr Ile Cys
               215                 220                 225
Asn Val Asn His Lys Pro Ser Asn Thr Lys Val Asp Lys Lys Val
               230                 235                 240
Glu Pro Lys Ser Cys Asp Lys Thr His Leu
               245                 250

<210> SEQ ID NO 109
<211> LENGTH: 6620
<212> TYPE: DNA
<213> ORGANISM: Artificial sequence
<220> FEATURE:
<223> OTHER INFORMATION: sequence is synthesized

<400> SEQUENCE: 109
gaattcaact tctccatact ttggataagg aaatacagac atgaaaaatc          50
tcattgctga gttgttattt aagcttgccc aaaaagaaga agagtcgaat         100
gaactgtgtg cgcaggtaga agctttggag attatcgtca ctgcaatgct         150
tcgcaatatg gcgcaaaatg accaacagcg gttgattgat caggtagagg         200
gggcgctgta cgaggtaaag cccgatgcca gcattcctga cgacgatacg         250
gagctgctgc gcgattacgt aaagaagtta ttgaagcatc ctcgtcagta         300
aaaagttaat cttttcaaca gctgtcataa agttgtcacg gccgagactt         350
atagtcgctt tgttttttatt ttttaatgta tttgtaacta gtacgcaagt        400
tcacgtaaaa agggtatgta gaggttgagg tgattttatg aaaaagaata         450
tcgcatttct tcttgcatct atgttcgttt tttctattgc tacaaatgcc         500
tatgcagata ccagatgac ccagtccccg agctccctgt ccgcctctgt          550
gggcgatagg gtcaccatca cctgccgtgc cagtcaggat gtgtccactg         600
ctgtagcctg gtatcaacag aaaccaggaa aagctccgaa gcttctgatt         650
tactcggcat ccttcctcta ctctggagtc ccttctcgct tctctggtag         700
cggttccggg acggatttca ctctgaccat cagcagtctg cagccggaag         750
acttcgcaac ttattactgt cagcaatctt atactactcc tcccacgttc         800
ggacagggta ccaaggtgga gatcaaacga actgtggctg caccatctgt         850
```

```
cttcatcttc cgccatctg atgagcagtt gaaatctgga actgcctctg          900
ttgtgtgcct gctgaataac ttctatccca gagaggccaa agtacagtgg          950
aaggtggata acgccctcca atcgggtaac tcccaggaga gtgtcacaga         1000
gcaggacagc aaggacagca cctacagcct cagcagcacc ctgacgctga         1050
gcaaagcaga ctacgagaaa cacaaagtct acgcctgcga agtcacccat         1100
cagggcctga gctcgcccgt cacaaagagc ttcaacaggg gagagtgtgg         1150
tgccagctcc ggtatggctg atccgaaccg tttccgcggt aaggacctgg         1200
cataactcga ggctgatcct ctacgccgga cgcatcgtgg ccctagtacg         1250
caagttcacg taaaagggt aactagaggt tgaggtgatt ttatgaaaaa         1300
gaatatcgca tttcttcttg catctatgtt cgttttttct attgctacaa         1350
acgcgtacgc tgaggttcag ctggtggagt ctggcggtgg cctggtgcag         1400 ccaggggct cactccgttt gtcctgtgca gcttctggct tcaccattag         1450
tggttcttgg atacactggg tgcgtcaggc cccgggtaag ggcctggaat         1500
gggttgcttg gattgctcct tatagcggcg ctactgacta tgccgatagc         1550
gtcaagggcc gtttcactat aagcgcagac acatccaaaa acacagccta         1600
cctacaaatg aacagcttaa gagctgagga cactgccgtc tattattgtg         1650
caagagaggg gggcttgtac tgggtgttcg actactgggg tcaaggaaca         1700
ctagtcaccg tctcctcggc ctccaccaag ggcccatcgg tcttccccct         1750
ggcaccctcc tccaagagca cctctggggg cacagcggcc ctgggctgcc         1800
tggtcaagga ctacttcccc gaaccggtga cggtgtcgtg gaactcaggc         1850
gccctgacca gcggcgtgca caccttcccg gctgtcctac agtcctcagg         1900
actctactcc ctcagcagcg tggtgaccgt gccctccagc agcttgggca         1950
cccagaccta catctgcaac gtgaatcaca agcccagcaa caccaaggtc         2000
gacaagaaag ttgagcccaa atcttgtgac aaaactcacc tctagagtgg         2050
cggtggctct ggttccggtg atgctcggtt gccgccgggc gttttttatg         2100
ctagcgccgc cctataccct tgtctgcctcc ccgcgttgcg tcgcggtgca         2150
tggagccggg ccacctcgac ctgaatggaa gccggcggca cctcgctaac         2200
ggattcacca ctccaagaat tggagccaat caattcttgc ggagaactgt         2250
gaatgcgcaa accaacccctt ggcagaacat atccatcgcg tccgccatct         2300
ccagcagccg cacgcggcgc atctcgggca gcgttgggtc ctggccacgg         2350
gtgcgcatga tcgtgctcct gtcgttgagg acccggctag gctggcgggg         2400
ttgccttact ggttagcaga atgaatcacc gatacgcgag cgaacgtgaa         2450
gcgactgctg ctgcaaaacg tctgcgacct gagcaacaac atgaatggtc         2500
ttcggtttcc gtgtttcgta aagtctggaa acgcggaagt cagcgccctg         2550
caccattatg ttccggatct gcatcgcagg atgctgctgg ctaccctgtg         2600
gaacacctac atctgtatta acgaagcgct ggcattgacc ctgagtgatt         2650
tttctctggt cccgccgcat ccataccgcc agttgtttac cctcacaacg         2700
ttccagtaac cggcatgtt catcatcagt aacccgtatc gtgagcatcc         2750
tctctcgttt catcggtatc attccccca tgaacagaaa ttccccctta         2800
cacggaggca tcaagtgacc aaacaggaaa aaaccgccct taacatggcc         2850
```

```
cgctttatca gaagccagac attaacgctt ctggagaaac tcaacgagct      2900
ggacgcggat gaacaggcag acatctgtga atcgcttcac gaccacgctg      2950
atgagcttta ccgcaggatc cggaaattgt aaacgttaat attttgttaa      3000
aattcgcgtt aaattttgt taaatcagct cattttttaa ccaataggcc       3050
gaaatcggca aaatcccta taaatcaaaa gaatagaccg atagggggtt       3100
gagtgttgtt ccagtttgga acaagagtcc actattaaag aacgtggact      3150
ccaacgtcaa agggcgaaaa accgtctatc agggctatgg cccactacgt      3200
gaaccatcac cctaatcaag ttttttgggg tcgaggtgcc gtaaagcact      3250
aaatcggaac cctaaaggga gcccccgatt tagagcttga cggggaaagc      3300
cggcgaacgt ggcgagaaag gaagggaaga agcgaaagg agcgggcgct       3350 agggcgctgg caagtgtagc ggtcacgctg cgcgtaacca ccacacccgc      3400
cgcgcttaat gcgccgctac agggcgcgtc cggatcctgc ctcgcgcgtt     3450
tcggtgatga cggtgaaaac ctctgacaca tgcagctccc ggagacggtc      3500
acagcttgtc tgtaagcgga tgccgggagc agacaagccc gtcagggcgc     3550
gtcagcgggt gttggcgggt gtcggggcgc agccatgacc cagtcacgta     3600
gcgatagcgg agtgtatact ggcttaacta tgcggcatca gagcagattg     3650
tactgagagt gcaccatatg cggtgtgaaa taccgcacag atgcgtaagg     3700
agaaaatacc gcatcaggcg ctcttccgct tcctcgctca ctgactcgct     3750
gcgctcggtc gttcggctgc ggcgagcggt atcagctcac tcaaaggcgg    3800
taatacggtt atccacagaa tcaggggata acgcaggaaa gaacatgtga     3850
gcaaaaggcc agcaaaaggc caggaaccgt aaaaaggccg cgttgctggc    3900 gttttttccat aggctccgcc ccctgacga gcatcacaaa aatcgacgct     3950
caagtcagag gtggcgaaac ccgacaggac tataaagata ccaggcgttt     4000 cccctggaa gctccctcgt gcgctctcct gttccgaccc tgccgcttac      4050
cggatacctg tccgcctttc tcccttcggg aagcgtggcg ctttctcata     4100
gctcacgctg taggtatctc agttcggtgt aggtcgttcg ctccaagctg     4150
ggctgtgtgc acgaaccccc cgttcagccc gaccgctgcg ccttatccgg     4200
taactatcgt cttgagtcca acccggtaag acacgactta tcgccactgg   4250
cagcagccac tggtaacagg attagcagag cgaggtatgt aggcggtgct    4300
acagagttct tgaagtggtg gcctaactac ggctacacta aaggacagt     4350 atttggtatc tgcgctctgc tgaagccagt taccttcgga aaaagagttg    4400
gtagctcttg atccggcaaa caaaccaccg ctggtagcgg tggttttttt   4450
gtttgcaagc agcagattac gcgcagaaaa aaaggatctc aagaagatcc    4500
tttgatcttt tctacggggt ctgacgctca gtggaacgaa aactcacgtt    4550
aagggatttt ggtcatgaga ttatcaaaaa ggatcttcac ctagatcctt    4600
ttaaattaaa aatgaagttt taaatcaatc taaagtatat atgagtaaac    4650
ttggtctgac agttaccaat gcttaatcag tgaggcacct atctcagcga   4700
tctgtctatt tcgttcatcc atagttgcct gactccccgt cgtgtagata    4750
actacgatac gggagggctt accatctggc cccagtgctg caatgatacc    4800
```

```
gcgagaccca cgctcaccgg ctccagattt atcagcaata aaccagccag      4850
ccggaagggc cgagcgcaga agtggtcctg caactttatc cgcctccatc      4900
cagtctatta attgttgccg ggaagctaga gtaagtagtt cgccagttaa      4950
tagtttgcgc aacgttgttg ccattgctgc aggcatcgtg gtgtcacgct      5000
cgtcgtttgg tatggcttca ttcagctccg gttcccaacg atcaaggcga      5050
gttacatgat cccccatgtt gtgcaaaaaa gcggttagct ccttcggtcc      5100
tccgatcgtt gtcagaagta agttggccgc agtgttatca ctcatggtta      5150
tggcagcact gcataattct cttactgtca tgccatccgt aagatgcttt      5200
tctgtgactg gtgagtactc aaccaagtca ttctgagaat agtgtatgcg      5250
gcgaccgagt tgctcttgcc cggcgtcaac acgggataat accgcgccac      5300
atagcagaac tttaaaagtg ctcatcattg gaaaacgttc ttcggggcga      5350
aaactctcaa ggatcttacc gctgttgaga tccagttcga tgtaacccac      5400
tcgtgcaccc aactgatctt cagcatcttt tactttcacc agcgtttctg      5450
ggtgagcaaa aacaggaagg caaaatgccg caaaaaaggg aataagggcg      5500
acacggaaat gttgaatact catactcttc ctttttcaat attattgaag      5550
catttatcag ggttattgtc tcatgagcgg atacatattt gaatgtatt      5600 agaaaaataa acaaataggg gttccgcgca catttccccg aaaagtgcca      5650
cctgacgtct aagaaaccat tattatcatg acattaacct ataaaaatag      5700
gcgtatcacg aggccctttc gtcttcaata caggtagacc tttcgtagag      5750
atgtacagtg aaatccccga aattatacac atgactgaag gaagggagct      5800
cgtcattccc tgccgggtta cgtcacctaa catcactgtt actttaaaaa      5850
agtttccact tgacactttg atccctgatg gaaaacgcat aatctgggac      5900
agtagaaagg gcttcatcat atcaaatgca acgtacaaag aaatagggct      5950
tctgacctgt gaagcaacag tcaatgggca tttgtataag acaaactatc      6000
tcacacatcg acaaaccaat acaatacagg tagaccttc gtagagatgt      6050 acagtgaaat ccccgaaatt atacacatga ctgaaggaag ggagctcgtc      6100
attccctgcc gggttacgtc acctaacatc actgttactt taaaaagtt      6150 tccacttgac actttgatcc ctgatggaaa acgcataatc tgggacagta      6200
gaaagggctt catcatatca aatgcaacgt acaaagaaat agggcttctg      6250
acctgtgaag caacagtcaa tgggcatttg tataagacaa actatctcac      6300
acatcgacaa accaatacaa tctacaggta gacctttcgt agagatgtac      6350
agtgaaatcc ccgaaattat acacatgact gaaggaaggg agctcgtcat      6400
tccctgccgg gttacgtcac ctaacatcac tgttacttta aaaagtttc      6450 cacttgacac tttgatccct gatggaaaac gcataatctg ggacagtaga      6500
aagggcttca tcatatcaaa tgcaacgtac aaagaaatag gcttctgac      6550 ctgtgaagca acagtcaatg gcatttgta taagacaaac tatctcacac      6600
atcgacaaac caatacaatc                                      6620

<210> SEQ ID NO 110
<211> LENGTH: 233
<212> TYPE: PRT
<213> ORGANISM: Artificial sequence
```

<220> FEATURE:
<223> OTHER INFORMATION: sequence is synthesized

<400> SEQUENCE: 110

```
Met Gly Trp Ser Cys Ile Ile Leu Phe Leu Val Ala Thr Ala Thr
  1               5                  10                  15

Gly Val His Ser Asp Ile Gln Met Thr Gln Ser Pro Ser Ser Leu
             20                  25                  30

Ser Ala Ser Val Gly Asp Arg Val Thr Ile Thr Cys Arg Ala Ser
             35                  40                  45

Gln Asp Val Ser Thr Ala Val Ala Trp Tyr Gln Gln Lys Pro Gly
             50                  55                  60

Lys Ala Pro Lys Leu Leu Ile Tyr Ser Ala Ser Phe Leu Tyr Ser
             65                  70                  75

Gly Val Pro Ser Arg Phe Ser Gly Ser Gly Ser Gly Thr Asp Phe
             80                  85                  90

Thr Leu Thr Ile Ser Ser Leu Gln Pro Glu Asp Phe Ala Thr Tyr
             95                 100                 105

Tyr Cys Gln Gln Ser Tyr Thr Thr Pro Pro Thr Phe Gly Gln Gly
            110                 115                 120

Thr Lys Val Glu Ile Lys Arg Thr Val Ala Ala Pro Ser Val Phe
            125                 130                 135

Ile Phe Pro Pro Ser Asp Glu Gln Leu Lys Ser Gly Thr Ala Ser
            140                 145                 150

Val Val Cys Leu Leu Asn Asn Phe Tyr Pro Arg Glu Ala Lys Val
            155                 160                 165

Gln Trp Lys Val Asp Asn Ala Leu Gln Ser Gly Asn Ser Gln Glu
            170                 175                 180

Ser Val Thr Glu Gln Asp Ser Lys Asp Ser Thr Tyr Ser Leu Ser
            185                 190                 195

Ser Thr Leu Thr Leu Ser Lys Ala Asp Tyr Glu Lys His Lys Val
            200                 205                 210

Tyr Ala Cys Glu Val Thr His Gln Gly Leu Ser Ser Pro Val Thr
            215                 220                 225

Lys Ser Phe Asn Arg Gly Glu Cys
            230
```

<210> SEQ ID NO 111
<211> LENGTH: 5387
<212> TYPE: DNA
<213> ORGANISM: Artificial sequence
<220> FEATURE:
<223> OTHER INFORMATION: sequence is synthesized

<400> SEQUENCE: 111

| | |
|---|---:|
| ttcgagctcg cccgacattg attattgact agttattaat agtaatcaat | 50 |
| tacgggtca ttagttcata gcccatatat ggagttccgc gttacataac | 100 |
| ttacggtaaa tggcccgcct ggctgaccgc ccaacgaccc ccgcccattg | 150 |
| acgtcaataa tgacgtatgt tcccatagta acgccaatag ggactttcca | 200 |
| ttgacgtcaa tgggtggagt atttacggta aactgcccac ttggcagtac | 250 |
| atcaagtgta tcatatgcca agtacgcccc ctattgacgt caatgacggt | 300 |
| aaatggcccg cctggcatta tgcccagtac atgaccttat ggactttcc | 350 |
| tacttggcag tacatctacg tattagtcat cgctattacc atggtgatgc | 400 |

| | |
|---|---|
| ggttttggca gtacatcaat gggcgtggat agcggtttga ctcacgggga | 450 |
| tttccaagtc tccaccccat tgacgtcaat gggagtttgt tttggcacca | 500 |
| aaatcaacgg gactttccaa aatgtcgtaa caactccgcc ccattgacgc | 550 |
| aaatgggcgg taggcgtgta cggtgggagg tctatataag cagagctcgt | 600 |
| ttagtgaacc gtcagatcgc ctggagacgc catccacgct gttttgacct | 650 |
| ccatagaaga caccgggacc gatccagcct ccgcggccgg gaacggtgca | 700 |
| ttggaacgcg gattccccgt gccaagagtg acgtaagtac cgcctataga | 750 |
| gtctataggc ccaccccctt ggcttcgtta aacgcggaca caattaata | 800 |
| cataacctta tgtatcatac acatacgatt taggtgacac tatagaataa | 850 |
| catccacttt gcctttctct ccacaggtgt ccactcccag gtccaactgc | 900 |
| acctcggttc tatcgattga attccaccat gggatggtca tgtatcatcc | 950 |
| tttttctagt agcaactgca actggagtac attcagatat ccagatgacc | 1000 |
| cagtccccga gctccctgtc cgcctctgtg ggcgataggg tcaccatcac | 1050 |
| ctgccgtgcc agtcaggatg tgtccactgc tgtagcctgg tatcaacaga | 1100 |
| aaccaggaaa agctccgaag cttctgattt actcggcatc cttcctctac | 1150 |
| tctggagtcc cttctcgctt ctctggtagc ggttccggga cggatttcac | 1200 |
| tctgaccatc agcagtctgc agccggaaga cttcgcaact tattactgtc | 1250 |
| agcaatctta tactactcct cccacgttcg gacagggtac caaggtggag | 1300 |
| atcaaacgaa ctgtggctgc accatctgtc ttcatcttcc cgccatctga | 1350 |
| tgagcagttg aaatctggaa ctgcttctgt tgtgtgcctg ctgaataact | 1400 |
| tctatcccag agaggccaaa gtacagtgga aggtggataa cgcccctccaa | 1450 |
| tcgggtaact cccaggagag tgtcacagag caggacagca aggacagcac | 1500 |
| ctacagcctc agcagcaccc tgacgctgag caaagcagac tacgagaaac | 1550 |
| acaaagtcta cgcctgcgaa gtcacccatc agggcctgag ctcgcccgtc | 1600 |
| acaaagagct tcaacagggg agagtgttaa gcttggccgc catggcccaa | 1650 |
| cttgtttatt gcagcttata atggttacaa ataaagcaat agcatcacaa | 1700 |
| atttcacaaa taaagcattt ttttcactgc attctagttg tggtttgtcc | 1750 |
| aaactcatca atgtatctta tcatgtctgg atcgggaatt aattcggcgc | 1800 |
| agcaccatgg cctgaaataa cctctgaaag aggaacttgg ttaggtatct | 1850 |
| tctgaggcgg aaagaaccag ctgtggaatg tgtgtcagtt agggtgtgga | 1900 |
| aagtccccag gctccccagc aggcagaagt atgcaaagca tgcatctcaa | 1950 |
| ttagtcagca accaggtgtg gaaagtcccc aggctcccca gcaggcagaa | 2000 |
| gtatgcaaag catgcatctc aattagtcag caaccatagt cccgccccta | 2050 |
| actccgccca tcccgcccct aactccgccc agttccgccc attctccgcc | 2100 |
| ccatggctga ctaattttt ttatttatgc agaggccgag gccgcctcgg | 2150 |
| cctctgagct attccagaag tagtgaggag gcttttttgg aggcctaggc | 2200 |
| ttttgcaaaa agctgttaac agcttggcac tggccgtcgt tttacaacgt | 2250 |
| cgtgactggg aaaaccctgg cgttacccaa cttaatcgcc ttgcagcaca | 2300 |
| tccccccttc gccagctggc gtaatagcga agaggcccgc accgatcgcc | 2350 |
| cttcccaaca gttgcgtagc ctgaatggcg aatggcgcct gatgcggtat | 2400 |

```
tttctcctta cgcatctgtg cggtatttca caccgcatac gtcaaagcaa        2450
ccatagtacg cgccctgtag cggcgcatta agcgcggcgg gtgtggtggt        2500
tacgcgcagc gtgaccgcta cacttgccag cgccctagcg cccgctcctt        2550
tcgctttctt cccttccttt ctcgccacgt tcgccggctt tccccgtcaa        2600
gctctaaatc gggggctccc tttagggttc cgatttagtg ctttacggca        2650
cctcgacccc aaaaaacttg atttgggtga tggttcacgt agtgggccat        2700
cgccctgata gacggttttt cgcccttga cgttggagtc cacgttcttt         2750
aatagtggac tcttgttcca aactggaaca acactcaacc ctatctcggg        2800
ctattctttt gatttataag ggattttgcc gatttcggcc tattggttaa        2850
aaaatgagct gatttaacaa aaatttaacg cgaattttaa caaaatatta        2900
acgtttacaa ttttatggtg cactctcagt acaatctgct ctgatgccgc        2950
atagttaagc caactccgct atcgctacgt gactgggtca tggctgcgcc        3000
ccgacacccg ccaacacccg ctgacgcgcc ctgacgggct tgtctgctcc        3050
cggcatccgc ttacagacaa gctgtgaccg tctccgggag ctgcatgtgt        3100
cagaggtttt caccgtcatc accgaaacgc gcgaggcagt attcttgaag        3150
acgaaagggc ctcgtgatac gcctattttt ataggttaat gtcatgataa        3200
taatggtttc ttagacgtca ggtggcactt ttcggggaaa tgtgcgcgga        3250
acccctattt gtttattttt ctaaatacat tcaaatatgt atccgctcat        3300
gagacaataa ccctgataaa tgcttcaata atattgaaaa aggaagagta        3350
tgagtattca catttccgt gtcgccctta ttccctttttt tgcggcattt        3400 tgccttcctg ttttttgctca cccagaaacg ctggtgaaag taaaagatgc        3450
tgaagatcag ttgggtgcac gagtgggtta catcgaactg gatctcaaca        3500
gcggtaagat ccttgagagt tttcgccccg aagaacgttt tccaatgatg        3550 agcacttta aagttctgct atgtggcgcg gtattatccc gtgatgacgc         3600
cgggcaagag caactcggtc gccgcataca ctattctcag aatgacttgg        3650
ttgagtactc accagtcaca gaaaagcatc ttacggatgg catgacagta        3700
agagaattat gcagtgctgc cataaccatg agtgataaca ctgcggccaa        3750
cttacttctg acaacgatcg gaggaccgaa ggagctaacc gcttttttgc        3800
acaacatggg ggatcatgta actcgccttg atcgttggga accggagctg        3850
aatgaagcca taccaaacga cgagcgtgac accacgatgc cagcagcaat        3900
ggcaacaacg ttgcgcaaac tattaactgg cgaactactt actctagctt        3950
cccggcaaca attaatagac tggatggagg cggataaagt tgcaggacca        4000
cttctgcgct cggcccttcc ggctggctgg tttattgctg ataaatctgg        4050
agccggtgag cgtgggtctc gcggtatcat tgcagcactg gggccagatg        4100
gtaagccctc ccgtatcgta gttatctaca cgacggggag tcaggcaact        4150
atggatgaac gaaatagaca gatcgctgag ataggtgcct cactgattaa        4200
gcattggtaa ctgtcagacc aagtttactc atatatactt tagattgatt        4250
taaaacttca ttttaattt aaaaggatct aggtgaagat cctttttgat        4300
aatctcatga ccaaaatccc ttaacgtgag ttttcgttcc actgagcgtc        4350
```

```
agaccccgta gaaaagatca aaggatcttc ttgagatcct ttttttctgc       4400
gcgtaatctg ctgcttgcaa acaaaaaaac caccgctacc agcggtggtt       4450
tgtttgccgg atcaagagct accaactctt tttccgaagg taactggctt       4500
cagcagagcg cagataccaa atactgtcct tctagtgtag ccgtagttag       4550
gccaccactt caagaactct gtagcaccgc ctacatacct cgctctgcta       4600
atcctgttac cagtggctgc tgccagtggc gataagtcgt gtcttaccgg       4650
gttggactca agacgatagt taccggataa ggcgcagcgg tcgggctgaa       4700
cggggggttc gtgcacacag cccagcttgg agcgaacgac ctacaccgaa       4750
ctgagatacc tacagcgtga gcattgagaa agcgccacgc ttcccgaagg       4800
gagaaaggcg gacaggtatc cggtaagcgg cagggtcgga acaggagagc       4850
gcacgaggga gcttccaggg ggaaacgcct ggtatcttta tagtcctgtc       4900
gggtttcgcc acctctgact tgagcgtcga ttttgtgat gctcgtcagg        4950
ggggcggagc ctatggaaaa acgccagcaa cgcggccttt ttacggttcc       5000
tggccttttg ctggcctttt gctcacatgt tctttcctgc gttatcccct       5050
gattctgtgg ataaccgtat taccgccttt gagtgagctg ataccgctcg       5100
ccgcagccga cgaccgagc gcagcgagtc agtgagcgag gaagcggaag        5150
agcgcccaat acgcaaaccg cctctccccg cgcgttggcc gattcattaa       5200
tccagctggc acgacaggtt tcccgactgg aaagcgggca gtgagcgcaa       5250
cgcaattaat gtgagttacc tcactcatta ggcaccccag gctttacact       5300
ttatgcttcc ggctcgtatg ttgtgtggaa ttgtgagcgg ataacaattt       5350
cacacaggaa acagctatga ccatgattac gaattaa                    5387
```

<210> SEQ ID NO 112
<211> LENGTH: 468
<212> TYPE: PRT
<213> ORGANISM: Artificial sequence
<220> FEATURE:
<223> OTHER INFORMATION: sequence is synthesized

<400> SEQUENCE: 112

```
Met Gly Trp Ser Cys Ile Ile Leu Phe Leu Val Ala Thr Ala Thr
  1               5                  10                  15

Gly Ala Tyr Ala Glu Val Gln Leu Val Glu Ser Gly Gly Gly Leu
                 20                  25                  30

Val Gln Pro Gly Gly Ser Leu Arg Leu Ser Cys Ala Ala Ser Gly
                 35                  40                  45

Phe Thr Ile Ser Gly Ser Trp Ile His Trp Val Arg Gln Ala Pro
                 50                  55                  60

Gly Lys Gly Leu Glu Trp Val Ala Trp Ile Ala Pro Tyr Ser Gly
                 65                  70                  75

Ala Thr Asp Tyr Ala Asp Ser Val Lys Gly Arg Phe Thr Ile Ser
                 80                  85                  90

Ala Asp Thr Ser Lys Asn Thr Ala Tyr Leu Gln Met Asn Ser Leu
                 95                 100                 105

Arg Ala Glu Asp Thr Ala Val Tyr Tyr Cys Ala Arg Glu Gly Gly
                110                 115                 120

Leu Tyr Trp Val Phe Asp Tyr Trp Gly Gln Gly Thr Leu Val Thr
                125                 130                 135
```

Val Ser Ser Ala Ser Thr Lys Gly Pro Ser Val Phe Pro Leu Ala
            140                 145                 150

Pro Ser Ser Lys Ser Thr Ser Gly Gly Thr Ala Ala Leu Gly Cys
            155                 160                 165

Leu Val Lys Asp Tyr Phe Pro Glu Pro Val Thr Val Ser Trp Asn
            170                 175                 180

Ser Gly Ala Leu Thr Ser Gly Val His Thr Phe Pro Ala Val Leu
            185                 190                 195

Gln Ser Ser Gly Leu Tyr Ser Leu Ser Ser Val Val Thr Val Pro
            200                 205                 210

Ser Ser Ser Leu Gly Thr Gln Thr Tyr Ile Cys Asn Val Asn His
            215                 220                 225

Lys Pro Ser Asn Thr Lys Val Asp Lys Lys Val Glu Pro Lys Ser
            230                 235                 240

Cys Asp Lys Thr His Thr Cys Pro Pro Cys Pro Ala Pro Glu Leu
            245                 250                 255

Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val
            290                 295                 300

Asp Gly Val Glu Val His Asn Ala Lys Thr Lys Pro Arg Glu Glu
            305                 310                 315

Gln Tyr Asn Ser Thr Tyr Arg Val Val Ser Val Leu Thr Val Leu
            320                 325                 330

His Gln Asp Trp Leu Asn Gly Lys Glu Tyr Lys Cys Lys Val Ser
            335                 340                 345

Asn Lys Ala Leu Pro Ala Pro Ile Glu Lys Thr Ile Ser Lys Ala
            350                 355                 360

Lys Gly Gln Pro Arg Glu Pro Gln Val Tyr Thr Leu Pro Pro Ser
            365                 370                 375

Arg Glu Glu Met Thr Lys Asn Gln Val Ser Leu Thr Cys Leu Val
            380                 385                 390

Lys Gly Phe Tyr Pro Ser Asp Ile Ala Val Glu Trp Glu Ser Asn
            395                 400                 405

Gly Gln Pro Glu Asn Asn Tyr Lys Thr Thr Pro Pro Val Leu Asp
            410                 415                 420

Ser Asp Gly Ser Phe Phe Leu Tyr Ser Lys Leu Thr Val Asp Lys
            425                 430                 435

Ser Arg Trp Gln Gln Gly Asn Val Phe Ser Cys Ser Val Met His
            440                 445                 450

Glu Ala Leu His Asn His Tyr Thr Gln Lys Ser Leu Ser Leu Ser
            455                 460                 465

Pro Gly Lys

<210> SEQ ID NO 113
<211> LENGTH: 6126
<212> TYPE: DNA
<213> ORGANISM: Artificial sequence
<220> FEATURE:
<223> OTHER INFORMATION: sequence is synthesized

<400> SEQUENCE: 113
attcgagctc gcccgacatt gattattgac tagttattaa tagtaatcaa            50

-continued

```
ttacggggtc attagttcat agcccatata tggagttccg cgttacataa        100
cttacggtaa atggcccgcc tggctgaccg cccaacgacc cccgcccatt        150
gacgtcaata atgacgtatg ttcccatagt aacgccaata gggactttcc        200
attgacgtca atgggtggag tatttacggt aaactgccca cttggcagta        250
catcaagtgt atcatatgcc aagtacgccc cctattgacg tcaatgacgg        300
taaatggccc gcctggcatt atgcccagta catgacctta tgggactttc        350
ctacttggca gtacatctac gtattagtca tcgctattac catggtgatg        400
cggttttggc agtacatcaa tgggcgtgga tagcggtttg actcacgggg        450
atttccaagt ctccacccca ttgacgtcaa tgggagtttg ttttggcacc        500
aaaatcaacg ggactttcca aaatgtcgta acaactccgc cccattgacg        550
caaatgggcg gtaggcgtgt acggtgggag gtctatataa gcagagctcg        600
tttagtgaac cgtcagatcg cctggagacg ccatccacgc tgttttgacc        650
tccatagaag acaccgggac cgatccagcc tccgcggccg gaacggtgc         700
attggaacgc ggattccccg tgccaagagt gacgtaagta ccgcctatag        750
agtctatagg cccaccccct tggcttcgtt agaacgcggc tacaattaat        800
acataacctt atgtatcata cacatacgat ttaggtgaca ctatagaata        850
acatccactt tgcctttctc tccacaggtg tccactccca ggtccaactg        900
cacctcggtt ctatcgattg aattccacca tgggatggtc atgtatcatc        950
ctttttctag tagcaactgc aactggagcg tacgctgagg ttcagctggt       1000
ggagtctggc ggtggcctgg tgcagccagg gggctcactc cgtttgtcct       1050
gtgcagcttc tggcttcacc attagtggtt cttggataca ctgggtgcgt       1100
caggccccgg gtaagggcct ggaatgggtt gcttggattg ctccttatag       1150
cggcgctact gactatgccg atagcgtcaa gggccgtttc actataagcg       1200
cagacacatc caaaaacaca gcctacctac aaatgaacag cttaagagct       1250
gaggacactg ccgtctatta ttgtgcaaga gaggggggct tgtactgggt       1300
gttcgactac tgggtcaag gaaccctggt caccgtctcc tcggcctcca       1350
ccaagggccc atcggtcttc cccctggcac cctcctccaa gagcacctct       1400
gggggcacag cggccctggg ctgcctggtc aaggactact ccccgaacc        1450
ggtgacggtg tcgtggaact caggcgccct gaccagcggc gtgcacacct       1500
tcccggctgt cctacagtcc tcaggactct actccctcag cagcgtggtg       1550
actgtgccct ctagcagctt gggcacccag acctacatct gcaacgtgaa       1600
tcacaagccc agcaacacca aggtggacaa gaaagttgag cccaaatctt       1650
gtgacaaaac tcacacatgc ccaccgtgcc cagcacctga actcctgggg       1700
ggaccgtcag tcttcctctt ccccccaaaa cccaaggaca cccctcatgat       1750
ctcccggacc cctgaggtca catgcgtggt ggtggacgtg agccacgaag       1800
accctgaggt caagttcaac tggtacgtgg acggcgtgga ggtgcataat       1850
gccaagacaa agccgcggga ggagcagtac aacagcacgt accgggtggt       1900
cagcgtcctc accgtcctgc accaggactg gctgaatggc aaggagtaca       1950
agtgcaaggt ctccaacaaa gccctcccag cccccatcga gaaaaccatc       2000
```

-continued

| | |
|---|---|
| tccaaagcca aagggcagcc ccgagaacca caggtgtaca ccctgccccc | 2050 |
| atcccgggaa gagatgacca agaaccaggt cagcctgacc tgcctggtca | 2100 |
| aaggcttcta tcccagcgac atcgccgtgg agtgggagag caatgggcag | 2150 |
| ccggagaaca actacaagac cacgcctccc gtgctggact ccgacggctc | 2200 |
| cttcttcctc tacagcaagc tcaccgtgga caagagcagg tggcagcagg | 2250 |
| ggaacgtctt ctcatgctcc gtgatgcatg aggctctgca caaccactac | 2300 |
| acgcagaaga gcctctccct gtctccgggt aaatgagtgc gacggcccta | 2350 |
| gagtcgacct gcagaagctt ggccgccatg gcccaacttg tttattgcag | 2400 |
| cttataatgg ttacaaataa agcaatagca tcacaaattt cacaaataaa | 2450 |
| gcatttttt cactgcattc tagttgtggt ttgtccaaac tcatcaatgt | 2500 |
| atcttatcat gtctggatcg atcgggaatt aattcggcgc agcaccatgg | 2550 |
| cctgaaataa cctctgaaag aggaacttgg ttaggtacct tctgaggcgg | 2600 |
| aaagaaccat ctgtggaatg tgtgtcagtt agggtgtgga aagtccccag | 2650 |
| gctccccagc aggcagaagt atgcaaagca tgcatctcaa ttagtcagca | 2700 |
| accaggtgtg gaaagtcccc aggctcccca gcaggcagaa gtatgcaaag | 2750 |
| catgcatctc aattagtcag caaccatagt cccgccccta actccgccca | 2800 |
| tcccgcccct aactccgccc agttccgccc attctccgcc ccatggctga | 2850 |
| ctaattttt ttatttatgc agaggccgag gccgcctcgg cctctgagct | 2900 |
| attccagaag tagtgaggag gctttttgg aggcctaggc ttttgcaaaa | 2950 |
| agctgttaac agcttggcac tggccgtcgt tttacaacgt cgtgactggg | 3000 |
| aaaaccctgg cgttacccaa cttaatcgcc ttgcagcaca tccccccttc | 3050 |
| gccagttggc gtaatagcga agaggcccgc accgatcgcc cttcccaaca | 3100 |
| gttgcgtagc ctgaatggcg aatggcgcct gatgcggtat tttctcctta | 3150 |
| cgcatctgtg cggtatttca caccgcatac gtcaaagcaa ccatagtacg | 3200 |
| cgccctgtag cggcgcatta agcgcggcgg gtgtggtggt tacgcgcagc | 3250 |
| gtgaccgcta cacttgccag cgccctagcg cccgctcctt tcgctttctt | 3300 |
| cccttccttt ctcgccacgt tcgccggctt tccccgtcaa gctctaaatc | 3350 |
| gggggctccc tttagggttc cgatttagtg ctttacggca cctcgacccc | 3400 |
| aaaaaacttg atttgggtga tggttcacgt agtgggccat cgccctgata | 3450 |
| gacggttttt cgccctttga cgttggagtc cacgttcttt aatagtggac | 3500 |
| tcttgttcca aactggaaca acactcaacc ctatctcggg ctattctttt | 3550 |
| gatttataag ggattttgcc gatttcggcc tattggttaa aaaatgagct | 3600 |
| gatttaacaa aaatttaacg cgaattttaa caaaatatta cgtttacaa | 3650 |
| ttttatggtg cactctcagt acaatctgct ctgatgccgc atagttaagc | 3700 |
| caactccgct atcgctacgt gactgggtca tggctgcgcc ccgacacccg | 3750 |
| ccaacacccg ctgacgcgcc ctgacgggct tgtctgctcc cggcatccgc | 3800 |
| ttacagacaa gctgtgaccg tctccgggag ctgcatgtgt cagaggtttt | 3850 |
| caccgtcatc accgaaacgc gcgaggcagt attcttgaag acgaaagggc | 3900 |
| ctcgtgatac gcctattttt ataggttaat gtcatgataa taatggtttc | 3950 |
| ttagacgtca ggtggcactt ttcggggaaa tgtgcgcgga acccctattt | 4000 |

```
gtttattttt ctaaatacat tcaaatatgt atccgctcat gagacaataa      4050
ccctgataaa tgcttcaata atattgaaaa aggaagagta tgagtattca      4100
acatttccgt gtcgccctta ttccttttt tgcggcattt tgccttcctg       4150
tttttgctca cccagaaacg ctggtgaaag taaaagatgc tgaagatcag      4200
ttgggtgcac gagtgggtta catcgaactg gatctcaaca gcggtaagat      4250
ccttgagagt tttcgccccg aagaacgttt tccaatgatg agcacttta      4300 aagttctgct atgtggcgcg gtattatccc gtgatgacgc cgggcaagag      4350
caactcggtc gccgcataca ctattctcag aatgacttgg ttgagtactc      4400
accagtcaca gaaaagcatc ttacggatgg catgacagta agagaattat      4450
gcagtgctgc cataaccatg agtgataaca ctgcggccaa cttacttctg      4500
acaacgatcg gaggaccgaa ggagctaacc gcttttttgc acaacatggg      4550
ggatcatgta actcgccttg atcgttggga accggagctg aatgaagcca      4600
taccaaacga cgagcgtgac accacgatgc cagcagcaat ggcaacaacg      4650
ttgcgcaaac tattaactgg cgaactactt actctagctt cccggcaaca      4700
attaatagac tggatggagg cggataaagt tgcaggacca cttctgcgct      4750
cggcccttcc ggctggctgg tttattgctg ataaatctgg agccggtgag      4800
cgtgggtctc gcggtatcat tgcagcactg gggccagatg gtaagccctc      4850
ccgtatcgta gttatctaca cgacggggag tcaggcaact atggatgaac      4900
gaaatagaca gatcgctgag ataggtgcct cactgattaa gcattggtaa      4950
ctgtcagacc aagtttactc atatatactt tagattgatt taaaacttca      5000
tttttaattt aaaaggatct aggtgaagat cctttttgat aatctcatga      5050
ccaaaatccc ttaacgtgag ttttcgttcc actgagcgtc agaccccgta      5100
gaaaagatca aaggatcttc ttgagatcct ttttttctgc gcgtaatctg      5150
ctgcttgcaa acaaaaaaac caccgctacc agcggtggtt tgtttgccgg      5200
atcaagagct accaactctt tttccgaagg taactggctt cagcagagcg      5250
cagataccaa atactgtcct tctagtgtag ccgtagttag gccaccactt      5300
caagaactct gtagcaccgc ctacatacct cgctctgcta atcctgttac      5350
cagtggctgc tgccagtggc gataagtcgt gtcttaccgg gttggactca      5400
agacgatagt taccggataa ggcgcagcgg tcgggctgaa cggggggttc      5450
gtgcacacag cccagcttgg agcgaacgac ctacaccgaa ctgagatacc      5500
tacagcgtga gcattgagaa agcgccacgc ttcccgaagg gagaaaggcg      5550
gacaggtatc cggtaagcgg cagggtcgga acaggagagc gcacgaggga      5600
gcttccaggg ggaaacgcct ggtatcttta tagtcctgtc gggtttcgcc      5650
acctctgact tgagcgtcga tttttgtgat gctcgtcagg gggcggagc      5700 ctatggaaaa acgccagcaa cgcggccttt ttacggttcc tggccttttg      5750
ctggcctttt gctcacatgt tctttcctgc gttatcccct gattctgtgg      5800
ataaccgtat taccgccttt gagtgagctg ataccgctcg ccgcagccga      5850
acgaccgagc gcagcgagtc agtgagcgag gaagcggaag agcgcccaat      5900
acgcaaaccg cctctccccg cgcgttggcc gattcattaa tccaactggc      5950
```

```
acgacaggtt tcccgactgg aaagcgggca gtgagcgcaa cgcaattaat        6000
gtgagttacc tcactcatta ggcaccccag gctttacact ttatgcttcc        6050
ggctcgtatg ttgtgtggaa ttgtgagcgg ataacaattt cacacaggaa        6100
acagctatga ccatgattac gaatta                                  6126
```

<210> SEQ ID NO 114
<211> LENGTH: 245
<212> TYPE: PRT
<213> ORGANISM: Artificial sequence
<220> FEATURE:
<223> OTHER INFORMATION: sequence is synthesized
<220> FEATURE:
<221> NAME/KEY: Xaa
<222> LOCATION: 1-19
<223> OTHER INFORMATION: Xaa is any amino acid and any one can be
      missing
<220> FEATURE:
<221> NAME/KEY: Unsure
<222> LOCATION: 1-19,22-28,30-36,38-52,54-56,58,61-62,64-65,70,73,88,
      96-97,99-100,103,105,108,112,114-115,127,133,136,144,152-153,164,
      169,174,176,178,181,187,198,207,213-215,221,225,238
<223> OTHER INFORMATION: Unknown amino acid
<220> FEATURE:
<221> NAME/KEY: Xaa
<222> LOCATION: 22-28
<223> OTHER INFORMATION: Xaa is any amino acid
<220> FEATURE:
<221> NAME/KEY: Xaa
<222> LOCATION: 30-36
<223> OTHER INFORMATION: Xaa is any amino acid and any one can be
      missing
<220> FEATURE:
<221> NAME/KEY: Xaa
<222> LOCATION: 38-44
<223> OTHER INFORMATION: Xaa is any amino acid
<220> FEATURE:
<221> NAME/KEY: Xaa
<222> LOCATION: 45
<223> OTHER INFORMATION: Xaa is R or K
<220> FEATURE:
<221> NAME/KEY: Xaa
<222> LOCATION: 46
<223> OTHER INFORMATION: Xaa is any amino acid
<220> FEATURE:
<221> NAME/KEY: Xaa
<222> LOCATION: 47
<223> OTHER INFORMATION: Xaa is R, P, or A
<220> FEATURE:
<221> NAME/KEY: Xaa
<222> LOCATION: 48
<223> OTHER INFORMATION: Xaa is B, D, E, N, Q or Z
<220> FEATURE:
<221> NAME/KEY: Xaa
<222> LOCATION: 49
<223> OTHER INFORMATION: Xaa is V, A or F
<220> FEATURE:
<221> NAME/KEY: Xaa
<222> LOCATION: 50-52
<223> OTHER INFORMATION: Xaa is any amino acid
<220> FEATURE:
<221> NAME/KEY: Y
<222> LOCATION: 53
<223> OTHER INFORMATION: Y can be missing
<220> FEATURE:
<221> NAME/KEY: Xaa
<222> LOCATION: 54
<223> OTHER INFORMATION: Xaa is Q or N or can be missing
<220> FEATURE:
<221> NAME/KEY: Xaa
<222> LOCATION: 55
<223> OTHER INFORMATION: Xaa is L or V
<220> FEATURE:
<221> NAME/KEY: Xaa
<222> LOCATION: 56, 62, 73, 88
<223> OTHER INFORMATION: Xaa is any amino acid

```
<220> FEATURE:
<221> NAME/KEY: Xaa
<222> LOCATION: 56
<223> OTHER INFORMATION: Xaa is any amino acid and any one can be
      missing
<220> FEATURE:
<221> NAME/KEY: Xaa
<222> LOCATION: 58
<223> OTHER INFORMATION: Xaa is L or V
<220> FEATURE:
<221> NAME/KEY: Xaa
<222> LOCATION: 61
<223> OTHER INFORMATION: Xaa is P or V
<220> FEATURE:
<221> NAME/KEY: Xaa
<222> LOCATION: 64
<223> OTHER INFORMATION: Xaa is V or T
<220> FEATURE:
<221> NAME/KEY: Xaa
<222> LOCATION: 65
<223> OTHER INFORMATION: Xaa is P or Q
<220> FEATURE:
<221> NAME/KEY: Xaa
<222> LOCATION: 70
<223> OTHER INFORMATION: Xaa is N or S
<220> FEATURE:
<221> NAME/KEY: Xaa
<222> LOCATION: 96
<223> OTHER INFORMATION: Xaa is L or V
<220> FEATURE:
<221> NAME/KEY: Xaa
<222> LOCATION: 97
<223> OTHER INFORMATION: Xaa is R or S
<220> FEATURE:
<221> NAME/KEY: Xaa
<222> LOCATION: 99
<223> OTHER INFORMATION: Xaa is S, R or V
<220> FEATURE:
<221> NAME/KEY: Xaa
<222> LOCATION: 100
<223> OTHER INFORMATION: Xaa is F or I
<220> FEATURE:
<221> NAME/KEY: Xaa
<222> LOCATION: 103
<223> OTHER INFORMATION: Xaa is S or P
<220> FEATURE:
<221> NAME/KEY: Xaa
<222> LOCATION: 105
<223> OTHER INFORMATION: Xaa is T or K
<220> FEATURE:
<221> NAME/KEY: Xaa
<222> LOCATION: 108
<223> OTHER INFORMATION: Xaa is F or Y
<220> FEATURE:
<221> NAME/KEY: Xaa
<222> LOCATION: 112
<223> OTHER INFORMATION: Xaa is S or A
<220> FEATURE:
<221> NAME/KEY: Xaa
<222> LOCATION: 114
<223> OTHER INFORMATION: Xaa is S or N
<220> FEATURE:
<221> NAME/KEY: Xaa
<222> LOCATION: 115
<223> OTHER INFORMATION: Xaa is S or A
<220> FEATURE:
<221> NAME/KEY: Xaa
<222> LOCATION: 127
<223> OTHER INFORMATION: Xaa is B, D, E, N, Q or Z
<220> FEATURE:
<221> NAME/KEY: Xaa
<222> LOCATION: 133
<223> OTHER INFORMATION: Xaa is M, L or Q
<220> FEATURE:
<221> NAME/KEY: Xaa
<222> LOCATION: 136
<223> OTHER INFORMATION: Xaa is B, D, E, N, Q or Z
<220> FEATURE:
<221> NAME/KEY: Xaa
```

```
<222> LOCATION: 144
<223> OTHER INFORMATION: Xaa is S or T
<220> FEATURE:
<221> NAME/KEY: Xaa
<222> LOCATION: 152
<223> OTHER INFORMATION: Xaa is K or R
<220> FEATURE:
<221> NAME/KEY: Xaa
<222> LOCATION: 153, 169, 207
<223> OTHER INFORMATION: Xaa is any amino acid
<220> FEATURE:
<221> NAME/KEY: Xaa
<222> LOCATION: 164
<223> OTHER INFORMATION: Xaa is B, D, E, N, Q or Z
<220> FEATURE:
<221> NAME/KEY: Xaa
<222> LOCATION: 174
<223> OTHER INFORMATION: Xaa is I or V
<220> FEATURE:
<221> NAME/KEY: Xaa
<222> LOCATION: 176
<223> OTHER INFORMATION: Xaa is A or S
<220> FEATURE:
<221> NAME/KEY: Xaa
<222> LOCATION: 178
<223> OTHER INFORMATION: Xaa is I or V
<220> FEATURE:
<221> NAME/KEY: Xaa
<222> LOCATION: 181
<223> OTHER INFORMATION: Xaa is B, D, E, N, Q or Z
<220> FEATURE:
<221> NAME/KEY: Xaa
<222> LOCATION: 187
<223> OTHER INFORMATION: Xaa is L or M
<220> FEATURE:
<221> NAME/KEY: Xaa
<222> LOCATION: 198
<223> OTHER INFORMATION: Xaa is S or T
<220> FEATURE:
<221> NAME/KEY: Xaa
<222> LOCATION: 213
<223> OTHER INFORMATION: Xaa is I or V
<220> FEATURE:
<221> NAME/KEY: Xaa
<222> LOCATION: 214
<223> OTHER INFORMATION: Xaa is A or G
<220> FEATURE:
<221> NAME/KEY: Xaa
<222> LOCATION: 215
<223> OTHER INFORMATION: Xaa is I or L
<220> FEATURE:
<221> NAME/KEY: Xaa
<222> LOCATION: 221
<223> OTHER INFORMATION: Xaa is S or A
<220> FEATURE:
<221> NAME/KEY: Xaa
<222> LOCATION: 225
<223> OTHER INFORMATION: Xaa is R or K
<220> FEATURE:
<221> NAME/KEY: Xaa
<222> LOCATION: 238
<223> OTHER INFORMATION: Xaa is I or V

<400> SEQUENCE: 114

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Leu Leu Xaa Xaa Xaa Xaa Xaa Xaa Xaa Pro Xaa
                20                  25                  30

Xaa Xaa Xaa Xaa Xaa Xaa Lys Xaa Xaa Xaa Xaa Xaa Xaa Xaa Xaa
                35                  40                  45

Xaa Xaa Xaa Xaa Xaa Xaa Xaa Tyr Xaa Xaa Xaa Cys Xaa Gln Gly
                50                  55                  60

Xaa Xaa Gly Xaa Xaa Gly Arg Asp Gly Xaa Pro Gly Xaa Asn Gly
                65                  70                  75
```

```
Ile Pro Gly Thr Pro Gly Ile Pro Gly Arg Asp Gly Xaa Lys Gly
                80                  85                  90

Glu Lys Gly Glu Cys Xaa Xaa Glu Xaa Xaa Glu Glu Xaa Trp Xaa
                95                 100                 105

Pro Asn Xaa Lys Gln Cys Xaa Trp Xaa Xaa Leu Asn Tyr Gly Ile
               110                 115                 120

Asp Leu Gly Lys Ile Ala Xaa Cys Thr Phe Thr Lys Xaa Arg Ser
               125                 130                 135

Xaa Ser Ala Leu Arg Val Leu Phe Xaa Gly Ser Leu Arg Leu Lys
               140                 145                 150

Cys Xaa Xaa Ala Cys Cys Gln Arg Trp Tyr Phe Thr Phe Xaa Gly
               155                 160                 165

Ala Glu Cys Xaa Gly Pro Leu Pro Xaa Glu Xaa Ile Xaa Tyr Leu
               170                 175                 180

Xaa Gln Gly Ser Pro Glu Xaa Asn Ser Thr Ile Asn Ile His Arg
               185                 190                 195

Thr Ser Xaa Val Glu Gly Leu Cys Glu Gly Ile Xaa Ala Gly Leu
               200                 205                 210

Val Asp Xaa Xaa Xaa Trp Val Gly Thr Cys Xaa Asp Tyr Pro Xaa
               215                 220                 225

Gly Asp Ala Ser Thr Gly Trp Asn Ser Val Ser Arg Xaa Ile Ile
               230                 235                 240

Glu Glu Leu Pro Lys
               245

<210> SEQ ID NO 115
<211> LENGTH: 11
<212> TYPE: PRT
<213> ORGANISM: Artificial sequence
<220> FEATURE:
<223> OTHER INFORMATION: sequence is synthesized
<220> FEATURE:
<221> NAME/KEY: Xaa
<222> LOCATION: 1
<223> OTHER INFORMATION: Xaa is G or A
<220> FEATURE:
<221> NAME/KEY: Xaa
<222> LOCATION: 2
<223> OTHER INFORMATION: Xaa is S, T, A, R, W or Y
<220> FEATURE:
<221> NAME/KEY: Xaa
<222> LOCATION: 4
<223> OTHER INFORMATION: Xaa is S, T, A, R, W or Y
<220> FEATURE:
<221> NAME/KEY: Xaa
<222> LOCATION: 6
<223> OTHER INFORMATION: Xaa is Y or F
<220> FEATURE:
<221> NAME/KEY: Xaa
<222> LOCATION: 7
<223> OTHER INFORMATION: Xaa is G, S, T or A
<220> FEATURE:
<221> NAME/KEY: Xaa
<222> LOCATION: 9
<223> OTHER INFORMATION: Xaa is N, Y or A
<220> FEATURE:
<221> NAME/KEY: Xaa
<222> LOCATION: 11
<223> OTHER INFORMATION: Xaa is N, Y, or D

<400> SEQUENCE: 115

Xaa Xaa Ile Xaa Pro Xaa Xaa Gly Xaa Thr Xaa
                 5                  10
```

```
<210> SEQ ID NO 116
<211> LENGTH: 14
<212> TYPE: PRT
<213> ORGANISM: Artificial sequence
<220> FEATURE:
<223> OTHER INFORMATION: sequence is synthesized
<220> FEATURE:
<221> NAME/KEY: Xaa
<222> LOCATION: 2
<223> OTHER INFORMATION: Xaa is A, S or T
<220> FEATURE:
<221> NAME/KEY: Xaa
<222> LOCATION: 3
<223> OTHER INFORMATION: Xaa is a basic amino acid
<220> FEATURE:
<221> NAME/KEY: Xaa
<222> LOCATION: 4
<223> OTHER INFORMATION: Xaa is any amino acid
<220> FEATURE:
<221> NAME/KEY: Xaa
<222> LOCATION: 7
<223> OTHER INFORMATION: Xaa is a hydrophobic amino acid
<220> FEATURE:
<221> NAME/KEY: Xaa
<222> LOCATION: 8-11
<223> OTHER INFORMATION: Xaa can be any amino acid or can be missing
<220> FEATURE:
<221> NAME/KEY: Xaa
<222> LOCATION: 8-11
<223> OTHER INFORMATION: at least one of X5-X8 is an aromatic amino
      acid or a hydrophobic amino acid
<220> FEATURE:
<221> NAME/KEY: Xaa
<222> LOCATION: 12
<223> OTHER INFORMATION: Xaa is an aromatic or hydrophobic amino acid
<220> FEATURE:
<221> NAME/KEY: Xaa
<222> LOCATION: 13
<223> OTHER INFORMATION: Xaa is D or A
<220> FEATURE:
<221> NAME/KEY: Xaa
<222> LOCATION: 14
<223> OTHER INFORMATION: Xaa is Y or V

<400> SEQUENCE: 116

Cys Xaa Xaa Xaa Gly Gly Xaa Xaa Xaa Xaa Xaa Xaa Xaa Xaa
                5                   10

<210> SEQ ID NO 117
<211> LENGTH: 15
<212> TYPE: PRT
<213> ORGANISM: Yeast

<400> SEQUENCE: 117

Gly Trp Asn Ser Val Ser Arg Ile Ile Ile Glu Glu Leu Pro Lys
1               5                   10                  15
```